(12) United States Patent
Lewis et al.

(10) Patent No.: US 10,723,782 B2
(45) Date of Patent: *Jul. 28, 2020

(54) EXOSOMES FOR IMMUNO-ONCOLOGY AND ANTI-INFLAMMATORY THERAPY

(71) Applicant: Codiak BioSciences, Inc., Cambridge, MA (US)

(72) Inventors: Nuruddeen D. Lewis, Andover, MA (US); Yu Zhou, Somerville, MA (US); Sriram Sathyanarayanan, Lexington, MA (US); John D. Kulman, Belmont, MA (US); Douglas E. Williams, Boston, MA (US); Leonid A. Gaydukov, Malden, MA (US); Ke Xu, Sudbury, MA (US); Shelly Martin, Stoneham, MA (US)

(73) Assignee: Codiak BioSciences, Inc., Cambridge, MA (US)

( * ) Notice: Subject to any disclaimer, the term of this patent is extended or adjusted under 35 U.S.C. 154(b) by 85 days.

This patent is subject to a terminal disclaimer.

(21) Appl. No.: 16/236,246

(22) Filed: Dec. 28, 2018

(65) Prior Publication Data

US 2019/0202892 A1    Jul. 4, 2019

Related U.S. Application Data

(60) Provisional application No. 62/723,267, filed on Aug. 27, 2018, provisional application No. 62/611,140, filed on Dec. 28, 2017.

(51) Int. Cl.

| C07K 14/715 | (2006.01) |
|---|---|
| C07K 14/705 | (2006.01) |
| C07K 14/54 | (2006.01) |
| C07K 14/52 | (2006.01) |
| C07K 14/47 | (2006.01) |
| C07K 16/28 | (2006.01) |
| C07K 14/475 | (2006.01) |
| C07K 14/57 | (2006.01) |
| A61K 39/00 | (2006.01) |

(52) U.S. Cl.
CPC ...... *C07K 14/7151* (2013.01); *C07K 14/4703* (2013.01); *C07K 14/475* (2013.01); *C07K 14/52* (2013.01); *C07K 14/5418* (2013.01); *C07K 14/5434* (2013.01); *C07K 14/5443* (2013.01); *C07K 14/57* (2013.01); *C07K 14/70532* (2013.01); *C07K 14/70575* (2013.01); *C07K 14/70578* (2013.01); *C07K 14/7155* (2013.01); *C07K 16/2809* (2013.01); *C07K 16/2818* (2013.01); *A61K 2039/505* (2013.01); *A61K 2039/6018* (2013.01); *A61K 2039/627* (2013.01); *C07K 2317/622* (2013.01); *C07K 2317/76* (2013.01); *C07K 2319/00* (2013.01); *C07K 2319/02* (2013.01); *C07K 2319/03* (2013.01); *C07K 2319/31* (2013.01); *C07K 2319/60* (2013.01)

(58) Field of Classification Search
None
See application file for complete search history.

(56) References Cited

U.S. PATENT DOCUMENTS

| 7,704,964 | B2 * | 4/2010 | Delcayre | C07K 14/47 424/93.2 |
|---|---|---|---|---|
| 9,518,125 | B2 | 12/2016 | Yong et al. | |
| 2005/0119215 | A1 | 6/2005 | Al-Mahmood et al. | |
| 2013/0156801 | A1 | 6/2013 | Bond et al. | |
| 2013/0280265 | A1 | 10/2013 | Rolland | |
| 2014/0179006 | A1 | 6/2014 | Zhang | |
| 2015/0174166 | A1 * | 6/2015 | Giampapa | A61K 35/15 424/520 |
| 2015/0190429 | A1 * | 7/2015 | Beelen | A61K 38/17 424/400 |
| 2015/0290343 | A1 | 10/2015 | Lotvall et al. | |
| 2015/0301058 | A1 | 10/2015 | Schettini et al. | |
| 2017/0173076 | A1 * | 6/2017 | Greco | A61K 35/15 |
| 2017/0333479 | A1 * | 11/2017 | Copik | A61K 35/13 |
| 2018/0042847 | A1 * | 2/2018 | Ross | A61K 31/625 |

FOREIGN PATENT DOCUMENTS

| WO | WO2001/093836 A3 | 10/2002 |
|---|---|---|
| WO | WO2007/126386 A1 | 11/2007 |
| WO | WO2012/048372 A1 | 4/2012 |
| WO | WO2016/057755 A1 | 4/2016 |
| WO | WO2016/077639 A2 | 5/2016 |
| WO | WO-2016168860 A1 | 10/2016 |
| WO | WO2017/161010 A1 | 9/2017 |
| WO | WO-2019133934 A2 | 7/2019 |

OTHER PUBLICATIONS

Bellavia et al., "Interleukin 3-receptor targeted exosomes inhibit in vitro and in vivo Chronic Myelogenous Leukemia cell growth," Theranostics, 2017, vol. 7, No. 5, pp. 1333-1345.

Chen et al., "Exosomal PD-L1 contributes to immunosuppression and is associated with anti-PD-1 response," Nature, 2018, vol. 560, No. 7718, 27 pages.

Ghazawi et al., "IL-7 downregulates IL-7Rα expression in human CD8 T cells by two independent mechanisms," Immunology and Cell Biology, 2013, vol. 91, pp. 149-158.

Kooijmans et al., "Modulation of tissue tropism and biological activity of exosomes and other extracellular vesicles: New nanotools for cancer treatment," Pharmacological Research, 2016, vol. 111, pp. 487-500.

Kordelas et al., "MSC-derived exosomes: a novel tool to treat therapy-refractory graft-versus-host disease," Leukemia, Jan. 21 2014, 12 pages.

(Continued)

*Primary Examiner* — Daniel C Gamett
(74) *Attorney, Agent, or Firm* — Sterne, Kessler, Goldstein & Fox P.L.L.C.

(57) ABSTRACT

Disclosed herein are extracellular vesicles comprising an immunomodulating component. Also provided are methods for producing the extracellular vesicles and methods for using the extracellular vesicles for treating cancer, GvHD, and autoimmune diseases.

19 Claims, 53 Drawing Sheets

Specification includes a Sequence Listing.

(56) References Cited

OTHER PUBLICATIONS

Lai et al. "Mesenchymal Stem Cell Exosome: a Novel Stem Cell Based Therapy for Cardiovascular Disease," Regenerative Medicine, Jul. 2011, vol. 6. No. 4, pp. 481-492.
Leonard et al.,"Effects of single-dose interleukin-12 exposure on interleukin-12—associated toxicity and interferon-y production," Blood, 1997, vol. 90, No. 7, pp. 2541-2548.
Moss et al. "Shedding of Membrane Proteins by ADAM Family Proteases." Essays in Biochemistry, Oct. 2002, vol. 38, pp. 141-154.
PCT Application No. PCT/US2018/048026, filed Aug. 24, 2018, Inventor Dooley, K.P. et al., (copy not enclosed).
PCT International Search Report and Written Opinion, PCT Application No. PCT/US2018/048026, dated Oct. 30, 2018, 23 pages.
U.S. Appl. No. 62/550,543, filed Aug. 25, 2017, Inventor Dooley, K.P. et al. (copy not enclosed).
Yang et al., "Exosome Mediated Delivery of miR-124 Promotes Neurogenesis after Ischemia," Molecular Therapy Nucleic Acids, Jun. 2017, vol. 7, pp. 278-287.
International Search Report and Written Opinion dated Jul. 12, 2019, in International Application No. PCT/US18/68062, ISA, Virginia, United States, 11 pages.

* cited by examiner

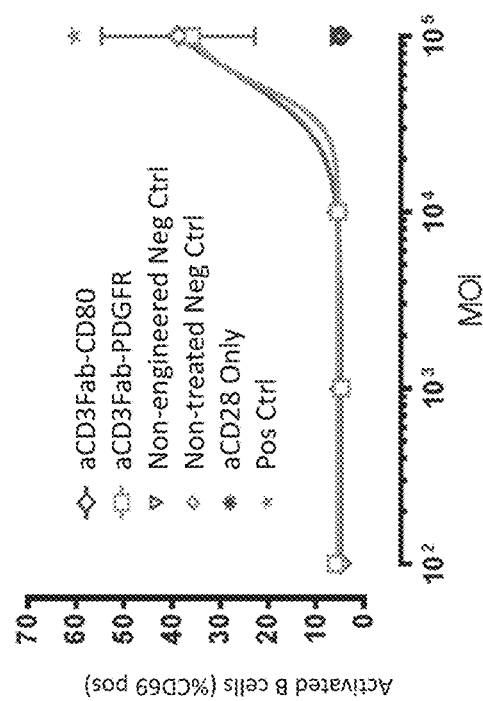
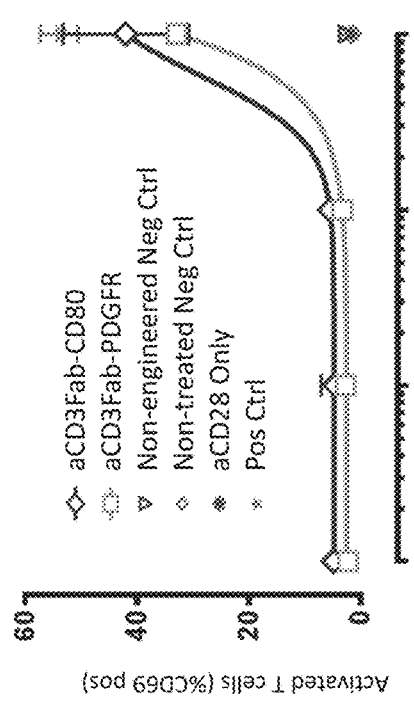
FIGURE 20A / FIGURE 20B

PTGFRN-IFNγ Monomer

PTGFRN-IFNγ Tandem Dimer

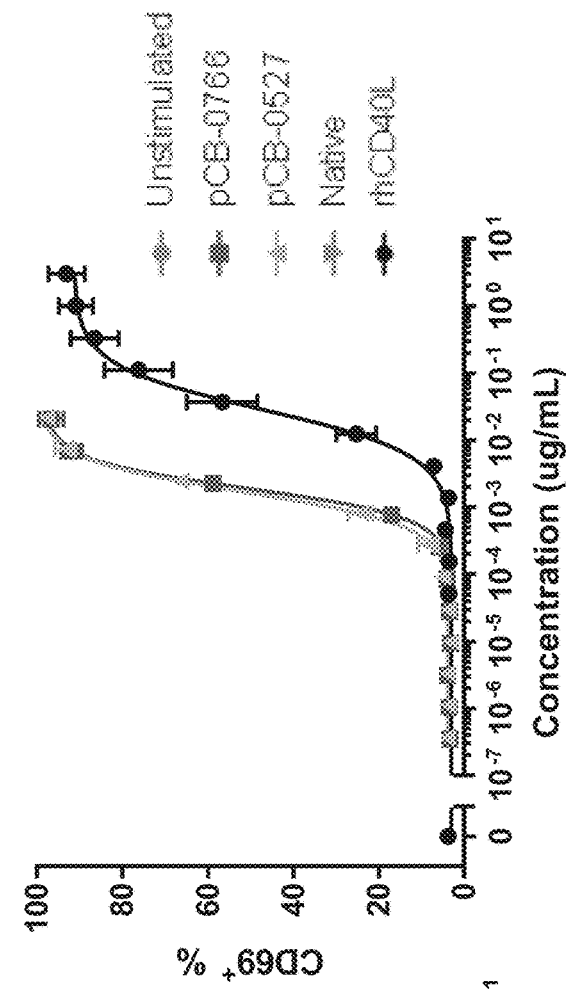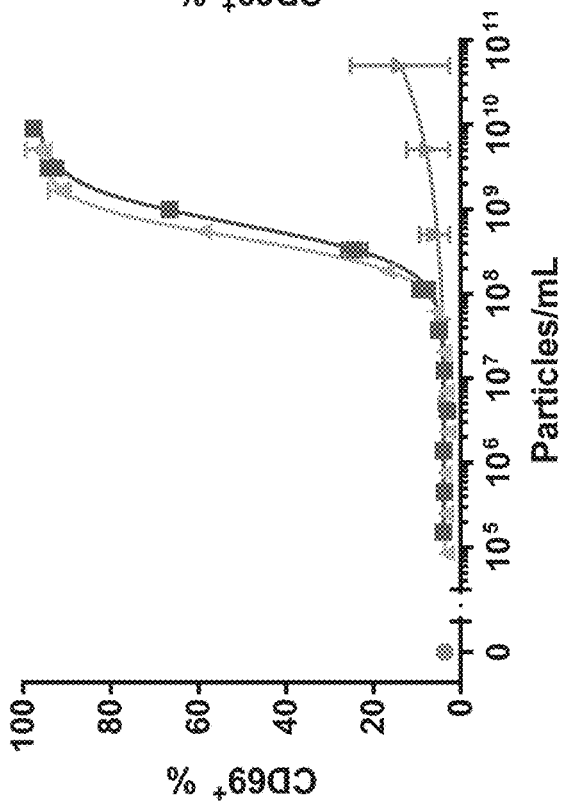
FIGURE 42A
FIGURE 42B

FIGURE 48

| IC50 (ug/ml) | dnLL2 | MLL2-hcD40L | EcnLL2 | EcnLL2/CD40L (L179) | EcnLL2-EcnCD40L |
|---|---|---|---|---|---|
| Donor 1 | 0.111 | 0.466 | 0.038 | 0.085 | 0.065 |
| Donor 2 | 0.124 | 0.233 | 0.034 | 0.047 | 0.058 |
| Average | 0.117 | 0.349 | 0.041 | 0.066 | 0.062 |

FIGURE 50

| EC50 (ng/mL) | rhIL12+rhCD40L | rhIL12/rhCD40L | Exo-rhCD40L | Exo-rhIL12/CD40L (1:79) | Exo-rhIL12+Exo-rhCD40L |
|---|---|---|---|---|---|
| Donor 1 | 70.08 | 124.9 | 2.518 | 1.034 | 2.441 |
| Donor 2 | 91.75 | 64.76 | 2.946 | 1.053 | 2.939 |
| Average | 80.915 | 94.830 | 2.732 | 1.044 | 2.690 |

EXOSOMES FOR IMMUNO-ONCOLOGY AND ANTI-INFLAMMATORY THERAPY

CROSS REFERENCE TO RELATED APPLICATIONS

This application claims the benefit of U.S. Provisional Application Nos. 62/723,267, filed Aug. 27, 2018; and 62/611,140, filed Dec. 28, 2017, each of which is hereby incorporated by reference in its entirety.

SEQUENCE LISTING

The instant application contains a Sequence Listing which has been submitted via EFS-Web and is hereby incorporated by reference in its entirety. Said ASCII copy, created on Feb. 21, 2019, is named 41775US_CRF_SequenceListing, and is 182,842 bytes in size.

FIELD OF THE INVENTION

The invention relates to compositions for interacting and modulating the human immune system, methods of making the compositions, and methods of using the compositions to treat cancer, GvHD, and autoimmune diseases.

BACKGROUND

Immunotherapy is the treatment of disease by inducing, enhancing, or suppressing the immune response. Immunotherapy can stimulate the patient's own immune system to attack cancer cells. Cancer immunotherapy usually has fewer side effects than traditional cancer therapies, such as chemotherapy and radiation therapy. Anti-inflammatory immunotherapy can down-regulate the patient's immune system for treating autoimmune diseases and graft-versus-host disease (GvHD). What is needed are improved methods for delivering immunomodulatory molecules to cells and tissues of the body.

SUMMARY

As drug delivery vehicles, extracellular vesicles offer many advantages over traditional drug delivery methods, especially for gene therapy. Systemic delivery of extracellular vesicles results in distribution of these lipid nanoparticles to various tissues. Studies have shown that extracellular vesicles can interact with various cells involved with the modulation of the human immune system. Extracellular vesicles that are selected, enriched, or engineered to deliver therapeutic molecules to activate, suppress, or influence the human immune system can be potent therapeutics for cancer and other immune system related diseases.

Provided herein are compositions comprising extracellular vesicles selected, enriched, or engineered with immunomodulating components that can up-regulate or down-regulate the human immune system, boosting the patient's immune system to fight cancer or suppressing the patient's immune system to alleviate the symptoms of GvHD and autoimmune diseases.

Also provided are methods of producing and utilizing the extracellular vesicles for modulating the human immune system.

Accordingly, in a first aspect, provided herein is a composition, comprising: an extracellular vesicle comprising a cell membrane bounding an enclosed volume, the cell membrane having an interior surface and an exterior surface; and a first immunomodulating component associated with the cell membrane or enclosed within the enclosed volume.

In various embodiments, the first immunomodulating component is an inhibitor for a negative checkpoint regulator or an inhibitor for a binding partner of a negative checkpoint regulator. In some of these embodiments, the negative checkpoint regulator is selected from the group consisting of: cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, and CD73.

In various embodiments, the first immunomodulating component is an activator for a positive co-stimulatory molecule or an activator for a binding partner of a positive co-stimulatory molecule. In some embodiments, the positive co-stimulatory molecule is a TNF receptor superfamily member. In some of these embodiments, the TNF receptor superfamily member is selected from the group consisting of: CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR. In some embodiments, the activator for a positive co-stimulatory molecule is a TNF superfamily member. In some of these embodiments, the TNF superfamily member is selected from the group consisting of: TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2. In certain embodiments, the TNF superfamily member is CD40L. In certain embodiments, the TNF superfamily member is CD27L. In certain embodiments, the TNF superfamily member is OX40L.

In some embodiments, the positive co-stimulatory molecule is a CD28-superfamily co-stimulatory molecule. In some of these embodiments, the CD28-superfamily co-stimulatory molecule is ICOS or CD28. In some embodiments, the activator for a positive co-stimulatory molecule is ICOSL, CD80, or CD86. In certain embodiments, the activator for a positive co-stimulatory molecule is CD80.

In some embodiments, the first immunomodulating component is a cytokine or a binding partner of a cytokine. In some embodiments, the cytokine is selected from the group consisting of: IL-2, IL-7, IL-10, IL-12, and IL-15. In certain embodiments, the cytokine is IL-7. In certain embodiment, the cytokine is IL-12. In certain embodiments, the cytokine is IL-15.

In some embodiments, the first immunomodulating component is a T-cell receptor (TCR), a T-cell co-receptor, a major histocompatibility complex (MHC), a human leukocyte antigen (HLA), or a derivative thereof.

In some embodiments, the first immunomodulating component is an activator of a T-cell receptor or co-receptor. In certain embodiments, the activator of a T-cell receptor or co-receptor is an activator of CD3, optionally an agonist antibody of CD3.

In some embodiments, the first immunomodulating component is a tumor antigen. In some embodiments, the tumor antigen is selected from the group consisting of: alphafetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand. In certain embodiments, the tumor antigen is derived from a reference genome sequence. In certain embodiments, the tumor antigen is derived from a genome sequence of a subject.

In some embodiments, the first immunomodulating component is an agonist or an antagonist of a selected target or activity.

In some embodiments, the first immunomodulating component is an antibody or an antigen-binding fragment.

In some embodiments, the first immunomodulating component is a polynucleotide. In some of these embodiments, the polynucleotide is selected from the group consisting of: an mRNA, a miRNA, an siRNA, an antisense RNA, an shRNA, a lncRNA, and a dsDNA.

In some embodiments, the first immunomodulating component is a protein, a peptide, a glycolipid, or a glycoprotein.

In some embodiments, the first immunomodulating component is expressed as a fusion protein displayed on the exterior surface of said extracellular vesicle. In some embodiments, the fusion protein comprises PTGFRN or a fragment or a variant thereof. In some embodiments, the sequence of the fusion protein is SEQ ID NO: 3.

In some embodiments, the extracellular vesicle is an exosome. In some other embodiments, the extracellular vesicle is a nanovesicle.

In certain embodiments, the composition further comprises a pharmaceutically-acceptable carrier.

In some embodiments, the extracellular vesicle additionally comprises a second immunomodulating component.

In various embodiments, the second immunomodulating component is an inhibitor for a negative checkpoint regulator or an inhibitor for a binding partner of a negative checkpoint regulator. In some of these embodiments, the negative checkpoint regulator is selected from the group consisting of: cytotoxic T-lymphocyte-associated protein 4 (CTLA-4), programmed cell death protein 1 (PD-1), lymphocyte-activated gene 3 (LAG-3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, and CD73.

In various embodiments, the second immunomodulating component is an activator for a positive co-stimulatory molecule or an activator for a binding partner of a positive co-stimulatory molecule. In some embodiments, the positive co-stimulatory molecule is a TNF receptor superfamily member. In some of these embodiments, the TNF receptor superfamily member is selected from the group consisting of: CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, AITR, TROY, CD358, TRAMP, and XEDAR. In some embodiments, the activator for a positive co-stimulatory molecule is a TNF superfamily member. In some of these embodiments, the TNF superfamily member is selected from the group consisting of: TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2. In certain embodiments, the TNF superfamily member is CD40L. In certain embodiments, the TNF superfamily member is CD27L. In certain embodiments, the TNF superfamily member is OX40L.

In some embodiments, the positive co-stimulatory molecule is a CD28-superfamily co-stimulatory molecule. In some of these embodiments, the CD28-superfamily co-stimulatory molecule is ICOS or CD28. In some embodiments, the activator for a positive co-stimulatory molecule is ICOSL, CD80, or CD86. In certain embodiments, the activator for a positive co-stimulatory molecule is CD80.

In some embodiments, the second immunomodulating component is a cytokine or a binding partner of a cytokine. In some embodiments, the cytokine is selected from the group consisting of: IL-2, IL-7, IL-10, IL-12, and IL-15. In certain embodiments, the cytokine is IL-7. In certain embodiment, the cytokine is IL-12. In certain embodiment, the cytokine is IL-15.

In some embodiments, the second immunomodulating component is a T-cell receptor (TCR), a T-cell co-receptor, a major histocompatibility complex (MHC), a human leukocyte antigen (HLA), or a derivative thereof.

In some embodiments, the second immunomodulating component is an activator of a T-cell receptor or co-receptor. In certain embodiments, the activator of a T-cell receptor or co-receptor is an activator of CD3, optionally an agonist antibody of CD3.

In some embodiments, the second immunomodulating component is a tumor antigen. In some embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand. In certain embodiments, the tumor antigen is derived from a reference genome sequence. In certain embodiments, the tumor antigen is derived from a genome sequence of a subject.

In some embodiments, the second immunomodulating component is an agonist or an antagonist of a selected target or activity.

In some embodiments, the second immunomodulating component is an antibody or an antigen-binding fragment.

In some embodiments, the second immunomodulating component is a polynucleotide. In some of these embodiments, the polynucleotide is selected from the group consisting of: an mRNA, a miRNA, an siRNA, an antisense RNA, an shRNA, a lncRNA, and a dsDNA.

In some embodiments, the second immunomodulating component is a protein, a peptide, a glycolipid, or a glycoprotein.

In some embodiments, the second immunomodulating component is expressed as a fusion protein displayed on the exterior surface of said extracellular vesicle. In some embodiments, the fusion protein comprises PTGFRN or a fragment or a variant thereof. In some embodiments, the sequence of said fusion protein is SEQ ID NO: 3.

In some embodiments, the second immunomodulating component is different from said first immunomodulating component.

In some embodiments, the extracellular vesicle additionally comprises a third immunomodulating component. In some embodiments, the third immunomodulating component is different from said first and second immunomodulating components.

In another aspect, provided herein is a method of producing the composition. In some embodiments, the method comprises modifying a producer cell with the first, second, and/or third immunomodulating components; obtaining the extracellular vesicle from the producer cell; and optionally isolating the obtained extracellular vesicles. In some other embodiments the method comprises obtaining the extracellular vesicle from a producer cell; isolating the obtained extracellular vesicles; and modifying the isolated extracellular vesicle with the first, second, and/or third immunomodulating components. In certain embodiments, the method further comprises formulating the isolated extracellular vesicles into a pharmaceutical composition.

In another aspect, provided herein is a method of treating cancer in a subject. The method comprises administering to the subject a therapeutically effective amount of the composition, wherein the composition is capable of up-regulating an immune response in the subject, thereby enhancing the tumor targeting of the subject's immune system.

In another aspect, provided herein is a method of treating graft-versus-host disease (GvHD) in a subject. The method comprises administering to the subject a therapeutically effective amount of the composition, wherein the composition is capable of down-regulating an immune response in the subject, thereby alleviating the symptoms of GvHD.

In another aspect, provided herein is a method of treating an autoimmune disease in a subject. The method comprises administering to the subject a therapeutically effective amount of the composition, wherein the composition is capable of down-regulating an immune response in the subject, thereby suppressing the immune activity of the subject.

In another aspect, provided herein is a method of treating or preventing cancer in a subject comprising administering to the subject a therapeutically effective amount of the composition comprising a tumor antigen, wherein the composition is capable of potentiating an immune response to the tumor antigen, thereby enhancing the immune response of the subject to cancer.

In some embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In certain embodiments, the tumor antigen is derived from a reference genome sequence. In certain embodiments, the tumor antigen is derived from a genome sequence of a subject.

BRIEF DESCRIPTION OF THE DRAWINGS

FIG. 1A shows the intravenous route of administration. FIG. 1B shows the intraperitoneal route of administration.

FIG. 6A shows the effect of CD80-expressing exosomes on the number of $CD8^+$ T-cells. FIG. 6B shows the effect of CD80-expressing exosomes on the number of $CD4^+$ T-cells.

FIG. 15A shows the effects of IL-7-expressing exosomes on CD8+ T-cell. FIG. 15B shows the effects of IL-7-expressing exosomes on memory CD8+ T-cell.

FIG. 16A shows the effects of IL-7-expressing exosomes on CD8+ T-cell. FIG. 16B shows the effects of IL-7-expressing exosomes on memory CD8+ T-cell.

FIG. 20A shows the effects of anti-CD3 scFab exosomes on T-cell activation in PBMCs. FIG. 20B shows the effects of anti-CD3 scFab exosomes on B-cell activation in PBMCs.

FIG. 42A shows B cell activation measured by the percentage of CD69 positive B cells after the addition of native exosomes, exosomes with trimeric CD40L-PTGFRN constructs pCB-527, and exosomes with trimeric CD40L-PTGFRN constructs pCB-766, respectively. FIG. 42B shows B cell activation measured by the percentage of CD69 positive B cells after the addition of exosomes with trimeric CD40L-PTGFRN constructs pCB-527 and pCB-766 respectively compared to concentration-matched CD40L.

FIG. 48 shows $EC_{50}$ of the IFNγ response in Donor 1 and Donor 2 human PBMCs after addition of recombinant IL-12, recombinant IL-12 mixed with recombinant CD40L, PTGFRN-IL-12 exosomes, double-positive PTGFRN-CD40L/IL-12 exosomes, and a mixture of PTGFRN-IL-12 exosomes and PTGFRN-CD40L exosomes, respectively.

FIG. 50 shows $EC_{50}$ of the IFNγ response in Donor 1 and Donor 2 human PBMCs after addition of recombinant CD40L, recombinant IL-12 mixed with recombinant CD40L, PTGFRN-CD40L exosomes, double-positive PTGFRN-CD40L/IL-12 exosomes, and a mixture of PTGFRN-IL-12 exosomes and PTGFRN-CD40L exosomes, respectively.

DETAILED DESCRIPTION

Figures 1A, 1B:
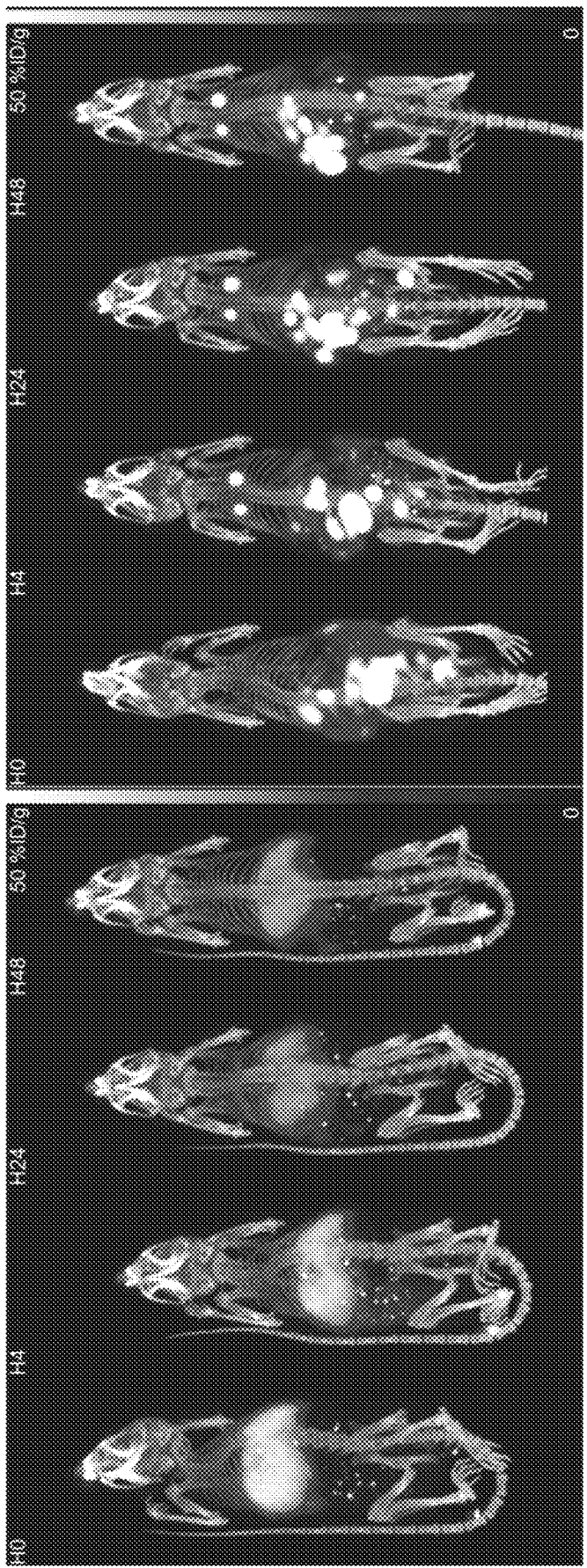
FIGS. 1A and 1B show a time course of mice injected with radio-labeled exosomes.

Disclosed herein are extracellular vesicles capable of modulating human immune system. Also provided are methods for producing the extracellular vesicles, and methods of using these extracellular vesicles to treat cancer and other immune system related diseases.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a negative limitation.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

In further describing the subject invention, subject systems for use in practicing the subject methods will be discussed in greater detail, followed by a review of associated methods.

As used herein, the term "extracellular vesicle" refers to a cell-derived vesicle comprising a membrane that encloses an internal space. Extracellular vesicles comprise all membrane-bound vesicles that have a smaller diameter than the cell from which they are derived. Generally extracellular vesicles range in diameter from 20 nm to 1000 nm, and can comprise various macromolecular cargo either within the internal space, displayed on the external surface of the extracellular vesicle, and/or spanning the membrane. The cargo can comprise nucleic acids, proteins, carbohydrates, lipids, small molecules, and/or combinations thereof. By way of example and without limitation, extracellular vesicles include apoptotic bodies, fragments of cells, vesicles derived from cells by direct or indirect manipulation (e.g., by serial extrusion or treatment with alkaline solutions), vesiculated organelles, and vesicles produced by living cells (e.g., by direct plasma membrane budding or fusion of the late endosome with the plasma membrane). Extracellular vesicles can be derived from a living or dead organism, explanted tissues or organs, and/or cultured cells.

As used herein the term "exosome" refers to a cell-derived small (between 20-300 nm in diameter, more preferably 40-200 nm in diameter) vesicle comprising a membrane that encloses an internal space, and which is generated from the cell by direct plasma membrane budding or by fusion of the late endosome with the plasma membrane. The exosome is a species of extracellular vesicle. The exosome comprises lipid or fatty acid and polypeptide and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The exosome can be derived from a producer cell, and isolated from the producer cell based on its size, density, biochemical parameters, or a combination thereof.

As used herein, the term "nanovesicle" refers to a cell-derived small (between 20-250 nm in diameter, more preferably 30-150 nm in diameter) vesicle comprising a membrane that encloses an internal space, and which is generated from the cell by direct or indirect manipulation such that the nanovesicle would not be produced by the producer cell without the manipulation. Appropriate manipulations of the producer cell include but are not limited to serial extrusion, treatment with alkaline solutions, sonication, or combinations thereof. The production of nanovesicles can, in some instances, result in the destruction of the producer cell. Preferably, populations of nanovesicles are substantially free of vesicles that are derived from producer cells by way of direct budding from the plasma membrane or fusion of the late endosome with the plasma membrane. The nanovesicle is a species of extracellular vesicle. The nanovesicle comprises lipid or fatty acid and polypeptide, and optionally comprises a payload (e.g., a therapeutic agent), a receiver (e.g., a targeting moiety), a polynucleotide (e.g., a nucleic acid, RNA, or DNA), a sugar (e.g., a simple sugar, polysaccharide, or glycan) or other molecules. The nanovesicle, once it is derived from a producer cell according to the manipulation, can be isolated from the producer cell based on its size, density, biochemical parameters, or a combination thereof.

The term "extracellular vesicle delivery" or "delivery of extracellular vesicles" refers to the administration and localization of extracellular vesicles to target tissues, cells, and/or organs of the subject. In some embodiments, the immunomodulating component can be delivered to the cytoplasm of a target cell. In other embodiments, the immunomodulating component is delivered to the membrane of the target cell. In some embodiments, the membrane of the extracellular vesicle fuses with a membrane of a target cell.

As used herein, the term "producer cell" refers to any cell from which an extracellular vesicle can be isolated. A producer cell is a cell which serves as a source for the extracellular vesicle. A producer cell can share a protein, lipid, sugar, or nucleic acid component with the extracellular vesicle. In some embodiments, the producer cell is a modified or synthetic cell. In some embodiments, the producer cell is a cultured or isolated cell. In certain embodiments, the producer cell is a cell line. In certain other embodiments, the producer cell is a primary cell. In some particular embodiments, the producer cell is an immune cell.

"Membrane" as used herein is a boundary layer that separates an interior space from an exterior space comprising one or more biological compounds, typically lipids, and optionally polypeptides and/or carbohydrates. In some embodiments, the membrane comprises lipids and fatty acids. In some embodiments, the membrane comprises phospholipids, glycolipids, fatty acids, sphingolipids, phosphoglycerides, sterols, cholesterols, and phosphatidylserines. In some of these embodiments, the membrane further comprises one or more polypeptide and/or one or more polysaccharide, such as glycan. The extracellular vesicle comprises a membrane as defined herein.

As used herein, the term "immunomodulating component" refers to a therapeutic agent that acts on a target (e.g., a target cell) that is contacted with the extracellular vesicle, and regulates the immune system. The immunomodulating component that can be introduced into an extracellular vesicle and/or a producer cell include therapeutic agents such as, modulators of checkpoint inhibitors or ligands of checkpoint inhibitors, surface antigens and derivatives thereof, cytokines and derivatives thereof. The immunomodulating component can also include an agonist, an antagonist, an antibody, and an antigen-binding fragment, or a polynucleotide, such as siRNA, miRNA, lncRNA, and DNA.

The term "receiver" refers to a molecule that directs the extracellular vesicle to a target and/or promotes the interaction of extracellular vesicle with the target in the subject. In some embodiments, the receiver is a polypeptide. In some embodiments, the receiver is capable of increasing the concentration of the immunomodulating component in the tissue of the subject. Examples of receivers include, but are not limited to, examples listed in Table 3.

The term "target" refers to, a cell, a pathogen, a metabolite, a polypeptide complex or any molecule or structure that resides in a tissue or circulates in the circulatory system or lymphatic system of the subject, such as an immune cell or a cancer cell. Examples of targets include, but are not limited to, examples listed in Table 4.

A "therapeutic agent" or "therapeutic molecule" includes a compound or molecule that, when present in an effective amount, produces a desired therapeutic effect, pharmacologic and/or physiologic effect on a subject in need thereof. It includes any compound, e.g., a small molecule drug, or a biologic (e.g., a polypeptide drug or a nucleic acid drug) that when administered to a subject has a measurable or conveyable effect on the subject, e.g., it alleviates or decreases a symptom of a disease, disorder or condition.

As used herein, the term "antibody" encompasses an immunoglobulin whether natural or partly or wholly synthetically produced, and fragments thereof. The term also covers any protein having a binding domain that is homologous to an immunoglobulin binding domain. "Antibody" further includes a polypeptide comprising a framework region from an immunoglobulin gene or fragments thereof that specifically binds and recognizes an antigen. Use of the term antibody is meant to include whole antibodies, polyclonal, monoclonal and recombinant antibodies, fragments thereof, and further includes single-chain antibodies, humanized antibodies, murine antibodies, chimeric, mouse-human, mouse-primate, primate-human monoclonal antibodies, anti-idiotype antibodies, antibody fragments, such as, e.g., scFv, (scFv)$_2$, Fab, Fab', and F(ab')$_2$, F(ab1)$_2$, Fv, dAb, and Fd fragments, diabodies, and antibody-related polypeptides. Antibody includes bispecific antibodies and multispecific antibodies so long as they exhibit the desired biological activity or function.

The term "antigen-binding fragment" used herein refers to fragments of an intact immunoglobulin, and any part of a polypeptide including antigen binding regions having the ability to specifically bind to the antigen. For example, the antigen-binding fragment can be a F(ab')$_2$ fragment, a Fab' fragment, a Fab fragment, a Fv fragment, or a scFv fragment, but is not limited thereto. A Fab fragment has one antigen binding site and contains the variable regions of a light chain and a heavy chain, the constant region of the light chain, and the first constant region CH1 of the heavy chain. A Fab' fragment differs from a Fab fragment in that the Fab' fragment additionally includes the hinge region of the heavy chain, including at least one cysteine residue at the C-terminal of the heavy chain CH1 region. The F(ab')$_2$ fragment is produced whereby cysteine residues of the Fab' fragment are joined by a disulfide bond at the hinge region. An Fv fragment is the minimal antibody fragment having only heavy chain variable regions and light chain variable regions, and a recombinant technique for producing the Fv fragment is well-known in the art. Two-chain Fv fragments can have a structure in which heavy chain variable regions are linked to light chain variable regions by a non-covalent bond. Single-chain Fv (scFv) fragments generally can have a dimer structure as in the two-chain Fv fragments in which heavy chain variable regions are covalently bound to light chain variable regions via a peptide linker or heavy and light chain variable regions are directly linked to each other at the C-terminal thereof. The antigen-binding fragment can be obtained using a protease (for example, a whole antibody is digested with papain to obtain Fab fragments, and is digested with pepsin to obtain F(ab')$_2$ fragments), and can be prepared by a genetic recombinant technique. A dAb fragment consists of a VH domain. Single-chain antibody molecules can comprise a polymer with a number of individual molecules, for example, dimer, trimer or other polymers.

The phrase "nucleic acid molecule" refers to a single or double-stranded polymer of deoxyribonucleotide or ribonucleotide bases. It includes chromosomal DNA and self-replicating plasmids, vectors, mRNA, tRNA, siRNA, miRNA, etc. The nucleic acid molecule can be recombinant and exogenous polypeptides can be expressed when the nucleic acid is introduced into a cell.

The term "agonist" refers to a molecule that binds to a receptor and activates the receptor to produce a biological response. Receptors can be activated by either an endogenous or an exogenous agonist. Non-limiting examples of endogenous agonist include hormones and neurotransmitters. Non-limiting examples of exogenous agonist include drugs. The agonist can be a full, partial, or inverse agonist.

The term "antagonist" refers to a molecule that blocks or dampens an agonist mediated response rather than provoking a biological response itself upon bind to a receptor. Many antagonists achieve their potency by competing with endogenous ligands or substrates at structurally defined binding sites on the receptors. Non-limiting examples of antagonists include alpha blockers, beta-blocker, and calcium channel blockers. The antagonist can be a competitive, non-competitive, or uncompetitive antagonist.

As used herein the term "a fragment" of a protein refers to a protein that is N- and/or C-terminally deleted in comparison to the naturally occurring protein. Preferably, a fragment of PTGFRN, BSG, IGSF2, IGSF3, IGSF8, ITGB1, ITGA4, SLC3A2, or ATP transporter retains the ability to be specifically targeted to exosomes. Such a fragment is also referred to as "functional fragment". Whether a fragment is a functional fragment in that sense can be assessed by any art known methods to determine the protein content of exosomes including Western Blots, FACS analysis and fusions of the fragments with autofluorescent proteins like, e.g. GFP. In a particular embodiment the fragment of PTGFRN, BSG, IGSF2, IGSF3, IGSF8, ITGB1, ITGA4, SLC3A2, ATP transporter retains at least 50%, 60%, 70%, 80%, 90% or 100% of the ability of the naturally occurring PTGFRN, BSG, IGSF2, IGSF3, IGSF8, ITGB1, ITGA4, SLC3A2, or ATP transporter to be specifically targeted to exosomes.

As used herein the term "variant" of a protein refers to a protein that shares a certain amino acid sequence identity with another protein upon alignment by a method known in the art. A variant of a protein can include a substitution, insertion, deletion, frameshift or rearrangement in another protein. In a particular embodiment, the variant is a variant having at least 70% identity to PTGFRN, BSG, IGSF2, IGSF3, IGSF8, ITGB1, ITGA4, SLC3A2, ATP transporter or a fragment of PTGFRN, BSG, IGSF2, IGSF3, IGSF8, ITGB1, ITGA4, SLC3A2, or ATP transporter. In some embodiments variants or variants of fragments of PTGFRN share at least 70%, 80%, 85%, 90%, 95% or 99% sequence identity with PTGFRN according to SEQ ID NO: 1 or with a functional fragment thereof. In some embodiments variants or variants of fragments of BSG share at least 70%, 80%, 85%, 90%, 95% or 99% sequence identity with BSG according to SEQ ID NO: 9 or with a functional fragment thereof. In some embodiments variants or variants of fragments of IGSF2 share at least 70%, 80%, 85%, 90%, 95% or 99% sequence identity with IGSF2 according to SEQ ID NO: 34 or with a functional fragment thereof. In some embodiments variants or variants of fragments of IGSF3 share at least 70%, 80%, 85%, 90%, 95% or 99% sequence identity with IGSF3 according to SEQ ID NO: 20 or with a functional fragment thereof. In some embodiments variants or variants of fragments of IGSF8 share at least 70%, 80%, 85%, 90%, 95% or 99% sequence identity with IGSF8 according to SEQ ID NO: 14 or with a functional fragment thereof. In some embodiments variants or variants of fragments of ITGB1 share at least 70%, 80%, 85%, 90%, 95% or 99% sequence identity with ITGB1 according to SEQ ID NO: 21 or with a functional fragment thereof. In some embodiments variants or variants of fragments of ITGA4 share at least 70%, 80%, 85%, 90%, 95% or 99% sequence identity with ITGA4 according to SEQ ID NO: 22 or with a functional fragment thereof. In some embodiments variants or variants of fragments of SLC3A2 share at least 70%, 80%, 85%, 90%, 95% or 99% sequence identity with SLC3A2 according to SEQ ID NO: 23 or with a functional fragment thereof. In some embodiments variants or variants of fragments of ATP1A1 share at least 70%, 80%, 85%, 90%, 95% or 99% sequence identity with ATP1A1 according to SEQ ID NO: 24 or with a functional fragment thereof. In some embodiments variants or variants of fragments of ATP1A2 share at least 70%, 80%, 85%, 90%, 95% or 99% sequence identity with ATP1A2 according to SEQ ID NO: 25 or with a functional fragment thereof. In some embodiments variants or variants of fragments of ATP1A3 share at least 70%, 80%, 85%, 90%, 95% or 99% sequence identity with ATP1A3 according to SEQ ID NO: 26 or with a functional fragment thereof. In some embodiments variants or variants of fragments of ATP1A4 share at least 70%, 80%, 85%, 90%, 95% or 99% sequence identity with ATP1A4 according to SEQ ID NO: 27 or with a functional fragment thereof. In some embodiments variants or variants of fragments of ATP1B3 share at least 70%, 80%, 85%, 90%, 95% or 99% sequence identity with ATP1B3 according to SEQ ID NO: 28 or with a functional fragment thereof. In some embodiments variants or variants of fragments of ATP2B1 share at least 70%, 80%, 85%, 90%, 95% or 99% sequence identity with ATP2B1 according to SEQ ID NO: 29 or with a functional fragment thereof. In some embodiments variants or variants of fragments of ATP2B2 share at least 70%, 80%, 85%, 90%, 95% or 99% sequence identity with ATP2B2 according to SEQ ID NO: 30 or with a functional fragment thereof. In some embodiments variants or variants of fragments of ATP2B3 share at least 70%, 80%, 85%, 90%, 95% or 99% sequence identity with ATP2B3 according to SEQ ID NO: 31 or with a functional fragment thereof. In some embodiments variants or variants of fragments of ATP2B4 share at least 70%, 80%, 85%, 90%, 95% or 99% sequence identity with ATP2B4 according to SEQ ID NO: 32 or with a functional fragment thereof. In each of above cases, it is preferred that the variant or variant of a fragment retains the ability to be specifically targeted to exosomes.

Methods of alignment of sequences for comparison are well-known in the art. Various programs and alignment algorithms are described in: Smith and Waterman, Adv. Appl. Math. 2: 482 (1981); Needleman and Wunsch, J. Mol. Bio. 48: 443 (1970); Pearson and Lipman, Methods in Mol. Biol. 24: 307-31 (1988); Higgins and Sharp, Gene 73: 15 237-44 (1988); Higgins and Sharp, CABIOS 5: 151-3 (1989) Corpet et al., Nuc. Acids Res. 16: 10881-90 (1988); Huang et al., Comp. Appl. BioSci. 8: 155-65 (1992); and Pearson et al., Meth. Mol. Biol. 24: 307-31 (1994). The NCBI Basic Local Alignment Search Tool (BLAST) [Altschul 20 et al., J. Mol. Biol. 215: 403-10 (1990) J is available from several sources, including the National Center for Biological Information (NBCI, Bethesda, Md.) and on the Internet, for use in connection with the sequence analysis programs blastp, blasm, blastx, tblastn and tblastx. BLAST and a description of how to determine sequence identify using the program can be accessed at the official website of NCBI (National Center for Biotechnology Information) under NIH (National Institute of Health).

Recitation of any protein provided herein encompasses a functional variant of the protein. The term "functional variant" of a protein refers to a variant of the protein that retains the ability to be specifically targeted to exosomes.

As used herein, the term "pharmaceutical composition" refers to one or more of the compounds described herein, such as, e.g., an extracellular vesicle mixed or intermingled with, or suspended in one or more other chemical components, such as pharmaceutically-acceptable carriers and excipients. One purpose of a pharmaceutical composition is to facilitate administration of preparations of extracellular vesicles to a subject. The term "pharmaceutically-acceptable" and grammatical variations thereof, refers to compositions, carriers, diluents and reagents capable of administration to or upon a subject without the production of undesirable physiological effects to a degree that prohibits administration of the composition. The term "excipient" or "carrier" refers to an inert substance added to a pharmaceutical composition to further facilitate administration of a compound. The term "pharmaceutically-acceptable carrier" or "pharmaceutically-acceptable excipient" encompasses any of the agents approved by a regulatory agency of the US Federal government or listed in the US Pharmacopeia for use in animals, including humans, as well as any carrier or diluent that does not cause significant irritation to a subject and does not abrogate the biological activity and properties of the administered compound. Included are excipients and carriers that are useful in preparing a pharmaceutical composition and are generally safe, non-toxic, and desirable.

As used herein, the terms "isolate," "isolated," and "isolating" or "purify," "purified," and "purifying" as well as "extracted" and "extracting" are used interchangeably and refer to the state of a preparation (e.g., a plurality of known or unknown amount and/or concentration) of desired extracellular vesicles, that have undergone one or more processes of purification, e.g., a selection or an enrichment of the desired extracellular vesicle preparation. In some embodiments, isolating or purifying as used herein is the process of removing, partially removing (e.g. a fraction) of the extracellular vesicles from a sample containing producer cells. In some embodiments, an isolated extracellular vesicle composition has no detectable undesired activity or, alternatively, the level or amount of the undesired activity is at or below an acceptable level or amount. In other embodiments, an isolated extracellular vesicle composition has an amount and/or concentration of desired extracellular vesicles at or above an acceptable amount and/or concentration. In other embodiments, the isolated extracellular vesicle composition is enriched as compared to the starting material (e.g. producer cell preparations) from which the composition is obtained. This enrichment can be by 10%, 20%, 30%, 40%, 50%, 60%, 70%, 80%, 90%, 95%, 96%, 97%, 98%, 99%, 99.9%, 99.99%, 99.999%, 99.9999%, or greater than 99.9999% as compared to the starting material. In some embodiments, isolated extracellular vesicle preparations are substantially free of residual biological products. In some embodiments, the isolated extracellular vesicle preparations are 100% free, 99% free, 98% free, 97% free, 96% free, or 95% free of any contaminating biological matter. Residual biological products can include abiotic materials (including chemicals) or unwanted nucleic acids, proteins, lipids, or metabolites. Substantially free of residual biological products can also mean that the extracellular vesicle composition contains no detectable producer cells and that only extracellular vesicles are detectable.

The terms "administration," "administering" and variants thereof refer to introducing a composition, such as an extracellular vesicle, or agent into a subject and includes concurrent and sequential introduction of a composition or agent. The introduction of a composition or agent into a subject is by any suitable route, including orally, pulmonarily, intranasally, parenterally (intravenously, intra-arterially, intramuscularly, intraperitoneally, or subcutaneously), rectally, intralymphatically, intrathecally, intratumorally, periocularly or topically. Administration includes self-administration and the administration by another. A suitable route of administration allows the composition or the agent to perform its intended function. For example, if a suitable route is intravenous, the composition is administered by introducing the composition or agent into a vein of the subject.

As used herein, the term "modulate," "modulating", "modify," and/or "modulator" generally refers to the ability to alter, by increase or decrease, e.g., directly or indirectly promoting/stimulating/up-regulating or interfering with/inhibiting/down-regulating a specific concentration, level, expression, function or behavior, such as, e.g., to act as an antagonist or agonist. In some instances a modulator can increase and/or decrease a certain concentration, level, activity or function relative to a control, or relative to the average level of activity that would generally be expected or relative to a control level of activity.

The term "sufficient amount" means an amount sufficient to produce a desired effect, e.g., an amount sufficient to modulate a condition in the subject.

The term "therapeutically effective amount" is an amount that is effective to ameliorate a symptom of a disease. A therapeutically effective amount can be a "prophylactically effective amount" as prophylaxis can be considered therapy.

As used herein, the term "substantially" or "substantial" refers, e.g., to the presence, level, or concentration of an entity in a particular space, the effect of one entity on another entity, or the effect of a treatment. For example, an activity, level or concentration of an entity is substantially increased if the increase is 2-fold, 3-fold, 4-fold, 5-fold, 10-fold, 50-fold, 100-fold, or 1000-fold relative to a baseline. An activity, level or concentration of an entity is also substantially increased if the increase is 5%, 10%, 20%, 30%, 40%, 50%, 60%, 70%, 80%, 90%, 100%, 200%, or 500% relative to a baseline.

The term "in vivo" refers to processes that occur in a living organism.

The term "mammal" as used herein includes both humans and non-human mammals.

Abbreviations used in this application include the following: "mRNA" refers to messenger RNA, "miRNA" refers to microRNA, "siRNA" refers to small interfering RNA, "antisense RNA" refers to single stranded RNA that is complementary to an mRNA, "shRNA" refers to small or short hairpin RNA, "lncRNA" refers to long non-coding RNA, and "dsDNA" refers to double stranded DNA.

Compositions

Aspects of the subject disclosure include a composition capable of regulating the immune system. The composition comprises an extracellular vesicle comprising a cell membrane, and an immunomodulating component associated with the cell membrane or enclosed within the membrane-bound enclosed volume.

The Extracellular Vesicle

In various embodiments, the composition comprises an extracellular vesicle. In certain embodiments, the extracellular vesicle is a cell-derived vesicle comprising a membrane that encloses an internal space.

In various embodiments, the extracellular vesicle can be a membrane-bound vesicle that has a smaller diameter than the cell from which it is derived. In some embodiments, the extracellular vesicle has a longest dimension between about 20-1000 nm, such as between about 20-100 nm, 20-200 nm, 20-300 nm, 20-400 nm, 20-500 nm, 20-600 nm, 20-700 nm, 20-800 nm, 20-900 nm, 30-100 nm, 30-200 nm, 30-300 nm, 30-400 nm, 30-500 nm, 30-600 nm, 30-700 nm, 30-800 nm, 30-900 nm, 40-100 nm, 40-200 nm, 40-300 nm, 40-400 nm, 40-500 nm, 40-600 nm, 40-700 nm, 40-800 nm, 40-900 nm, 50-150 nm, 50-500 nm, 50-750 nm, 100-200 nm, 100-500 nm, or 500-1000 nm.

In certain embodiments, the extracellular vesicle is an exosome. In certain embodiments, the extracellular vesicle is a nanovesicle. In certain embodiments, the extracellular vesicle is an apoptotic body. In certain embodiments, the extracellular vesicle is a fragment of cell. In certain embodiments, the extracellular vesicle is a vesicle derived from cell by direct or indirect manipulation. In certain embodiments, the extracellular vesicle is a vesiculated organelle. In various embodiments, the extracellular vesicle is a vesicle produced by living cells.

In some embodiments, the extracellular vesicle is derived from a living organism. In some embodiments, the extracellular vesicle is derived from a dead organism. In some embodiments, the extracellular vesicle is derived from an explanted tissue. In some embodiments, the extracellular vesicle is derived from an explanted organ. In some embodiments, the extracellular vesicle is derived from cultured cells. In some of these embodiments, when the extracellular vesicle is generated in a cell culture system, the extracellular vesicle is further isolated (e.g., by separating the extracellular vesicle from the cultured cells). Separation can be achieved by sedimentation. For example, the extracellular vesicle can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$. Separation can also be achieved by affinity purification. For example, the extracellular vesicle can be purified by binding a population comprising extracellular vesicles to a resin, said resin comprising a plurality of ligands that have specific affinity for one or more target proteins on the surface of the extracellular vesicle. The target proteins may be a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc. The target protein may additionally be the immunomodulating component that is displayed on the surface of the exosomes.

In various embodiments, the extracellular vesicle comprises lipids or fatty acids and polypeptides. In certain embodiments, the extracellular vesicle further comprises a sugar. In certain embodiments, the extracellular vesicle further comprises a polynucleotide.

In various embodiments, the extracellular vesicle membrane comprises an interior surface and an exterior surface and encloses an internal space. In some embodiments, the extracellular vesicle further comprises a payload. In certain embodiments, the payload is enclosed within the internal space. In certain embodiments, the payload is displayed on the external surface of the extracellular vesicle. In certain embodiments, the payload is spanning the membrane of the extracellular vesicle. In various embodiments, the payload comprises nucleic acids, proteins, carbohydrates, lipids, small molecules, and/or combinations thereof. In some embodiments, the extracellular vesicle further comprises a receiver.

The Exosome

In various embodiments, the extracellular vesicle is an exosome. In certain embodiments, the exosome is a small membrane-bound vesicle secreted by producer cells.

In some embodiments, the exosome from the producer cell has a longest dimension between about 20-300 nm, such as between about 20-290 nm, 20-280 nm, 20-270 nm, 20-260 nm, 20-250 nm, 20-240 nm, 20-230 nm, 20-220 nm, 20-210 nm, 20-200 nm, 20-190 nm, 20-180 nm, 20-170 nm, 20-160 nm, 20-150 nm, 20-140 nm, 20-130 nm, 20-120 nm, 20-110 nm, 20-100 nm, 20-90 nm, 20-80 nm, 20-70 nm, 20-60 nm, 20-50 nm, 20-40 nm, 20-30 nm, 30-300 nm, 30-290 nm, 30-280 nm, 30-270 nm, 30-260 nm, 30-250 nm, 30-240 nm, 30-230 nm, 30-220 nm, 30-210 nm, 30-200 nm, 30-190 nm, 30-180 nm, 30-170 nm, 30-160 nm, 30-150 nm, 30-140 nm, 30-130 nm, 30-120 nm, 30-110 nm, 30-100 nm, 30-90 nm, 30-80 nm, 30-70 nm, 30-60 nm, 30-50 nm, 30-40 nm, 40-300 nm, 40-290 nm, 40-280 nm, 40-270 nm, 40-260 nm, 40-250 nm, 40-240 nm, 40-230 nm, 40-220 nm, 40-210 nm, 40-200 nm, 40-190 nm, 40-180 nm, 40-170 nm, 40-160 nm, 40-150 nm, 40-140 nm, 40-130 nm, 40-120 nm, 40-110 nm, 40-100 nm, 40-90 nm, 40-80 nm, 40-70 nm, 40-60 nm, 40-50 nm, 50-300 nm, 50-290 nm, 50-280 nm, 50-270 nm, 50-260 nm, 50-250 nm, 50-240 nm, 50-230 nm, 50-220 nm, 50-210 nm, 50-200 nm, 50-190 nm, 50-180 nm, 50-170 nm, 50-160 nm, 50-150 nm, 50-140 nm, 50-130 nm, 50-120 nm, 50-110 nm, 50-100 nm, 50-90 nm, 50-80 nm, 50-70 nm, 50-60 nm, 60-300 nm, 60-290 nm, 60-280 nm, 60-270 nm, 60-260 nm, 60-250 nm, 60-240 nm, 60-230 nm, 60-220 nm, 60-210 nm, 60-200 nm, 60-190 nm, 60-180 nm, 60-170 nm, 60-160 nm, 60-150 nm, 60-140 nm, 60-130 nm, 60-120 nm, 60-110 nm, 60-100 nm, 60-90 nm, 60-80 nm, 60-70 nm, 70-300 nm, 70-290 nm, 70-280 nm, 70-270 nm, 70-260 nm, 70-250 nm, 70-240 nm, 70-230 nm, 70-220 nm, 70-210 nm, 70-200 nm, 70-190 nm, 70-180 nm, 70-170 nm, 70-160 nm, 70-150 nm, 70-140 nm, 70-130 nm, 70-120 nm, 70-110 nm, 70-100 nm, 70-90 nm, 70-80 nm, 80-300 nm, 80-290 nm, 80-280 nm, 80-270 nm, 80-260 nm, 80-250 nm, 80-240 nm, 80-230 nm, 80-220 nm, 80-210 nm, 80-200 nm, 80-190 nm, 80-180 nm, 80-170 nm, 80-160 nm, 80-150 nm, 80-140 nm, 80-130 nm, 80-120 nm, 80-110 nm, 80-100 nm, 80-90 nm, 90-300 nm, 90-290 nm, 90-280 nm, 90-270 nm, 90-260 nm, 90-250 nm, 90-240 nm, 90-230 nm, 90-220 nm, 90-210 nm, 90-200 nm, 90-190 nm, 90-180 nm, 90-170 nm, 90-160 nm, 90-150 nm, 90-140 nm, 90-130 nm, 90-120 nm, 90-110 nm, 90-100 nm, 100-300 nm, 110-290 nm, 120-280 nm, 130-270 nm, 140-260 nm, 150-250 nm, 160-240 nm, 170-230 nm, 180-220 nm, or 190-210 nm.

In particularly preferred embodiments, the exosome from the producer cell described herein has a longest dimension between about 30-100 nm. In another preferred embodiment, the exosome from the producer cell has a longest dimension between about 20-300 nm. In another preferred embodiment, the exosome from the producer cell has a longest dimension between about 40-200 nm. In another embodiment, a population of the exosomes described herein comprise a population wherein 90% of the exosomes have a longest dimension 20-300 nm. In another embodiment, a population of the exosomes described herein comprise a population wherein 95% of the exosomes have a longest dimension 20-300 nm. In another embodiment, a population of the exosomes described herein comprise a population wherein 99% of the exosomes have a longest dimension 20-300 nm. In another embodiment, a population of the exosomes described herein comprise a population wherein 90% of the exosomes have a longest dimension 40-200 nm. In another embodiment, a population of the exosomes described herein comprise a population wherein 95% of the exosomes have a longest dimension 40-200 nm. In another embodiment, a population of the exosomes described herein comprise a population wherein 99% of the exosomes have a longest dimension 40-200 nm. In other preferred embodiments, the size of the exosome or population of exosomes described herein is measured according to methods described, infra.

In some embodiments, the exosome is generated by a producer cell. In some embodiments, the membrane of the exosome comprises one or more molecules derived from the producer cell. In some embodiments, the exosome is generated in a cell culture system and isolated (e.g., by separating the exosome from the producer cell). Separation can be achieved by sedimentation. For example, the exosome can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$. Separation can also be achieved by affinity purification. For example, the extracellular vesicle can be purified by binding a population comprising extracellular vesicles to a resin, said resin comprising a plurality of ligands that have specific affinity for one or more target proteins on the surface of the extracellular vesicle. The one or more target protein may be a tetraspanin (e.g., CD63, CD81 and/or CD9), an EWI protein/immunoglobulin superfamily member (e.g., PTGFRN, IGSF8 and/or IGSF3), an integrin (e.g., ITGB1 and/or ITGA4), an ATP transporter protein (e.g., ATP1A1, ATP1A2, ATP1A3, ATP1A4, ATP1B3, ATP2B1, ATP2B2, ATP2B3 and/or ATP2B4), SLC3A2, BSG, or CD98hc. The target protein may additionally be the immunomodulating component that is displayed on the surface of the exosomes.

In some embodiments, the exosome membrane comprises an interior surface and an exterior surface. In certain embodiments, the interior surface faces the inner core of the exosome. In certain embodiments, the exterior surface can be in contact with the endosome, the multivesicular bodies, or the membrane/cytoplasm of a producer cell or a target cell.

In some embodiments, the exosome membrane comprises lipids and fatty acids. In some embodiments, the exosome membrane comprises phospholipids, glycolipids, fatty acids, sphingolipids, phosphoglycerides, sterols, cholesterols, and phosphatidylserines. In some embodiments, the lipid and fatty acid can be one or more of those listed in Table 1.

In certain embodiments, the exosome comprises a lipid bilayer composed of an inner leaflet and an outer leaflet. The composition of the inner and outer leaflet can be determined by transbilayer distribution assays known in the art, see e.g., Kuypers et al. Biohim Biophys Acta 1985 819:170. In some embodiments, the composition of the outer leaflet is between approximately 70-90% choline phospholipids, between approximately 0-15% acidic phospholipids, and between approximately 5-30% phosphatidylethanolamine. In some embodiments, the composition of the inner leaflet is between approximately 15-40% choline phospholipids, between approximately 10-50% acidic phospholipids, and between approximately 30-60% phosphatidylethanolamine.

In some embodiments, the exosome membrane further comprises one or more polypeptide. In certain embodiments, the exosome comprises one or more polypeptide selected from the following list, including but not limited to, spectrin, myosin-like polypeptide, band 3, SLC4A1, actin, actin-like polypeptide, glyceraldehyde 3-P dehydrogenase (G3PD), tetraspanins (e.g., CD63, CD81 and/or CD9), Alix and TSG101, integrins (e.g., ITGB1 and/or ITGA4), selectins, CR1, TNFRI, proteolytic enzymes, glycosylphosphatidylinositol (GPI)-linked proteins or histones, EWI protein/immunoglobulin superfamily members (e.g., PTGFRN, IGSF8 and/or IGSF3), ATP transporter proteins (e.g., ATP1A1, ATP1A2, ATP1A3, ATP1A4, ATP1B3, ATP2B1, ATP2B2, ATP2B3 and/or ATP2B4), SLC3A2, BSG, or CD98hc. In some embodiments, the exosome comprises at least one polypeptide selected from Table 2.

In some embodiments, the exosome comprises polypeptides on its surface. In some embodiments, the exosome is modified to contain the one or more polypeptides. In some embodiments, the producer cell is modified to contain the one or more polypeptides. In some embodiments, the producer cell naturally contains the one or more polypeptides and exosomes derived therefrom also contain the polypeptides. The levels of any desired surface marker can be modified directly on the exosome (e.g., by contacting the complex with recombinantly produced polypeptides to bring about insertion in or conjugation to the membrane of the complex). Alternatively or in addition, the levels of any desired surface marker can be modified directly on the producer cell (e.g., by contacting the complex with recombinantly produced polypeptides to bring about insertion in or conjugation to the membrane of the cell). Alternatively, the producer cell can be modified by transducing an exogenous nucleic acid into the producer cell to express a desired surface marker. The surface marker can already be naturally present on the producer cell, in which case the exogenous construct can lead to overexpression of the marker and increased concentration of the marker in or on the producer cell. Alternatively, a naturally expressed surface marker can be removed from the producer cell (e.g., by inducing gene silencing in the producer cell). The polypeptides can confer different functionalities to the exosome (e.g., specific targeting capabilities, delivery functions (e.g., fusion molecules), enzymatic functions, increased or decreased half-life in vivo, etc.). In some embodiments, the polypeptides include, but are not limited to CD47, CD55, CD49, CD40, CD133, CD59, glypican-1, CD9, CD63, CD81, integrins, selectins, lectins, and cadherins.

In specific embodiments, the exosomes comprise one or more polypeptides on their surface, wherein said polypeptides are selected from a group of proteins that was recently identified to be enriched on the surface of exosomes (described in detail in U.S. Patent Application 62/550,543, which is incorporated herein by reference in its entirety). This group of polypeptides includes prostaglandin F2 receptor negative regulator (PTGFRN); basigin (BSG); immunoglobulin superfamily member 3 (IGSF3); immunoglobulin superfamily member 8 (IGSF8); integrin beta-1 (ITGB1); integrin alpha-4 (ITGA4); 4F2 cell-surface antigen heavy chain (SLC3A2); and a class of ATP transporter proteins (ATP1A1, ATP1A2, ATP1A3, ATP1A4, ATP1B3, ATP2B1, ATP2B2, ATP2B3, ATP2B4)).

In some embodiments, the exosome membrane further comprises one or more polysaccharide, such as glycan.

In some embodiments, the exosome delivers the payload (therapeutic agent) to a target. The payload is a therapeutic agent that acts on a target (e.g., a target cell) that is contacted with the exosome. Contacting can occur in vitro or in a subject. Payloads that can be introduced into an exosome and/or a producer cell include therapeutic agents such as, nucleotides (e.g., nucleotides comprising a detectable moiety or a toxin or that disrupt transcription), nucleic acids (e.g., DNA or mRNA molecules that encode a polypeptide such as an enzyme, or RNA molecules that have regulatory function such as miRNA, dsDNA, lncRNA, or siRNA), amino acids (e.g., amino acids comprising a detectable moiety or a toxin that disrupt translation), polypeptides (e.g., enzymes), lipids, carbohydrates, and small molecules (e.g., small molecule drugs and toxins).

The exosome can interact with the target cell via membrane fusion and deliver payloads (e.g., therapeutic agents) in an exosome composition to the surface or cytoplasm of a target cell. In some embodiments, membrane fusion occurs between the exosome and the plasma membrane of a target cell. In other embodiments, membrane fusion occurs between the exosome and an endosomal membrane of a target cell.

In some embodiments, the exosome comprises a receiver polypeptide. The receiver polypeptide can be synthetic. In some embodiments, the receiver polypeptide is introduced into the producer cell (e.g., an exogenous nucleic acid that encodes the receiver polypeptide is introduced into the producer cell) or a recombinant receiver polypeptide that is made outside the producer cell (e.g., synthesized by a protein expression system). In some embodiments, the receiver polypeptide (e.g., a recombinantly produced polypeptide) is introduced into the exosome directly (e.g., after the exosome is isolated from the producer cell). In some embodiments, the receiver polypeptide can be on the surface of the exosomes. In some embodiments, the receiver polypeptide is capable of targeting the exosome to a specific target (e.g., a target such as a pathogen, a metabolite, a polypeptide complex or a cell such as non-functional cell or cancer cell) that circulates in the circulatory system of the subject, such as the blood, or a target that resides in a tissue (such as a diseased tissue).

In some embodiments, the exosome is synthetic. For example, the exosome can comprise a payload, such as, e.g., a therapeutic polypeptide, nucleic acid (such as DNA or RNA) or other polynucleotide, polysaccharide or glycan, lipid or fatty acid, large biologic, small molecule or toxin such that the exosome is not naturally occurring. In some embodiments, the exosome is modified (e.g., by introducing a payload or otherwise modifying the content of the complex, such as by changing the protein, lipid or glycan content of the membrane). For example, exosomes are first isolated from a producer cell and then modified as desired, thereby generating synthetic exosomes. In some embodiments, the producer cell is modified. For example, an exogenous nucleic acid, an exogenous polypeptide or small molecule or toxin can be introduced into the producer cell. Alternatively or in addition, the producer cell can otherwise be modified (e.g., by modifying the cellular or membrane content, such as by changing the lipid or glycan content of the cell membrane). Exosomes generated from the modified producer cells comprise one or more of the modifications of the producer cell. The process produces synthetic exosomes. In some embodiments, both the producer cell and the exosome isolated from the producer cell are modified as described herein.

Nanovesicle

In various embodiments, the extracellular vesicle is a nanovesicle. In certain embodiments, the nanovesicle is a cell-derived small vesicle comprising a membrane that encloses an internal space, and which is generated from the cell by direct or indirect manipulation such that the nanovesicle would not be produced by the cell without the manipulation. Appropriate manipulations of the cell include but are not limited to serial extrusion, treatment with alkaline solutions, sonication, or combinations thereof and can, in some instances, result in the destruction of the producer cell.

In various embodiments, the nanovesicle has a longest dimension between about 20-250 nm, such as between about 20-100 nm, 20-150 nm, 20-200 nm, 30-100 nm, 30-150 nm, 30-200 nm, 30-250 nm, 40-100 nm, 40-150 nm, 40-200 nm, 40-250 nm, 50-100 nm, 50-150 nm, 50-200 nm, 50-250 nm, 100-200 nm, or 150-250 nm.

In various embodiments, the nanovesicle is derived from a producer cell. In certain embodiments, the nanovesicle is generated from a producer cell by direct or indirect manipulation. Appropriate manipulations include but are not limited to serial extrusion, treatment with alkaline solutions, sonication, or combinations thereof. In some of these embodiments, the manipulation can result in the destruction of the producer cell. In some preferred embodiments, the population of the nanovesicle is substantially free of vesicles that are derived from producer cells by way of direct budding from the plasma membrane or fusion of the late endosome with the plasma membrane.

In some embodiments, the nanovesicle is isolated from the producer cell based on its size, density, biochemical parameters, or a combination thereof. In certain embodiments, the isolation can be achieved by sedimentation. For example, the nanovesicle can have a specific density between 0.5-2.0, 0.6-1.0, 0.7-1.0, 0.8-1.0, 0.9-1.0, 1.0-1.1, 1.1-1.2, 1.2-1.3, 1.4-1.5, 1.0-1.5, 1.5-2.0, and 1.0-2.0 kg/m$^3$.

In various embodiments, the nanovesicle comprises lipids or fatty acids and polypeptides. In certain embodiments, the nanovesicle further comprises a sugar. In certain embodiments, the nanovesicle further comprises a polynucleotide. In some embodiments, the nanovesicle further comprises a receiver. In some embodiments, the nanovesicle further comprises a payload. In some of these embodiments, the payload comprises nucleic acids, proteins, carbohydrates, lipids, small molecules, and/or combinations thereof.

The Immunomodulating Component

In various embodiments, the composition further comprises an immunomodulating component.

In some embodiments, the immunomodulating compound is a protein that is expressed as a translational fusion protein to an exosome surface protein, such that said protein is retained on the surface of the exosome. In certain embodiments, the immunomodulating compound is a membrane protein. In certain embodiments, the immunomodulating compound is a soluble protein. In some embodiments, the exosome surface protein is a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc or a fragment or variant thereof.

In some embodiments, the immunomodulating compound is a soluble protein that is expressed as a translational fusion protein to an exosome surface protein, such that said soluble protein is retained on the surface of the exosome. In some embodiments, the exosome surface protein is a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc or a fragment or variant thereof.

In certain embodiments, the immunomodulating component has anti-tumor activity. In some embodiments, the immunomodulating component regulates the innate immune response. In some of these embodiments, the immunomodulating component targets the natural killer cells. In some other embodiments, the immunomodulating component regulates the adaptive immune response. In some of these embodiments, the immunomodulating component targets the cytotoxic T cells.

In some embodiments, the immunomodulating component is expressed in the producer cell in its full-length form. In other embodiments, the immunomodulating component is expressed as a translational fusion protein to an exosome surface protein, which results in a higher level of expression of the biologically active portion of the immunomodulating compound on the surface of the exosome. In some embodiments, the immunomodulating compound is a soluble protein that is expressed as a translational fusion protein to an exosome surface protein, such that said soluble protein is retained on the surface of the exosome. In some embodiments, the exosome surface protein is a tetraspanin (e.g., CD63, CD81, CD9), an EWI protein/immunoglobulin superfamily member (e.g., PTGFRN, IGSF8, IGSF3), an integrin (e.g., ITGB1, ITGA4), an ATP transporter protein (e.g., ATP1A1, ATP1A2, ATP1A3, ATP1A4, ATP1B3, ATP2B1, ATP2B2, ATP2B3, ATP2B4), SLC3A2, BSG, or CD98hc or a fragment or variant thereof.

In some embodiments, the immunomodulating component is an inhibitor for a negative checkpoint regulator. In some embodiments, the immunomodulating component is an inhibitor for a binding partner of a negative checkpoint regulator.

In certain embodiments, the immunomodulating component is an inhibitor of cytotoxic T-lymphocyte-associate protein 4 (CTLA-4). In some of these embodiments, the CTLA-4 inhibitor is a monoclonal antibody of CTLA-4. In certain embodiments, the inhibitor is a fragment of a monoclonal antibody of CTLA-4. In certain embodiments, the antibody fragment is a scFv, (scFv)$_2$, Fab, Fab', and F(ab')$_2$, F(ab1)$_2$, Fv, dAb, or Fd of a monoclonal antibody of CTLA-4. In certain embodiments, the inhibitor is a nanobody, a bispecific antibody, or a multispecific antibody against CTLA-4. In some specific embodiments, the monoclonal antibody is ipilimumab. In some specific embodiments, the monoclonal antibody is tremelimumab.

In certain embodiments, the immunomodulating component is an inhibitor of programmed cell death protein 1 (PD-1). In certain embodiments, the immunomodulating component is an inhibitor of programmed death-ligand 1 (PD-L1). In certain embodiments, the immunomodulating component is an inhibitor of programmed death-ligand 2 (PD-L2). In some embodiments, the inhibitor of PD-1, PD-L1, or PD-L2 is a monoclonal antibody of PD-1, PD-L1, or PD-L2. In certain embodiments, the inhibitor is a fragment of a monoclonal antibody of PD-1, PD-L1, or PD-L2. In certain embodiments, the antibody fragment is a scFv, (scFv)$_2$, Fab, Fab', and F(ab')$_2$, F(ab1)$_2$, Fv, dAb, or Fd of a monoclonal antibody of PD-1, PD-L1, or PD-L2. In certain embodiments, the inhibitor is a nanobody, a bispecific antibody, or a multispecific antibody against PD-1, PD-L1, or PD-L2. In some specific embodiments, the monoclonal antibody is nivolumab. In some specific embodiments, the monoclonal antibody is pembrolizumab. In some specific embodiments, the monoclonal antibody is pidilizumab. In some specific embodiments, the monoclonal antibody is atezolizumab. In some specific embodiments, the monoclonal antibody is avelumab.

In certain embodiments, the immunomodulating component is an inhibitor of lymphocyte-activated gene 3 (LAG3). In some of these embodiments, the inhibitor of LAG3 is a monoclonal antibody of LAG3.

In certain embodiments, the immunomodulating component is an inhibitor of T-cell immunoglobulin mucin-containing protein 3 (TIM-3). In certain embodiments, the immunomodulating component is an inhibitor of B and T lymphocyte attenuator (BTLA). In certain embodiments, the immunomodulating component is an inhibitor of T cell immunoreceptor with Ig and ITIM domains (TIGIT). In certain embodiments, the immunomodulating component is an inhibitor of V-domain Ig suppressor of T cell activation (VISTA). In certain embodiments, the immunomodulating component is an inhibitor of adenosine A2a receptor (A2aR). In certain embodiments, the immunomodulating component is an inhibitor of killer cell immunoglobulin like receptor (KIR). In certain embodiments, the immunomodulating component is an inhibitor of indoleamine 2,3-dioxygenase (IDO). In certain embodiments, the immunomodulating component is an inhibitor of CD20, CD39, or CD73.

In some embodiments, the immunomodulating component is an activator for a positive co-stimulatory molecule.

In some embodiments, the immunomodulating component is an activator for a binding partner of a positive co-stimulatory molecule.

In some embodiments, the immunomodulating component is an activator of a TNF receptor superfamily member. In certain embodiments, the TNF receptor superfamily member is selected from the group consisting of: CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, GITR, TROY, CD358, TRAMP, and XEDAR. In some embodiments, the immunomodulating component is a TNF superfamily member. In certain embodiments, the TNF superfamily member is selected from the group consisting of: TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, and EDA-2.

In some embodiments, the activator of a TNF receptor superfamily member is expressed as a monomeric protein. In some embodiments, the activator of a TNF receptor superfamily member is expressed as trimeric proteins. In some embodiments, the TNF receptor superfamily member is expressed as a monomeric protein. In some embodiments, the TNF receptor superfamily member is expressed as trimeric proteins.

In certain embodiments, the immunomodulating component is an activator of TNF Receptor Superfamily Member 4 (OX40). In some of these embodiments, the activator of OX40 is an agonist antibody of OX40. In some other of these embodiments, the activator of OX40 is OX40 ligand (OX40L).

In certain embodiments, the immunomodulating component is an activator of CD27. In some of these embodiments, the activator of CD27 is an agonist antibody of CD27. In some other of these embodiments, the activator of CD27 is CD27 ligand (CD27L).

In certain embodiments, the immunomodulating component is an activator of CD40. In some of these embodiments, the activator of CD40 is an agonist antibody of CD40. In some other of these embodiments, the activator of CD40 is CD40 ligand (CD40L). In some embodiments, the CD40L is monomeric CD40L. In some embodiments, the CD40L is trimeric CD40L.

In some embodiments, trimeric CD40L is fused to PTGFRN or a fragment thereof. In some embodiments, trimeric CD40L is fused to the N-terminus of PTGFRN or a fragment thereof. In some embodiments, trimeric CD40L is expressed as a fusion protein to PTGFRN, wherein the polypeptide has the sequence of SEQ ID NO: 19 or SEQ ID NO: 20.

In certain embodiments, the immunomodulating component is an activator of glucocorticoid-induced TNFR-related protein (GITR). In some of these embodiments, the activator of GITR is an agonist antibody of GITR. In some other of these embodiments, the activator of GITR is a natural ligand of GITR.

In certain embodiments, the immunomodulating component is an activator of 4-1BB. In some of these embodiments, the activator of 4-1BB is an agonist antibody of 4-1BB. In some other of these embodiments, the activator of 4-1BB is a natural ligand of 4-1BB.

In some embodiments, the immunomodulating component is Fas receptor (Fas). In some of these embodiments, the Fas receptor is displayed on the surface of the extracellular vesicle. In some other embodiments, the immunomodulating component is Fas ligand (FasL). In some of these embodiments, the Fas ligand is displayed on the surface of the extracellular vesicle. In certain embodiments, the immunomodulating component is an antibody of Fas receptor. In certain embodiments, the immunomodulating component is an antibody of Fas ligand.

In some embodiments, the immunomodulating component is an activator of a CD28-superfamily co-stimulatory molecule. In certain embodiments, the CD28-superfamily co-stimulatory molecule is ICOS or CD28. In certain embodiments, the immunomodulating component is ICOSL, CD80, or CD86.

In certain embodiments, the immunomodulating component is an activator of inducible T cell co-stimulator (ICOS). In some of these embodiments, the activator of ICOS is an agonist antibody of ICOS. In some other of these embodiments, the activator of ICOS is ICOS ligand (ICOSL).

In certain embodiments, the immunomodulating component is an activator of CD28. In some of these embodiments, the activator of CD28 is an agonist antibody of CD28. In some other of these embodiments, the activator of CD28 is a natural ligand of CD28. In certain embodiments, the ligand of CD28 is CD80.

In certain embodiments, the composition comprises an inhibitor for a negative checkpoint regulator or an inhibitor for a binding partner of a negative checkpoint regulator and an activator for a positive co-stimulatory molecule or an activator for a binding partner of a positive co-stimulatory molecule.

In certain embodiments, the immunomodulating component is a cytokine. In some embodiments, the cytokine is a soluble cytokine that has been translationally fused to an exosome surface protein or fragment thereof. In some embodiments, the cytokine is interleukin 2 (IL-2). In some embodiments, the cytokine is interleukin 7 (IL-7). In some embodiments, the cytokine is interleukin 12 (IL-12). In some embodiments, the cytokine is interleukin 15 (IL-15).

In certain embodiments, the cytokine is fused to PTGFRN or a fragment thereof. In some embodiments, IL-7 is fused to PTGFRN or a fragment thereof. In some embodiments, IL-7 is fused to the N-terminus of PTGFRN or a fragment thereof. In some embodiments, IL-7 is expressed as a fusion protein to PTGFRN, wherein the polypeptide has the sequence of SEQ ID NO: 1 or SEQ ID NO: 2.

In certain embodiments, the cytokine is fused to PTGFRN or a fragment thereof. In some embodiments, IL-12 is fused to PTGFRN or a fragment thereof. In some embodiments, IL-12 is fused to the N-terminus of PTGFRN or a fragment thereof. In some embodiments, IL-12 is expressed as a fusion protein to PTGFRN, wherein the polypeptide has the sequence of SEQ ID NO: 3, SEQ ID NO: 4, SEQ ID NO: 5, or SEQ ID NO: 6.

In certain embodiments, the cytokine is fused to PTGFRN or a fragment thereof. In some embodiments, IL-15 is fused to PTGFRN or a fragment thereof. In some embodiments, IL-15 is fused to the N-terminus of PTGFRN or a fragment thereof. In some embodiments, IL-15 is expressed as a fusion protein to PTGFRN, wherein the polypeptide has the sequence of SEQ ID NO: 15 or SEQ ID NO: 16.

In some embodiments, the cytokine is an interferon (IFN). In certain embodiments, the interferon is fused to PTGFRN or a fragment thereof. In certain embodiments, the interferon is interferon γ (IFNγ). In some embodiments, IFNγ is fused to PTGFRN or a fragment thereof. In some embodiments, IFNγ is fused to the N-terminus of PTGFRN or a fragment thereof. In some embodiments, IFNγ is expressed as a fusion protein to PTGFRN, wherein the polypeptide has the sequence of SEQ ID NO: 7 or SEQ ID NO: 8.

In some embodiments, the immunomodulating component is a T-cell receptor (TCR) or a derivative thereof. In certain embodiments, the immunomodulating component is a TCR α-chain or a derivative thereof. In certain embodiments, the immunomodulating component is a TCR β-chain or a derivative thereof. In some embodiments, the immunomodulating component is a co-receptor of the T-cell or a derivative thereof.

In some embodiments, the immunomodulating component is a tumor antigen. In certain embodiments, the tumor antigen is selected from the group consisting of: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In certain embodiments, the tumor antigen is a carcinoembryonic antigen (CEA). In certain embodiments, the tumor antigen is an epithelial tumor antigen (ETA).

In certain embodiments, the tumor antigen is a mucin. In some of these embodiments, the mucin is a secreted mucin. In some other of these embodiments, the mucin is a transmembrane mucin. In specific embodiments, the tumor antigen is mucin 1 (MUC1). In specific embodiments, the tumor antigen is Tn-MUC1. In specific embodiments, the tumor antigen is mucin 16 (MUC16).

In certain embodiments, the tumor antigen is a melanoma-associated antigen (MAGE). In some of these embodiments, the MAGE is a type-I MAGE. In some other of these embodiments, the MAGE is a type-II MAGE. In specific embodiments, the type-I MAGE is MAGE-A2. In specific embodiments, the type-I MAGE is MAGE-A4.

In certain embodiments, the tumor antigen is alpha-fetoprotein (AFP). In certain embodiments, the tumor antigen is tumor protein p53 (p53). In certain embodiments, the tumor antigen is tyrosinase. In certain embodiments, the tumor antigen is a tyrosinase-related protein (TRP). In some embodiments, the tumor antigen is programmed death ligand 1 (PD-L1) or programmed death ligand 2 (PD-L2). In various embodiments, the tumor antigen is selected from the group consisting of CD4, CD8, CD45, CD80, and CD86.

In some embodiments, the immunomodulating component is a chimeric antigen receptor (CAR) or a derivative thereof. In some embodiments, the CAR binds to one or more of alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand.

In some embodiments, the immunomodulating component is an activator of a T-cell receptor or co-receptor. In certain embodiments, the immunomodulating component is an activator of CD3. In certain embodiments, the activator is a fragment of a monoclonal antibody of CD3. In certain embodiments, the antibody fragment is a scFv, (scFv)$_2$, Fab, Fab', and F(ab')$_2$, F(ab1)$_2$, Fv, dAb, or Fd of a monoclonal antibody against CD3. In certain embodiments, the activator is a nanobody, a bispecific antibody, or a multispecific antibody against CD3. In some embodiments, the anti-CD3 antibody fragment is fused to PTGFRN or a fragment thereof. In some embodiments, the anti-CD3 antibody fragment is fused to the N-terminus of PTGFRN or a fragment thereof. In some embodiments, the anti-CD3 antibody fragment is expressed as a fusion protein to PTGFRN, wherein the polypeptide has the sequence of SEQ ID NO: 18 or SEQ ID NO: 21. In certain embodiments, the immunomodulating component is an activator of CD28. In certain embodiments, the inhibitor is a fragment of a monoclonal antibody of CD28. In certain embodiments, the antibody fragment is a scFv, (scFv)$_2$, Fab, Fab', and F(ab')$_2$, F(ab1)$_2$, Fv, dAb, or Fd of a monoclonal antibody of CD28. In certain embodiments, the inhibitor is a nanobody, a bispecific antibody, or a multispecific antibody against CD28.

In some embodiments, the immunomodulating component is a major histocompatibility complex (MHC) or a derivative thereof. In some of these embodiments, the immunomodulating component is an MHC class I or a derivative thereof. In some of these embodiments, the immunomodulating component is an MHC class II or a derivative thereof. In some of these embodiments, the immunomodulating component is an MHC class III or a derivative thereof.

In some embodiments, the immunomodulating component is a human leukocyte antigen (HLA) or a derivative thereof. In some of these embodiments, the immunomodulating component is an HLA-A, HLA-B, HLA-C, or derivative thereof. In some of these embodiments, the immunomodulating component is an HLA-E, HLA-F, HLA-G, or a derivative thereof. In some of these embodiments, the immunomodulating component is an HLA-DP, HLA-DQ, HLA-DR, or a derivative thereof.

In various embodiments, the immunomodulating component can be a polypeptide, a polynucleotide, a polysaccharide, a lipid, a small molecule, or a toxin.

In some embodiments, the immunomodulating component can be a protein, a peptide, a glycolipid, or a glycoprotein.

In certain embodiments, the immunomodulating component is an agonist. In some of these embodiments, the agonist is an endogenous agonist, such as a hormone, or a neurotransmitter. In some other of these embodiments, the agonist is an exogenous agonist, such as a drug. In some embodiments, the agonist is a physical agonist, which can create an agonist response without binding to the receptor. In some embodiments, the agonist is a superagonist, which can produce a greater maximal response than the endogenous agonist. In certain embodiments, the agonist is a full agonist with full efficacy at the receptor. In certain other embodiments, the agonist is a partial agonist having only partial efficacy at the receptor relative to a full agonist. In some embodiments, the agonist is an inverse agonist that can inhibit the constitutive activity of the receptor. In some embodiments, the agonist is a co-agonist that works with other co-agonists to produce an effect on the receptor. In certain embodiments, the agonist is an irreversible agonist that binds permanently to a receptor through formation of covalent bond. In certain embodiments, the agonist is selective agonist for a specific type of receptor.

In certain embodiments, the immunomodulating component is an antagonist. In some of these embodiments, the antagonist is a competitive antagonist, which reversibly binds to the receptor at the same binding site as the endogenous ligand or agonist without activating the receptor. Competitive antagonist can affect the amount of agonist necessary to achieve a maximal response. In some other of these embodiments, the antagonist is a non-competitive antagonist, which binds to an active site of the receptor or an allosteric site of the receptor. Non-competitive antagonist can reduce the magnitude of the maximum response that can be attained by any amount of agonist. In some other embodiments, the antagonist is an uncompetitive antagonist, which requires receptor activation by an agonist before its binding to a separate allosteric binding site.

In various embodiments, the immunomodulating component comprises an antibody or an antigen-binding fragment. The immunomodulating component can be a full length protein or a fragment thereof. The antibody or antigen-binding fragment can be derived from natural sources, or partly or wholly synthetically produced. In some embodiments, the antibody is a monoclonal antibody. In some of these embodiments, the monoclonal antibody is an IgG antibody. In certain embodiments, the monoclonal antibody is an IgG1, IgG2, IgG3, or IgG4. In some other embodiments, the antibody is a polyclonal antibody. In certain embodiments, the antigen-binding fragment is selected from Fab, Fab', and F(ab')$_2$, F(ab1)$_2$, Fv, dAb, and Fd fragments. In certain embodiments, the antigen-binding fragment is an scFv or (scFv)$_2$ fragment. In certain other embodiments, the antibody or antigen-binding fragment is a Nanobody® (single-domain antibody). In some embodiments, the antibody or antigen-binding fragment is a bispecific or multi-specific antibody.

In various embodiments, the antibody or antigen-binding fragment is fully human. In some embodiments, the antibody or antigen-binding fragment is humanized. In some embodiments, the antibody or antigen-binding fragment is chimeric. In some of these embodiments, the chimeric antibody has non-human V region domains and human C region domains. In some embodiments, the antibody or antigen-binding fragment is non-human, such as murine or veterinary.

In certain embodiments, the immunomodulating component is a polynucleotide. In some of these embodiments, the polynucleotide includes, but is not limited to, an mRNA, a miRNA, an siRNA, an antisense RNA, an shRNA, a lncRNA, and a dsDNA. In some embodiments, the polynucleotide is an RNA (e.g., an mRNA, a miRNA, an siRNA, an antisense RNA, an shRNA, or an lncRNA). In some of these embodiments, when the polynucleotide is an mRNA, it can be translated into a desired polypeptide. In some embodiments, the polynucleotide is a microRNA (miRNA) or pre-miRNA molecule. In some of these embodiments, the miRNA is delivered to the cytoplasm of the target cell, such that the miRNA molecule can silence a native mRNA in the target cell. In some embodiments, the polynucleotide is a small interfering RNA (siRNA) or a short hairpin RNA (shRNA) capable of interfering with the expression of an oncogene or other dysregulating polypeptides. In some of these embodiments, the siRNA is delivered to the cytoplasm of the target cell, such that the siRNA molecule can silence a native mRNA in the target cell. In some embodiments, the polynucleotide is an antisense RNA that is complementary to an mRNA. In some embodiments, the polynucleotide is a long non-coding RNA (lncRNA) capable of regulating gene expression and modulating diseases. In some embodiments, the polynucleotide is a DNA that can be transcribed into an RNA. In some of these embodiments, the transcribed RNA can be translated into a desired polypeptide.

In some embodiments, the immunomodulating component is a protein, a peptide, a glycolipid, or a glycoprotein.

In various embodiments, the composition comprises two or more above mentioned immunomodulating components, including mixtures, fusions, combinations and conjugates, of atoms, molecules, etc. In some embodiments, the composition comprises one, two, three, four, five, six, seven, eight, nine, ten, eleven, or twelve different immunomodulating components associated with the membrane or enclosed within the enclosed volume of said extracellular vesicle. In certain embodiments, the composition comprises a nucleic acid combined with a polypeptide. In certain embodiments, the composition comprises two or more polypeptides conjugated to each other. In certain embodiments, the composition comprises a protein conjugated to a biologically active molecule. In some of these embodiments, the biologically active molecule is a prodrug.

In some embodiments, the composition comprises two different immunomodulating components associated with the membrane or enclosed within the enclosed volume of said extracellular vesicle. In certain embodiments, the two different immunomodulating components are IL-12 and CD40L. In some embodiments, the CD40L and IL-12 are fused to PTGFRN or a fragment thereof respectively. In some embodiments, the CD40L and IL-12 are fused to the N-terminus of PTGFRN or a fragment thereof respectively. In some embodiments, the CD40L and IL-12 are expressed as fusion proteins to PTGFRN, wherein the polypeptides have the sequences of SEQ ID NO: 20 and SEQ ID NO: 3 respectively.

In some embodiments, the composition comprises three different immunomodulating components associated with the membrane or enclosed within the enclosed volume of said extracellular vesicle. In certain embodiments, the two different immunomodulating components are IL-12, CD40L, and FMS-like tyrosine kinase 3 ligand (FLT3L). In some embodiments, the CD40L, IL-12, and FLT3L are fused to PTGFRN or a fragment thereof respectively. In some embodiments, the CD40L, IL-12, and FLT3L are fused to the N-terminus of PTGFRN or a fragment thereof respectively. In some embodiments, the CD40L, IL-12, and FLT3L are expressed as fusion proteins to PTGFRN, wherein the polypeptides have the sequences of SEQ ID NO: 20, SEQ ID NO: 3, and SEQ ID NO: 22 respectively.

The Pharmaceutical Composition

The pharmaceutical compositions generally comprise a plurality of extracellular vesicles and a pharmaceutically-acceptable excipient or carrier in a form suitable for administration to a subject. Pharmaceutically-acceptable excipients or carriers are determined in part by the particular composition being administered, as well as by the particular method used to administer the composition. Accordingly, there is a wide variety of suitable formulations of pharmaceutical compositions comprising a plurality of extracellular vesicles. (See, e.g., Remington's Pharmaceutical Sciences, Mack Publishing Co., Easton, Pa. 21st ed. (2005)). The pharmaceutical compositions are generally formulated sterile and in full compliance with all Good Manufacturing Practice (GMP) regulations of the U.S. Food and Drug Administration.

In some embodiments, the pharmaceutical composition comprises one or more therapeutic agents and the extracellular vesicle described herein. In some embodiments, the extracellular vesicles are co-administered with of one or more separate therapeutic agents, wherein co-administration includes administration of the separate therapeutic agent before, after or concurrent with administration of the extracellular vesicles.

Pharmaceutically-acceptable excipients include excipients that are generally safe, non-toxic, and desirable, including excipients that are acceptable for veterinary use as well as for human pharmaceutical use.

Examples of carriers or diluents include, but are not limited to, water, saline, Ringer's solutions, dextrose solution, and 5% human serum albumin. The use of such media and compounds for pharmaceutically active substances is well known in the art. Except insofar as any conventional media or compound is incompatible with the extracellular vesicles described herein, use thereof in the compositions is contemplated. Supplementary therapeutic agents can also be incorporated into the compositions. Typically, a pharmaceutical composition is formulated to be compatible with its intended route of administration. The extracellular vesicles can be administered by parenteral, topical, intravenous, oral, subcutaneous, intra-arterial, intradermal, transdermal, rectal, intracranial, intraperitoneal, intranasal, intratumoral, intramuscular route or as inhalants. In certain embodiments, the pharmaceutical composition comprising extracellular vesicles is administered intravenously, e.g. by injection. The extracellular vesicles can optionally be administered in combination with other therapeutic agents that are at least partly effective in treating the disease, disorder or condition for which the extracellular vesicles are intended.

Solutions or suspensions can include the following components: a sterile diluent such as water, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. The preparation can be enclosed in ampoules, disposable syringes or multiple dose vials made of glass or plastic.

Pharmaceutical compositions suitable for injectable use include sterile aqueous solutions (if water soluble) or dispersions and sterile powders. For intravenous administration, suitable carriers include physiological saline, bacteriostatic water, Cremophor EL™ (BASF, Parsippany, N.J.) or phosphate buffered saline (PBS). The composition is generally sterile and fluid to the extent that easy syringeability exists. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. If desired, isotonic compounds, e.g., sugars, polyalcohols such as mannitol, sorbitol, and sodium chloride can be added to the composition. Prolonged absorption of the injectable compositions can be brought about by including in the composition a compound which delays absorption, e.g., aluminum monostearate and gelatin.

Sterile injectable solutions can be prepared by incorporating the extracellular vesicles in an effective amount and in an appropriate solvent with one or a combination of ingredients enumerated herein, as desired. Generally, dispersions are prepared by incorporating the extracellular vesicles into a sterile vehicle that contains a basic dispersion medium and any desired other ingredients. In the case of sterile powders for the preparation of sterile injectable solutions, methods of preparation are vacuum drying and freeze-drying that yields a powder of the active ingredient plus any additional desired ingredient from a previously sterile-filtered solution thereof. The extracellular vesicles can be administered in the form of a depot injection or implant preparation which can be formulated in such a manner to permit a sustained or pulsatile release of the extracellular vesicles.

Systemic administration of compositions comprising extracellular vesicles can also be by transmucosal means. For transmucosal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of, e.g., nasal sprays.

In certain embodiments the pharmaceutical composition comprising extracellular vesicles is administered intravenously into a subject that would benefit from the pharmaceutical composition. In certain other embodiments, the composition is administered to the lymphatic system, e.g., by intralymphatic injection or by intranodal injection (see e.g., Senti et al., PNAS 105(46): 17908 (2008)), or by intramuscular injection, by subcutaneous administration, by intratumoral injection, by direct injection into the thymus, or into the liver.

In certain embodiments, the pharmaceutical composition comprising extracellular vesicles is administered as a liquid suspension. In certain embodiments, the pharmaceutical composition is administered as a formulation that is capable of forming a depot following administration. In certain preferred embodiments, the depot slowly releases the extracellular vesicles into circulation, or remains in depot form.

Typically, pharmaceutically-acceptable compositions are highly purified to be free of contaminants, are biocompatible and not toxic, and are suited to administration to a subject. If water is a constituent of the carrier, the water is highly purified and processed to be free of contaminants, e.g., endotoxins.

The pharmaceutically-acceptable carrier can be lactose, dextrose, sucrose, sorbitol, mannitol, starch, gum acacia, calcium phosphate, alginates, gelatin, calcium silicate, micro-crystalline cellulose, polyvinylpyrrolidone, cellulose, water, syrup, methyl cellulose, methylhydroxy benzoate, propylhydroxy benzoate, talc, magnesium stearate, and/or mineral oil, but is not limited thereto. The pharmaceutical composition can further include a lubricant, a wetting agent, a sweetener, a flavor enhancer, an emulsifying agent, a suspension agent, and/or a preservative.

The pharmaceutical compositions described herein comprise the extracellular vesicles described herein and optionally a pharmaceutically active or therapeutic agent. The therapeutic agent can be a biological agent, a small molecule agent, or a nucleic acid agent.

Dosage forms are provided that comprise a pharmaceutical composition comprising the extracellular vesicles described herein. In some embodiments, the dosage form is formulated as a liquid suspension for intravenous injection. In some embodiments, the dosage form is formulated as a liquid suspension for intratumoral injection.

In certain embodiments, the preparation of extracellular vesicles is subjected to radiation, e.g., X rays, gamma rays, beta particles, alpha particles, neutrons, protons, elemental nuclei, UV rays in order to damage residual replication-competent nucleic acids.

In certain embodiments, the preparation of extracellular vesicles is subjected to gamma irradiation using an irradiation dose of more than 1, 5, 10, 15, 20, 25, 30, 35, 40, 50, 60, 70, 80, 90, 100, or more than 100 kGy.

In certain embodiments, the preparation of extracellular vesicles is subjected to X-ray irradiation using an irradiation dose of more than 0.1, 0.5, 1, 5, 10, 15, 20, 25, 30, 35, 40, 50, 60, 70, 80, 90, 100, 200, 300, 400, 500, 600, 700, 800, 900, 1000, 2000, 3000, 4000, 5000, 6000, 7000, 8000, 9000, 10000, or greater than 10000 mSv.

Methods

Aspects of the subject disclosure also include methods of producing the composition comprising the extracellular vesicle and the immunomodulating component. In some embodiments, the method comprises: obtaining the extracellular vesicle from the producer cell, wherein the producer cell naturally contains the immunomodulating component; and optionally isolating the obtained extracellular vesicle. In some embodiments, the method comprises: modifying a producer cell with the immunomodulating component; obtaining the extracellular vesicle from the modified producer cell; and optionally isolating the obtained extracellular vesicles. In some other embodiments, the method comprises: obtaining the extracellular vesicle from a producer cell; isolating the obtained extracellular vesicles; and modifying the isolated extracellular vesicle with the immunomodulating component. In certain embodiments, the method further comprises formulating the isolated extracellular vesicles into a pharmaceutical composition.

Methods of Producing the Extracellular Vesicles
Methods of Modifying the Producer Cell with the Immunomodulating Component In various embodiments, the method comprises modifying a producer cell with the immunomodulating component.

The producer cell can be a mammalian cell line, a plant cell line, an insect cell line, a fungi cell line, or a prokaryotic cell line. In certain embodiments, the producer cell is a mammalian cell line. The mammalian cell lines include but are not limited to a human embryonic kidney (HEK) cell line, a Chinese hamster ovary (CHO) cell line, an HT-1080 cell line, a HeLa cell line, a PERC-6 cell line, a CEVEC cell line, a fibroblast cell line, an amniocyte cell line, an epithelial cell line, and a mesenchymal stem cell (MSC) cell line. In some preferred embodiments, the mammalian cell line can be HEK-293 cells, BJ human foreskin fibroblast cells, fHDF fibroblast cells, AGE.HN® neuronal precursor cells, CAP® amniocyte cells, adipose mesenchymal stem cells, or RPTEC/TERT1 cells. The producer cell can also be a primary cell. In various embodiments, the primary cell can be a primary mammalian cell, a primary plant cell, a primary insect cell, a primary fungi cell, or a primary prokaryotic cell.

In certain preferred embodiments, the producer cell is an immune cell, such as a dendritic cell, a T cell, a B cell, a natural killer cell (NK cell), an antigen presenting cell, a macrophage, a T helper cell, or a regulatory T cell (Treg cell).

In various embodiments, the immunomodulating component can be expressed in a producer cell from a transgene or mRNA introduced into the producer cell by transfection, viral transduction, electroporation, extrusion, sonication, cell fusion, or other methods that are known to the skilled in the art.

In certain embodiments, the immunomodulating component is introduced to the producer cell by transfection. In some embodiments, the immunomodulating component can be introduced into suitable producer cells using synthetic macromolecules such as cationic lipids and polymers (Papapetrou et al., Gene Therapy 12: S118-S130 (2005)). In some embodiments, the cationic lipids form complexes with the immunomodulating component through charge interactions. In some of these embodiments, the positively charged complexes bind to the negatively charged cell surface and are taken up by the cell by endocytosis. In some other embodiments, a cationic polymer can be used to transfect producer cells. In some of these embodiments, the cationic polymer is polyethylenimine (PEI). In certain embodiments, chemicals such as calcium phosphate, cyclodextrin, or polybrene, can be used to introduce the immunomodulating component to the producer cells. The immunomodulating component can also be introduced into a producer cell using a physical method such as particle-mediated transfection, "gene gun", biolistics, or particle bombardment technology (Papapetrou et al., Gene Therapy 12: S118-S130 (2005)). A reporter gene such as, for example, beta-galactosidase, chloramphenicol acetyltransferase, luciferase, or green fluorescent protein can be used to assess the transfection efficiency of the producer cell.

In certain embodiments, the immunomodulating component is introduced to the producer cell by viral transduction. A number of viruses can be used as gene transfer vehicles, including moloney murine leukemia virus (MMLV), adenovirus, adeno-associated virus (AAV), herpes simplex virus (HSV), lentiviruses, and spumaviruses. The viral mediated gene transfer vehicles comprise vectors based on DNA viruses, such as adenovirus, adeno-associated virus and herpes virus, as well as retroviral based vectors.

In certain embodiments, the immunomodulating component is introduced to the producer cell by electroporation. Electroporation creates transient pores in the cell membrane, allowing for the introduction of various molecules into the cell. In some embodiments, DNA and RNA as well as polypeptides and non-polypeptide therapeutic agents can be introduced into the producer cell by electroporation.

In certain embodiments, the immunomodulating component is introduced to the producer cell by microinjection. In some embodiments, a glass micropipette can be used to inject the immunomodulating component into the producer cell at the microscopic level.

In certain embodiments, the immunomodulating component is introduced to the producer cell by extrusion.

In certain embodiments, the immunomodulating component is introduced to the producer cell by sonication. In some embodiments, the producer cell is exposed to high intensity sound waves, causing transient disruption of the cell membrane allowing loading of an immunomodulating component.

In certain embodiments, the immunomodulating component is introduced to the producer cell by cell fusion. In some embodiments, the immunomodulating component is introduced by electrical cell fusion. In some other embodiments, polyethylene glycol (PEG) is used to fuse the producer cells. In some other embodiments, sendai virus is used to fuse the producer cells.

In some embodiments, the immunomodulating component is introduced to the producer cell by hypotonic lysis. In some of these embodiments, the producer cell is exposed to low ionic strength buffer causing them to burst allowing loading of an immunomodulating component. In some alternative embodiments, controlled dialysis against a hypotonic solution is used to swell the producer cell and to create pores in the producer cell membrane. The producer cell is subsequently exposed to conditions that allow resealing of the membrane.

In some embodiments, the immunomodulating component is introduced to the producer cell by detergent treatment. In certain embodiments, producer cell is treated with a mild detergent which transiently compromises the producer cell membrane by creating pores allowing loading of an immunomodulating component. After producer cells are loaded, the detergent is washed away thereby resealing the membrane.

In some embodiments, the immunomodulating component is introduced to the producer cell by receptor mediated endocytosis. In certain embodiments, producer cells have a surface receptor which upon binding of the immunomodulating component induces internalization of the receptor and the associated immunomodulating component.

In some embodiments, the immunomodulating component is introduced to the producer cell by filtration. In certain embodiments, the producer cells and the immunomodulating component can be forced through a filter of pore size smaller than the producer cell causing transient disruption of the producer cell membrane and allowing the immunomodulating component to enter the producer cell.

In some embodiments, the producer cell is subjected to several freeze thaw cycles, resulting in cell membrane disruption allowing loading of an immunomodulating component.

Methods of Modifying the Extracellular Vesicle with the Immunomodulating Component In various alternative embodiments, the immunomodulating component is introduced directly to the extracellular vesicles after the isolation of the extracellular vesicles.

In certain embodiments, the immunomodulating component is introduced to the extracellular vesicle by transfection. In some embodiments, the immunomodulating component can be introduced into the extracellular vesicles using synthetic macromolecules such as cationic lipids and polymers (Papapetrou et al., Gene Therapy 12: S118-S130 (2005)). In certain embodiments, chemicals such as calcium phosphate, cyclodextrin, or polybrene, can be used to introduce the immunomodulating component to the extracellular vesicles.

In certain embodiments, the immunomodulating component is introduced to the extracellular vesicle by electroporation. In some embodiments, extracellular vesicles are exposed to an electrical field which causes transient holes in the extracellular vesicle membrane, allowing loading of an immunomodulating component.

In certain embodiments, the immunomodulating component is introduced to the extracellular vesicle by microinjection. In some embodiments, a glass micropipette can be used to inject the immunomodulating component directly into the extracellular vesicle at the microscopic level.

In certain embodiments, the immunomodulating component is introduced to the extracellular vesicle by extrusion.

In certain embodiments, the immunomodulating component is introduced to the extracellular vesicle by sonication. In some embodiments, extracellular vesicles are exposed to high intensity sound waves, causing transient disruption of the extracellular vesicle membrane allowing loading of an immunomodulating component.

In some embodiments, the immunomodulating component can be conjugated to the surface of the extracellular vesicle. Conjugation can be achieved chemically or enzymatically, by methods known in the art.

In some embodiments, the extracellular vesicle comprises an immunomodulating component that is chemically conjugated. Chemical conjugation can be accomplished by covalent bonding of the immunomodulating component to another molecule, with or without use of a linker. The formation of such conjugates is within the skill of artisans and various techniques are known for accomplishing the conjugation, with the choice of the particular technique being guided by the materials to be conjugated. In certain embodiments, polypeptides are conjugated to the extracellular vesicle. In certain other embodiments, non-polypeptides, such as lipids, carbohydrates, nucleic acids, and small molecules, are conjugated to the extracellular vesicle.

In some embodiments, the immunomodulating component is introduced to the extracellular vesicle by hypotonic lysis. In some of these embodiments, the extracellular vesicles are exposed to low ionic strength buffer causing them to burst allowing loading of an immunomodulating component. In some alternative embodiments, controlled dialysis against a hypotonic solution is used to swell the extracellular vesicle and to create pores in the extracellular vesicle membrane. The extracellular vesicle is subsequently exposed to conditions that allow resealing of the membrane.

In some embodiments, the immunomodulating component is introduced to the extracellular vesicle by detergent treatment. In certain embodiments, extracellular vesicles are treated with a mild detergent which transiently compromises the extracellular vesicle membrane by creating pores allowing loading of an immunomodulating component. After extracellular vesicles are loaded, the detergent is washed away thereby resealing the membrane.

In some embodiments, the immunomodulating component is introduced to the extracellular vesicle by receptor mediated endocytosis. In certain embodiments, extracellular vesicles have a surface receptor which upon binding of the immunomodulating component induces internalization of the receptor and the associated immunomodulating component.

In some embodiments, the immunomodulating component is introduced to the extracellular vesicle by mechanical firing. In certain embodiments, extracellular vesicles can be bombarded with an immunomodulating component attached to a heavy or charged particle such as gold microcarriers. In some of these embodiments, the particle can be mechanically or electrically accelerated such that it traverses the extracellular vesicle membrane.

In some embodiments, the immunomodulating component is introduced to the extracellular vesicle by filtration. In certain embodiments, the extracellular vesicles and the immunomodulating component can be forced through a filter of pore size smaller than the extracellular vesicle causing transient disruption of the extracellular vesicle membrane and allowing the immunomodulating component to enter the extracellular vesicle.

In some embodiments, extracellular vesicles are subjected to several freeze thaw cycles, resulting in extracellular vesicle membrane disruption allowing loading of an immunomodulating component.

Methods of Isolating the Extracellular Vesicles

The extracellular vesicles can be isolated from the producer cells. In certain embodiments, the extracellular vesicle is released by the producer cell into the cell culture medium. It is contemplated that all known manners of isolation of extracellular vesicles are deemed suitable for use herein. For example, physical properties of extracellular vesicles can be employed to separate them from a medium or other source material, including separation on the basis of electrical charge (e.g., electrophoretic separation), size (e.g., filtration, molecular sieving, etc.), density (e.g., regular or gradient centrifugation), Svedberg constant (e.g., sedimentation with or without external force, etc.). Alternatively, or additionally, isolation can be based on one or more biological properties, and include methods that can employ surface markers (e.g., for precipitation, reversible binding to solid phase, FACS separation, specific ligand binding, non-specific ligand binding, affinity purification etc.).

Isolation and enrichment can be done in a general and non-selective manner, typically including serial centrifugation. Alternatively, isolation and enrichment can be done in a more specific and selective manner, such as using extracellular vesicle or producer cell-specific surface markers. For example, specific surface markers can be used in immunoprecipitation, FACS sorting, affinity purification, and magnetic separation with bead-bound ligands.

In some embodiments, size exclusion chromatography can be utilized to isolate the extracellular vesicles. Size exclusion chromatography techniques are known in the art. Exemplary, non-limiting techniques are provided herein. In some embodiments, a void volume fraction is isolated and comprises the extracellular vesicles of interest. Further, in some embodiments, the extracellular vesicles can be further isolated after chromatographic separation by centrifugation techniques (of one or more chromatography fractions), as is generally known in the art. In some embodiments, for example, density gradient centrifugation can be utilized to further isolate the extracellular vesicles. In certain embodiments, it can be desirable to further separate the producer cell-derived extracellular vesicles from extracellular vesicles of other origin. For example, the producer cell-derived extracellular vesicles can be separated from non-producer cell-derived extracellular vesicles by immunosorbent capture using an antigen antibody specific for the producer cell.

In some embodiments, the isolation of extracellular vesicles can involve combinations of methods that include, but are not limited to, differential centrifugation, size-based membrane filtration, immunoprecipitation, FACS sorting, and magnetic separation.

Methods of Measuring the Size of Extracellular Vesicles

In some embodiments, the methods described herein comprise measuring the size of extracellular vesicles and/or populations of extracellular vesicles. Generally, extracellular vesicle size is measured as the longest measurable dimension. Generally, the longest measurable dimension of an extracellular vesicle is also referred to as its diameter.

Extracellular vesicle size can be measured using dynamic light scattering (DLS) and/or multiangle light scattering (MALS). Methods of using DLS and/or MALS to measure the size of extracellular vesicles are known to those of skill in the art, and include the nanoparticle tracking assay (NTA, e.g., using a Malvem NanoSight NS300 nanoparticle tracking device). In a specific embodiment, the extracellular vesicle size is determined using a Malvem NanoSight NS300. In some embodiments, the extracellular vesicles described herein have a longest dimension of about 20-300 nm as measured by NTA (e.g., using a Malvem NanoSight NS300). In other embodiments, the extracellular vesicles described herein have a longest dimension of about 40-200 nm as measured by NTA (e.g., using a Malvem NanoSight NS300). In other embodiments, the extracellular vesicle populations described herein comprise a population, wherein 90% of the extracellular vesicles have a longest dimension of about 20-300 nm as measured by NTA (e.g., using a Malvem NanoSight NS300). In other embodiments, the extracellular vesicle populations described herein comprise a population, wherein 95% of the extracellular vesicles have a longest dimension of about 20-300 nm as measured by NTA (e.g., using a Malvem NanoSight NS300). In other embodiments, the extracellular vesicle populations described herein comprise a population, wherein 99% of the extracellular vesicles have a longest dimension of about 20-300 nm as measured by NTA (e.g., using a Malvem NanoSight NS300). In other embodiments, the extracellular vesicle populations described herein comprise a population, wherein 90% of the extracellular vesicles have a longest dimension of about 40-200 nm as measured by NTA (e.g., using a Malvem NanoSight NS300). In other embodiments, the extracellular vesicle populations described herein comprise a population, wherein 95% of the extracellular vesicles have a longest dimension of about 40-200 nm as measured by NTA (e.g., using a Malvem NanoSight NS300). In other embodiments, the extracellular vesicle populations described herein comprise a population, wherein 99% of the extracellular vesicles have a longest dimension of about 40-200 nm as measured by NTA (e.g., using a Malvem NanoSight NS300).

Extracellular vesicle size can be measured using tunable resistive pulse sensing (TRPS). In a specific embodiment, extracellular vesicle size as measured by TRPS is determined using an iZON qNANO Gold. In some embodiments, the extracellular vesicles described herein have a longest dimension of about 20-300 nm as measured by TRPS (e.g., using an iZON qNano Gold). In other embodiments, the extracellular vesicles described herein have a longest dimension of about 40-200 nm as measured by TRPS (e.g., an iZON qNano Gold). In other embodiments, the extracellular vesicle populations described herein comprise a population, wherein 90% of the extracellular vesicles have a longest dimension of about 20-300 nm as measured by TRPS (e.g., using an iZON qNano Gold). In other embodiments, the extracellular vesicle populations described herein comprise a population, wherein 95% of the extracellular vesicles have a longest dimension of about 20-300 nm as measured by TRPS (e.g., using an iZON qNano Gold). In other embodiments, the extracellular vesicle populations described herein comprise a population, wherein 99% of the extracellular vesicles have a longest dimension of about 20-300 nm as measured by TRPS (e.g., using an iZON qNano Gold). In other embodiments, the extracellular vesicle populations described herein comprise a population, wherein 90% of the extracellular vesicles have a longest dimension of about 40-200 nm as measured by TRPS (e.g., using an iZON qNano Gold). In other embodiments, the extracellular vesicle populations described herein comprise a population, wherein 95% of the extracellular vesicles have a longest dimension of about 40-200 nm as measured by TRPS (e.g., using an iZON qNano Gold). In other embodiments, the extracellular vesicle populations described herein comprise a population, wherein 99% of the extracellular vesicles have a longest dimension of about 40-200 nm as measured by TRPS (e.g., using an iZON qNano Gold).

Extracellular vesicles size can be measured using electron microscopy. In some embodiments, the method of electron microscopy used to measure extracellular vesicle size is transmission electron microscopy. In a specific embodiment, the transmission electron microscope used to measure extracellular vesicle size is a Tecnai™ $G^2$ Spirit BioTWIN. Methods of measuring extracellular vesicle size using an electron microscope are well-known to those of skill in the art, and any such method can be appropriate for measuring extracellular vesicle size. In some embodiments, the extracellular vesicles described herein have a longest dimension of about 20-300 nm as measured by a scanning electron microscope (e.g., a Tecnai™ $G^2$ Spirit BioTWIN scanning electron microscope). In other embodiments, the extracellular vesicles described herein have a longest dimension of about 40-200 nm as measured by a scanning electron microscope (e.g., a Tecnai™ $G^2$ Spirit BioTWIN scanning electron microscope). In other embodiments, the extracellular vesicle populations described herein comprise a population, wherein 90% of the extracellular vesicles have a longest dimension of about 20-300 nm as measured by a scanning electron microscope (e.g., a Tecnai™ G² Spirit BioTWIN scanning electron microscope). In other embodiments, the extracellular vesicle populations described herein comprise a population, wherein 95% of the extracellular vesicles have a longest dimension of about 20-300 nm as measured by a scanning electron microscope (e.g., a Tecnai™ G² Spirit BioTWIN scanning electron microscope). In other embodiments, the extracellular vesicle populations described herein comprise a population, wherein 99% of the extracellular vesicles have a longest dimension of about 20-300 nm as measured by a scanning electron microscope (e.g., a Tecnai™ G² Spirit BioTWIN scanning electron microscope). In other embodiments, the extracellular vesicle populations described herein comprise a population wherein 90% of the extracellular vesicles have a longest dimension of about 40-200 nm as measured by a scanning electron microscope (e.g., a Tecnai™ G² Spirit BioTWIN scanning electron microscope). In other embodiments, the extracellular vesicle populations described herein comprise a population wherein 95% of the extracellular vesicles have a longest dimension of about 40-200 nm as measured by a scanning electron microscope (e.g., a Tecnai™ G² Spirit BioTWIN scanning electron microscope). In other embodiments, the extracellular vesicle populations described herein comprise a population wherein 99% of the extracellular vesicles have a longest dimension of about 40-200 nm as measured by a scanning electron microscope (e.g., a Tecnai™ G² Spirit BioTWIN scanning electron microscope).

Methods of Treating Cancer, GvHD, and Autoimmune Disease

Also, provided herein are methods of treating cancer, graft-versus-host-disease (GvHD) and autoimmune disease in a subject.

In various embodiments, the composition is administered to a subject with cancer. In some of these embodiments, the composition can up-regulate an immune response and enhance the tumor targeting of the subject's immune system. In some embodiments, the cancer being treated is characterized by infiltration of leukocytes (T-cells, B-cells, macrophages, dendritic cells, monocytes) into the tumor microenvironment, or so-called "hot tumors" or "inflammatory tumors". In some embodiments, the cancer being treated is characterized by low levels or undetectable levels of leukocyte infiltration into the tumor microenvironment, or so-called "cold tumors" or "non-inflammatory tumors". In some embodiments, the composition is administered in an amount and for a time sufficient to convert a "cold tumor" into a "hot tumor", i.e., said administering results in the infiltration of leukocytes (such as T-cells) into the tumor microenvironment.

In some embodiments, the composition comprising an extracellular vesicle and an immunomodulating component is administered to a subject as a cancer vaccine. In some of these embodiments, the composition is administered to a subject as a personalized cancer vaccine. In some embodiments, the immunomodulating component is a tumor antigen or a peptide derived from a tumor antigen. Examples of suitable tumor antigens include: alpha-fetoprotein (AFP), carcinoembryonic antigen (CEA), epithelial tumor antigen (ETA), mucin 1 (MUC1), Tn-MUC1, mucin 16 (MUC16), tyrosinase, melanoma-associated antigen (MAGE), tumor protein p53 (p53), CD4, CD8, CD45, CD80, CD86, programmed death ligand 1 (PD-L1), programmed death ligand 2 (PD-L2), NY-ESO-1, PSMA, TAG-72, HER2, GD2, cMET, EGFR, Mesothelin, VEGFR, alpha-folate receptor, CE7R, IL-3, Cancer-testis antigen, MART-1 gp100, and TNF-related apoptosis-inducing ligand. In certain embodiments, the tumor antigen is derived from a reference genome sequence. In certain embodiments, the tumor antigen is derived a genome sequence of the subject receiving the composition.

The cancers that can be treated with the composition include but are not limited to the cancers listed in Table 5.

In certain embodiments, the composition is administered to a subject with graft-versus-host disease (GvHD). In some of these embodiments, the composition can down-regulate an immune response and alleviate the symptoms of GvHD. In some specific embodiments, the composition alleviates the symptoms of GvHD through activation of apoptotic signaling. In certain embodiments, the composition for treating GvHD comprises Fas ligand (FasL). In some of these embodiments, the FasL is expressed on the surface of the extracellular vesicle.

In various embodiments, the composition is administered to a subject with an autoimmune disease. In some of these embodiments, the composition can down-regulate an immune response and suppress the immune activity of the subject.

The autoimmune diseases include but are not limited to multiple sclerosis, peripheral neuritis, Sjogren's syndrome, rheumatoid arthritis, alopecia, autoimmune pancreatitis, Behcet's disease, Bullous pemphigoid, Celiac disease, Devic's disease (neuromyelitis optica), Glomerulonephritis, IgA nephropathy, assorted vasculitides, scleroderma, diabetes, arteritis, vitiligo, ulcerative colitis, irritable bowel syndrome, psoriasis, uveitis, and systemic lupus erythematosus.

In some embodiments, the composition is administered intravenously to the circulatory system of the subject. In some embodiments, the composition is infused in suitable liquid and administered into a vein of the subject.

In some embodiments, the composition is administered intra-arterialy to the circulatory system of the subject. In some embodiments, the composition is infused in suitable liquid and administered into an artery of the subject.

In some embodiments, the composition is administered to the subject by intrathecal administration. In some embodiments, the composition is administered via an injection into the spinal canal, or into the subarachnoid space so that it reaches the cerebrospinal fluid (CSF).

In some embodiments, the composition is administered intratumorally into one or more tumors of the subject.

In some embodiments, the composition is administered to the subject by intranasal administration. In some embodiments, the composition can be insufflated through the nose in a form of either topical administration or systemic administration. In certain embodiments, the composition is administered as nasal spray.

In some embodiments, the composition is administered to the subject by intraperitoneal administration. In some embodiments, the composition is infused in suitable liquid and injected into the peritoneum of the subject. In some embodiments, said intraperitoneal administration results in distribution of the composition (e.g., the extracellular vesicles in the composition) to the lymphatics. In some embodiments, said intraperitoneal administration results in distribution of the composition (e.g., the extracellular vesicles in the composition) to the thymus, spleen, and/or bone marrow. In some embodiments, said intraperitoneal administration results in distribution of the composition (e.g., the extracellular vesicles in the composition) to one or more lymph nodes. In some embodiments, said intraperitoneal administration results in distribution of the composition (e.g., the extracellular vesicles in the composition) to one or more of the cervical lymph node, the inguinal lymph node, the mediastinal lymph node, or the sternal lymph node. In some embodiments, said intraperitoneal administration results in distribution of the composition (e.g., the extracellular vesicles in the composition) to the pancreas.

In some embodiments, the composition is administered to the subject by periocular administration. In some embodiments, the composition is injected into the periocular tissues. Periocular drug administration includes the routes of subconjunctival, anterior sub-Tenon's, posterior sub-Tenon's, and retrobulbar administration.

In some embodiments, the composition is administered into the same subject by multiple routes of administration. In some embodiments, said multiple routes of administration comprise intravenous administration, intra-arterial administration, intrathecal administration, intranasal administration, intratumoral administration, intraperitoneal administration, and/or periocular administration. In a preferred embodiment, said multiple routes of administration comprise intravenous administration and intraperitoneal administration.

In certain embodiments, the dosage of the extracellular vesicles is between 1 ng to 10 ng, 10 ng to 100 ng, 100 ng to 1 μg, 1 μg to 5 μg, 5 μg to 10 μg, 10 μg to 50 μg, 50 μg to 75 μg, 75 μg to 100 μg, 100 μg to 150 μg, 150 μg to 200 μg, 200 μg to 300 μg, 300 μg to 500 μg, 500 μg to 1 mg, or 1 mg to 10 mg.

The compositions can be administered once to the subject. Alternatively, multiple administrations can be performed over a period of time. For example, two, three, four, five, or more administrations can be given to the subject. In some embodiments, administrations can be given as needed, e.g., for as long as symptoms associated with the disease, disorder or condition persists. In some embodiments, repeated administrations can be indicated for the remainder of the subject's life. Treatment periods can vary and can be, e.g., no longer than a year, six months, three months, two months, one month, two weeks, one week, three days, two days, or no longer than one day.

In certain embodiments, doses of extracellular vesicles are administered at intervals such as once daily, every other day, once weekly, twice weekly, once monthly or twice monthly.

In some embodiments, the pharmaceutical composition is administered at a frequency sufficient to effectively increase the concentration of the immunomodulating component in the target cell or tissue above a level that is associated with a symptom of the disease, disorder or condition.

In some embodiments, the compositions are administered at least twice over a treatment period such that the disease, disorder or condition is treated, or a symptom thereof is ameliorated. In some embodiments, the compositions are administered at least twice over a treatment period such that the disease, disorder or condition is treated or a symptom thereof is prevented. In some embodiments, the pharmaceutical composition is administered a sufficient number of times over a treatment period such that a sufficient amount of immunomodulating component is delivered to the target cell or tissue during the treatment period. In some embodiments, the pharmaceutical composition is administered a sufficient number of times over a treatment period such that a sufficient amount of immunomodulating component is delivered to the target cell or tissue during the treatment period such that one or more symptoms of the disease, disorder or condition is prevented, decreased, ameliorated or delayed. In some embodiments, increasing the immunomodulating component concentration in the target cell or tissue includes increasing the peak concentration, while in others it includes increasing the average concentration. In some embodiments, a substantial increase during the treatment period can be determined by comparing a pretreatment or post-treatment period in the subject, or by comparing measurements made in a population undergoing treatment with a matched, untreated control population.

In some embodiments, the pharmaceutical composition is administered a sufficient number of times per treatment period such that the concentration of immunomodulating component in the target cell or tissue is increased for at least about one week, two weeks, three weeks, four weeks, one month, two months, three months, four months, five months, six months or greater than six months. In some embodiments, the pharmaceutical composition is administered a sufficient number of times per treatment period such that the concentration of immunomodulating component in the target cell or tissue is increased for a period of time at least as long as the treatment period.

In some embodiments, the time interval between repeated administrations within a treatment period is no longer than the period in which the number of extracellular vesicles in circulation is reduced to less than about 5%, 10%, 15%, 20%, 25%, 30%, 35%, 40%, 45%, 50%, 55%, 60%, 65%, 70%, 75%, 80%, 85%, 90%, or 95% of the number of extracellular vesicles present in the administered pharmaceutical composition.

In some embodiments, the methods further comprise one or multiple doses of non-therapeutic extracellular vesicles prior to the injection of a suitable therapeutic dose of extracellular vesicles harboring a therapeutic agent. In certain embodiments, the non-therapeutic extracellular vesicle is administered separately to and at a different dosage than the therapeutic extracellular vesicles. In certain embodiments, the dosage of the non-therapeutic extracellular vesicle is greater than the dosage of the therapeutic extracellular vesicle. In certain other embodiments, the dosage of the non-therapeutic extracellular vesicle is smaller than the dosage of the therapeutic extracellular vesicle. In certain embodiments, the dosage of the non-therapeutic extracellular vesicle is the same as the therapeutic extracellular vesicle. In various embodiments, the methods of non-therapeutic extracellular vesicles prior to injection of a suitable dose of therapeutic extracellular vesicles reduce the update of the therapeutic extracellular vesicles in the liver, lung, and/or spleen.

An effective amount of the composition is provided based, at least in part, on the target tissue, target cell type, means of administration, physical characteristics of the extracellular vesicle (e.g., size, and in some cases the extent of molecules to be delivered) and other determinants. In general, an effective amount of the composition provides efficient cellular response of the target cell. Increased efficiency can be demonstrated by increased cell transfection (i.e., the percentage of cells transfected with the extracellular vesicle constituents), increased cellular response or reduced innate immune response of the host subject.

The dosing and frequency of the administration of the extracellular vesicles and pharmaceutical compositions thereof can be determined, e.g., by the attending physician based on various factors such as the severity of disease, the patient's age, sex and diet, the severity of any inflammation, time of administration and other clinical factors. In an example, an intravenous administration is initiated at a dose which is minimally effective, and the dose is increased over a pre-selected time course until a positive effect is observed. Subsequently, incremental increases in dosage are made limiting to levels that produce a corresponding increase in effect while taking into account any adverse effects that can appear.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W.H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 21th Edition (Easton, Pa.: Mack Publishing Company, 2005); Carey and Sundberg Advanced Organic Chemistry $3^{rd}$ Ed. (Plenum Press) Vols A and B (1992).

Methods

Exosome Purification

Conditioned culture media was collected and centrifuged at 300-800×g for 5 minutes at room temperature to remove cells and large debris. Media supernatant was then supplemented with 1000 U/L Benzonase® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and any residual media was aspirated from the bottom of the tube. The pellet was resuspended in 200-1000 μL PBS (—Ca—Mg).

To further enrich exosome populations, the pellet was processed via density gradient purification (sucrose or Optiprep™). For sucrose gradient purification, the exosome pellet was layered on top of a sucrose gradient as defined in Table 6 below:

TABLE 6

| Sucrose Density Gradient: | | |
|---|---|---|
| Working Percentage (%) | 65% Stock Vol. (mL) | Milli-Q Vol. (mL) |
| 50 | 3.85 | 1.15 |
| 40 | 3.08 | 1.92 |

TABLE 6-continued

| Sucrose Density Gradient: | | |
|---|---|---|
| Working Percentage (%) | 65% Stock Vol. (mL) | Milli-Q Vol. (mL) |
| 25 | 1.92 | 3.08 |
| 10 | 0.46 | 2.54 |

The gradient was spun at 200,000×g for 16 hours at 4° C. in a 12 mL Ultra-Clear (344059) tube placed in a SW 41 Ti rotor to separate the exosome fraction.

The exosome layer was gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet was resuspended in a minimal volume of PBS (~200 μL) and stored at 4° C.

For Optiprep™ gradient, a 3-tier sterile gradient was prepared with equal volumes of 10%, 30%, and 45% Optiprep in a 12 mL Ultra-Clear (344059) tube for a SW 41 Ti rotor. The pellet was added to the Optiprep™ gradient and ultracentrifuged at 200,000×g for 16 hours at 4° C. to separate the exosome fraction. The exosome layer was then gently collected from the top ~3 mL of the tube.

The exosome fraction was diluted in ~32 mL PBS in a 38.5 mL Ultra-Clear (344058) tube and ultracentrifuged at 133,900×g for 3 hours at 4° C. to pellet the purified exosomes. The pelleted exosomes were then resuspended in a minimal volume of PBS (~200 μL) and store at 4° C.

Example 1: Engineering Exosomes to Display an Immune Checkpoint Regulator Antibody A human embryonic kidney (HEK) cell line is grown to high density, and the resulting exosomes are isolated from culture medium according to methods known to those of skill in the art (e.g., the methods described herein). Exosomes engineered with cytotoxic T-lymphocyte-associated protein 4 (CTLA-4) antibody are prepared by chemical conjugation according to the techniques known in the art. The exosomes modified with CTLA4 antibody are selected by flow cytometry. At the same time, unmodified exosomes are isolated according to the same standard methods.

The two exosome populations are labeled with a radioactive tracer, and 150 μg of each preparation is injected into live mice (e.g. mouse model of melanoma). The mice receiving either the exosomes displaying the CTLA-4 antibody or the unmodified exosomes are monitored continuously for 30 minutes, and again at four hour intervals by whole-animal PET/CT. Whole-animal imaging allows for real-time, high resolution tracking of labeled exosomes to various tissues.

150 μg of each exosome population are injected into two mouse cohorts intravenously without first labeling with a radioactive tracer. The mice are euthanized five weeks post-administration. The tumor samples are collected and analyzed by immunohistochemistry and real-time PCR.

Example 2: Engineering Exosomes to Display Fas Ligand

Human antigen-presenting cells are transfected with a plasmid encoding a puromycin-resistant selectable marker and Fas ligand. Transfected cells are treated with puromycin, and resistant colonies are selected and assayed for surface expression of Fas ligand by flow cytometry. Stable Fas ligand-expressing cells are grown to high concentration, and the resulting exosomes are isolated from culture medium according to methods known to those of skill in the art (e.g., the methods described herein). At the same time, untransfected producer cells are cultured and the resulting exosomes are isolated according to the same standard methods.

The two exosome populations are labeled with a radioactive tracer, and 150 µg of each preparation is injected into live mice (e.g. mouse model of GvHD). The mice receiving either the exosomes derived from unmodified cells or the exosomes derived from Fas ligand-expressing cells are monitored continuously for 30 minutes, and again at four hour intervals by whole-animal PET/CT. Whole-animal imaging allows for real-time, high resolution tracking of labeled exosomes to various tissues.

Purified exosome populations from unmodified producer cells and producer cells engineered to express Fas ligand are purified according to the methods described herein. 150 µg of each exosome population are injected into two mouse cohorts without first labeling with a radioactive tracer. Animals of both cohorts are euthanized three to five weeks post-administration for immunohistochemical analysis and real-time PCR.

Example 3: Lymphatic Uptake of Exosomes after Intraperitoneal Administration To determine the biodistribution of purified exosomes in vivo, the following experiment was performed:

Conditioned culture media from 293T cells was collected and centrifuged at 300-800×g for 5 minutes at room temperature to remove cells and large debris. Media supernatant was then supplemented with 1000 U/L Benzonase® and incubated at 37° C. for 1 hour in a water bath. Supernatant was collected and centrifuged at 16,000×g for 30 minutes at 4° C. to remove residual cell debris and other large contaminants. Supernatant was then ultracentrifuged at 133,900×g for 3 hours at 4° C. to pellet the exosomes. Supernatant was discarded and residual media was aspirated from the bottom of the tube. The pellet was then resuspended in 200-1000 µL PBS (—Ca—Mg).

To further enrich exosome populations, the pellet was processed via sucrose density gradient purification as defined in Table 6.

The gradient was spun at 200,000×g for 16 hours at 4° C. in a 12 mL Ultra-Clear (344059) tube placed in a SW 41 Ti rotor to separate the exosome fraction.

The exosome layer was gently removed from the top layer and diluted in ~32.5 mL PBS in a 38.5 mL Ultra-Clear (344058) tube and ultracentrifuged again at 133,900×g for 3 hours at 4° C. to pellet the purified exosomes. The resulting pellet was resuspended in a minimal volume of PBS (~200 µL) and stored at 4° C.

To radiolabel the purified exosomes for in vivo imaging, $1\times10^{11}$ purified exosomes in 100 µL were diluted with HEPES (200 µL, 0.1M, pH 8.5) and conjugated to p-SCN-Bn-DFO (5 µg) for one hour at 37° C. followed by overnight incubation at 4° C., separately. DFO-exosomes were incubated with 89Zr (7.5 mCi) diluted in HEPES (100 µL, 1M, pH 7.3) for one hour at 37° C. and purified on a qEv column. This resulted in a total yield (0.4 mCi of 89Zr-DFO-exosomes in up to 0.8 mL PBS) at 100 µCi/$1\times10^{10}$ exosomes. Quality control (HPLC) was performed prior to release to ensure >95% RCP.

In Vitro Stability

Exosomes (20 µCi/$2\times10^{10}$) were incubated at room temperature in:
a. Formulation buffer
b. Mouse serum (10% v/v exosome solution in serum, if possible)

2 hours after initiation of incubation solutions were injected into HPLC to determine stability of tracer.

In Vivo Imaging

Mice (SKH-1, n=8, age 5-8 weeks) were randomized into two groups, weighed and injected (with the second group injected immediately after the first group's dynamic scan is over) with $1\times10^{10}$/g exosomes to give a minimum radioactive dose of 100 µCi/mouse. Group 1 was injected intravenously (IV) while group 2 was injected intraperitoneally (IP).

Mice receive a whole-body PET/CT scan in a 4-mouse hotel using the following schedule: 1 h dynamic (5×60, 5×180, 8×300 seconds) and static imaging at 4 h (20 min), 24 h (Thursday, 20 min) and 48 h (Friday, 30 min). Each imaging time point was followed by CT for anatomical reference.

After the last imaging time point, mice were euthanized and the following organs were collected, weighed and counted in the gamma counter: blood, lung (one), liver (lobe), spleen, pancreas, kidney (one), liver, colon and additional organs of high uptake.

Organs were allowed to decay for 2-3 days if counts were extremely high and counted again.

TABLE 7

| Group (mouse # and type) | Tracer | Injection route | Imaging | Imaging time points |
|---|---|---|---|---|
| 1 (n = 4, SKH-1) | 89Zr-DFO-exosomes (100 µCi, <200 µL) | IV | Whole body PET/CT using a 4 mouse hotel | 1 h dynamic followed by static at 4 h and 24 h (20 min) 48 h (30 min) |
| 2 (n = 4, SKH-1) | 89Zr-DFO-exosomes (100 µCi, <200 µL) | IP | Whole body PET/CT using a 4 mouse hotel | 1 h dynamic followed by static at 4 h and 24 h (20 min) 48 h (30 min) |

Results

Figure 2:
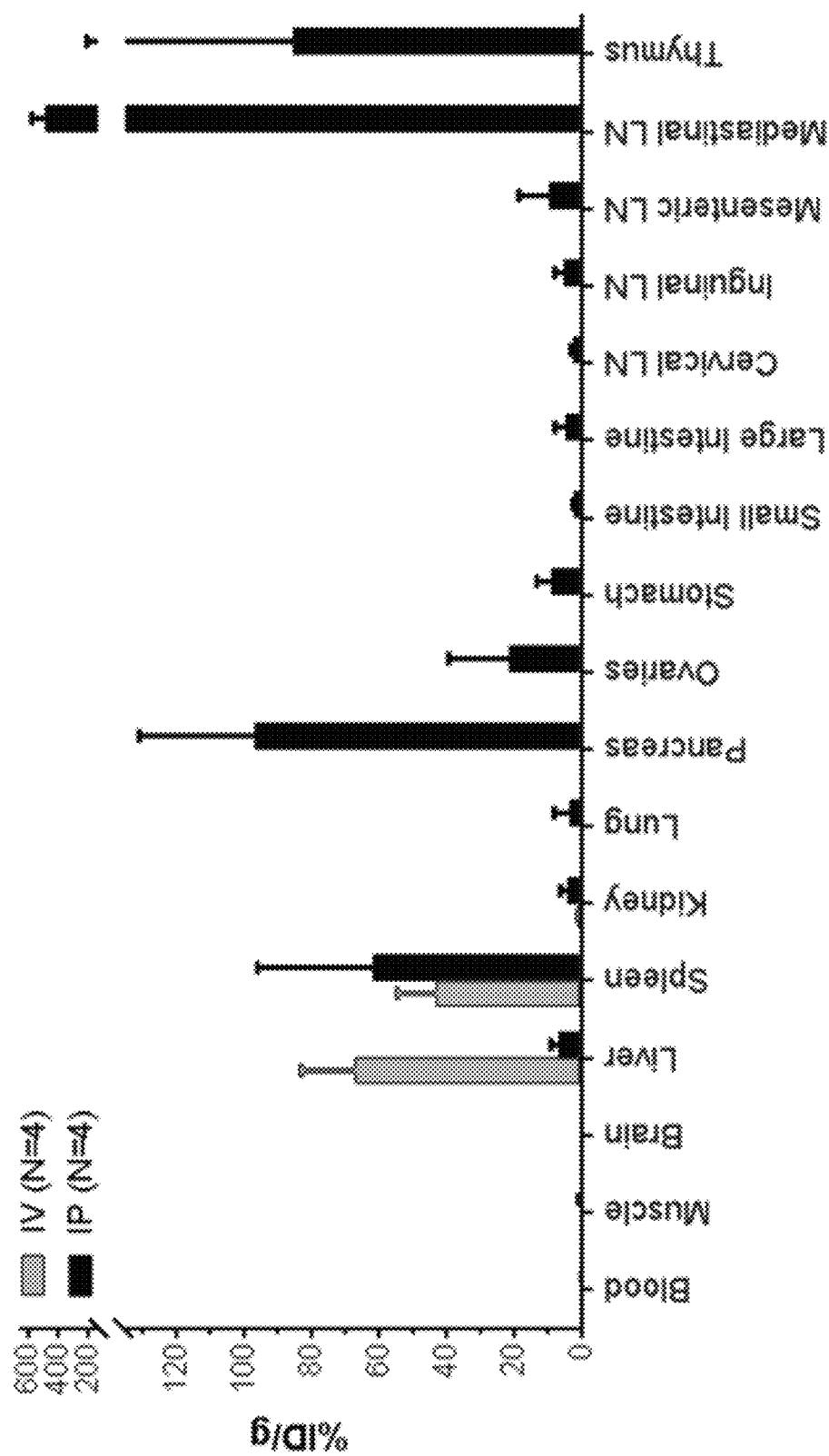
FIG. 2 is a quantitation of exosome distribution in different mouse tissues after intravenous and intraperitoneal administration of radiolabeled exosomes.

The two cohorts of treated mice were imaged 4 hours, 24 hours, and 48 hours after treatment. Whole body PET/CT imaging revealed robust delivery to the livers of all mice in group 1 treated IV (FIG. 1A), and a distinct non-overlapping distribution for mice in group 2 treated IP (FIG. 1B). Organs were dissected and analyzed by radiographic gamma counter, which revealed significant liver and spleen uptake in mice treated IV (FIG. 2). In contrast, for mice treated IP, uptake was primarily observed in the pancreas, spleen, thymus, and lymph nodes, with additional uptake in the liver and ovaries. These results demonstrate that different routes of administration result in substantially different biodistribution profiles. Importantly, IP administration led to significant uptake in the lymphatics, suggesting that IP administration can be a suitable route of administration to reach immune cells.

Example 4: B-Cell Activation by Engineered CD40L Exosomes

Figure 3A:
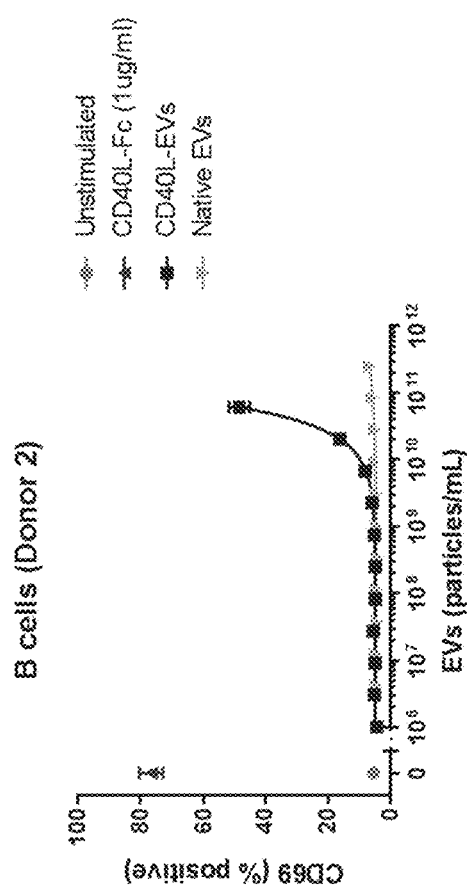
FIGS. 3A and 3B show the effects of B-cell activation in peripheral blood mononuclear cells (PBMCs) from two human donors after incubation with CD40L-expressing exosomes.
Figure 3B:
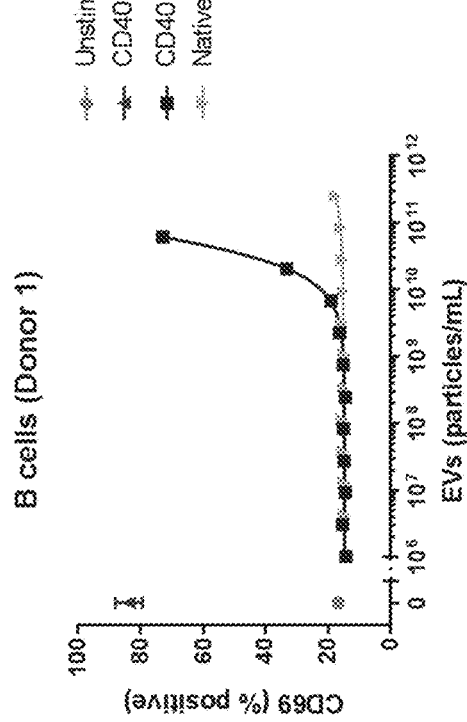

CD40L is a member of the tumor necrosis factor (TNF) superfamily primarily expressed on T-cells. The CD40L receptor, CD40, is expressed on antigen presenting cells including macrophages, dendritic cells and B-cells. Signaling through CD40 activates B-cells and induces an antigen-specific response. Activating the CD40 pathway therefore has implications in the development of anti-tumor immunity in a broad array of tumor types. To determine whether engineered exosomes could be generated to induce a specific immunological effect, exosomes were generated from HEK293SF cells transfected with a plasmid containing full-length human CD40L. Transfected cells were put under puromycin selection and resistant cell populations were grown to high density. The resulting exosomes were collected from the conditioned culture medium and purified over an Optiprep™ gradient as described above. Exosomes from unmodified HEK293SF cells were also isolated to be used as a control. Human peripheral blood mononuclear cells (PBMCs) were plated at 150,000 cells per well of a 96-well plate, and incubated with purified CD40L exosomes or native exosomes overnight at 37° C. One sample of PBMCs was incubated with 1 µg/mL of soluble recombinant CD40L-Fc as a positive control. As shown in FIGS. 3A and 3B, CD40L exosomes activated B-cells in a dose-dependent manner, as measured by CD69 expression in two different donor samples. Native exosomes failed to induce B-cell activation. Importantly, the level of B-cell activation by CD40L exosomes was comparable to the activation caused by the CD40L-Fc.

Figure 4B:
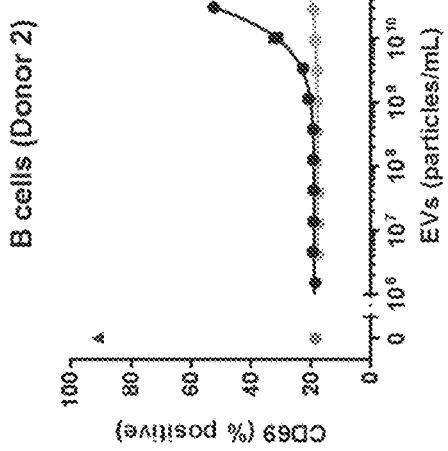
FIGS. 4A and 4B show the effects of B-cell activation of purified B-cells from two human donors after incubation with CD40L-expressing exosomes.
Figure 4A:
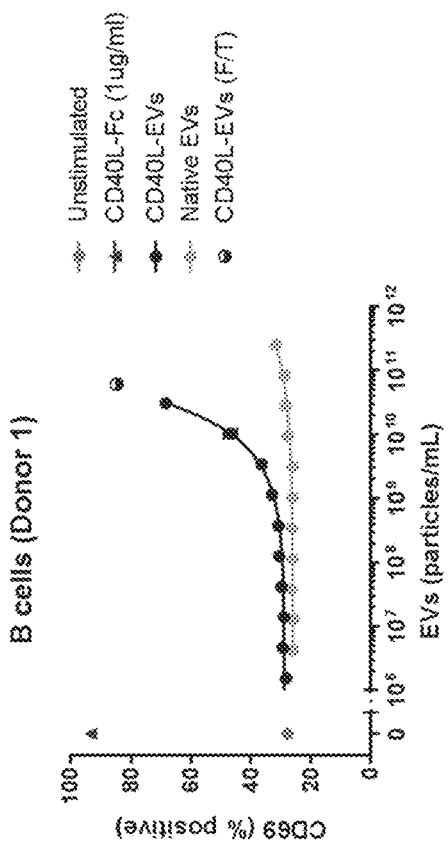

To determine whether the observed exosome-mediated B-cell activation was due to direct activation of B-cells or through trans-acting immune cells, a similar experiment was carried out using purified human B-cells. 50,000 purified human B-cells were plated in a 96-well plate and incubated with either CD40L exosomes, native exosomes, or CD40L-Fc. One sample of high concentration CD40L exosomes was put through a freeze-thaw cycle (CD40L-EVs [F/T]) and tested for B-cell activation as well. As shown in FIGS. 4A and 4B, CD40L exosomes activated purified B-cells from two donors to a similar extent as CD40L-Fc. Native exosomes failed to activate B-cells, while the CD40L exosome freeze-thaw samples successfully activated B-cells, indicating that the effect of CD40L exosomes is mediated directly through B-cells, and that the presence of CD40L is sufficient for B-cell activation. Additionally, the engineered exosomes remain stable and active for at least one freeze-thaw cycle.

Figure 5C:
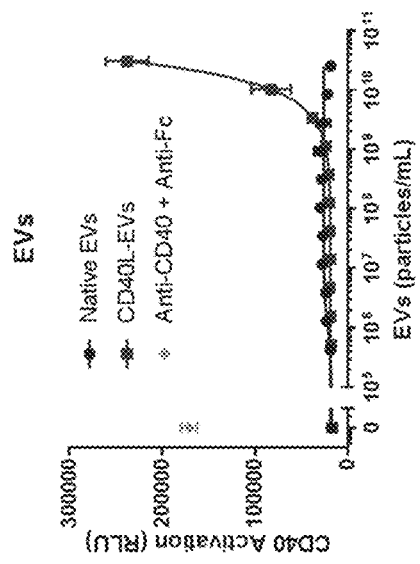
FIG. 5C shows the effects of CD40L-expressing exosomes on a CD40 reporter cell line.
Figure 5B:
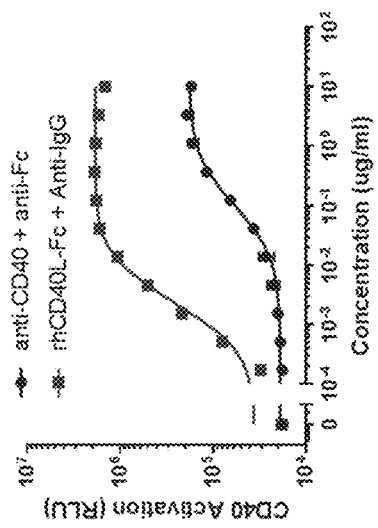
FIG. 5B shows the concentration-dependent activation of a CD40 reporter cell line treated with an anti-CD40 agonistic antibody or recombinant human CD40L.
Figure 5A:
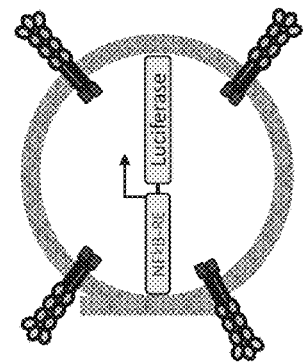
FIG. 5A is a schematic of a CD40 reporter cell line.

To further validate the CD40L exosomes, a reporter system was used to measure the activity of the engineered exosomes. Activation of CD40 pathway results in activation of NF-κB. Using a modified U2OS cell line engineered to overexpress CD40 on its surface and contain a luciferase reporter downstream of the NF-κB promoter (Promega Corporation), CD40 activation was confirmed by incubating the cells in the presence of an agonistic anti-CD40 antibody (BioLegend, Inc.) crosslinked with an anti-Fc antibody (Jackson ImmunoResearch, Inc.) or recombinant human CD40L (ACROBiosystems) cross-linked with an anti-IgG antibody (Jackson ImmunoResearch, Inc.) (FIGS. 5A and 5B). CD40L engineered exosomes were incubated with the engineered cells and resulted in a robust increase in luciferase activity comparable to the effects of anti-CD40+ anti-Fc. Importantly, the engineered exosomes did not require a cross-linking antibody, demonstrating that CD40L on the surface of exosomes can form functional CD40L trimers sufficient to activate CD40.

Example 5: T-Cell Activation by Engineered CD80 Exosomes

Figure 6A:
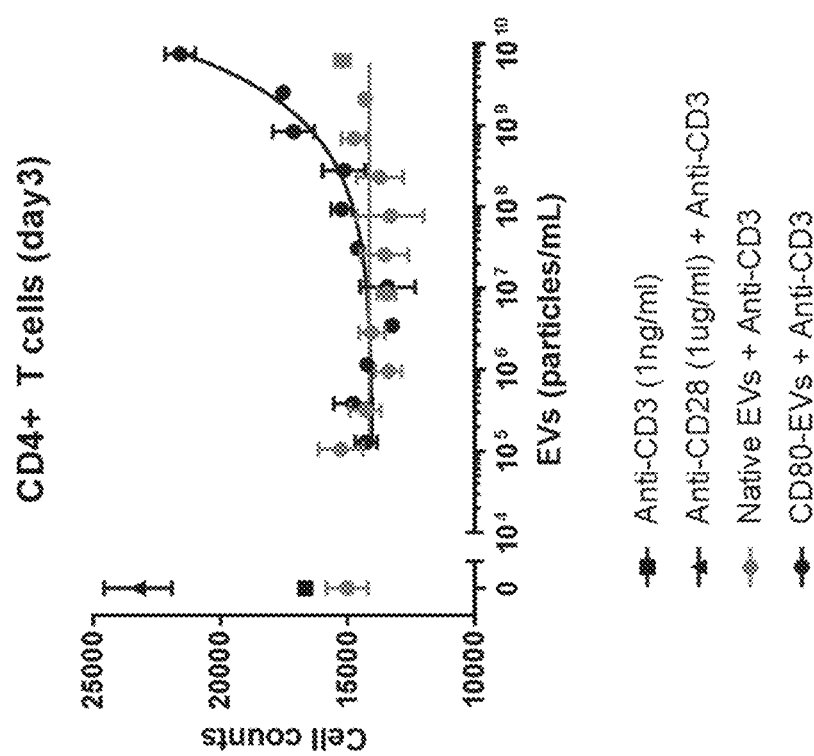
FIGS. 6A and 6B show the effects of T-cell activation in peripheral blood mononuclear cells (PBMCs) with CD80-expressing exosomes.
Figure 6B:
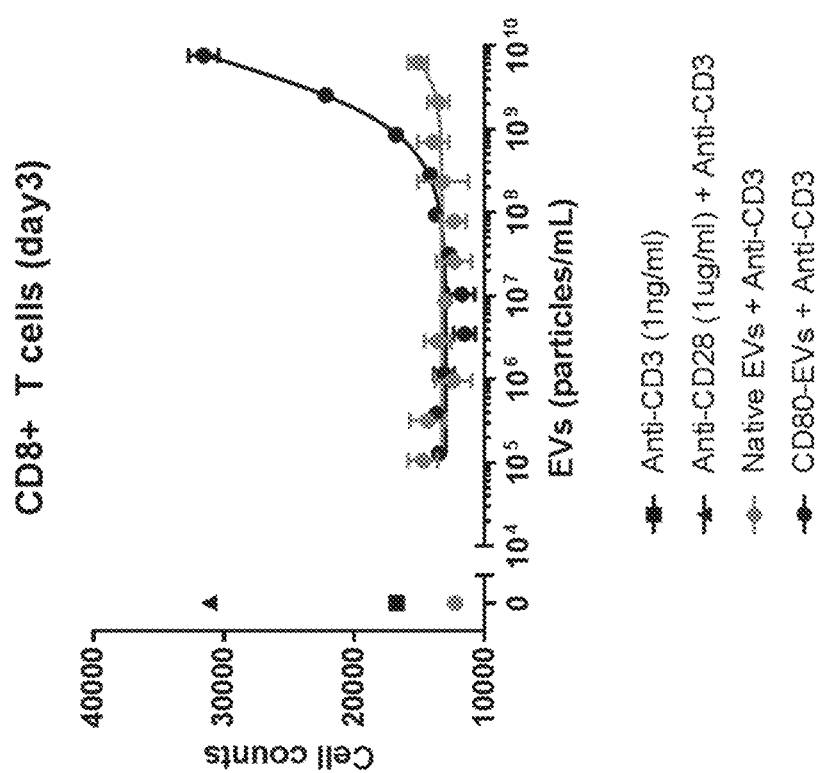

CD80 is expressed on antigen presenting cells and binds to CD28 and CTLA-4 on the surface of T-cells. Stimulation by CD80 (and CD86) through CD28 and CTLA-4 activates T-cells during the initiation of an immune response. To determine whether exosomes could be engineered to activate T-cells, CD80-containing exosomes were generated by transfection and selection of HEK293SF cells as described in Example 4. To validate the activity of CD80 exosomes, human PBMCs were plated at 150,000 cells per well of a 96-well plate, and incubated with (i) purified CD80 exosomes and anti-CD3 antibody, (ii) native exosomes and anti-CD3 antibody, (iii) anti-CD3 antibody alone, or (iv) a combination of anti-CD28 and anti-CD3 antibodies. The samples were incubated at 37° C. for three days and assayed for T-cell counts for both $CD4^+$ T-cells (FIG. 6A) and $CD8^+$ T-cells (FIG. 6B). CD80 exosomes activated T-cells in a dose-dependent manner and to an extent comparable to the positive control of CD3 and CD28 antibodies. In contrast, the native exosomes had no effect on T-cell proliferation.

Figure 7B:
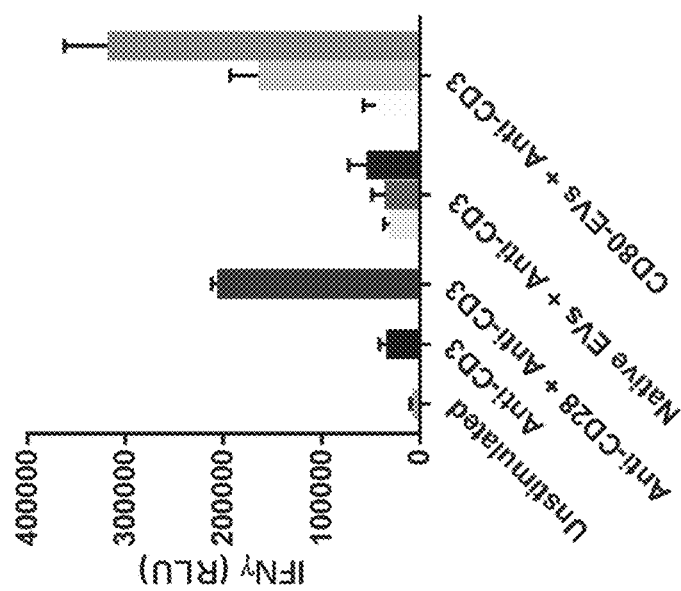
FIGS. 7A and 7B show the effects of CD80-expressing exosomes on IFNγ expression in human PBMCs.
Figure 7A:
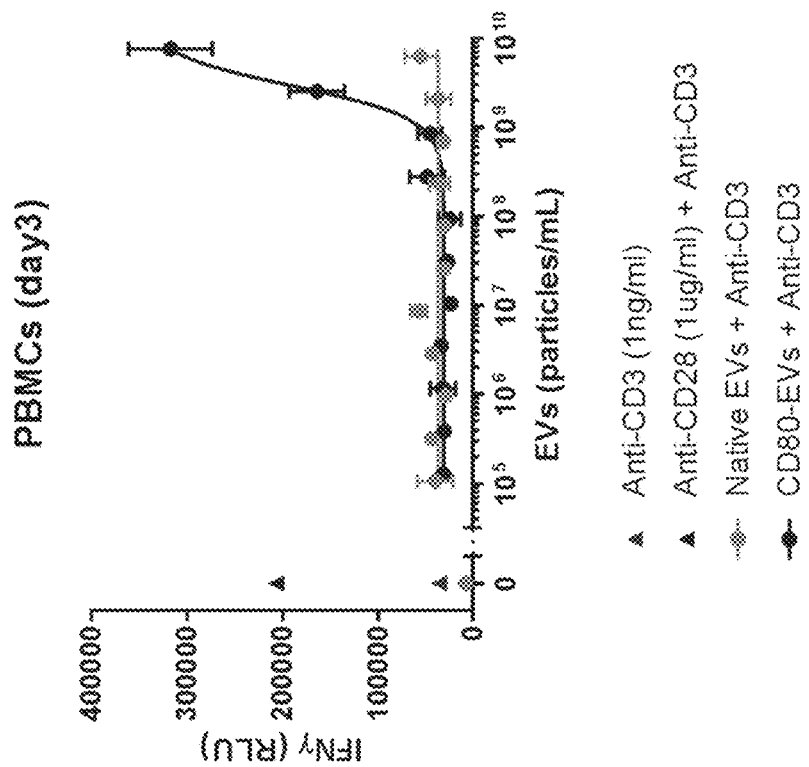

To confirm that CD80 exosomes induce a functional activation of T-cells, IFNγ levels were measured by AlphaLISA in PBMCs incubated with native exosomes and CD80 exosomes with additional anti-CD3 antibody. As shown in FIG. 7A, there was a dose-dependent increase in IFNγ levels for the CD80 exosomes but not for the native exosomes. As shown in FIG. 7B, the highest concentrations of CD80 exosomes resulted in greater IFNγ levels than any other condition, including the positive control (anti-CD28/ anti-CD3). These results demonstrate that exosomes can be engineered with specific activity that results in immune cell activation.

Figure 8A:
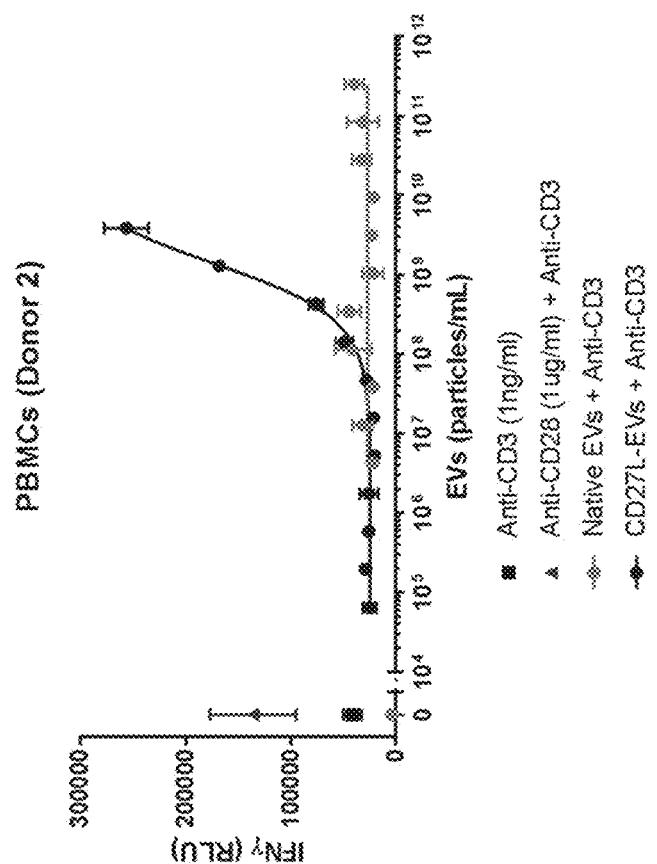
FIGS. 8A and 8B show the effects of CD27L-expressing exosomes on IFNγ expression in human PBMCs from two donors.
Figure 8B:
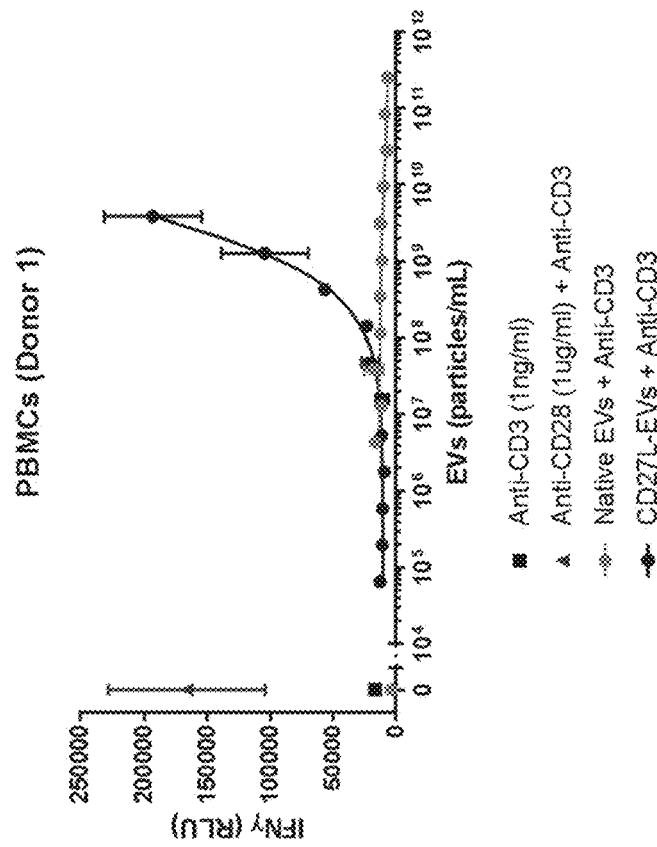
Figure 9A:
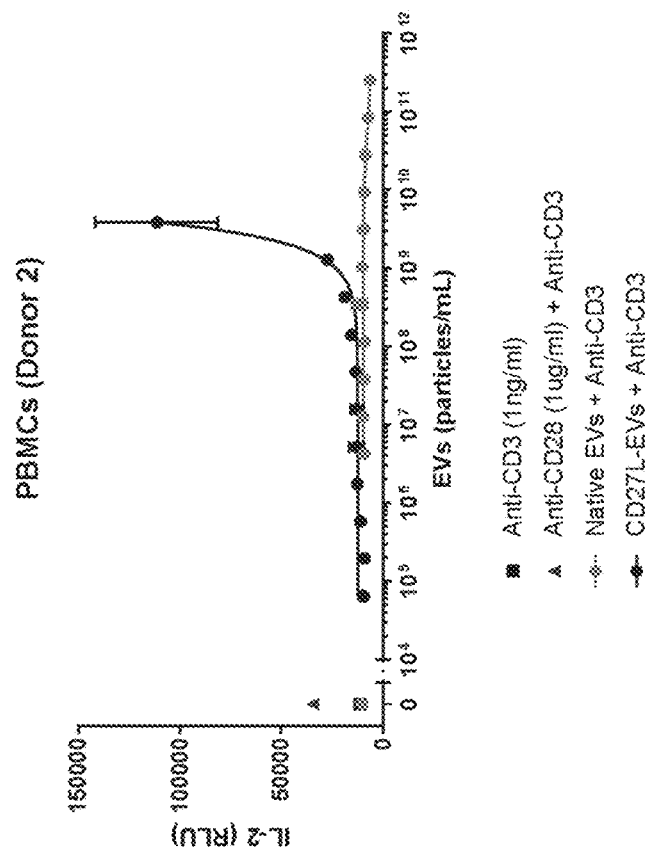
FIGS. 9A and 9B show the effects of CD27L-expressing exosomes on IL-2 expression in human PBMCs from two donors.
Figure 9B:
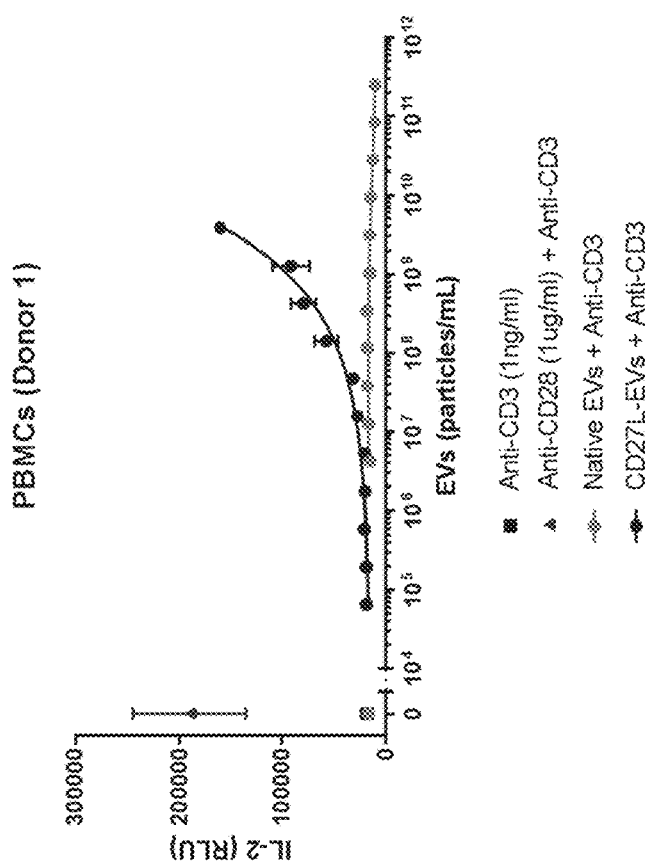
Figure 10A:
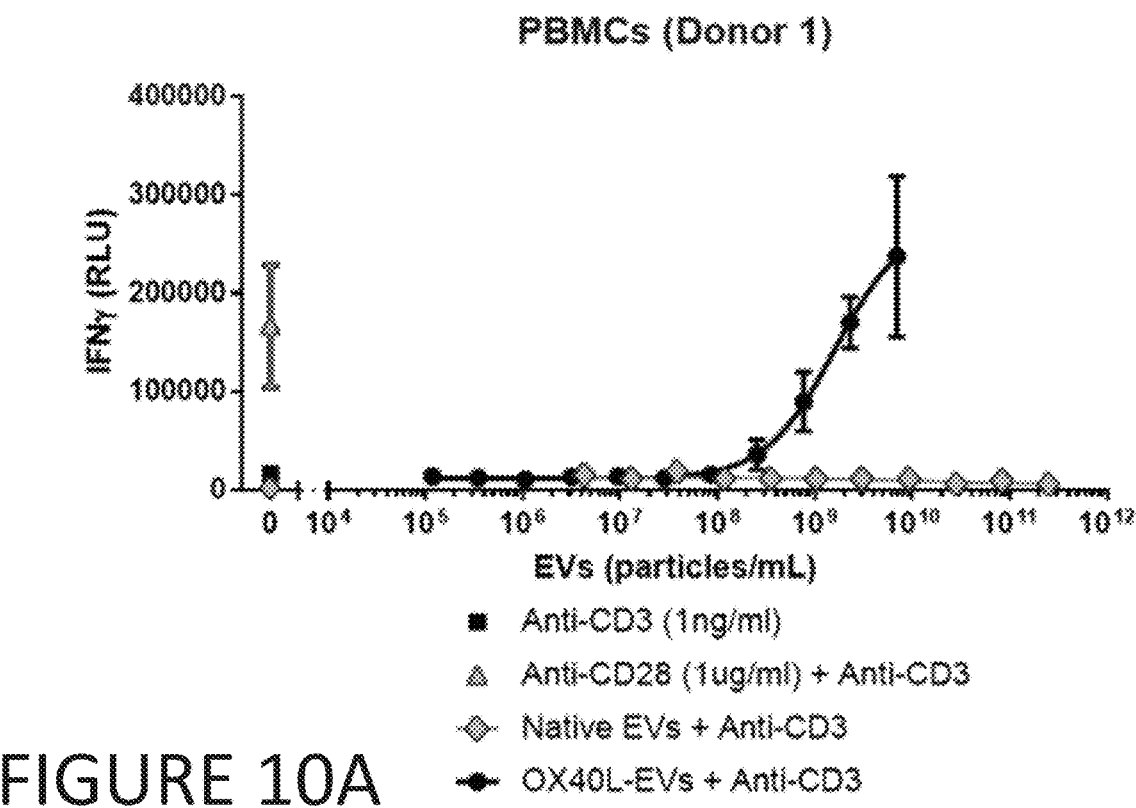
FIGS. 10A and 10B show the effects of OX40L-expressing exosomes on IFNγ expression in human PBMCs from two donors.
Figure 10B:
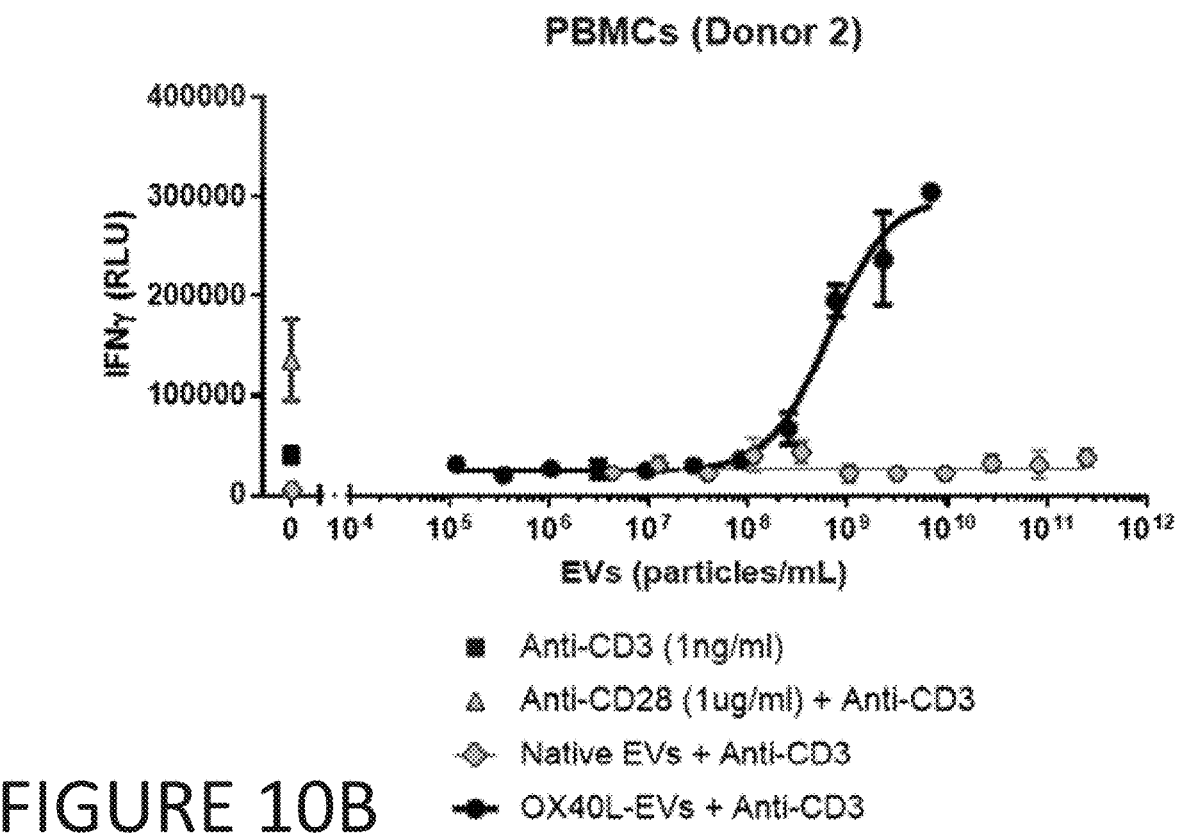
Figure 11A:
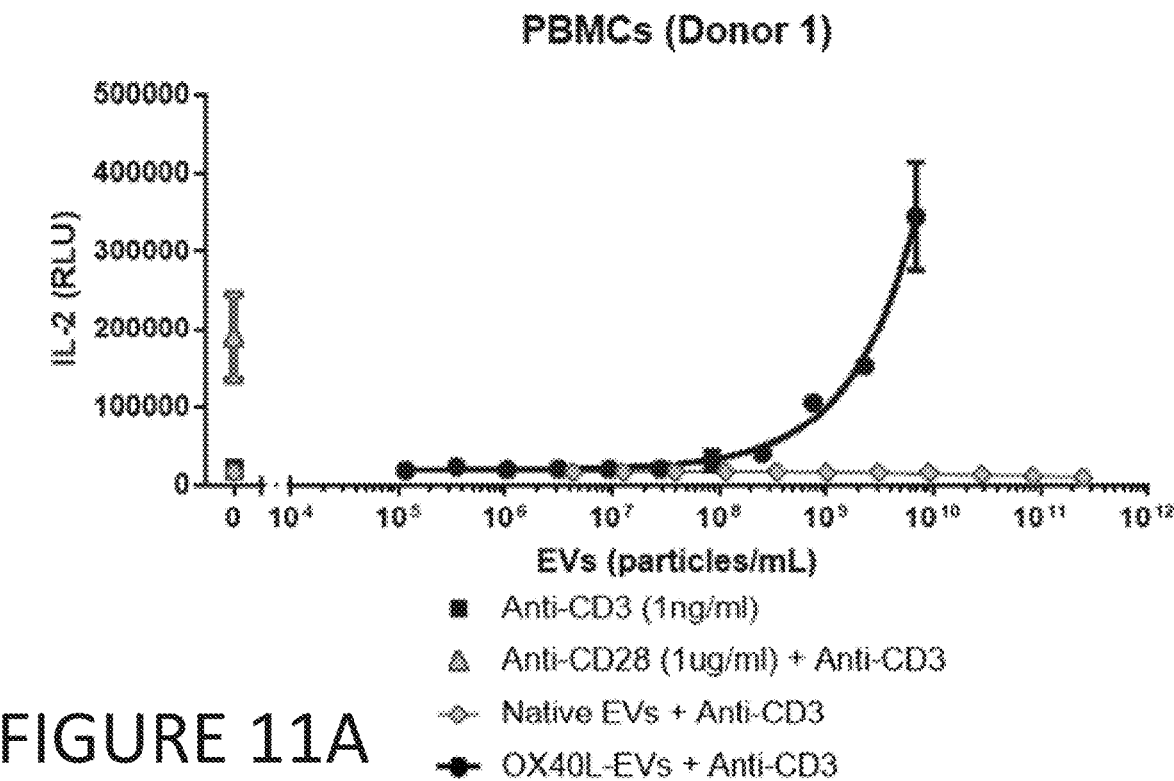
FIGS. 11A and 11B show the effects of OX40L-expressing exosomes on IL-2 expression in human PBMCs from two donors.
Figure 11B:
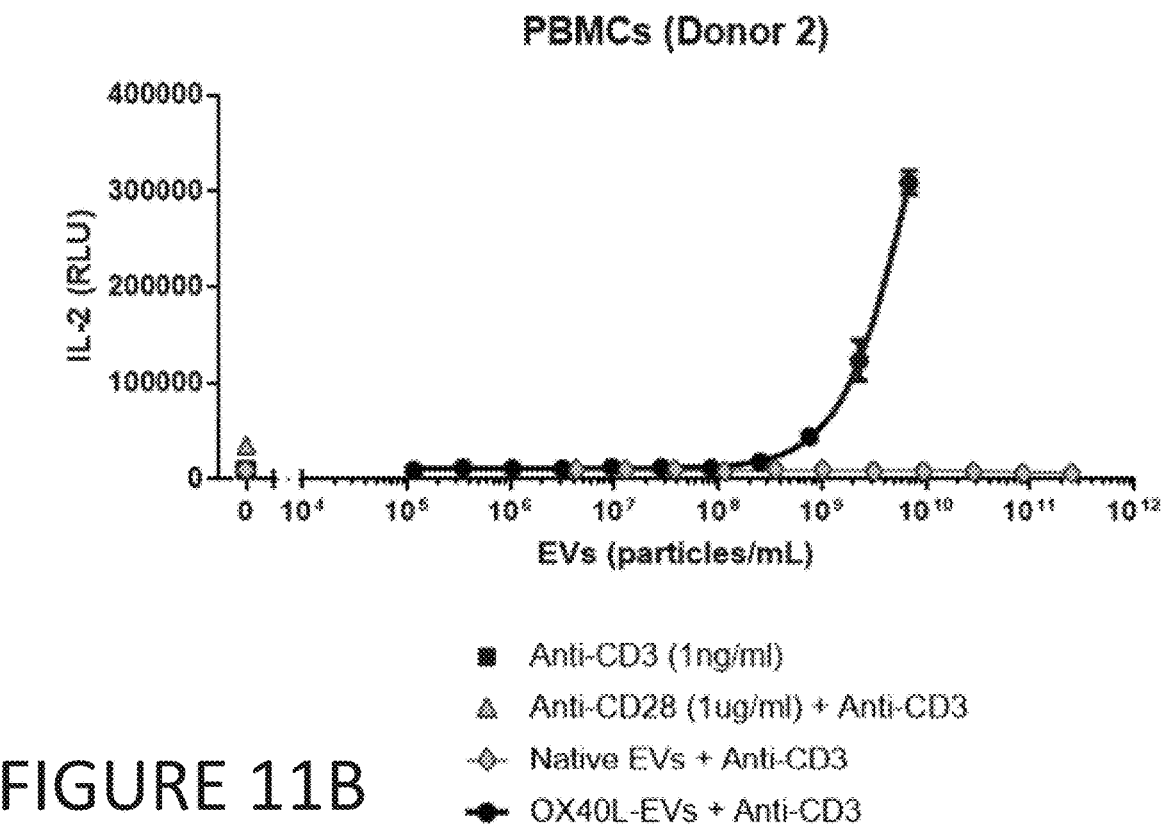

Example 6: Pro-Inflammatory Cytokine Production by Engineered CD27L and OX40L Exosomes CD27L (CD70) and OX40L are members of the TNF super-family, and bind to cognate receptors (CD27 and OX40, respectively) on T-cells. CD27L is expressed by certain populations of T- and B-cells, while OX40L is expressed by certain populations of antigen presenting cells. Signaling through CD27 or OX40 therefore have implications in immuno-oncology, specifically as a method of activating anergic T-cells. To determine whether exosomes could be engineered to induce pro-inflammatory cytokine production in PBMCs, CD27L- and OX40L-containing exosomes were generated by transfection and selection of HEK293SF cells as described in Example 4. To validate the activity of CD27L exosomes, human PBMCs were plated in a 96-well plate, and incubated with purified CD27L exosomes and anti-CD3 antibody, native exosomes and anti-CD3 antibody, anti-CD3 antibody alone, or a combination of anti-CD28 and anti-CD3 antibodies. The samples were incubated at 37 C for two days and assayed for Interferon Gamma (IFNγ) production (FIGS. 8A and 8B) and IL-2 production (FIGS. 9A and 9B) in two different donors. CD27L exosomes induced IFNγ and IL-2 production in a dose-dependent manner and to an extent comparable to (Donor 1) or significantly more than (Donor 2) the positive control of CD3 and CD28 antibodies. In contrast, the native exosomes had no effect on IFNγ or IL-2 production. Similarly, OX40L exosomes were sufficient to induce IFNγ and IL-2 production in two different donors to a similar or greater extent (FIGS. 10A and 10B and FIGS. 11A and 11B).

Figure 12A:
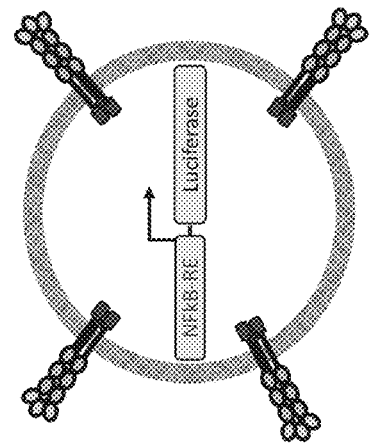
FIG. 12A is a schematic of an OX40 reporter cell line.
Figure 12B:
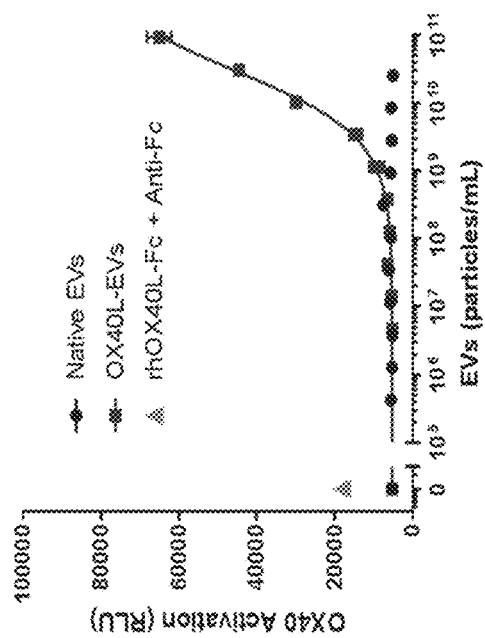
FIG. 12B shows the concentration-dependent activation of an OX40 reporter cell line treated with an anti-OX40 agonistic antibody or recombinant human OX40L.
Figure 12C:
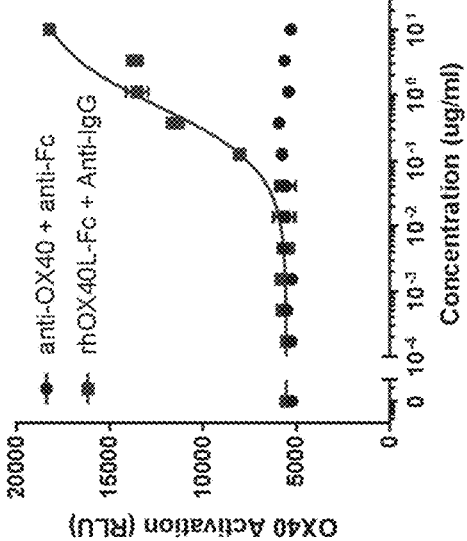
FIG. 12C shows the effects of OX40L-expressing exosomes on an OX40 reporter cell line.

To further validate the OX40L exosomes, a report system was used to measure the activity of the engineered exosomes. Activation of the OX40 pathway results in activation of NF-κB. Using a modified Jurkat T-cell line engineered to overexpress OX40 on its surface and contain a luciferase reporter downstream of the NF-κB promoter (Promega Corporation), OX40 activation was confirmed by incubating the cells in the presence of an agonistic anti-OX40 antibody (Biolegend) crosslinked with an anti-Fc antibody (Jackson ImmunoResearch, Inc.) or recombinant human OX40L (AC-ROBiosystems) cross-linked with an anti-IgG antibody (Jackson Immunoresearch) (FIGS. 12A and 12B). The anti-OX40L antibody crosslinked with anti-IgG failed to activate the reporter cells, while the recombinant OX40L crosslinked with anti-Fc led to a robust activation of the reporter gene (FIG. 12B). Strikingly, the engineered OX40L exosomes induced reporter gene expression to a greater extent than either the anti-OX40 antibody or the recombinant OX40L (FIG. 12C). Importantly, the engineered exosomes did not require a cross-linking antibody, demonstrating that OX40L on the surface of exosomes can form functional OX40L trimers sufficient to activate OX40.

Example 7: T-Cell Activation by IL-7 Engineered Exosomes

Figures 13A, 13B:
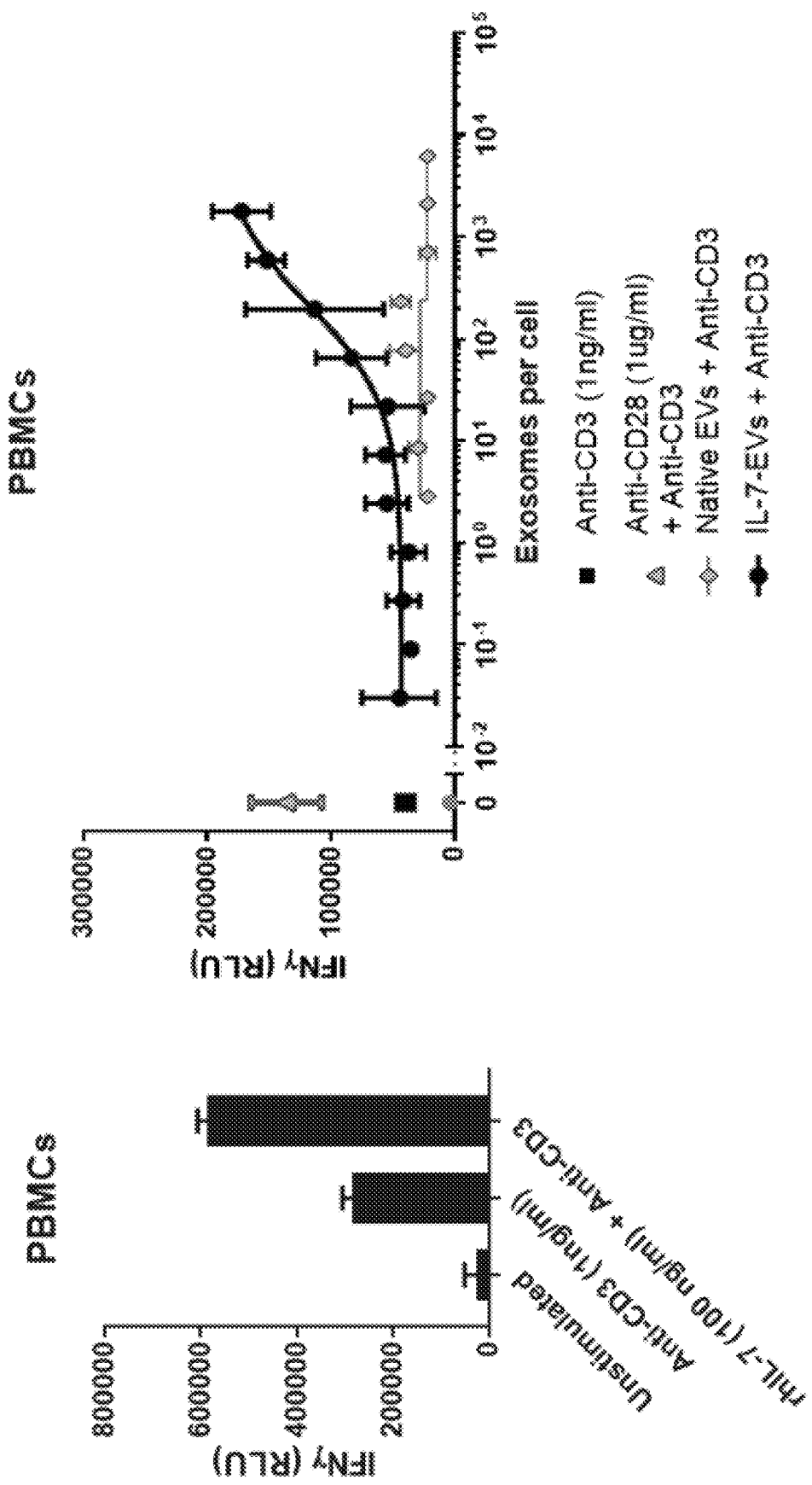
FIGS. 13A and 13B show the effects of IL-7-expressing exosomes in combination with an anti-CD3 antibody on IFNγ expression in human PBMCs.

IL-7 is a cytokine involved in B-cell and T-cell proliferation and has implications in immunotherapy. Specifically, IL-7 may activate T-cells and induce a tumor antigen response in tumors that are poorly infiltrated by leukocytes or in tumor microenvironments that have induced T-cell anergy. IL-7 signaling through the heterodimeric IL-7 receptor induces Interferon Gamma (IFNγ) signaling, which can enhance tumor-specific antigen response by T-cells. To determine whether exosomes could be engineered to induce T-cell activation, IL-7-containing exosomes were generated by transfection and selection of HEK293SF cells with the pDisplay™ plasmid (ThermoFisher) encoding a fusion of IL-7 and PDGF Receptor. The engineered exosomes were purified as described in the Methods. To validate the activity of IL-7 exosomes, human PBMCs were plated in a 96-well plate, and incubated with purified IL-7 exosomes and anti-CD3 antibody, native exosomes and anti-CD3 antibody, anti-CD3 antibody alone, or a combination of anti-CD28 and anti-CD3 antibodies. The samples were incubated at 37° C. for two days and assayed for IFNγ (FIGS. 13A and 13B). IL-7 exosomes in combination with anti-CD3 antibody induced peak IFNγ production to a greater extent than anti-CD3 alone (FIG. 13A). Additionally, IL-7 exosomes induced IFNγ in a dose-dependent manner and to an extent comparable to the positive control of CD3 and CD28 antibodies. In contrast, the native exosomes had no effect on IFNγ production (FIG. 13B).

Figure 14C:
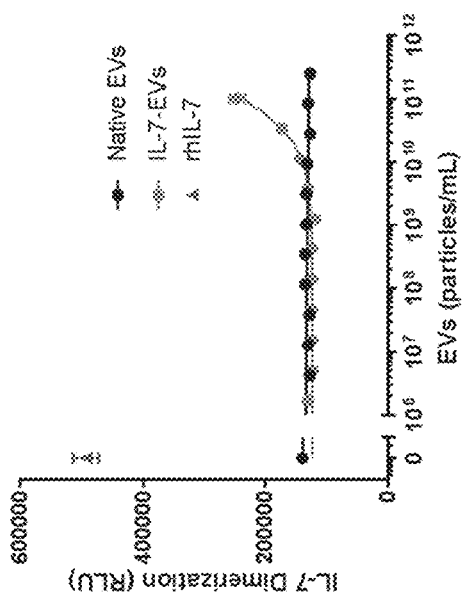
FIG. 14C shows the effects of IL-7-expressing exosomes on an IL-7 receptor reporter cell line.
Figure 14B:
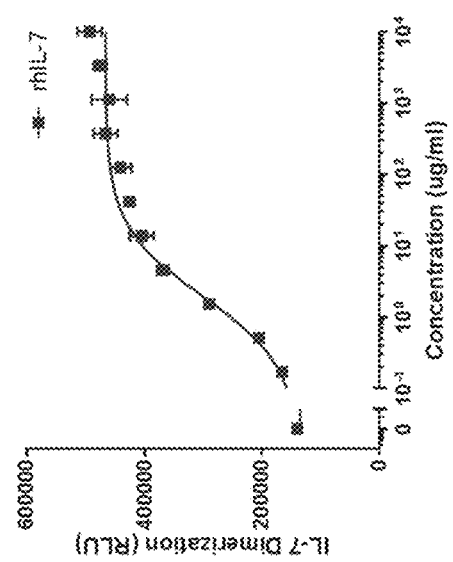
FIG. 14B shows the concentration-dependent activation of an IL-7 receptor reporter cell line treated with recombinant human IL-7.
Figure 14A:
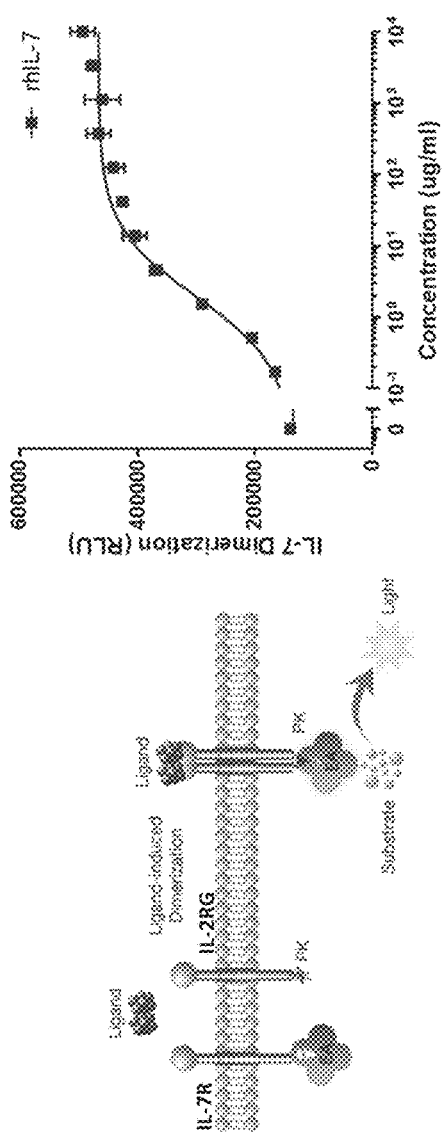
FIG. 14A is a schematic of an IL-7 receptor reporter cell line.

The IL-7 receptor is a heterodimeric complex consisting of IL-7R and IL-2RG, which form a ternary complex in the presence of IL-7 and induces downstream signaling through the JAK/STAT pathway, resulting in cell proliferation. A synthetic cell-based assay was used to measure IL-7 signaling through the IL-7 receptor to assess the functional activity of engineered IL-7 exosomes (DiscoverX Corporation) (FIG. 14A). Recombinant human IL-7 (rhIL-7) was sufficient to increase signaling through the IL-7 receptor (FIG. 14B), and engineered IL-7 exosomes were able to induce signaling through the IL-7 receptor while native exosomes were not (FIG. 14C). These data demonstrate that IL-7-expressing exosomes are sufficient to induce signaling through the IL-7 receptor in vitro.

To determine whether the effects of IL-7 exosomes observed in vitro could be recapitulated in an in vivo model, the IL-7 exosomes were administered to C57BL/6 mice. A cohort of 20 mice were separated into the following groups: (1) PBS, (2) recombinant human IL-7 (rhIL-7), (3) IL-7 engineered exosomes, and (4) unmodified native exosomes.

Figure 15A:
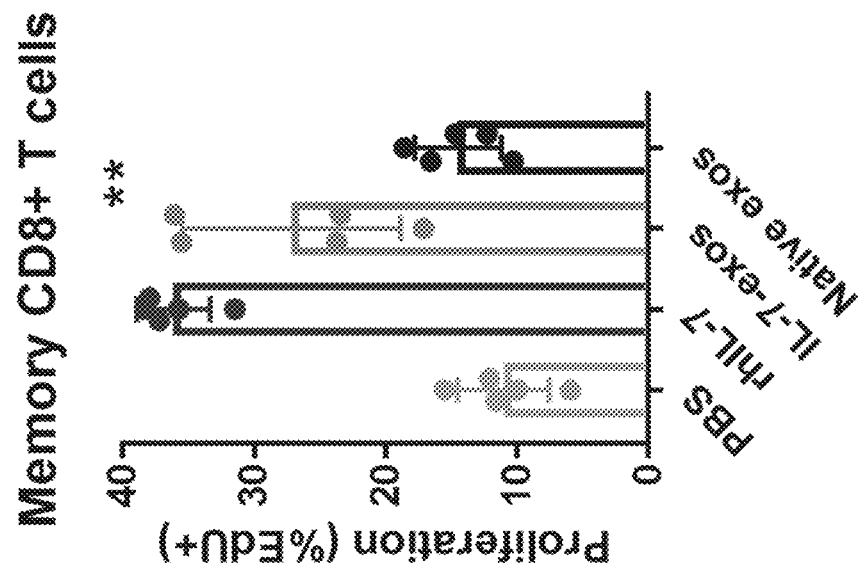
FIGS. 15A and 15B show the effects of IL-7-expressing exosomes on T-cell proliferation in mice in vivo as measured by EdU incorporation.
Figure 15B:
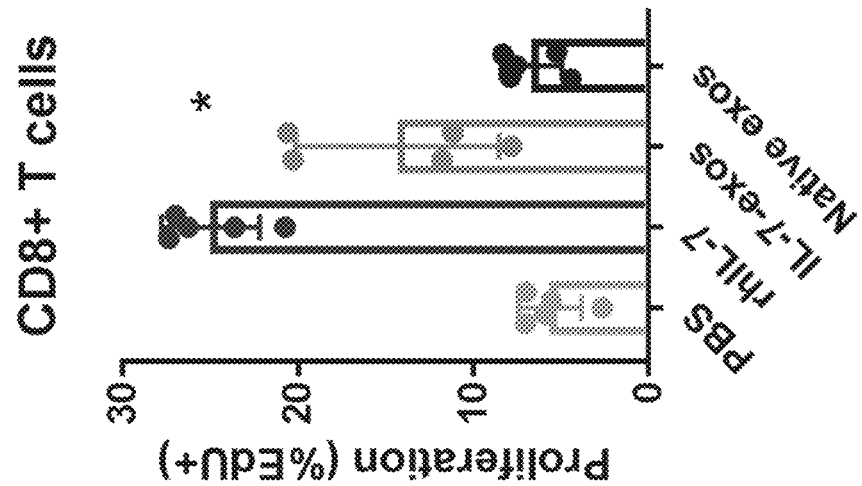

Five mice in each group were injected intraperitoneally (IP) with 1 mg of EdU and either PBS, $1 \times 10^{11}$ native or IL-7 exosomes, or 10 µg of rhIL-7 once daily for three days. Mice were sacrificed, spleens were isolated, and EdU levels were measured in splenic cells by flow cytometry. As shown in FIG. 15A, the percent-positive CD8+ T-cell were significantly increased in the IL-7 exosome mice and the rhIL-7 mice compared to the control cohorts. Although the T-cell counts in IL-7 exosome mice were lower than the rhIL-7 cohort, it is estimated that there was five-fold fewer IL-7 molecules administered in the IL-7 exosome cohort (data not shown). A similar trend was observed for Memory CD8+ T-cells by measuring the levels of the memory marker CD45RO (FIG. 15B).

Figure 16A:
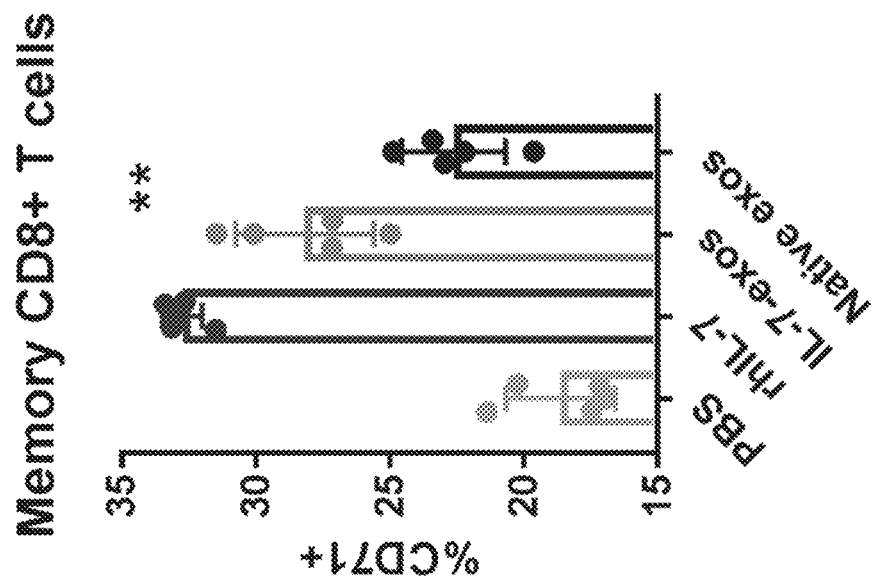
FIGS. 16A and 16B show the effects of IL-7-expressing exosomes on T-cell proliferation in mice in vivo as measured by CD71 positivity.
Figure 16B:
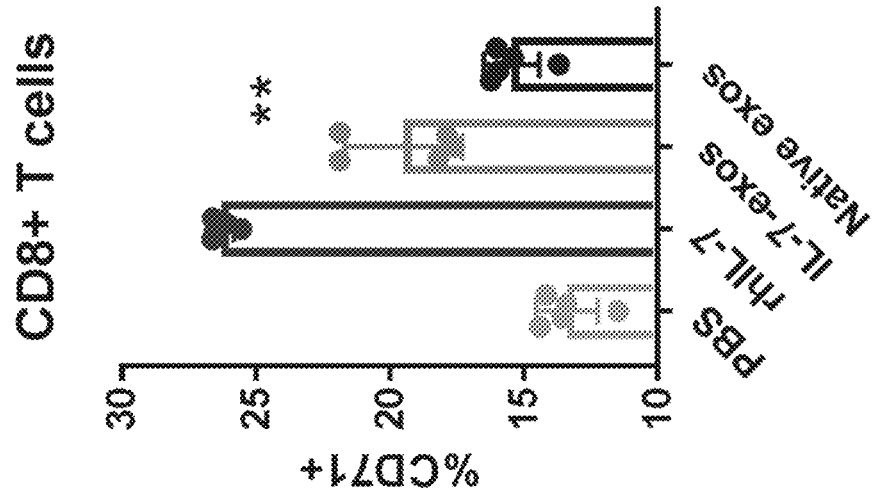

As an orthogonal approach, the levels of CD71 (Transferrin receptor) were measured in splenic cells isolated from exosome-treated mice. CD71 is required for proliferation, and CD71 levels correlate with T-cell number. As shown in FIGS. 15A and 15B, CD8+ T-cell and Memory CD-8+ T-cell numbers followed the same trend as observed in FIGS. 16A and 16B. Together, these data demonstrate that engineered exosomes can induce a specific immune cell effect in vivo, and that this activation can be more potent on a per-molecule basis compared to recombinant agonists.

Example 8: IL-7 Fusion to Proprietary Scaffolds Enhances Specific Activity

Figure 17A:
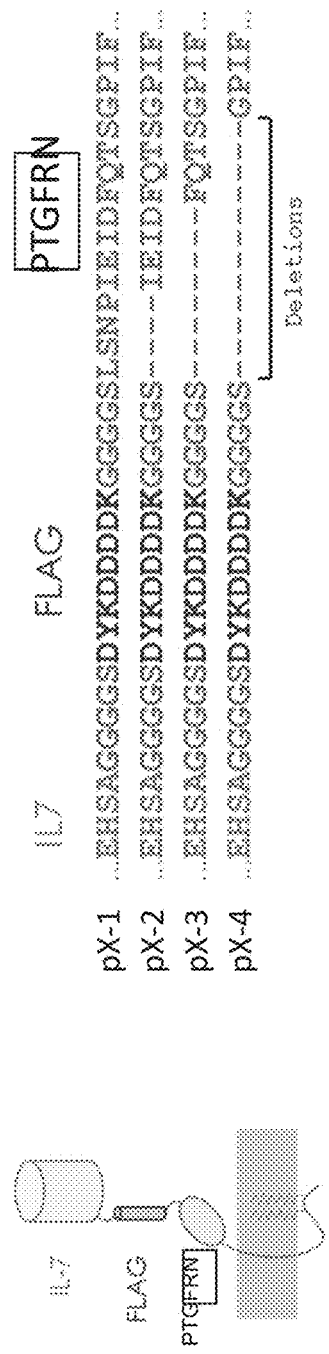
FIG. 17A shows a schematic of a PTGFRN/IL-7 fusion protein expressed at high density on the surface of an exosome, and variants of the fusion protein.
Figure 17B:
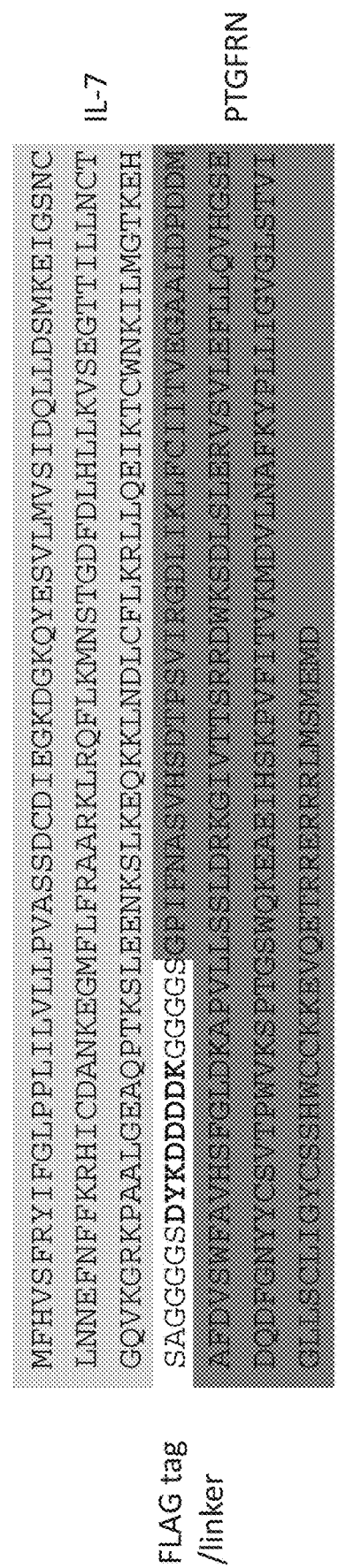
FIG. 17B is the sequence of the optimized PTGFRN/IL-7 fusion protein.
Figure 18A:
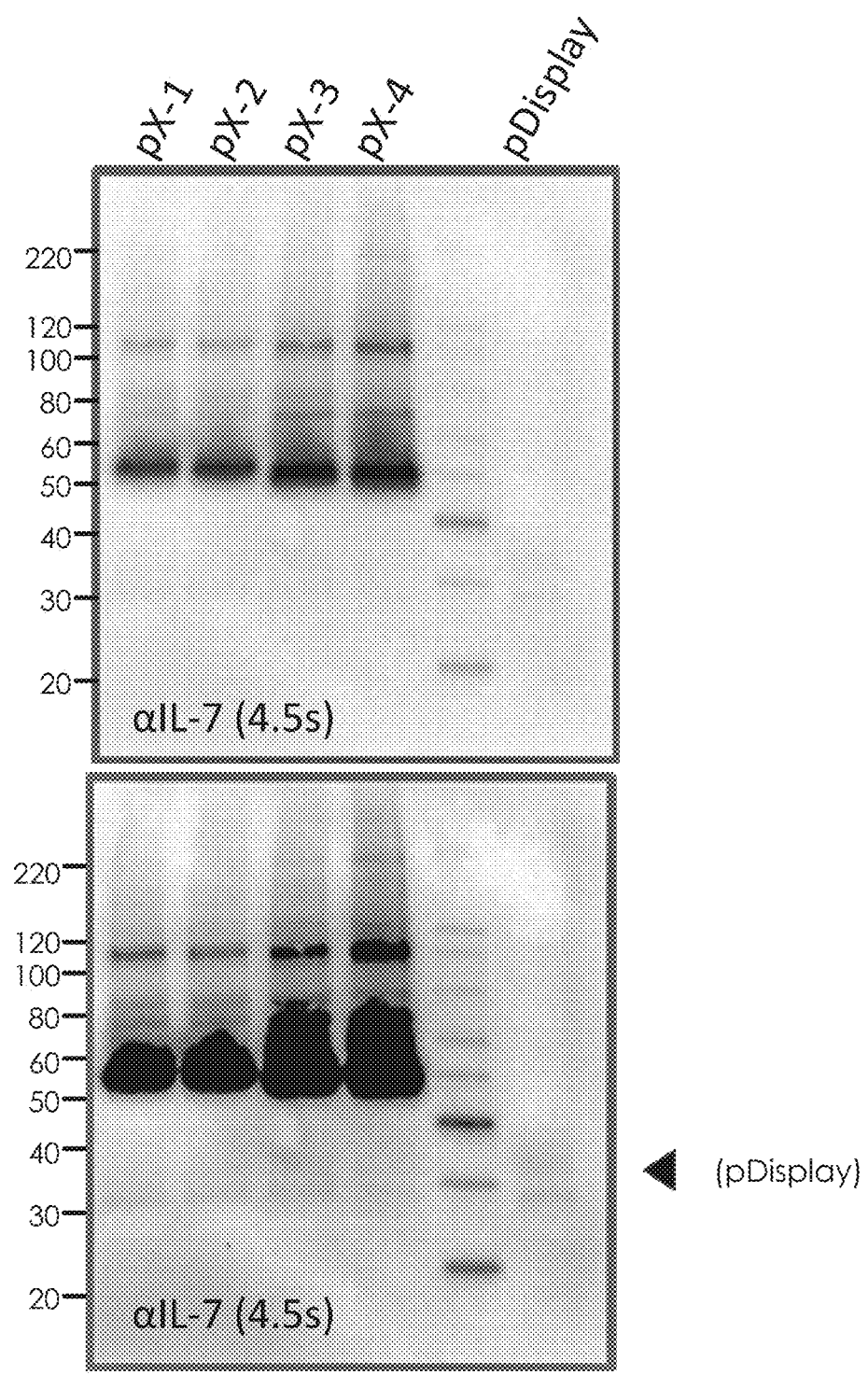
FIG. 18A is a Western blot showing the relative expression of different IL-7 fusion proteins on the surface of purified exosomes.
Figure 18B:
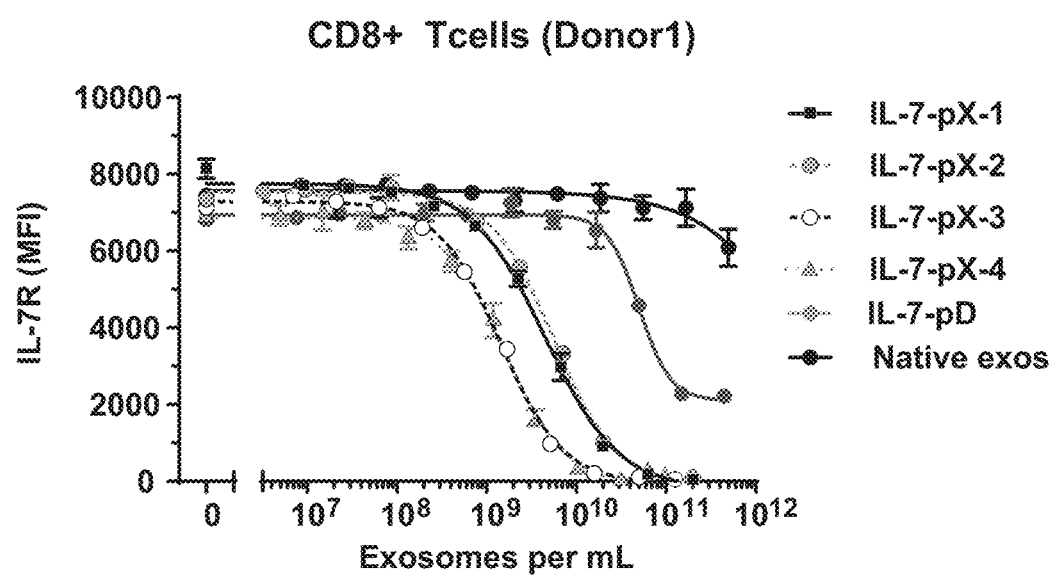
FIG. 18B shows the effects of IL-7-expressing exosomes on IL-7 receptor down-regulation as a model of IL-7-mediated T-cell activation.

To enhance the activity of IL-7 engineered exosomes, the IL-7 sequence was fused to a truncated portion of PTGFRN, a novel exosome transmembrane protein that is highly expressed on the surface of HEK293SF exosomes. IL-7 was expressed as a translational fusion upstream of a short fragment of PTGFRN encompassing the region before the C-terminal-most IgV domain, the transmembrane domain, and the intracellular domain of PTGFRN, as well as a FLAG tag. A series of expression constructs was generated by introducing a series of four amino acid deletions between IL-7 and PTGFRN (FIG. 17A). The resulting constructs were numbered pX-1 through pX-4 (pX-4 complete sequence shown in FIG. 17B). As shown by Western blot analysis using an anti-IL-7 antibody, constructs pX-3 and pX-4 showed the highest levels of expression. The level of IL-7 expression in the PTGFRN backbone was dramatically higher than pDisplay-IL-7, which was used in Example 7 (FIG. 18A). The increased expression of IL-7 suggested that these novel fusion proteins could induce a much greater level of IL-7-mediated T-cell activation. To determine the potency of PTGFRN-IL-7 fusions, an in vitro model of T-cell activation was carried out. Upon IL-7-mediated activation of T-cells, IL-7 receptor (IL-7R) levels decrease in a dose-dependent manner within 24 hours (Ghawazi et al., Immunol Cell Biol. 2013 February; 91(2):149-58). Thus, IL-7R levels were monitored after incubation of PBMCs with various IL-7 engineered exosomes. As shown in FIG. 18B, native exosomes failed to reduce IL-7R levels, while pDisplay-IL-7 exosomes (IL-7-pD) reduced IL-7R levels only at high doses. In contrast, PTGFRN-IL-7 exosomes (IL-7-pX3 to pX4) completely reduced IL-7R levels at much lower doses, demonstrating an increased potency of these engineered exosomes. As a measure of IC50, the PTGFRN-IL-7 exosomes were 20- to 76-fold more potent than the IL-7-pD exosomes (Table 2), demonstrating that increased ligand density is sufficient to increase biological potency. Furthermore, these results demonstrate that specific truncations of PTGFRN may be ideal scaffolds for use in engineering therapeutic exosomes.

TABLE 8

| Exosomes | pX1 | pX2 | pX3 | pX4 | pD |
|---|---|---|---|---|---|
| IC50 (p/ml) | 4.2E+09 | 5.4E+09 | 1.4E+09 | 1.5E+09 | 1.1E+11 |
| Fold increase in potency | 25.6 | 19.8 | 76.5 | 71.0 | N/A |

Example 9: Exosomes Engineered with Anti-CD3 Antibody Fragments

Figure 19B:
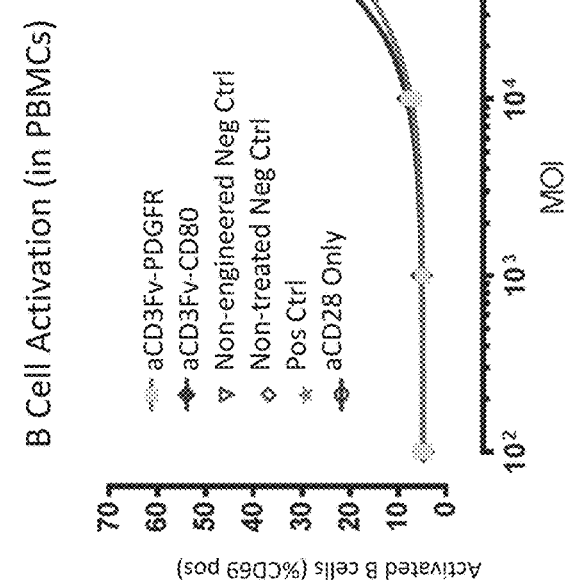
FIG. 19B shows the effects of anti-CD3 scFv exosomes on B-cell activation in PBMCs.
Figure 19A:
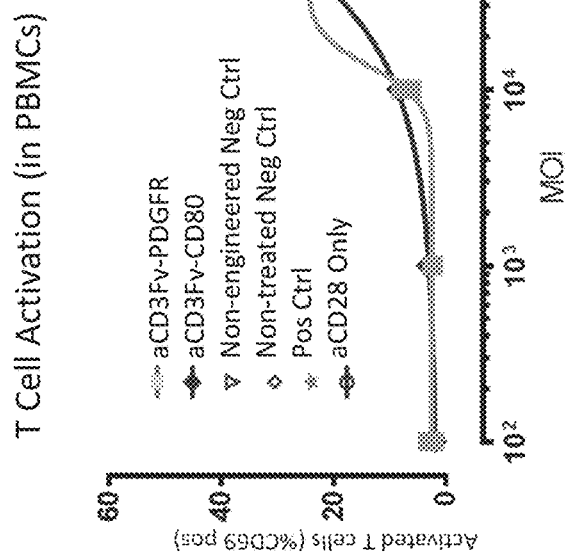
FIG. 19A shows the effects of anti-CD3 scFv exosomes on T-cell activation in PBMCs.
Figure 21A:
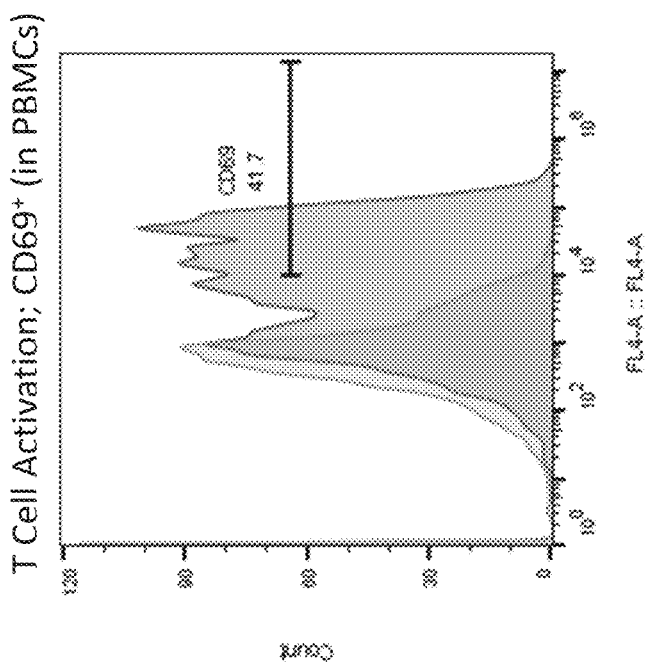
FIG. 21A is a histogram showing the extent of T-cell activation after treatment with anti-CD3 scFv exosomes.
Figure 21B:
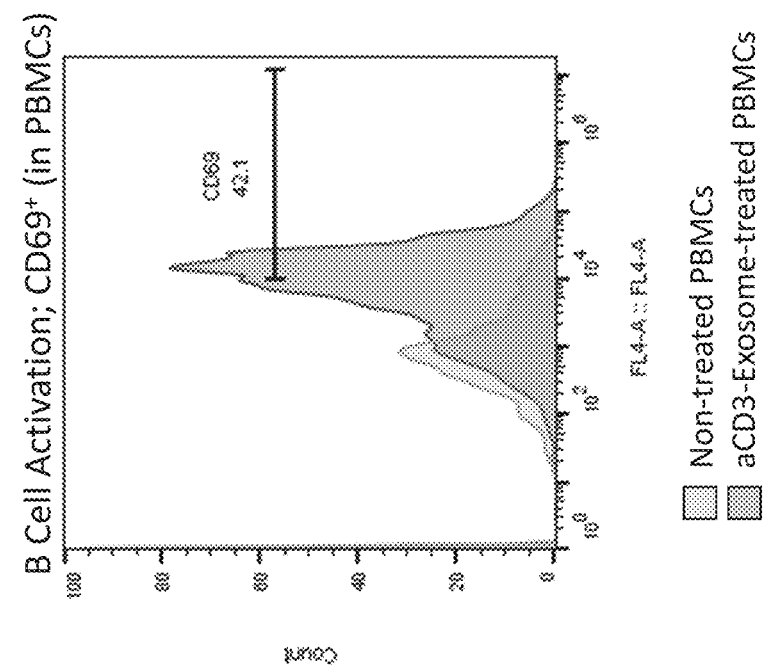
FIG. 21B is a histogram showing the extent of B-cell activation after treatment with anti-CD3 scFv exosomes.

As shown in the previous examples, exosomes can be engineered to overexpress functional endogenous sequences of immunomodulatory proteins. To determine if synthetic agonists can be engineered on the surface of exosomes, anti-CD-3 antibodies were expressed as fusions to either pDisplay as described in Example 4, or the transmembrane domain of CD80. Human PBMCs were plated in a 96-well plate at 100,000 cells per well and incubated overnight with exosomes engineered to express an anti-CD3 single chain Fv (scFv) (FIGS. 19A and 19B) or single chain Fab (scFab) (FIGS. 20A and 20B). As a positive control, PBMCs were incubated with ImmunoCult™ CD3/CD28 Activator (Stem Cell Technologies) according to the manufacturers' protocol. In the presence of anti-CD28 co-stimulation, all engineered exosomes induced T-cell (FIGS. 19A and 20A) and B-cell (FIGS. 19B and 20B) activation comparable to the positive control, while the non-engineered exosome controls did not. To measure the effects of anti-CD3 exosomes on immune cell populations, T-cell and B-cells were assayed for CD69 positivity by flow cytometry. As shown in FIG. 21A, PBMCs incubated with exosomes expressing anti-CD3 scFv fused to the CD80 transmembrane domain led to activation of ~40% of T-cells. Similar effects were observed for the activation of B-cells (FIG. 21B).

Figure 22B:
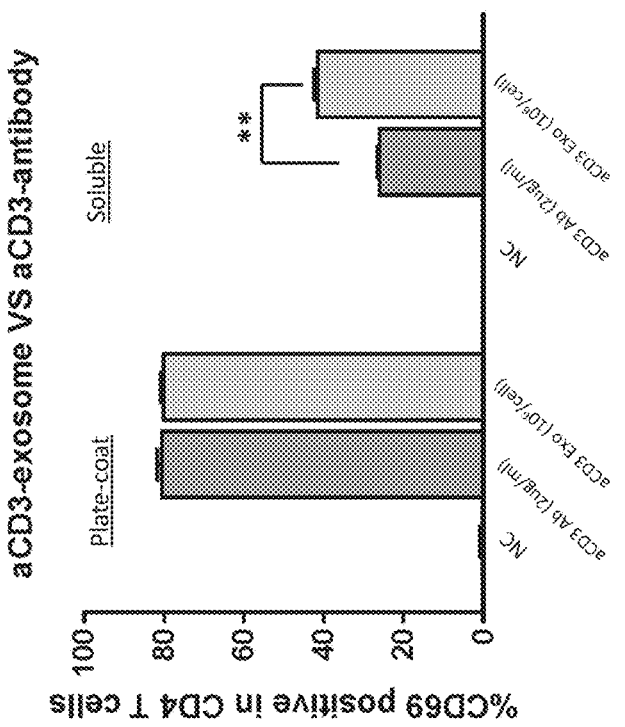
FIG. 22B is a bar chart quantitating the results of a separate experiment carried out as in FIG. 22A.
Figure 22A:
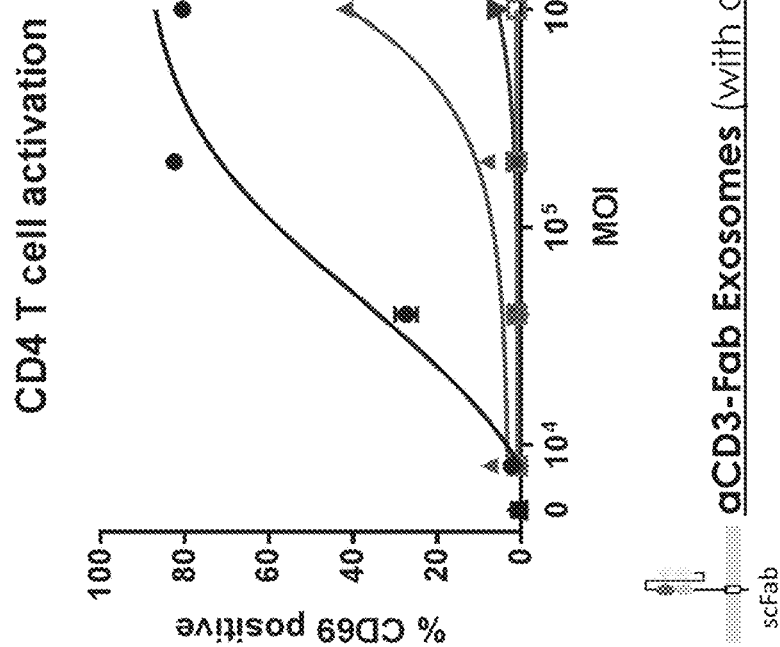
FIG. 22A shows the effects of anti-CD3 scFab exosomes on T-cell activation in a plate-coated activation assay compared to soluble anti-CD3 antibody or plate-coated anti-CD3 antibody.

To determine whether anti-CD-3 exosome-mediated T-cell activation was due to direct T-cell activation or through trans-acting immune cells, activation of purified T-cells was measured. 100,000 purified human T-cells were plated in 96-well format in wells that were pre-coated with a non-targeting antibody or anti-CD3 exosomes in the presence or absence of anti-CD28 antibody, or in wells that were incubated with soluble anti-CD3 exosomes in the presence or absence of anti-CD28 antibody. As shown in FIG. 22A, both soluble and plate-coated anti-CD3 scFv exosomes activated T-cells in the presence of anti-CD28 antibody as measured by CD69 expression. As shown in FIG. 22B, plate-coated anti-CD3 antibody in the presence of anti-CD28 antibody activated T-cells to the same extent as plate-coated anti-CD3 scFv in the presence of anti-CD28 antibody. Strikingly, while soluble anti-CD3 antibody in the presence of anti-CD28 antibody was sufficient to activate ~30% of T-cells, soluble anti-CD3 scFv exosomes in the presence of anti-CD28 antibody activated a significantly higher proportion of T-cells, demonstrating that exosomes engineered to overexpress an antibody fragment can induce higher levels of T-cell activation compared to soluble antibody. Together, these results demonstrate that exosomes can be engineered to overexpress antibody fragments with functional activity against specific cell types.

Example 10: IL-12-PTGFRN Exosomes Have Potent Immunomodulatory Activity In Vitro and In Vivo IL-12 is a potent immunostimulatory cytokine produced by antigen presenting cells in response to infection and other antigenic stimulation. IL-12 production by activated dendritic cells, macrophages, and neutrophils induces IFNγ production by both CD8+ and CD4+ T-cells and induces cytotoxic effects of Natural Killer (NK) cells. The combined impact of IL-12 secretion in the tumor microenvironment results in the secretion of Th1 cytokines including IFNγ, leading to tumor cell killing, reprogramming of myeloid-derived suppressor cells (MDSCs) and anti-angiogenic effects. IL-12-mediated anti-tumor effects result in a durable T-cell response and anti-tumor immunity in numerous animal models. IL-12 has previously been tested as an immunotherapy agent in humans but resulted in significant toxicity in renal cell carcinoma patients despite a detectable induction of a robust IFNγ response (Leonard et al., Blood. 1997 Oct. 1; 90(7):2541-8). Exosomes therefore may represent an ideal delivery modality for IL-12 due to the high local concentration of the cytokine and presumed tumor-retained pharmacology.

Figure 23A:
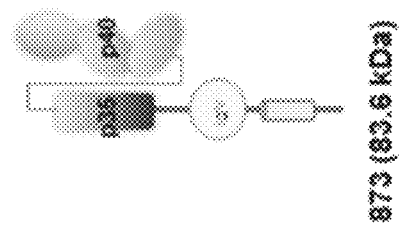
FIG. 23A shows a schematic of a full-length PTGFRN/IL-12 fusion protein.
Figure 23B:
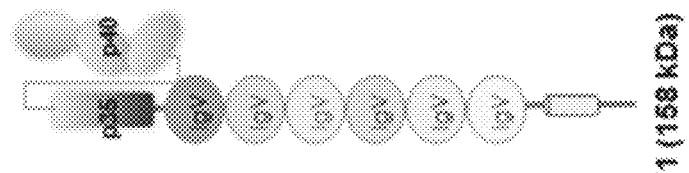
FIG. 23B shows a schematic of a shortened PTGFRN/IL-12 fusion protein.
Figure 24A:
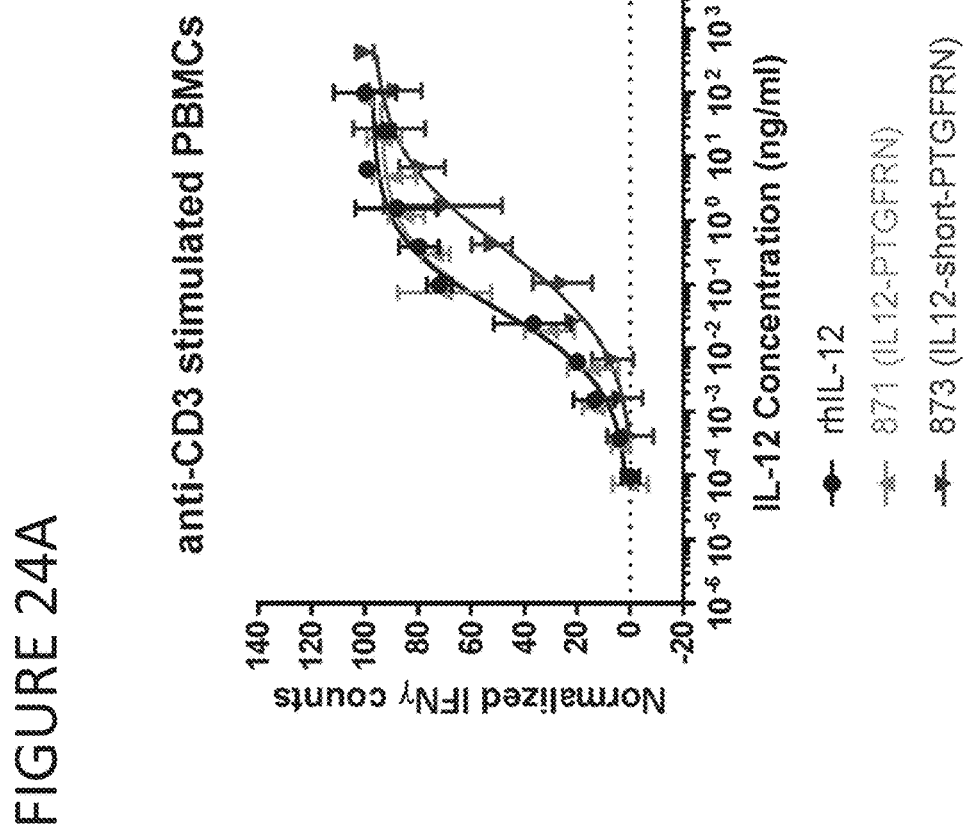
FIG. 24A shows the effects of recombinant human IL-12 or exosomes overexpressing either short or full-length PTGFRN-IL-12 inducing IFNγ in human PBMCs.
Figure 24B:
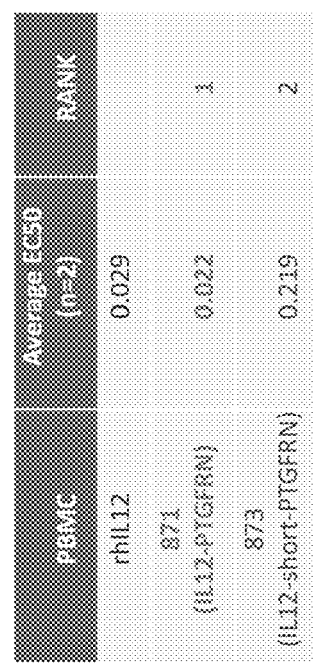
FIG. 24B is a table summarizing the potency of recombinant IL-12 and IL-12-containing exosomes.

IL-12 consists of two domains, p35 and p40. The human IL-12 dimer was encoded as a fusion protein to either full-length PTGFRN (FIG. 23A, construct 871, SEQ ID NO: 3) or a shortened fragment of PTGFRN that enables high-density surface display (FIG. 23B, construct 873, SEQ ID NO: 5), and the constructs were stably expressed in HEK293SF cells. Stable cell lines were grown in chemically defined media and the exosomes from the culture supernatant were purified over an Optiprep™ gradient as described in the Methods. The amount of IL-12 protein on the surface of the exosomes was measured by ELISA and concentration-matched to the rIL-12 for all functional studies. Purified full-length and short hIL-12-PTGFRN exosomes or recombinant hIL-12 (rhIL-12; BioLegend, Catalog No. 573004) were titrated in human PBMCs in the presence of a sub-optimal concentration anti-CD3 antibody to induce IFNγ expression. rhIL-12 resulted in robust IFNγ expression with an $EC_{50}$ of 0.029 ng/ml, which was comparable to full-length IL12-PTGFRN, both of which were ~10× more potent than IL12-short-PTGFRN (FIG. 24A-B). These results suggest that IL-12 displayed on the full-length PTGFRN scaffold may be a more potent immunomodulating reagent than the short PTGFRN construct.

Figure 25:
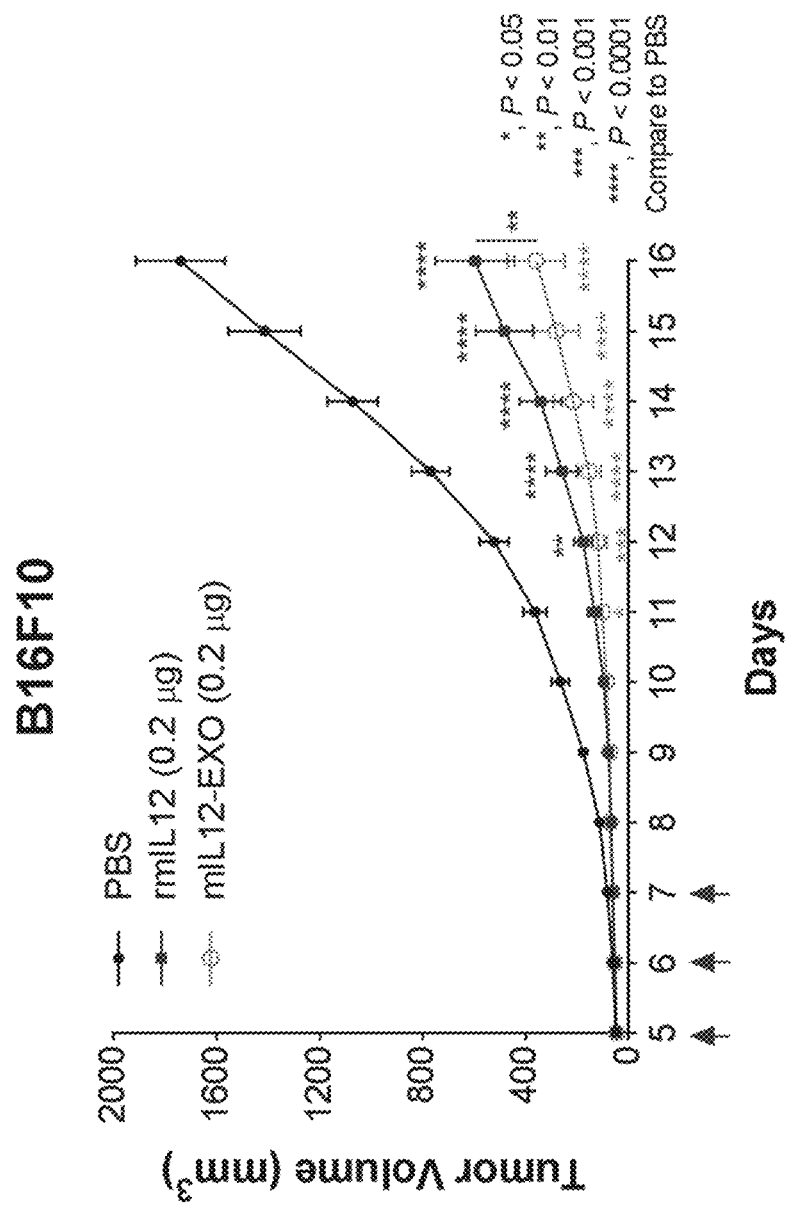
FIG. 25 shows the effects of recombinant IL-12 and IL-12-PTGFRN exosomes on reducing tumor growth in a murine model of melanoma.
Figure 26C:
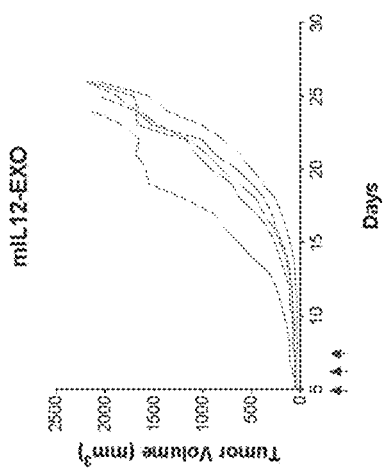
FIG. 26C shows the tumor growth curves for each of the tumor-bearing mice shown in FIG. 25 treated with IL-12-PTGFRN exosomes.
Figure 26B:
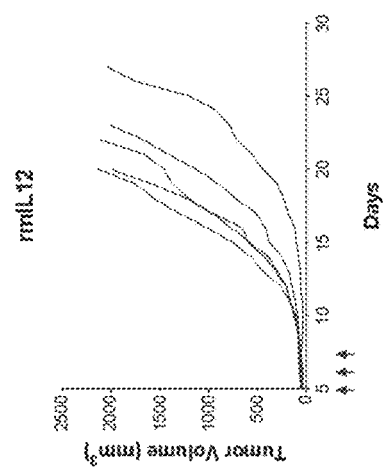
FIG. 26B shows the tumor growth curves for each of the tumor-bearing mice shown in FIG. 25 treated with recombinant IL-12.
Figure 26A:
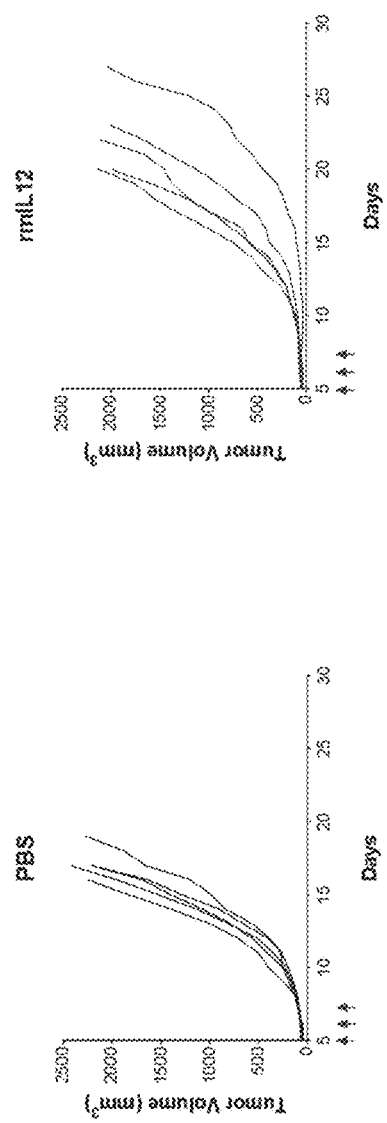
FIG. 26A shows the tumor growth curves for each of the tumor-bearing mice shown in FIG. 25 treated with PBS.
Figure 27:
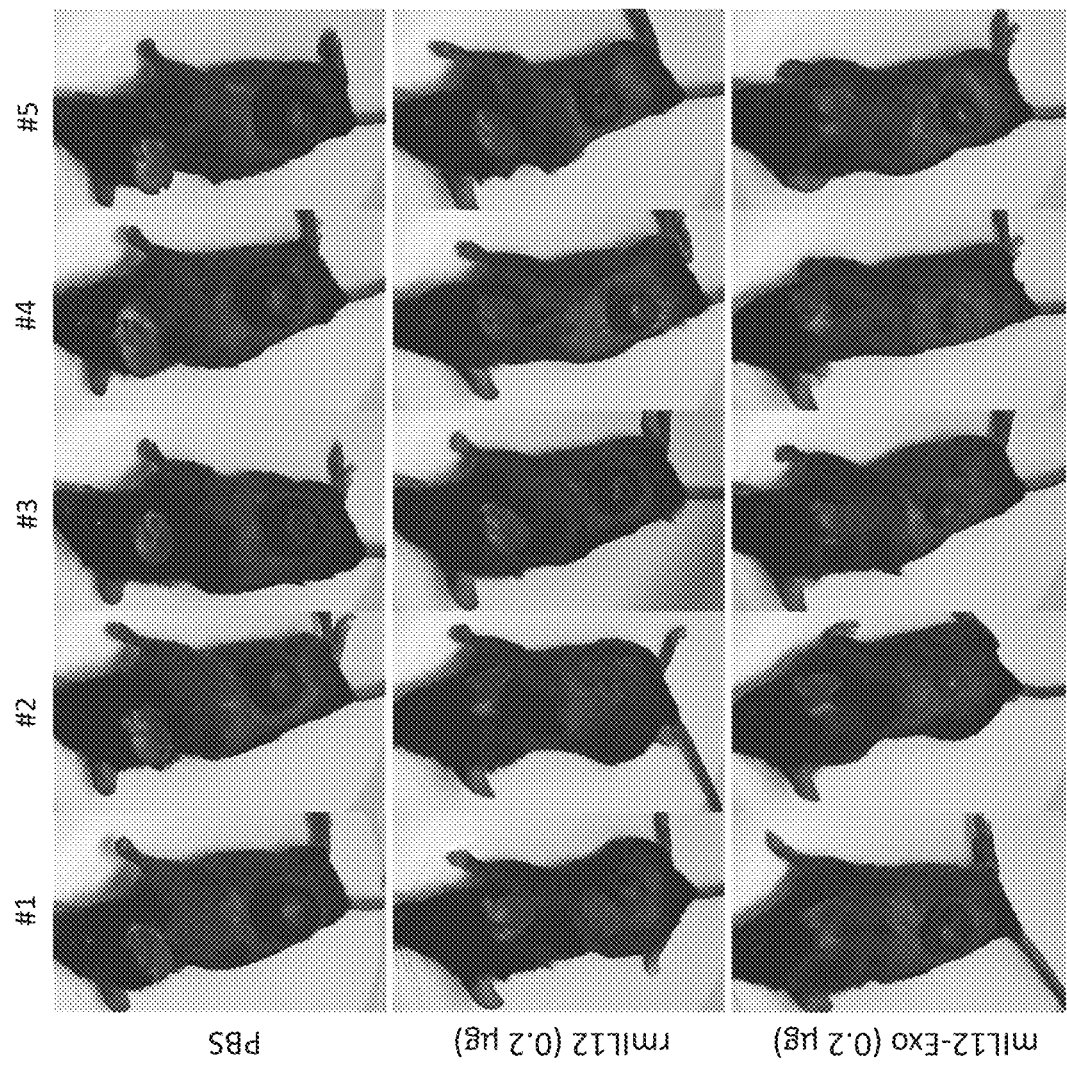
FIG. 27 shows images of all B16F10 tumor-bearing mice in the efficacy study shown in FIG. 25.
Figure 28:
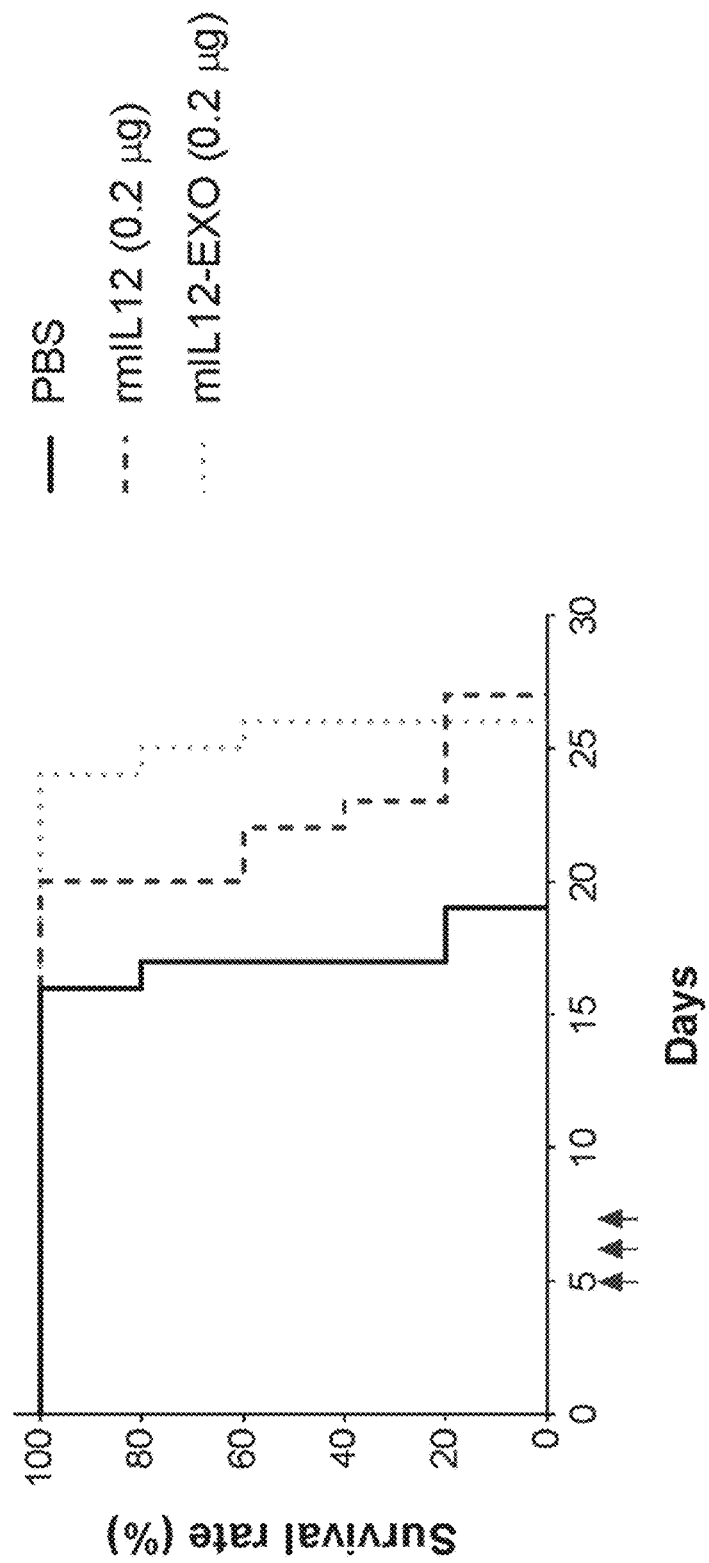
FIG. 28 shows the survival curves of the B16F10 tumor-bearing mice shown in FIG. 25.

Mouse and human IL-12 proteins do not cross-react, and the in vitro data shown in FIG. 24 suggest that mIL-12 fused to full-length PTGFRN would be more a more potent than using the short scaffold of PTGFRN. To determine the potency of mIL-12-PTGFRN exosomes in an in vivo model of cancer, C57BL/6 mice were implanted subcutaneously with $1 \times 10^6$ B16F10 murine melanoma cells (n=5 mice per group). On days 5, 6, and 7 after tumor inoculation the animals were injected intratumorally with PBS, 0.2 μg of recombinant murine IL-12 (mIL12; BioLegend, Catalog No. 577004), or $1 \times 10^{11}$ exosomes displaying full-length IL-12-PTGFRN (mIL12-Exosomes; SEQ ID NO: 4). Animals were sacrificed once tumor volumes reached 2,000 mm³. As shown in FIGS. 25-27, tumors in the PBS group grew rapidly while tumors in the rmIL12 and mIL12-Exo groups were dramatically reduced (~65-80% reduction in volume). Importantly, by day 16, tumors in the mIL12-Exo group were smaller than those in the rmIL12 group demonstrating superior efficacy of IL-12 when displayed on the surface of exosomes compared to the soluble cytokine. There was also a survival advantage for the IL-12 treated groups compared to the PBS treated groups (FIG. 28).

Figure 29A:
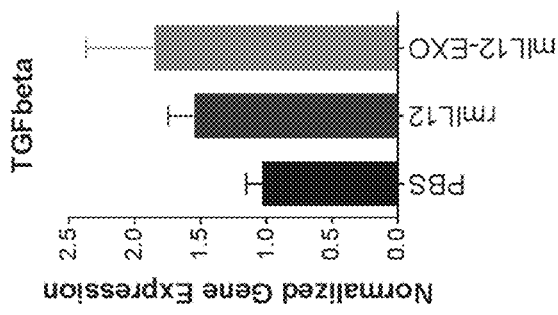
FIG. 29A shows the levels of IFNγ gene expression in tumors of mice treated with PBS, rIL-12 or IL-12-PTGFRN exosomes.
Figure 29B:
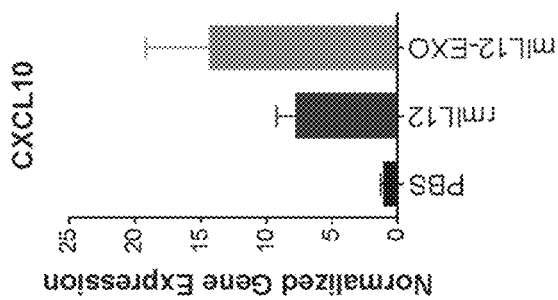
FIG. 29B shows the levels of CXCL9 gene expression in tumors of mice treated with PBS, rIL-12 or IL-12-PTGFRN exosomes.
Figure 29C:
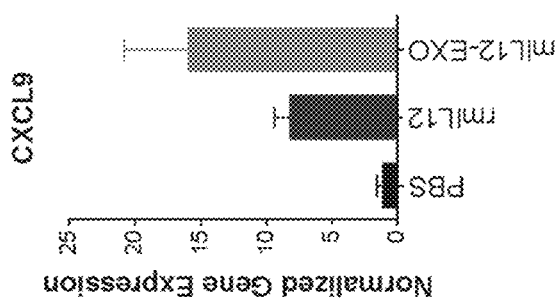
FIG. 29C shows the levels of CXCL10 gene expression in tumors of mice treated with PBS, rIL-12 or IL-12-PTGFRN exosomes.
Figure 29D:
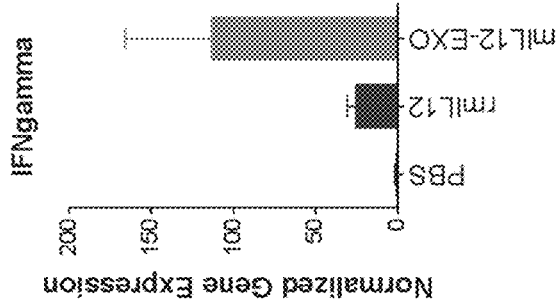
FIG. 29D shows the levels of TGFβ gene expression in tumors of mice treated with PBS, rIL-12 or IL-12-PTGFRN exosomes.
Figure 30:
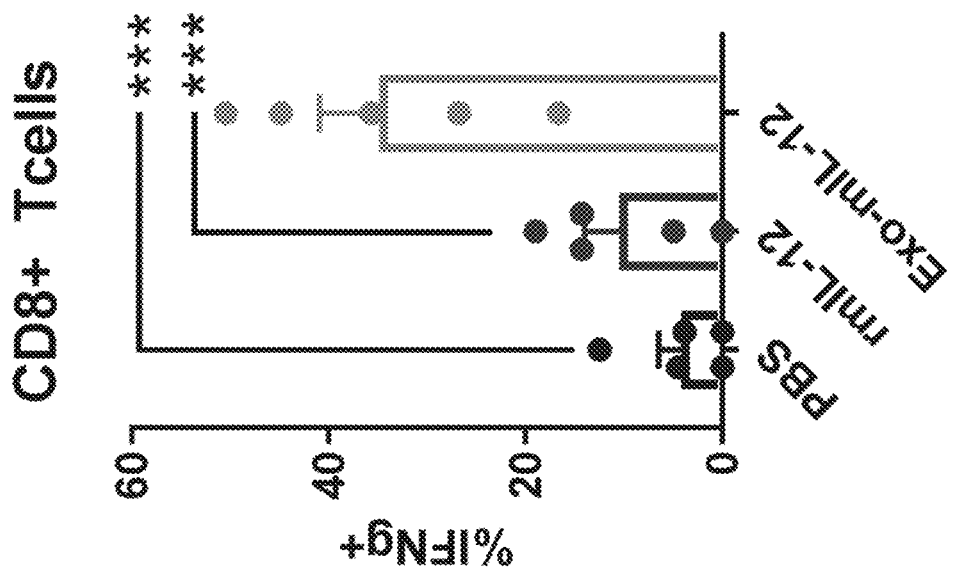
FIG. 30 shows the percent of IFNγ-positive CD8+ splenic T-cells in tumor-bearing mice treated with PBS, rIL-12 or IL-12-PTGFRN exosomes.

To understand the mechanistic advantage of IL-12-PTGFRN-exosomes over rmIL12, Th1 gene expression was profiled in the tumors of the control and treated groups. IFNγ (FIG. 29A), the T-cell chemoattractants CXCL9 (FIG. 29B)

and CXCL10 (FIG. 29C), and TGFβ (FIG. 29D) were all increased in the IL-12 treated groups compared to the control group. In most cases, the cytokine signals were higher in the animals treated with mIL12-Exo compared to rmIL-12. IFNγ levels in splenic CD8+ T-cells were measured by flow cytometry, and the Exo-mIL-12-treated mice showed significantly greater signal than either the PBS group or the rmIL-12 group (FIG. 30). Together, these data demonstrate that IL-12 displayed on the surface of an exosome represents a novel and potent immunomodulatory strategy that promotes robust T-cell activation in vitro and can be used to elicit potent anti-tumor effects in an aggressive model of murine melanoma in vivo. Mechanistically, the IL-12 exosomes show superiority over rIL-12, and thus represent a novel, differentiated therapeutic modality in cancer immunotherapy.

Figure 31A:
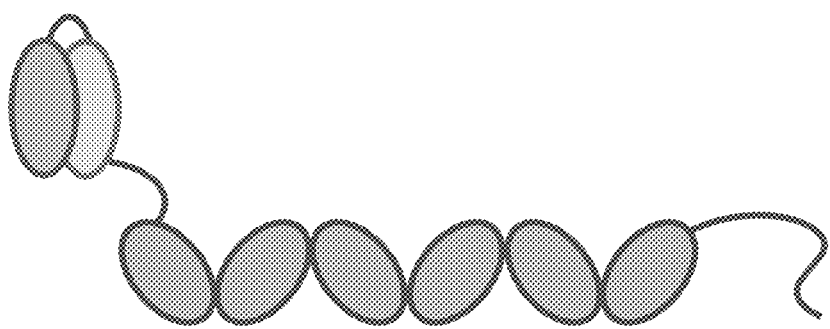
FIG. 31A shows a schematic of a full-length PTGFRN fused to an IFNγ monomer.
Figure 31B:
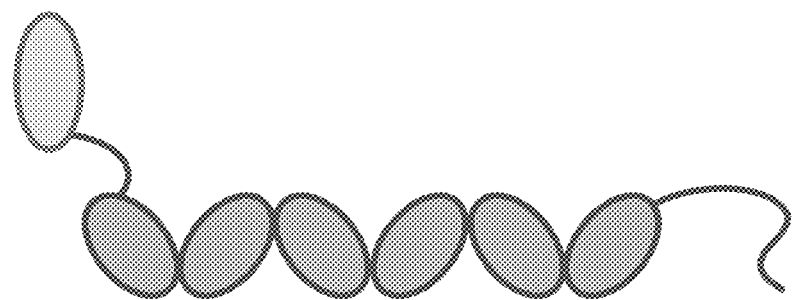
FIG. 31B shows a schematic of a full-length PTGFRN fused to an IFNγ tandem dimer.
Figure 32:
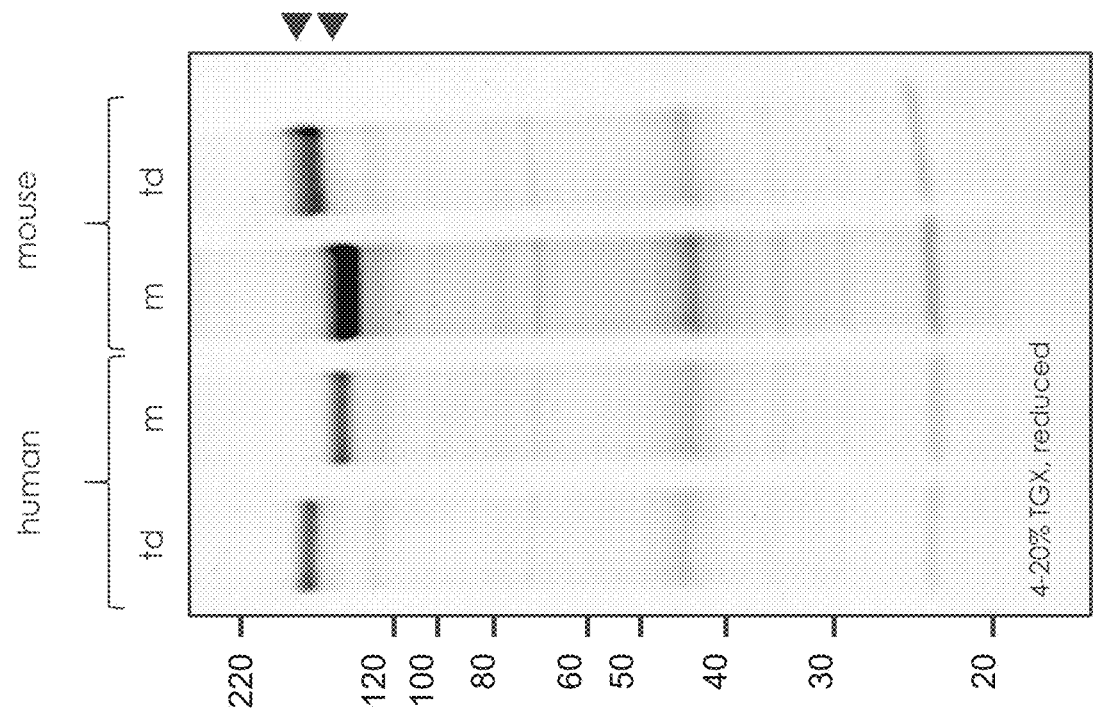
FIG. 32 shows the PAGE analysis results of purified human and mouse monomeric (m) and tandem dimer (td) PTGFRN IFNγ exosomes.

Example 11: Interferon Gamma-Displaying Exosomes are Potent Immune Cell Activators Interferon gamma (IFNγ) is a cytokine involved in priming innate and adaptive immune responses. It is expressed from a variety of cell types in response to numerous signals including IL-12, and is sufficient to activate NK cells, drive antigen presentation in antigen presenting cells, and promote leukocyte activation and invasion. IFNγ is naturally expressed as a homodimer and is secreted as a soluble factor. IFNγ expressing exosomes were generated by stably transfecting HEK293SF cells with full-length PTGFRN fused to monomeric or dimeric human and mouse IFNγ (FIGS. 31A and 31B, respectively). Exosomes from suspension cell cultures were purified as described above and analyzed by PAGE. Monomeric (m) and tandem dimer (td) PTGFRN IFNγ exosomes were expressed at the predicted molecular weights (arrow heads) at comparable levels (FIG. 32). The purified exosomes were analyzed by ELISA and compared to a standard curve using recombinant IFNγ (Biolegend, Catalog No. 570206) to calculate the number of IFNγ molecules per exosome. The results in Table 9 show the number of IFNγ molecules in each of the four types of purified exosomes. Notably, the tandem dimer IFNγ PTGFRN exosomes contain at least twice as many IFNγ molecules as the monomeric IFNγ PTGFRN exosomes, suggesting that the tandem dimer exosomes are appropriately expressing the dimeric IFNγ constructs.

TABLE 9

| Construct | IFN γ molecules/exosome |
| --- | --- |
| h-mIFNγ-PTGFRN | 53 |
| h-tdIFNγ-PTGFRN | 173 |
| m-mIFNγ-PTGFRN | 47 |
| m-tdIFNγ-PTGFRN | 113 |

Figure 33:
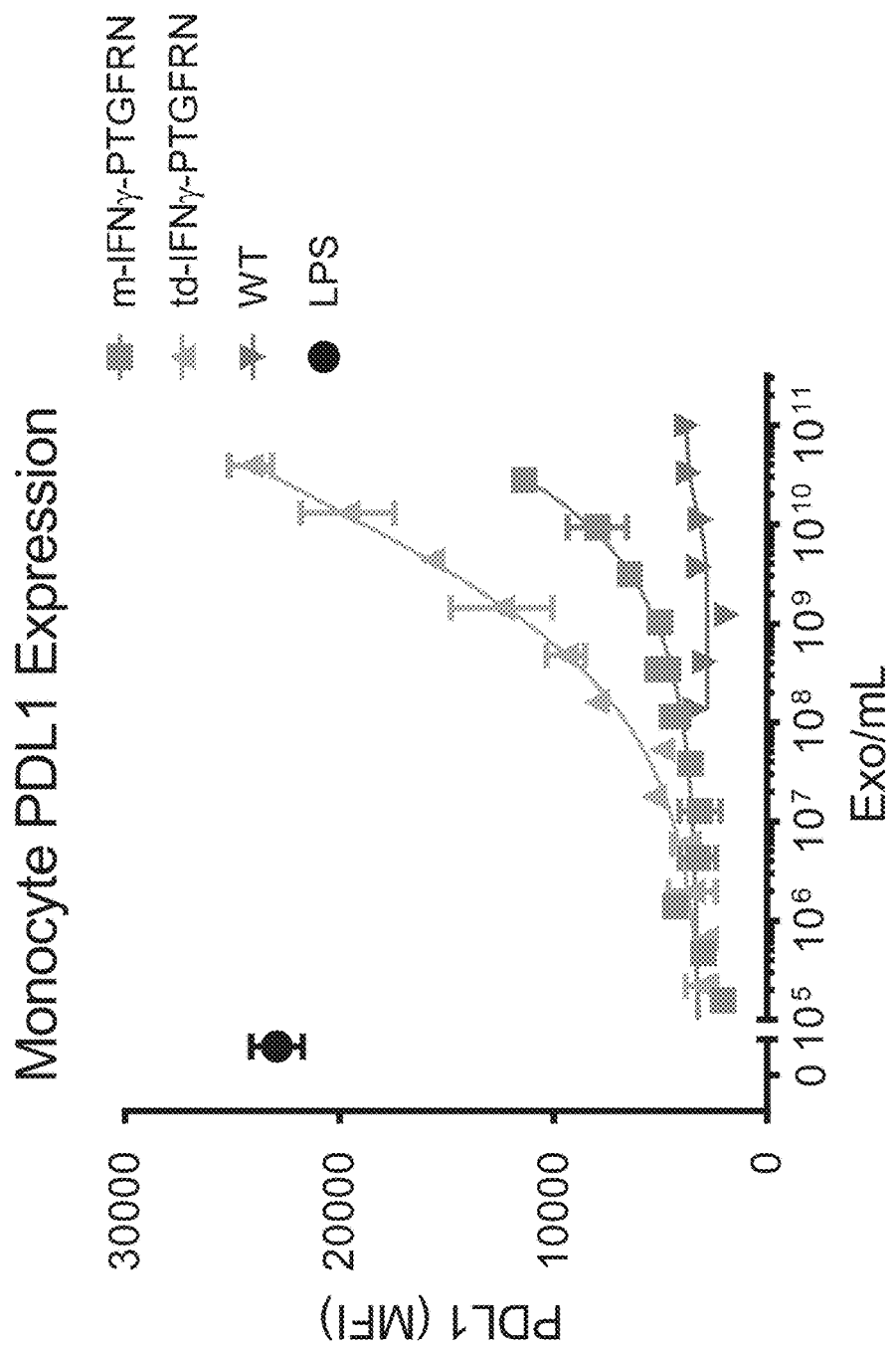
FIG. 33 shows the monocyte PD-L1 expression after addition of native exosomes (WT), monomeric IFNγ PTGFRN exosomes (m-IFNγ-PTGFRN), and tandem dimer IFNγ PTGFRN exosomes (td-IFNγ-PTGFRN) respectively. LPS-induced PD-L1 activation was used as positive control.

Human monomeric and tandem dimer PTGFRN-IFNγ exosomes were incubated with human PBMCs for 24 hours at increasing concentrations. Monocyte activation was measured by PD-L1 expression, a downstream surface protein induced by IFNγ signaling. As shown in FIG. 33, native HEK293SF exosomes (WT) failed to induce PD-L1 expression, while both monomeric and tandem dimer IFNγ PTGFRN exosomes induced PD-L1 in a dose-dependent manner, with greater activation by the tandem dimer IFNγ PTGFRN exosomes. Exosome-mediated PD-L1 activation was comparable to LPS-induced activation (FIG. 33). These data demonstrate that a soluble cytokine, in either monomeric or dimeric format, can be functionally expressed on the surface of an exosome and induce immune cell activation. The use of IFNγ expressing exosomes in immuno-oncology may be useful for the induction of NK and T-cell responses against tumor cells.

Example 12: IL-15 Expressing Exosomes Induce NK Cell Activation

Figure 34:
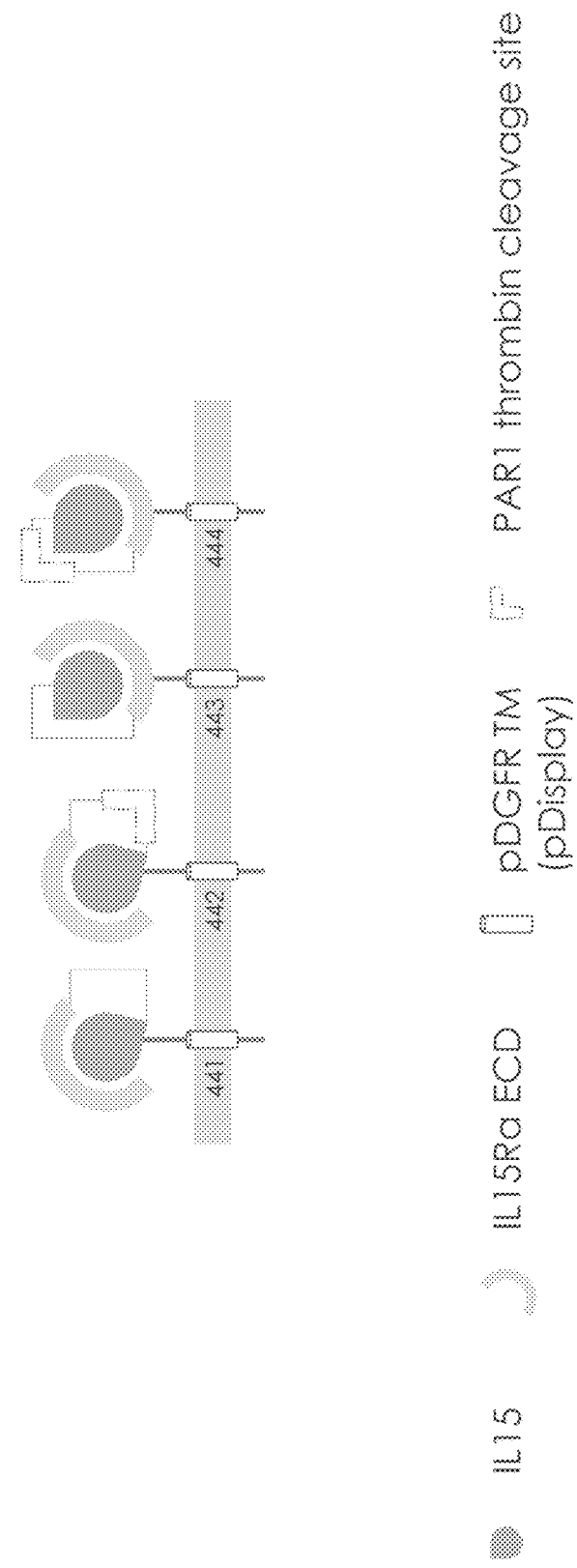
FIG. 34 shows the schematics of 15/IL-15Rt fusion proteins fused to the transmembrane domain of PDGFR.
Figure 35:
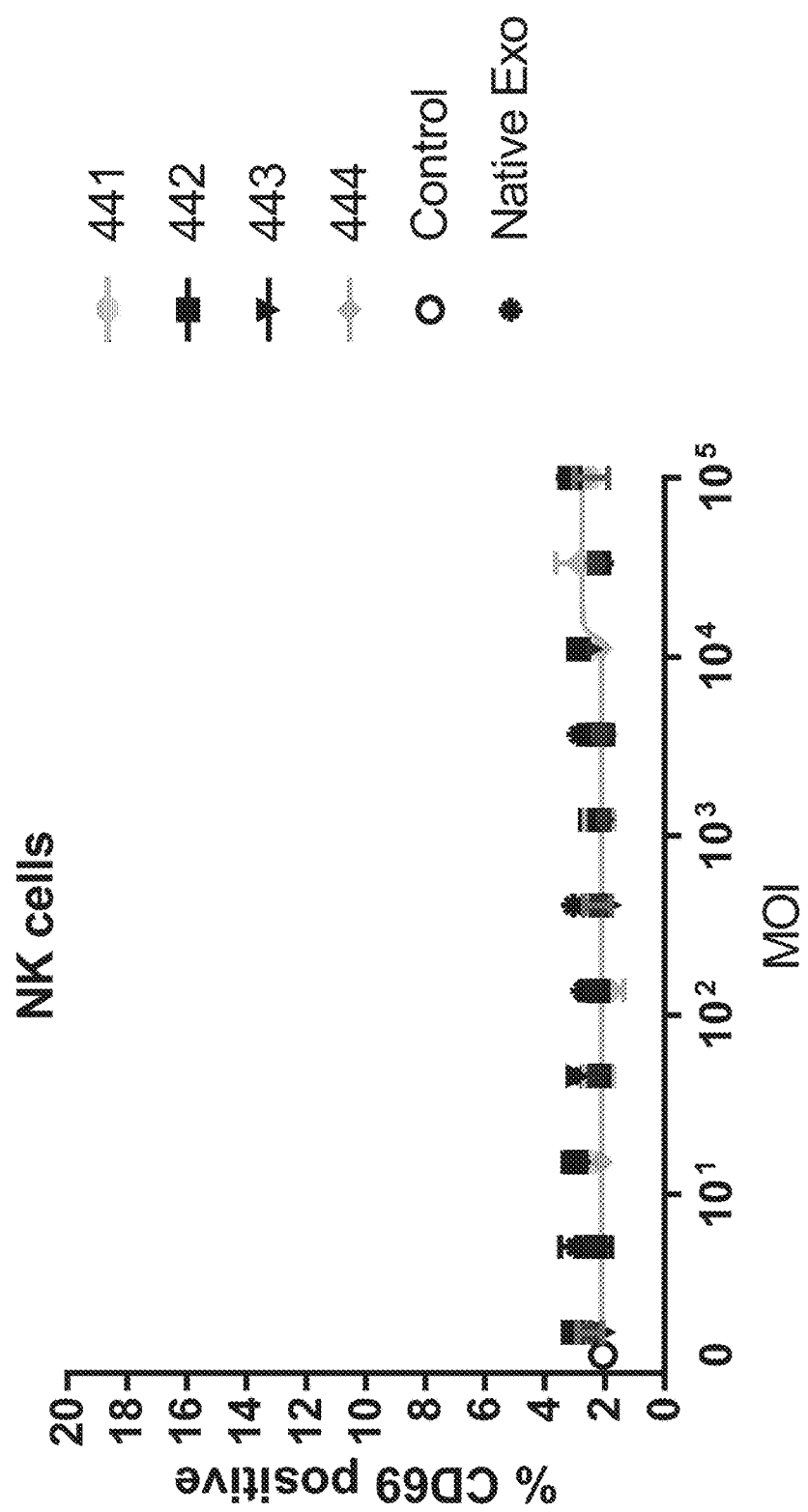
FIG. 35 shows the NK cell activation measured by the percentage of CD69 positive NK cells after the addition of pDisplay IL-15 exosomes.
Figure 36B:
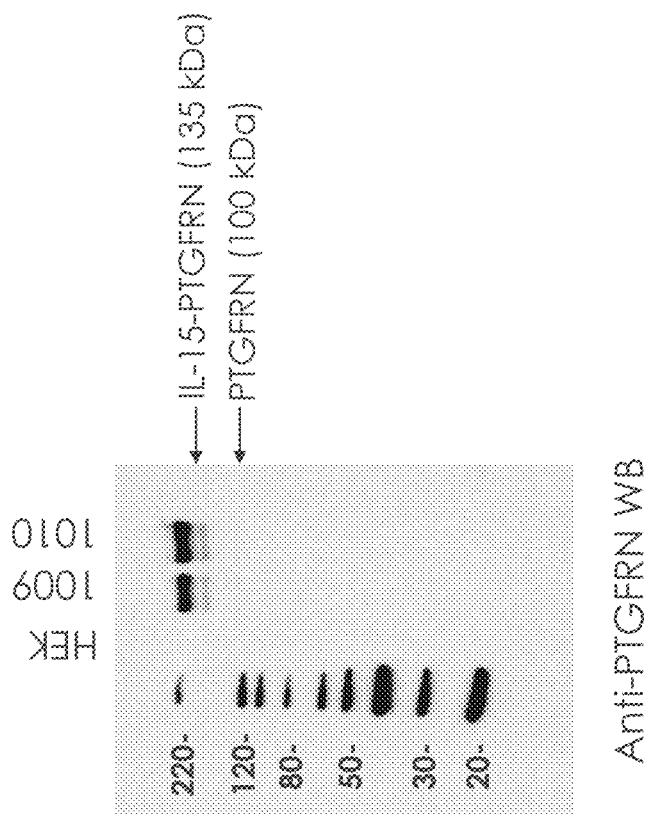
FIG. 36B shows the Western blotting of IL-15 fused to full-length PTGFRN and IL-15 N72D fused to full-length PTGFRN.
Figure 36A:
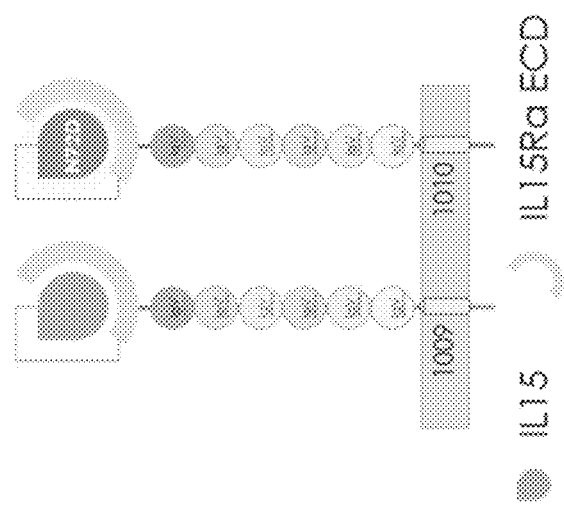
FIG. 36A shows the schematics of IL-15 fused to full-length PTGFRN and IL-15 N72D fused to full-length PTGFRN.
Figure 37:
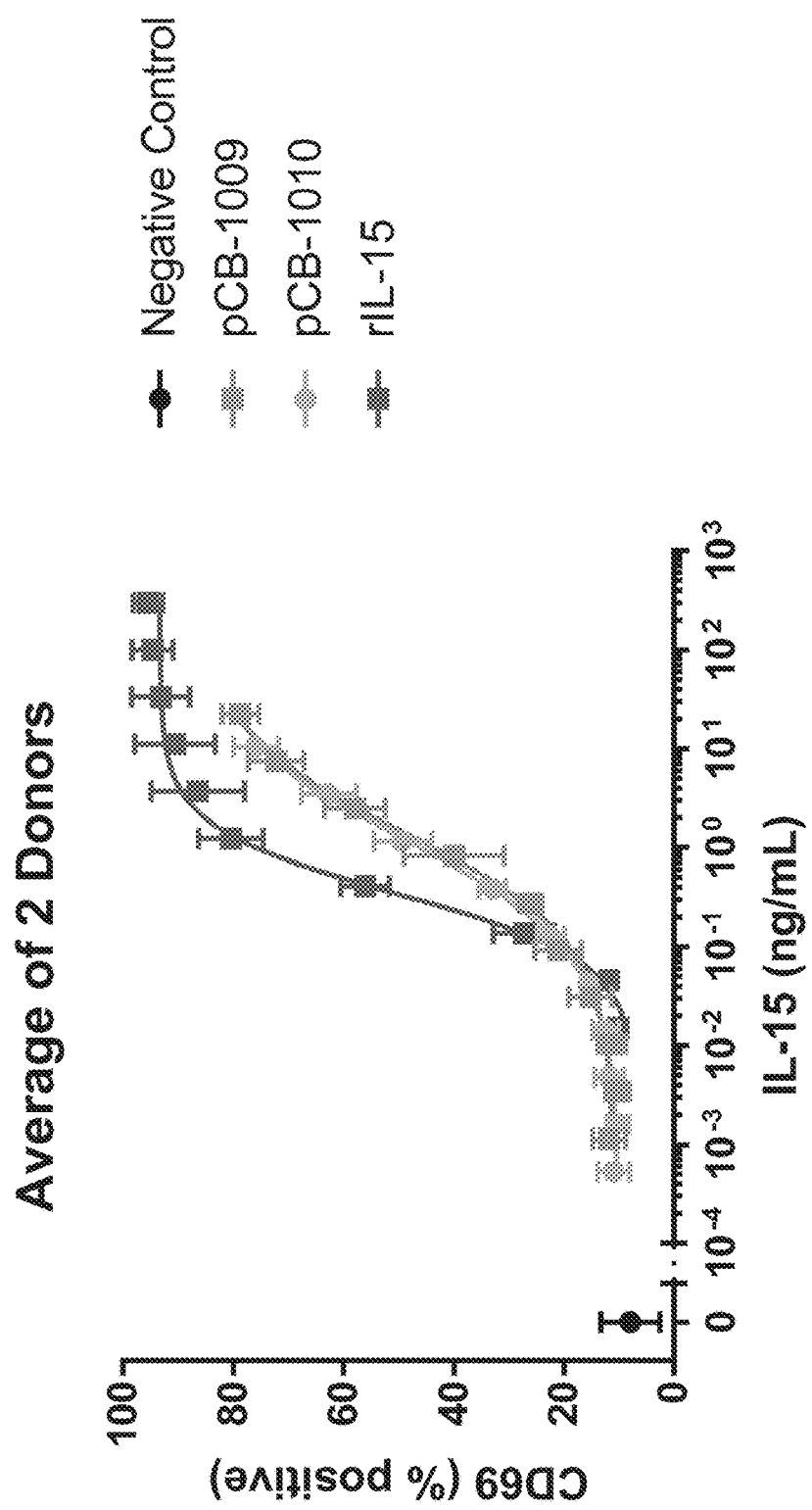
FIG. 37 shows NK cell activation measured by the percentage of CD69 positive NK cells after the addition of IL-15 fused to full-length PTGFRN and IL-15 N72D fused to full-length PTGFRN.

Interleukin 15 (IL-15) is a cytokine produced by mononuclear cells after pathogenic infection. IL-15 can be secreted as a soluble protein or presented as a dimeric membrane-anchored protein bound to IL-15Rα. IL-15 activates NK cells and T-cells and is implicated as a potential therapeutic molecule in immuno-oncology and other immune intervention therapies. IL-15-expressing exosomes were produced by stably transfecting HEK293SF cells with expression plasmids encoding the transmembrane domain of PDGFR (pDisplay) fused to IL-15/IL-15Rα fusion proteins (FIG. 34). Exosomes were purified by Optiprep™ density-gradient ultracentrifugation as described in the Methods above. Purified exosomes were incubated with human PBMCs for 24 hours, and NK cell activation was measured as percent positive for CD69 by flow cytometry. None of the pDisplay IL-15 exosomes induced NK cell activation at doses up to $10^5$ exosomes per cell of PBMC culture (FIG. 35; exosome construct number as in FIG. 34). To investigate whether higher density IL-15 display was required to induce NK cell activation, HEK293SF cells were stably transfected with an expression plasmid encoding IL-15 fused to full-length PTGFRN. Additionally, HEK293SF cells were stably transfected with an expression plasmid encoding a more potent IL-15 fused to full-length PTGFRN (IL-15 N72D, as described in J Immunol. 2009 Sep. 15; 183(6):3598-607; FIG. 36A). Expression was confirmed by anti-PTGFRN Western blotting (FIG. 36B). IL-15 levels were quantified by ELISA (R&D Systems, Catalog No. D1500), normalized to recombinant IL-15 (Biolegend, Catalog No. 570302). The IL-15 PTGFGN exosomes were added to two independent PBMC cultures overnight and compared to concentration-matched recombinant IL-15. All three IL-15 sources induced NK cell activation in PBMCs in a dose-dependent manner as measured by the percentage of NK cells positive for CD69. Furthermore, all constructs were comparable to each other across both donors demonstrating meaningful comparative efficacy (FIG. 37; exosome construct number as in FIG. 36). These data demonstrate that IL-15 can be actively and potently displayed on the surface of exosomes, but this requires high expression levels such as those bestowed by PTGFRN.

Figure 38:
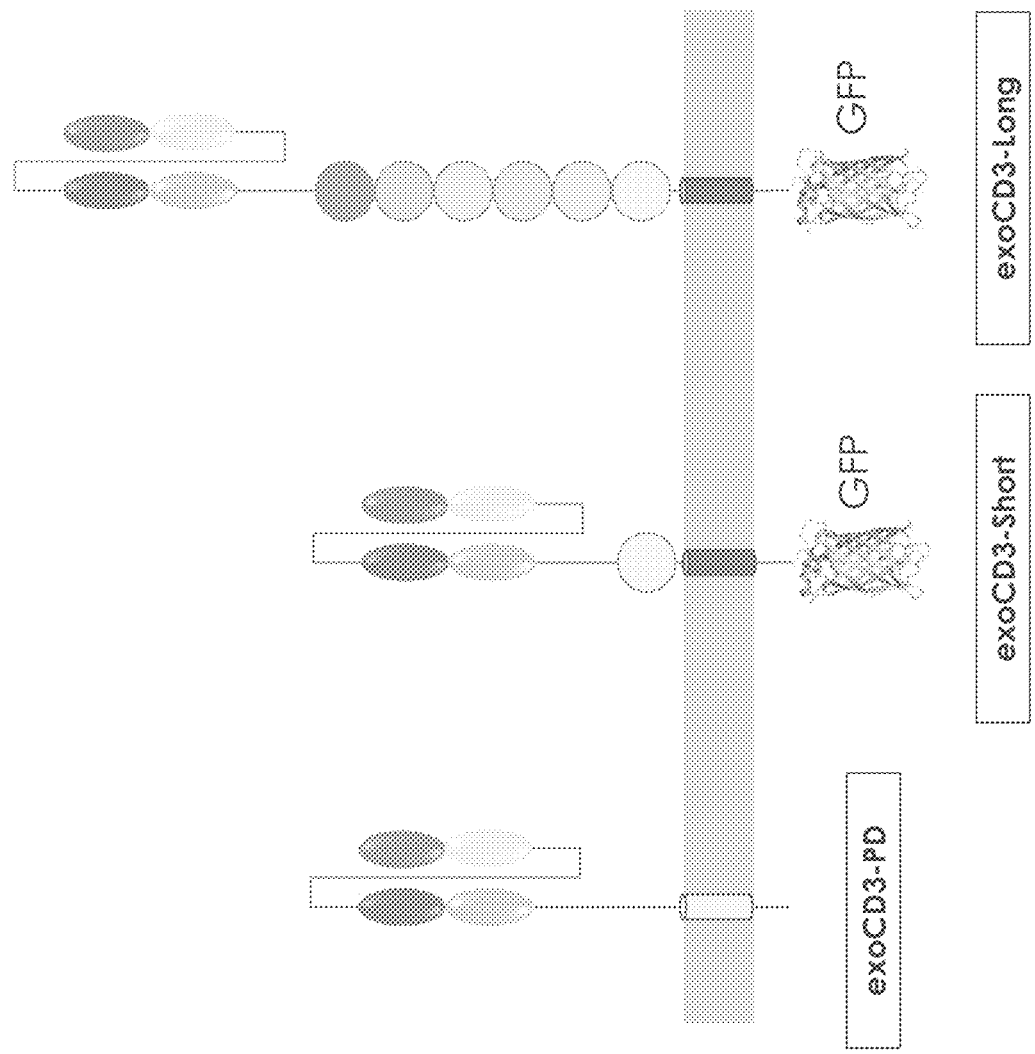
FIG. 38 shows the schematics of anti-CD3 antibody fragment fused to the PDGFR transmembrane region (exoCD3-PD), a full-length PTGFRN (exoCD3-long), and a PTGFRN fragment (exoCD3-short) respectively.
Figure 39:
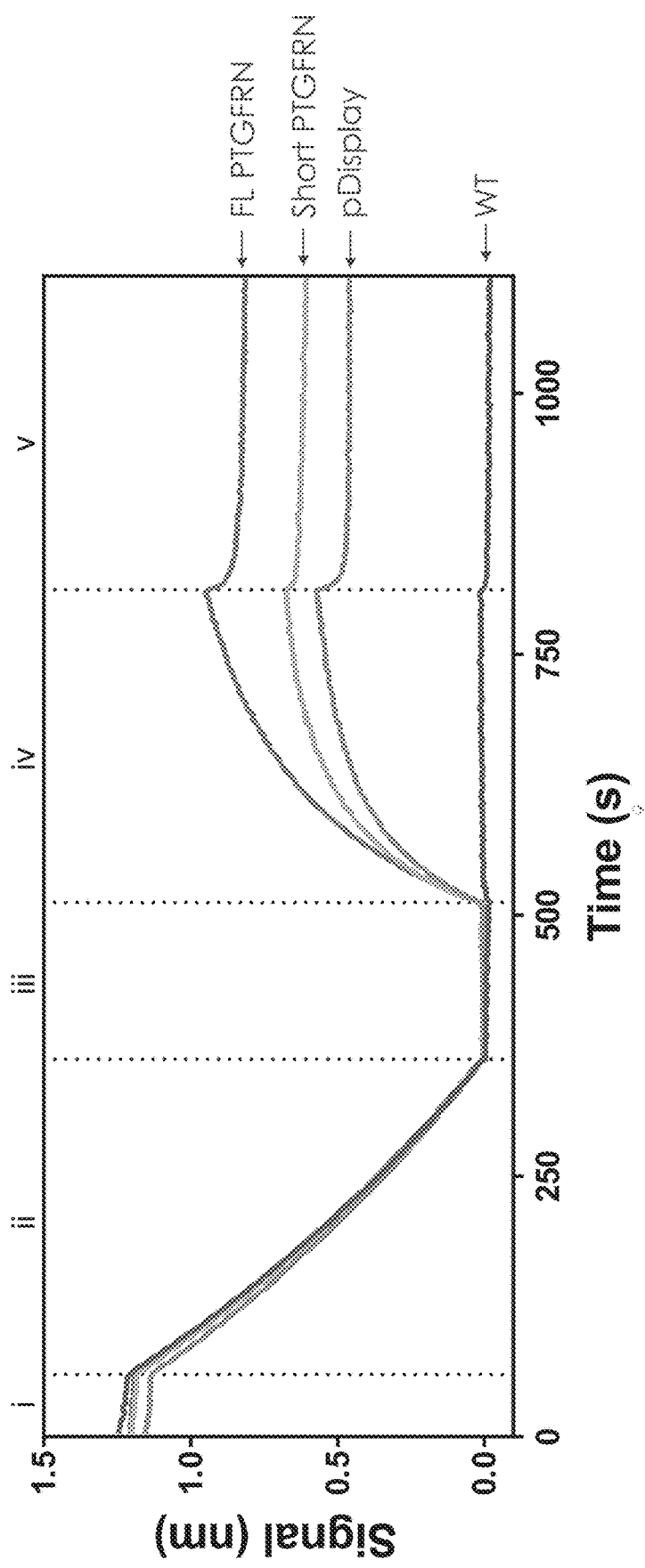
FIG. 39 shows the results of bio-layer interferometry (BLI) after addition of native exosomes (WT), exosomes with anti-CD3 antibody fragment fused to the PDGFR transmembrane region (pDisplay), exosomes with anti-CD3 antibody fragment fused to a full-length PTGFRN (FL PTGFRN), and exosomes with anti-CD3 antibody fragment fused to a PTGFRN fragment (Short PTGFRN), respectively.

Example 13: Exosomes Displaying Anti-CD-3 Antibody Fragments on a PTGFRN Scaffold Activate T-Cells The results in Example 9 demonstrate that exosomes displaying anti-CD3 antibody fragments can activate T-cells. To determine whether the PTGFRN scaffold supports this activity, anti-CD3 antibody fragments (OKT3 variants) were fused to the PDGFR transmembrane region (exoCD3-PD), full-length PTGFRN (exoCD3-long), or a PTGFRN fragment (exoCD3-short) and stably expressed in HEK293SF cells (FIG. 38). Exosome binding was confirmed by biolayer interferometry (BLI) using an Octet® RED96 (Pall). A CD3 fragment was bound to the BLI probe (FIG. 39, ii), washed (FIG. 39, iii), and the exosome constructs were added (FIG. 39, iv). Exosomes from WT HEK293SF cells did not bind the BLI probe, but all engineered constructs did.

Figure 40A:
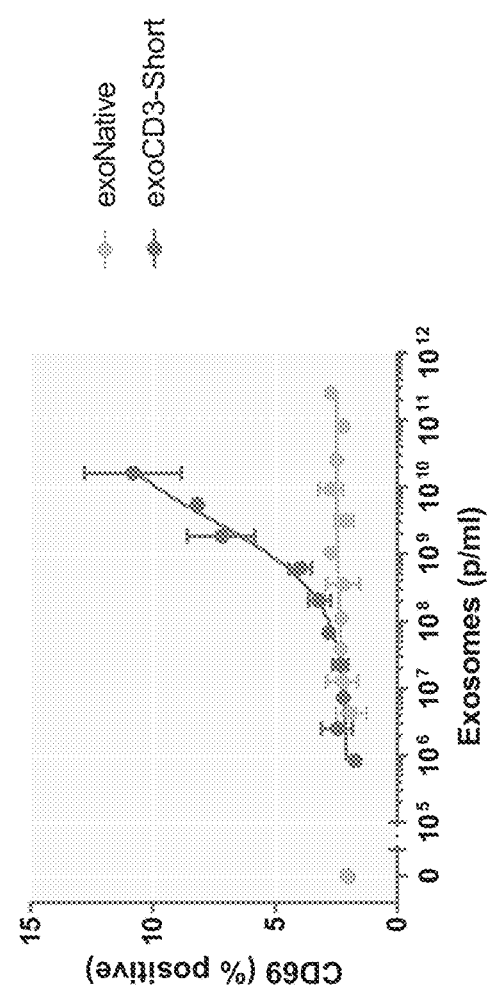
FIG. 40A shows CD4+ T cell activation measured by the percentage of CD69 positive CD4+ T cells after the addition of anti-CD3 antibody fragment.
Figure 40B:
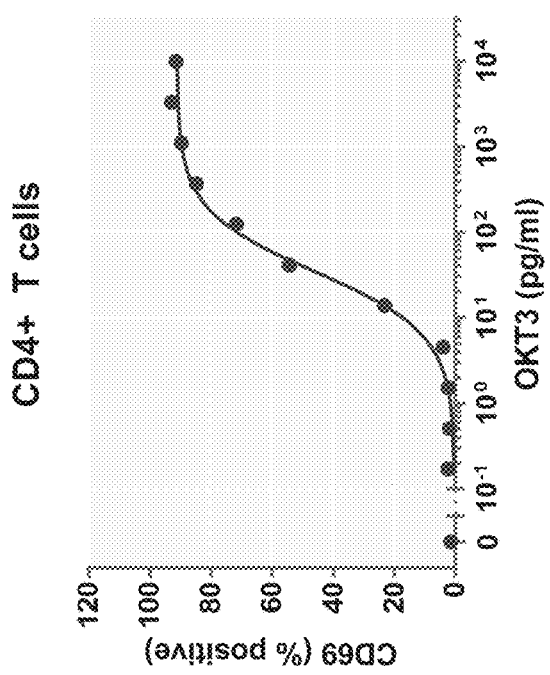
FIG. 40B shows CD4+ T cell activation measured by the percentage of CD69 positive CD4+ T cells after the addition of native exosomes (ex-oNative) and exosomes with anti-CD3 antibody fragment fused to a PTGFRN fragment (exoCD3-Short), respectively.

Both PTGFRN fragments bound to the probe with a greater affinity and remained stably bound (FIG. 39, v). Anti-CD3 display exosomes were tested for in vitro activity. T-cell activation was measured by CD69 positivity on CD4+ T-cells as measured by flow cytometry. In contrast to the unmodified native exosomes (exoNative), the exosomes with anti-CD3 fused to the PTGFRN fragment (exoCD3-short) were effective in activating CD4+ T-cells in vitro (FIG. 40).

Example 14: Exosomes Displaying CD40L are Potent Activators of B-Cells

Figure 41:
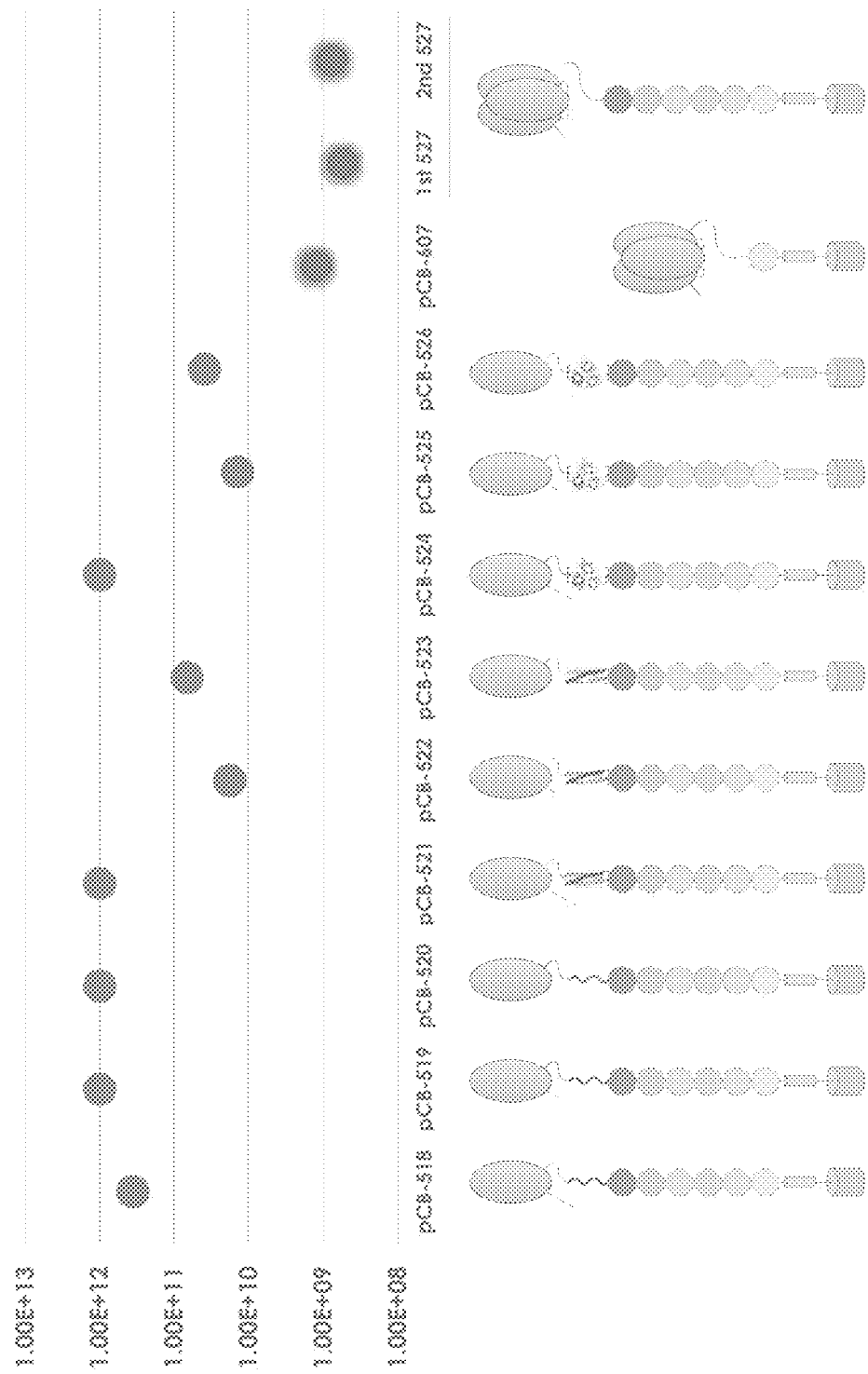
FIG. 41 shows the schematics of CD40L-GFP PTGFRN fusion proteins and the $EC_{50}$ for each construct in the B-cell activation assay measured by CD69 positivity on B-cells.

CD40 ligand (CD40L) is a ligand of the tumor necrosis superfamily (TNFSF) that binds to the costimulatory receptor CD40, which is highly expressed on B-cells and other antigen presenting cells. TNFSF ligand-mediated cellular activation requires the formation of trimeric ligand complexes that form on the cell surface and bind to cognate receptors. To investigate whether exosomes displaying different conformations of CD40L on their surface were sufficient to activate B-cells, over 40 different CD40L expression constructs were designed and individually transfected in HEK293SF cells. CD40L was expressed as a fusion to the transmembrane domain of PDGFR, full-length PTGFRN, and a short single-domain fragment of PTGFRN (FIG. 41A, bottom). CD40L-GFP PTGFRN fusions were expressed as a monomer (pCB-518 to pCB-526) or as a forced trimer (pCB-607 and pCB-527) (FIG. 41A, bottom). To promote trimerization of monomeric CD40L, constructs were designed which expressed a fusion to multimerization domains from TRAF2 (pCB-521 to pCB-523) or Collagen XV (pCB-524 to pCB-526). Among the monomeric CD40L constructs, pCB-518/521/524 contained full-length N-terminal stem sequences from endogenous CD40L; pCB-519/522/525 contained a truncated N-terminal stem sequence from endogenous CD40L; and pCB-520/523/526 contained only the soluble portion of CD40L. Each of the engineered exosome populations was incubated with purified B-cells, isolated from human peripheral blood by using RosetteSep™ Human B Cell Enrichment Cocktail (Stemcell Technologies #15064) and B-cell activation was measured by CD69 positivity on B-cells by flow cytometry. The $EC_{50}$ for each of the constructs was calculated as a function of particles concentration of cell culture and is plotted in the graph shown in FIG. 41, top. Interestingly, all of the monomeric CD40L constructs had modest potency, while the trimeric constructs were at least ten-fold more potent than the monomers (FIG. 41, top). These results demonstrate that monomeric CD40L is a poor activator of B-cells when presented on the surface of exosomes, but that forced trimeric CD40L can induce robust B-cell activation. Furthermore, PTGFRN has been shown to form dimeric structures (PCT/US2018/048026), suggesting that higher order multimeric structures may be forming on the exosome surface to further promote target engagement and immune cell activation.

The results shown in FIG. 41 all employed exosomes containing luminal GFP fused to the C-terminus of PTGFRN. With the goal of generating a tag-less CD40L exosome, the same trimeric CD40L-PTGFRN construct as the lead construct pCB-527 but lacking the C-terminal GFP was stably expressed in HEK293SF cells (pCB-766). The absolute concentration of CD40L on the surface of the engineered exosomes was quantified using ELISA (R&D Systems, Catalog No., DCDL40), as shown in Table 10, below.

TABLE 10

| EC50 | pCB-0766 | pCB-0527 | rhCD40L |
|---|---|---|---|
| particles/mL | 6.63E+08 | 4.53E+08 | N/A |
| ng/mL | 1.68 | 1.89 | 28.51 |

The purified CD40L-PTGFRN exosomes were tested in B-cell activation assays as described above, compared to concentration-matched recombinant human CD40L (Biolegend, Catalog No. 591702). The GFP-containing and the tag-less CD40L exosomes were comparable B-cell activators when measured as a function of particle number or CD40L concentration (FIG. 42A), and both exosome preparations were more potent than concentration-matched CD40L (FIG. 42B). Native, non-engineered exosomes from HEK293SF cells failed to activate B-cells, demonstrating that the engineered CD40L trimeric constructs on the exosome surface were sufficient to potently activate B-cells.

Figure 43A:
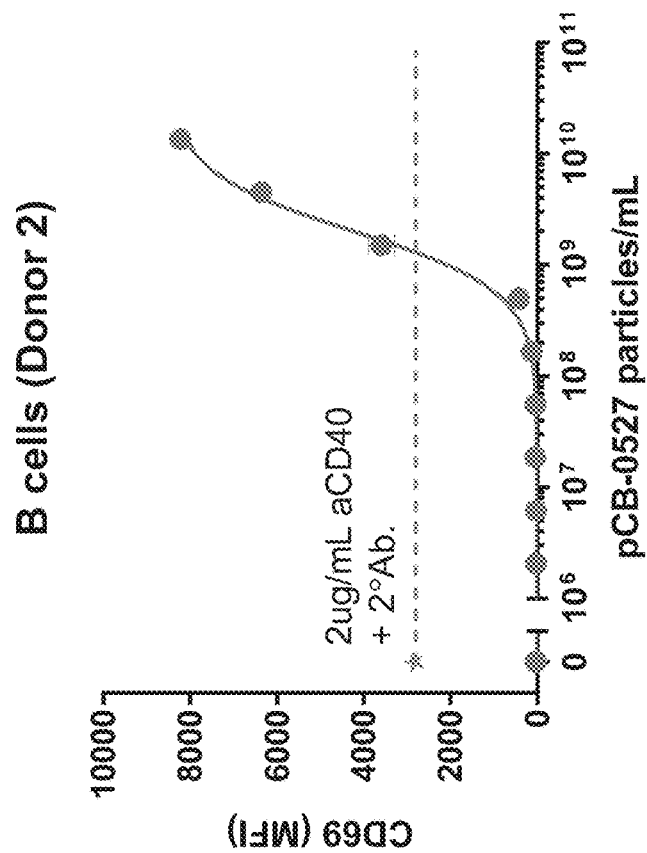
FIG. 43A shows B cell activation in Donor 1 measured by the percentage of CD69 positive B cells after the addition of exosomes with trimeric CD40L-PTGFRN constructs pCB-527.
Figure 43B:
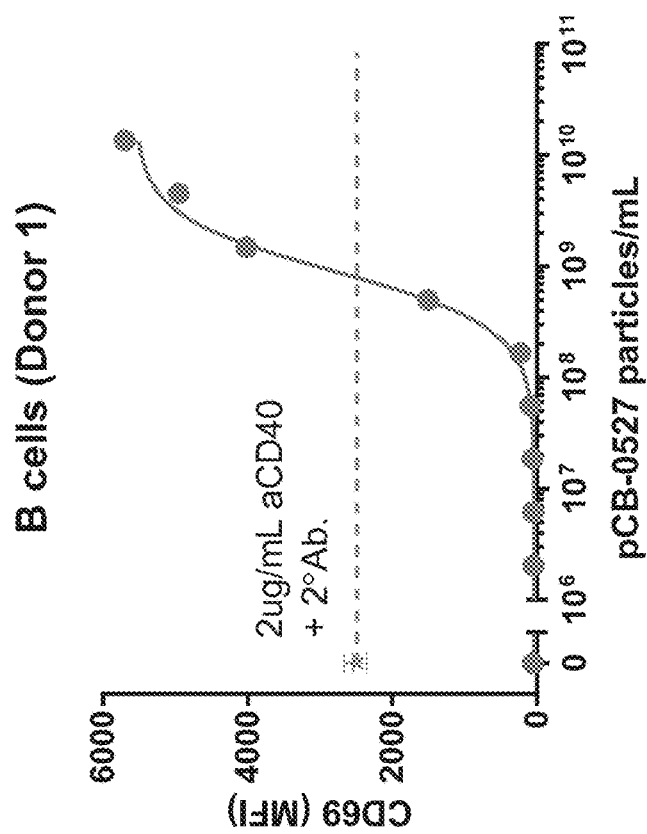
FIG. 43B shows B cell activation in Donor 2 measured by the percentage of CD69 positive B cells after the addition of exosomes with trimeric CD40L-PTGFRN constructs pCB-527.

An alternative modality to agonize CD40 and activate B-cells is to use an agonistic antibody cross-linked with a secondary antibody. To compare the potency of trimeric CD40L-expressing exosomes to an agonistic CD40L antibody, PBMC cultures were incubated with 2 g/ml anti-CD40L antibody (Biolegend®; Clone 5C3) with a secondary cross-linking antibody (JacksonImmuno Research, Catalog No. 115-006-071). Maximal B-cell activation is shown as the dotted line in FIGS. 43A and 43B. pCB-527 exosomes (PTGFRN-trimeric CD40L-GFP) induced a greater maximal B-cell activation than the cross-linked agonistic antibody in two independent donor PBMC pools (FIGS. 43A and 43B) demonstrating superiority of trimeric CD40L exosomes in activating immune cells.

Example 15: Simultaneous Display of Multiple Immuno-Oncology Molecules on Individual Exosomes The previous examples demonstrate that individual immune-modulating proteins can be displayed on the surface of an exosome and induce functional changes in one or more immune cell types. In certain applications, the use of combinatorially engineered exosomes may be required, i.e., an exosome containing more than one molecule on the exosome surface, each of which is capable of signaling a distinct immune cell pathway. HEK293SF cells were stably transfected with a plasmid expressing both PTGFRN-IL-12 and PTGFRN-CD40L fusion proteins. Exosomes were isolated and purified as described above. Exosomes from unmodified HEK293SF cells were used as negative controls.

To demonstrate simultaneous loading of different ligands, a pull-down co-stain assay was developed:
Reagents:
Dynabeads (Thermofisher Exosome-Streptavidin Isolation/Detection Reagent, Catalog No. 10608D): $1\times10^7$ beads/mL, 50% slurry
Isolation buffer: 0.5% BSA/PBS (1:4 from 2% BSA)
Block buffer: 2% BSA/PBS (1 gr/50 mL, filter)
Wash 0.5 ml beads with 0.5 ml isolation buffer and resuspend in 0.5 mL isolation buffer
Add 1 g biotinylated capture antibody (2.2 ul of 0.5 ug/ul stock)
1 hr rotation, RT
Wash 500 μl isolation buffer
Resuspend in 500 μl block buffer, 10 min rotation RT
Incubate in 500 μl isolation buffer ($1\times10^7$ beads/mL, 50% slurry)
Store at 4 C A. Exosome Capture and Flow
    1×10⁵ beads per sample (10 μl beads, 20 μl slurry)
    50,000 exosomes per bead; 5×10⁹ exosomes per sample
        (1.2×10⁹ exosomes/μL stock)
    5 μl of each fluorescently labeled detection antibody for flow
    Mix 5×10⁹ exosomes+20 μl Dynabeads slurry+0.7 ml 0.1% BSA/PBS
Procedure:
1. 120 μl slurry beads, remove sup, add 0.7 ml block buffer, mix, rotate 10 min RT, remove sup
2. Suspend beads in 0.7 ml isolation buffer+25.2 μl exosomes, rotate ON @ 4C
3. Next day: quick spin exosomes and beads, 5 sec
4. Place tube on magnet, remove sup
5. Block in 700 μl, 10 min rotate RT
6. Place tube on magnet, remove sup
7. Resuspend in 600 μl isolation buffer: 6×100 μl per tube
8. Add 1 μl labeled detection antibody, mix, incubate 30 min @ 4C in dark
9. Spin 2 min @ 500 g, remove sup
10. Wash 2× isolation buffer
11. Resuspend in 200 μl isolation buffer, run flow.

Figure 44A:
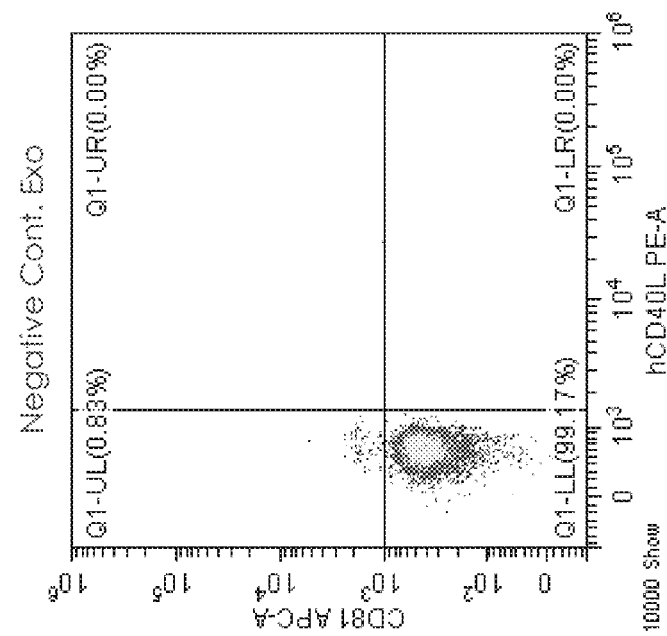
FIG. 44A shows the FACS analysis of native exosomes isolated with anti-CD40L-decorated beads and labeled with fluorescent antibodies against IL-12 and CD40L.
Figure 44B:
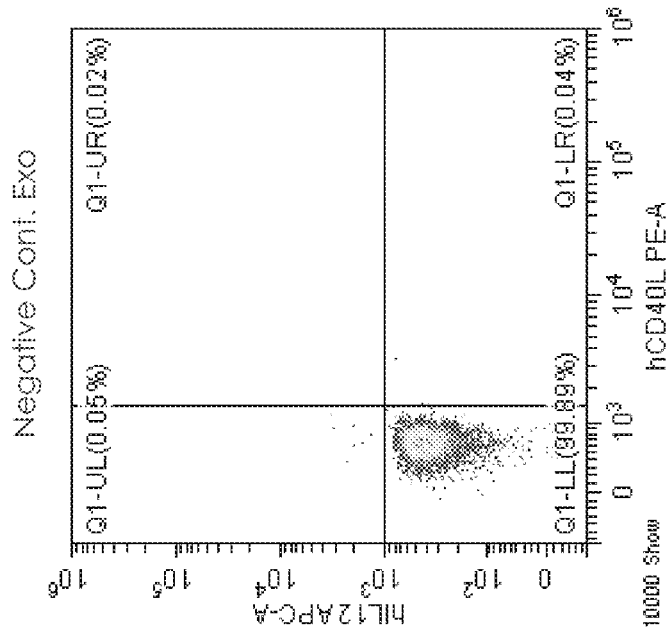
FIG. 44B shows the FACS analysis of native exosomes isolated with anti-CD40L-decorated beads and labeled fluorescent antibodies with against CD81 and CD40L.
Figure 45B:
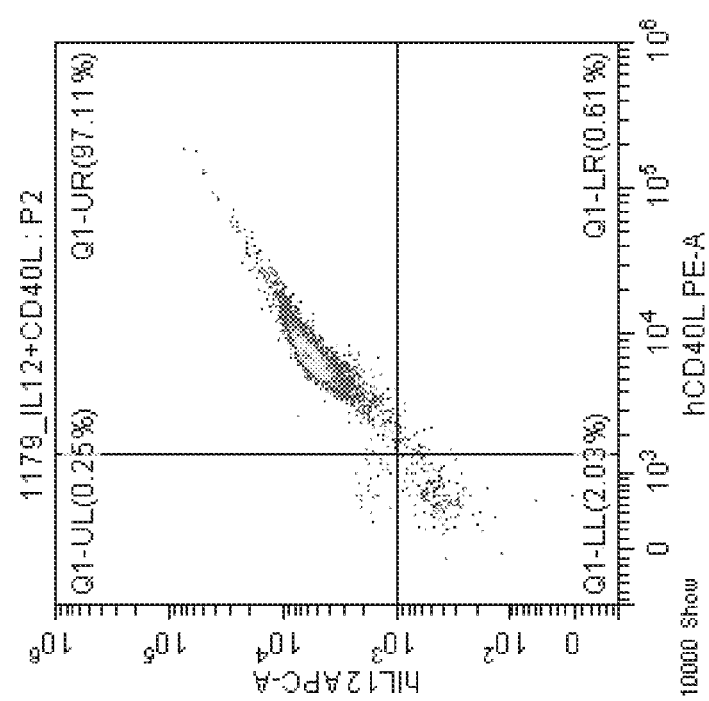
FIG. 45B shows the FACS analysis of PTGFRN-CD40L/IL-12 double engineered exosomes isolated with anti-CD40L-decorated beads and labeled with fluorescent antibodies against IL-12 and CD40L.
Figure 45A:
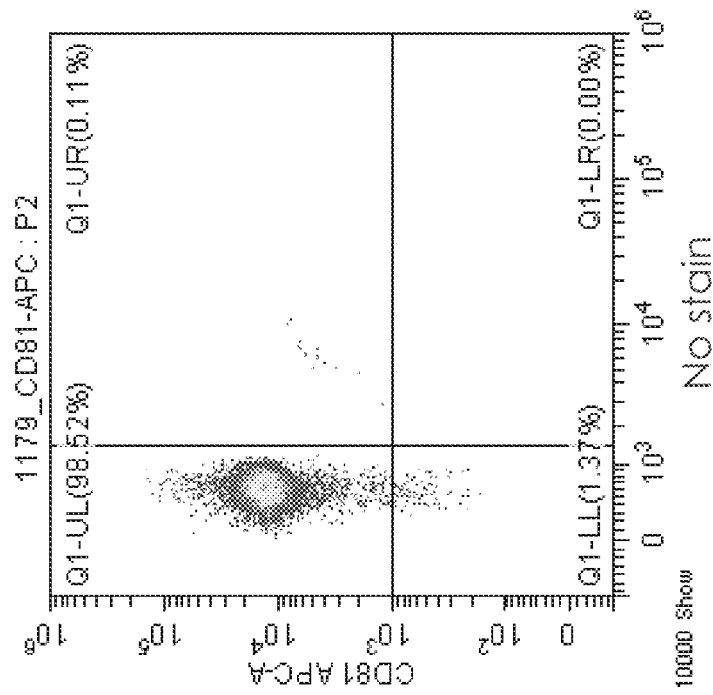
FIG. 45A shows the FACS analysis of PTGFRN-CD40L/IL-12 double engineered exosomes isolated with anti-CD40L-decorated beads and labeled with fluorescent antibody against CD81.
Figure 46B:
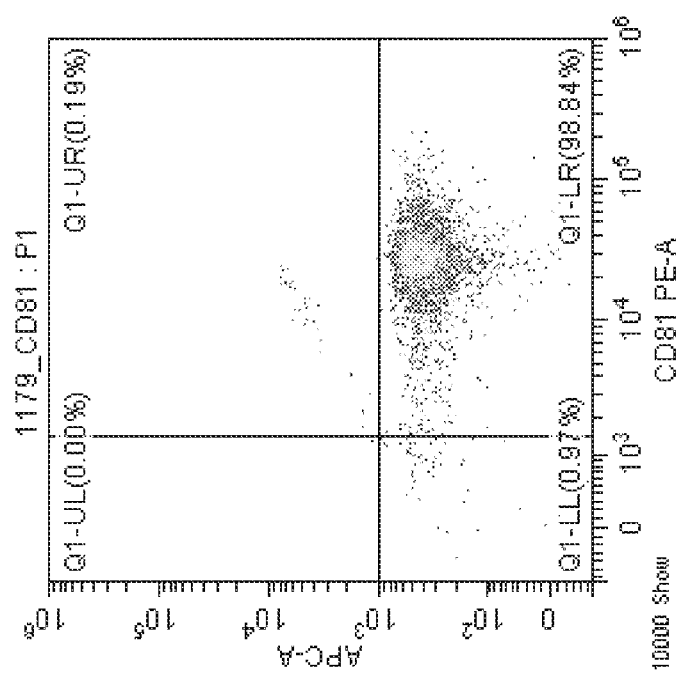
FIG. 46B shows the FACS analysis of PTGFRN-CD40L/IL-12 double engineered exosomes isolated with anti-IL-12-decorated beads and labeled with fluorescent antibody against CD81.
Figure 46A:
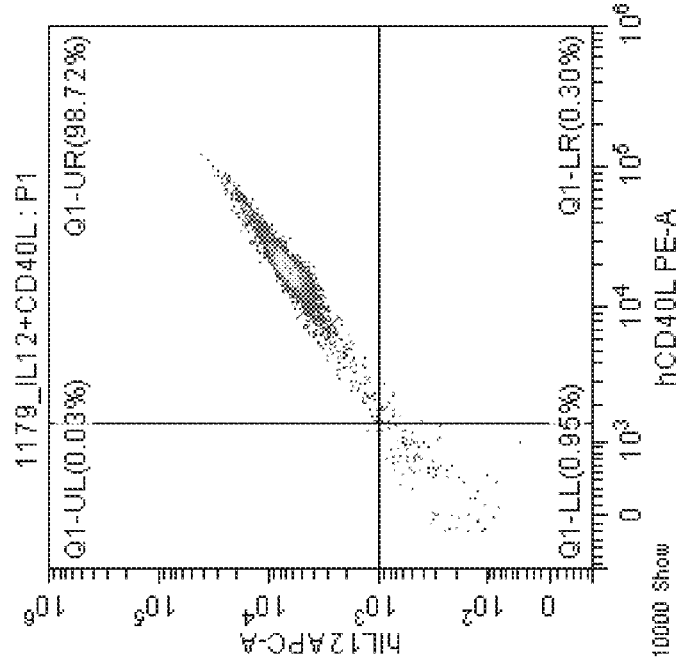
FIG. 46A shows the FACS analysis of PTGFRN-CD40L/IL-12 double engineered exosomes isolated with anti-IL-12-decorated beads and labeled with fluorescent antibodies against IL-12 and CD40L.

Native exosomes were isolated with anti-CD40L-decorated beads and labeled fluorescent antibodies against IL-12 and CD40L (FIG. 44A) or CD81, an exosome marker present on native and engineered exosomes, and CD40L (FIG. 44B). The CD40L beads did not pull down any of the native exosomes, since no fluorescent signal was detected for IL-12, CD40L or CD81. In contrast, PTGFRN-CD40L/IL-12 double engineered exosomes were incubated with anti-CD40L beads and isolated as above. Staining for CD81 (FIG. 45A), IL-12 or CD40L (FIG. 45B) were all detected with the engineered exosomes (greater than 97% of counted beads), indicating that CD40L-mediated isolation could also isolate IL-12 exosomes. Similarly, anti-IL-12-decorated beads were incubated with the IL-12/CD40L engineered exosomes and stained for IL-12, CD40L, and CD81. Greater than 98% of all beads were positive for both CD40L and IL-12 or for CD81 (FIGS. 46A and 46B), demonstrating that the exosomes contained both IL-12 and CD40L on their surface.

Figure 47B:
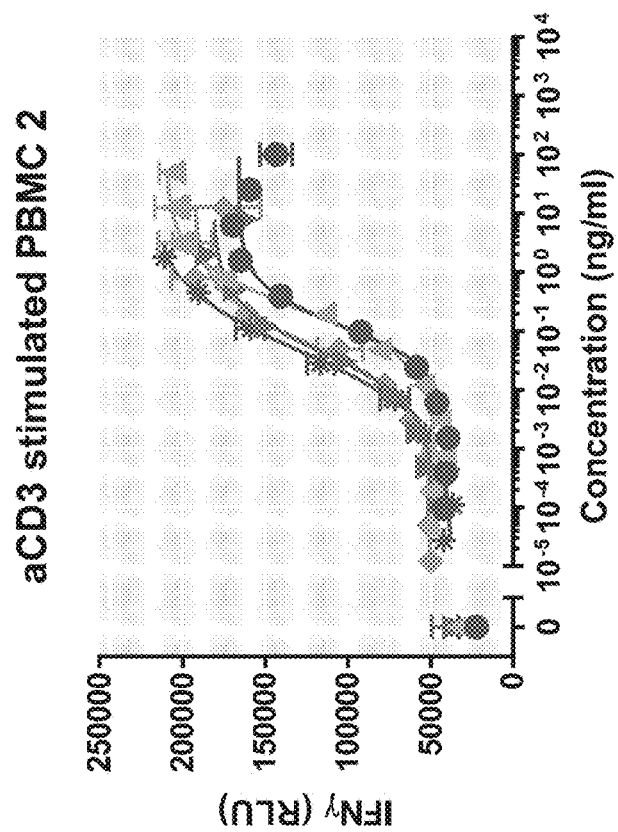
FIG. 47B shows the IFNγ response in Donor 2 human PBMCs after addition of recombinant IL-12, recombinant IL-12 mixed with recombinant CD40L, PTGFRN-IL-12 exosomes, double-positive PTGFRN-CD40L/IL-12 exosomes, and a mixture of PTGFRN-IL-12 exosomes and PTGFRN-CD40L exosomes, respectively.
Figure 47A:
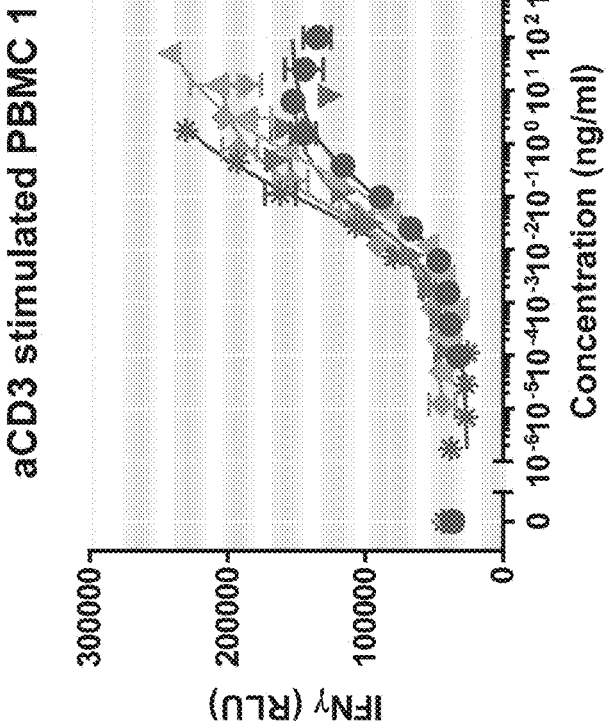
FIG. 47A shows the IFNγ response in Donor 1 human PBMCs after addition of recombinant IL-12, recombinant IL-12 mixed with recombinant CD40L, PTGFRN-IL-12 exosomes, double-positive PTGFRN-CD40L/IL-12 exosomes, and a mixture of PTGFRN-IL-12 exosomes and PTGFRN-CD40L exosomes, respectively.
Figure 49B:
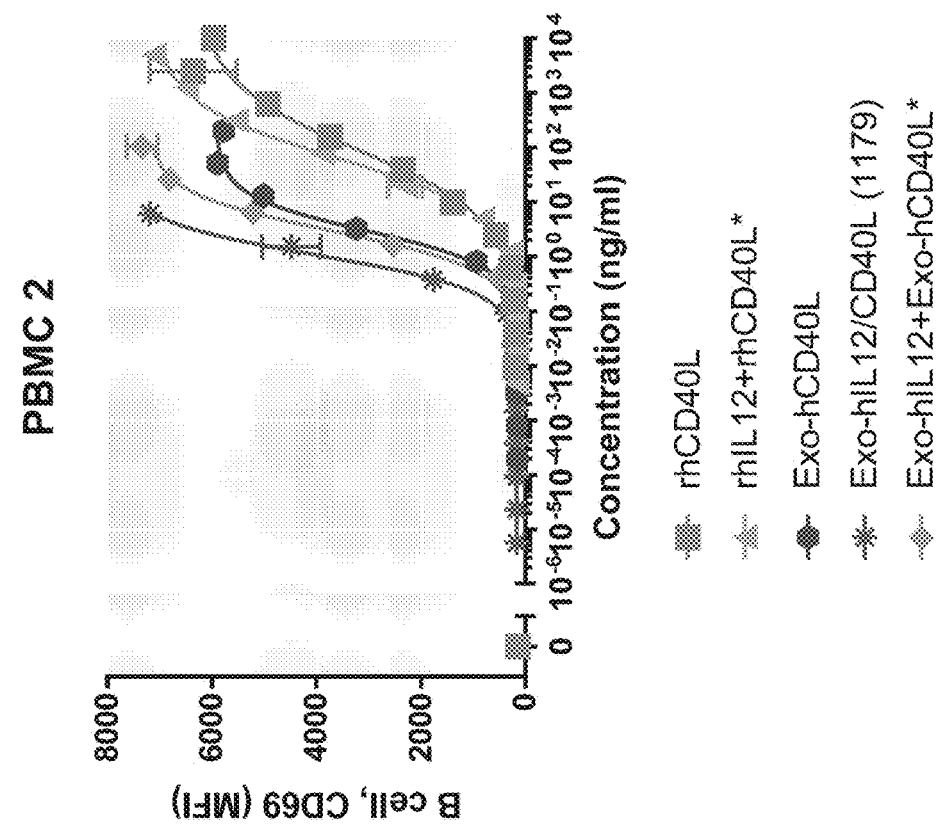
FIG. 49B shows the B cell activation in Donor 2 human PBMCs after addition of recombinant CD40L, recombinant IL-12 mixed with recombinant CD40L, PTGFRN-CD40L exosomes, double-positive PTGFRN-CD40L/IL-12 exosomes, and a mixture of PTGFRN-IL-12 exosomes and PTGFRN-CD40L exosomes, respectively.
Figure 49A:
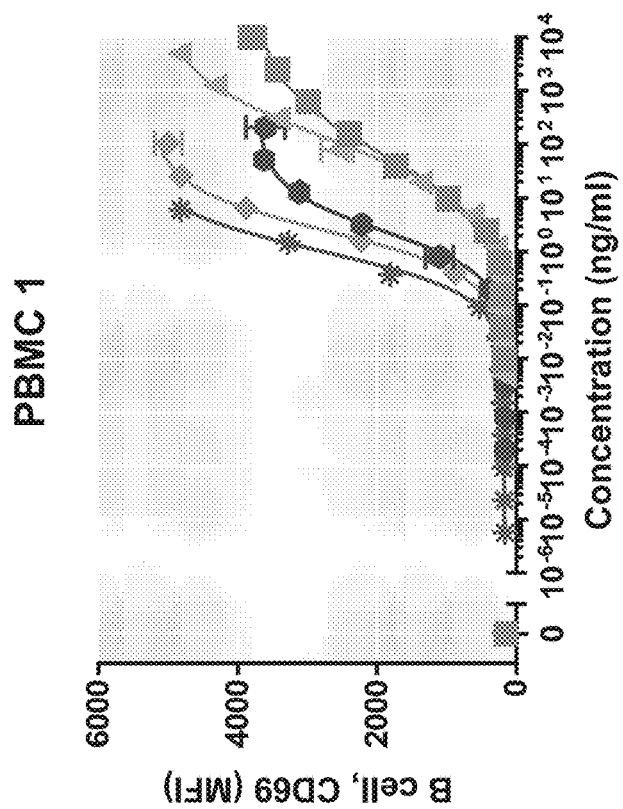
FIG. 49A shows the B cell activation in Donor 1 human PBMCs after addition of recombinant CD40L, recombinant IL-12 mixed with recombinant CD40L, PTGFRN-CD40L exosomes, double-positive PTGFRN-CD40L/IL-12 exosomes, and a mixture of PTGFRN-IL-12 exosomes and PTGFRN-CD40L exosomes, respectively.

IL-12 and CD40L concentration was quantified by ELISA (Abcam Catalog No. ab119517) for testing the engineered exosomes for potency in vitro. Equal concentrations of recombinant IL-12, recombinant IL-12 mixed with recombinant CD40L, PTGFRN-IL-12 exosomes, double-positive PTGFRN-CD40L/IL-12 exosomes, or a mixture of PTGFRN-IL-12 exosomes and PTGFRN-CD40L exosomes were added to human PBMCs at increasing concentrations (rhIL-12—BioLegend, Catalog No. 573004; rhCD40L—Biolegend, Catalog No. 591702). The cells were co-stimulated with anti-CD3 antibody, and IFNγ production was measured by (PerkinElmer, Catalog No. AL217C). As shown in FIGS. 47A and 47B, all IL-12-containing exosome preparations elicited an IFNγ response comparable to the recombinant cytokines. Calculation of the EC50 for the various conditions revealed that exosome-associated IL-12 was more potent than concentration-matched IL-12, whether expressed singly or combinatorially on the exosome surface (FIG. 48). Similar results were achieved with recombinant CD40L and singly or doubly engineered CD40L exosomes in the context of B-cell activation (FIGS. 49A and B). Again, the CD40L engineered exosomes were more potent than the soluble recombinant cytokine, and in this case the doubly engineered exosomes were the most potent construct tested in the assay (FIG. 50).

Figure 51A:
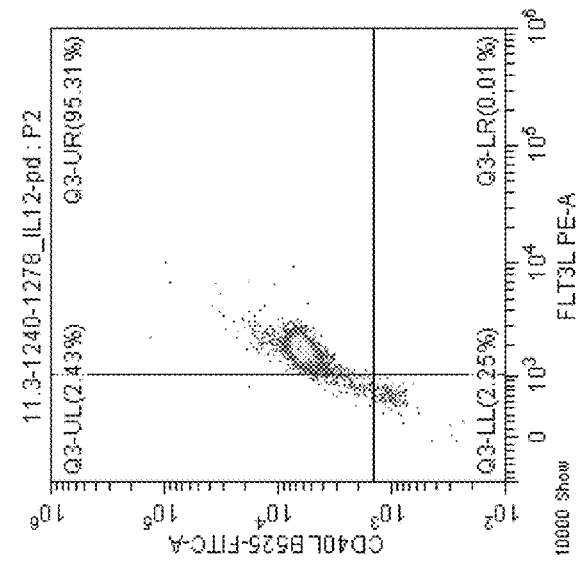
FIG. 51A shows the FACS analysis of PTGFRN-CD40L/IL-12/FLT3L triple engineered exosomes isolated with anti-IL-12-decorated beads and labeled with fluorescent antibodies against IL-12 and CD40L.
Figure 51B:
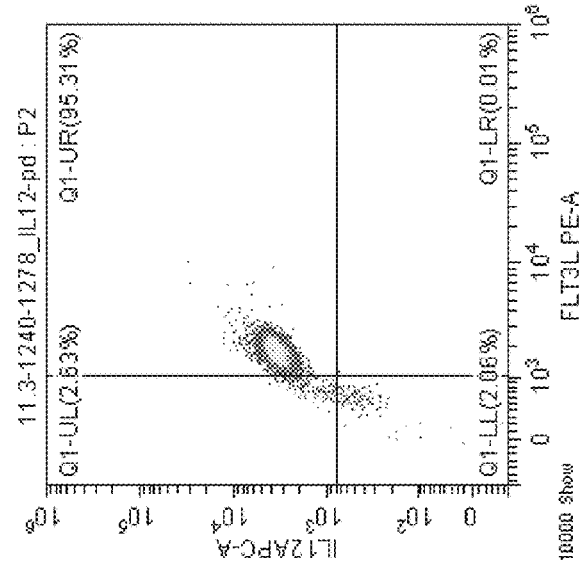
FIG. 51B shows the FACS analysis of PTGFRN-CD40L/IL-12/FLT3L triple engineered exosomes isolated with anti-IL-12-decorated beads and labeled with fluorescent antibodies against IL-12 and FLT3L.
Figure 51C:
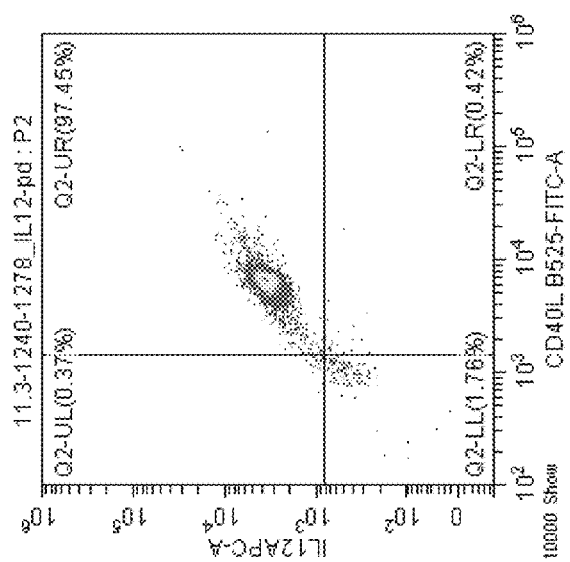
FIG. 51C shows the FACS analysis of PTGFRN-CD40L/IL-12/FLT3L triple engineered exosomes isolated with anti-IL-12-decorated beads and labeled with fluorescent antibodies against CD40L and FLT3L.
Figure 52A:
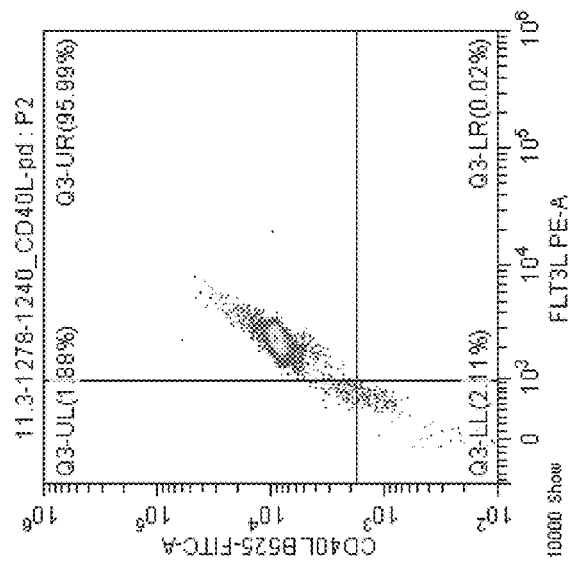
FIG. 52A shows the FACS analysis of PTGFRN-CD40L/IL-12/FLT3L triple engineered exosomes isolated with anti-CD40L-decorated beads and labeled with fluorescent antibodies against IL-12 and CD40L.
Figure 52B:
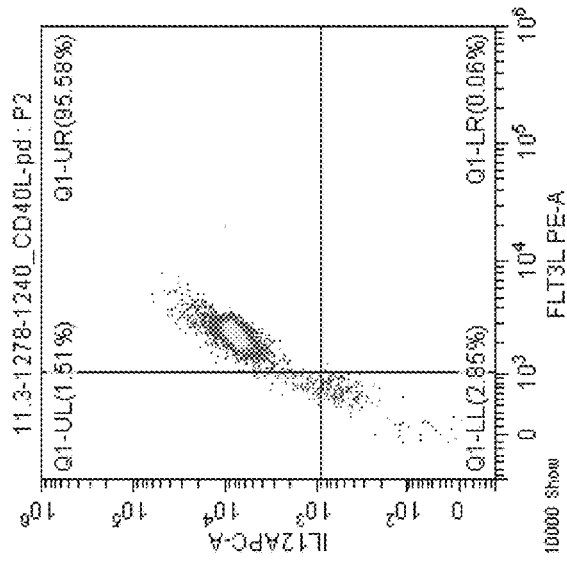
FIG. 52B shows the FACS analysis of PTGFRN-CD40L/IL-12/FLT3L triple engineered exosomes isolated with anti-CD40L-decorated beads and labeled with fluorescent antibodies against IL-12 and FLT3L.
Figure 52C:
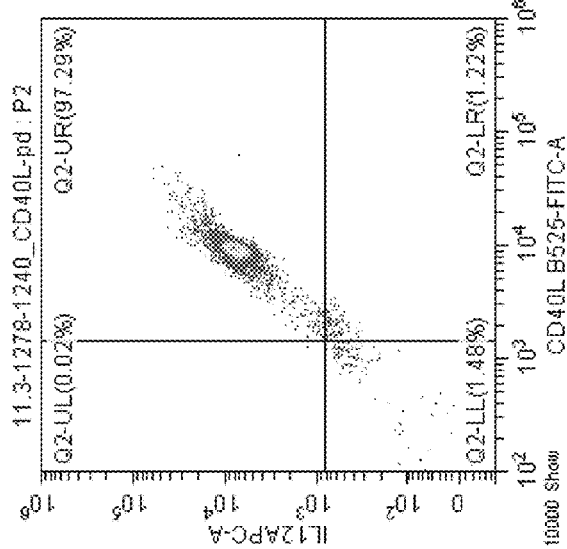
FIG. 52C shows the FACS analysis of PTGFRN-CD40L/IL-12/FLT3L triple engineered exosomes isolated with anti-CD40L-decorated beads and labeled with fluorescent antibodies against CD40L and FLT3L.

To further explore the possibility of combinatorial surface display exosomes, HEK293SF cells were stably transfected with three independent constructs expressing either PTGFRN-IL-12, PTGFRN-CD40L, or PTGFRN-FLT3L fusion proteins. Exosomes were purified and isolated by the affinity bead methods as described above, but were also interrogated for the presence of surface FLT3L using an anti-FLT3L-PE conjugated antibody. Exosomes isolated with anti-IL-12 beads were doubly positive for IL-12 and CD40L (FIG. 51A), IL-12 and FLT3L (FIG. 51B), and CD40L and FLT3L (FIG. 51C). Exosomes isolated with anti-CD40L beads were doubly positive for IL-12 and CD40L (FIG. 52A), IL-12 and FLT3L (FIG. 52B), and CD40L and FLT3L (FIG. 52C), confirming that individual exosomes expressed each of the three immunomodulatory ligands. These results demonstrate that multiply engineered immuno-modulatory exosomes are a feasible therapeutic modality, and that they are comparable or more potent than soluble cytokines in immune cell activation.

Although the foregoing invention has been described in some detail by way of illustration and example for purposes of clarity of understanding, it is readily apparent to those of ordinary skill in the art in light of the teachings of this disclosure that certain changes and modifications can be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

SEQUENCE LISTING

>SEQ ID NO: 1
MFHVSFRYIFGLPPLILVLLPVASSDCDIEGKDGKQYESVLMVSIDQLLDSMKEIGSNCLNNEFNFFKRHICDANK
EGMPLFRAARKLRQFLKMNSTGDFDLHLLKVSEGTTILLNCTGQVKGRKPAALGEAQPTKSLEENKSLKEQKKLND
LCFLKRLLQEIKTCWNKILMGTKEHSAGGGGSDYKDDDDKGGGGSGPIFNASVHSDTPSVIRGDLIKLFCIITVEG
AALDPDDMAFDVSWFAVHSFGLDKAPVLLSSLDRKGIVTTSRRDWKSDLSLERVSVLEFLLQVHGSEDQDFGNYYC
SVTPWVKSPTGSWQKEAEIHSKPVFITVKMDVLNAFKYPLLIGVGLSTVIGLLSCLIGYCSSHWCCKKEVQETRRE
RRRLMSMEMD

SEQUENCE LISTING

>SEQ ID NO: 2
MPHVSFRYIFGLPPLILVLLPVASSDCDIEGKDGKQYESVLMVSIDQLLDSMKEIGSNCLNNEFNFFKRHICDANK
EGMFLFRAARKLRQFLKMNSTGDFDLHLLKVSEGTTILLNCTGQVKGRKPAALGEAQPTKSLEENKSLKEQKKLND
LCFLKRLLQEIKTCWNKILMGTKEHSAGGGGSGGGGSGPIFNASVHDTPSVIRGDLIKLFCIITVEGAALDPDDM
AFDVSWFAVHSFGLDKAPVLLSSLDRKGIVTTSRRDWKSDLSLERVSVLEFLLQVHGSEDQDFGNYYCSVTPWVKS
PTGSWQKEAEIHSKPVFITVKMDVLNAFKYPLLIGVGLSTVIGLLSCLIGYCSSHWCCKKEVQETRRERRRLMSME
MD

>hIL-12-PTGFRN; 871 (SEQ ID NO: 3)
MCHQQLVISW FSLVFLASPL VAIWELKKDV YVVELDWYPD APGEMVVLTC DTPEEDGITW TLDQSSEVLG
SGKTLTIQVK EFGDAGQYTC HKGGEVLSHS LLLLHKKEDG IWSTDILKDQ KEPKNKTFLR CEAKNYSGRF
TCWWLTTIST DLTFSVKSSR GSSDPQGVTC GAATLSAERV RGDNKEYEYS VECQEDSACP AAEESLPIEV
MVDAVHKLKY ENYTSSFFIR DIIKPDPPKN LQLKPLKNSR QVEVSWEYPD TWSTPHSYFS LTFCVQVQGK
SKREKKDRVF TDKTSATVIC RKNASISVRA QDRYYSSSWS EWASVPCSGG SGGGSGGGGS GGGGSGGGSG
GRNLPVATPD PGMFPCLHHS QNLLRAVSNM LQKARQTLEF YPCTSEEIDH EDITKDKTST VEACLPLELT
KNESCLNSRE TSFITNGSCL ASRKTSFMMA LCLSSIYEDL KMYQVEFKTM NAKLLMDPKR QIFLDQNMLA
VIDELMQALN FNSETVPQKS SLEEPDFYKT KIKLCILLHA FRIRAVTIDR VMSYLNASSA GGGGSGGGGS
RVVRVPTATL VRVVGTELVI PCNVSDYDGP SEQNFDWSFS SLGSSFVELA STWEVGFPAQ LYQERLQRGE
ILLRRTANDA VELHIKNVQP SDQGHYKCST PSTDATVQGN YEDTVQVKVL ADSLHVGPSA RPPPSLSLRE
GEPFELRCTA ASASPLHTHL ALLWEVHRGP ARRSVLALTH EGRFHPGLGY EQRYHSGDVR LDTVGSDAYR
LSVSRALSAD QGSYRCIVSE WIAEQGNWQE IQEKAVEVAT VVIQPSVLRA AVPKNVSVAE GKELDLTCNI
TTDRADDVRP EVTWSFSRMP DSTLPGSRVL ARLDRDSLVH SSPHVALSHV DARSYHLLVR DVSKENSGYY
YCHVSLWAPG HNRSWHKVAE AVSSPAGVGV TWLEPDYQVY LNASKVPGFA DDPTELACRV VDTKSGEANV
RFTVSWYYRM NRRSDNVVTS ELLAVMDGDW TLKYGERSKQ RAQDGDFIFS KEHTDTFNFR IQRTTEEDRG
NYYCVVSAWT KQRNNSWVKS KDVFSKPVNI FWALEDSVLV VKARQPKPFF AAGNTFEMTC KVSSKNIKSP
RYSVLIMAEK PVGDLSSPNE TKYIISLDQD SVVKLENWTD ASRVDGVVLE KVQEDEFRYR MYQTQVSDAG
LYRCMVTAWS PVRGSLWREA ATSLSNPIEI DFQTSGPIFN ASVHSDTPSV IRGDLIKLFC IITVEGAALD
PDDMAFDVSW FAVHSFGLDK APVLLSSLDR KGIVTTSRRD WKSDLSLERV SVLEFLLQVH GSEDQDFGNY
YCSVTPWVKS PTGSWQKEAE IHSKPVFITV KMDVLNAFKY PLLIGVGLST VIGLLSCLIG YCSSHWCCKK
EVQETRRERR RLMSMEMD*

>mIL-12-PTGFRN; 872 (SEQ ID NO: 4)
MCPQKLTISW FAIVLLVSPL MAMWELEKDV YVVEVDWTPD APGETVNLTC DTPEEDDITW TSDQRHGVIG
SGKTLTITVK EFLDAGQYTC HKGGETLSHS HLLLHKKENG IWSTEILKNF KNKTFLKCEA PNYSGRFTCS
WLVQRNMDLK FNIKSSSSSP DSRAVTCGMA SLSAEKVTLD QRDYEKYSVS CQEDVTCPTA EETLPIELAL
EARQQNKYEN YSTSFFIRDI IKPDPPKNLQ MKPLKNSQVE VSWEYPDSWS TPHSYFSLKF FVRIQRKKEK
MKETEEGCNQ KGAFLVEKTS TEVQCKGGNV CVQAQDRYYN SSCSKWACVP CRVRSGGSGG SGGGGGSGGG
GSGGGGSGGRV IPVSGPARCL SQSRNLLKTT DDMVKTAREK LKHYSCTAED IDHEDITRDQ TSTLKTCLPL
ELHKNESCLA TRETSSTTRG SCLPPQKTSL MMTLCLGSIY EDLKMYQTEF QAINAALQNH NHQQIILDKG
MLVAIDELMQ SLNHNGETLR QKPPVGEADP YRVKMKLCIL LHAFSTRVVT INRVMGYLSS ASAGGGGSGG
GGSRVVRVPT ATLVRVVGTE LVIPCNVSDY DGPSEQNFDW SFSSLGSSFV ELASTWEVGF PAQLYQERLQ
RGEILLRRTA NDAVELHIKN VQPSDQGHYK CSTPSTDATV QGNYEDTQVQ KVLADSLHVG PSARPPPSLS
LREGEPFELR CTAASASPLH THLALLWEVH RGPARRSVLA LTHEGRFHPG LGYEQRYHSG DVRLDTVGSD
AYRLSVSRAL SADQGSYRCI VSEWIAEQGN WQEIQEKAVE VATVVIQPSV LRAAVPKNVS VAEGKELDLT
CNITTDRADD VRPEVTWSFS RMPDSTLPGS RVLARLDRDS LVHSSPHVAL SHVDARSYHL LVRDVSKENS
GYYYCHVSLW APGHNRSWHK VAEAVSSPAG VGVTWLEPDY QVYLNASKVP GFADDPTELA CRVVDTKSGE
ANVRFTVSWY YRMNRRSDNV VTSELLAVMD GDWTLKYGER SKQRAQDGDF IFSKEHTDTF NFRIQRTTEE
DRGNYYCVVS AWTKQRNNSW VKSKDVFSKP VNIFWALEDS VLVVKARQPK PFFAAGNTFE MTCKVSSKNI
KSPRYSVLIM AEKPVGDLSS PNETKYIISL DQDSVVKLEN WTDASRVDGV VLEKVQEDEF RYRMYQTQVS
DAGLYRCMVT AWSPVRGSLW REAATSLSNP IEIDFQTSGP_IFNASVHSDT PSVIRGDLIK LFCIITVEGA
ALDPDDMAFD VSWFAVHSFG LDKAPVLLSS LDRKGIVTTS RRDWKSDLSL ERVSVLEFLL QVHGSEDQDF
GNYYCSVTPW VKSPTGSWQK EAEIHSKPVF ITVKMDVLNA FKYPLLIGVG LSTVIGLLSC LIGYCSSHWC
CKKEVQETRR ERRRLMSMEM D*

>hIL-12-short PTGFRN; 873 (SEQ ID NO: 5)
MCHQQLVISW FSLVFLASPL VAIWELKKDV YVVELDWYPD APGEMVVLTC DTPEEDGITW TLDQSSEVLG
SGKTLTIQVK EFGDAGQYTC HKGGEVLSHS LLLLHKKEDG IWSTDILKDQ KEPKNKTFLR CEAKNYSGRF
TCWWLTTIST DLTFSVKSSR GSSDPQGVTC GAATLSAERV RGDNKEYEYS VECQEDSACP AAEESLPIEV
MVDAVHKLKY ENYTSSFFIR DIIKPDPPKN LQLKPLKNSR QVEVSWEYPD TWSTPHSYFS LTFCVQVQGK
SKREKKDRVF TDKTSATVIC RKNASISVRA QDRYYSSSWS EWASVPCSGG SGGGSGGGGS GGGGSGGGSG
GRNLPVATPD PGMFPCLHHS QNLLRAVSNM LQKARQTLEF YPCTSEEIDH EDITKDKTST VEACLPLELT
KNESCLNSRE TSFITNGSCL ASRKTSFMMA LCLSSIYEDL KMYQVEFKTM NAKLLMDPKR QIFLDQNMLA
VIDELMQALN FNSETVPQKS SLEEPDFYKT KIKLCILLHA FRIRAVTIDR VMSYLNASSA GGGGSGGGGS
GPIFNASVHS DTPSVIRGDL IKLFCIITVE GAALDPDDMA FDVSWFAVHS FGLDKAPVLL SSLDRKGIVT
TSRRDWKSDL SLERVSVLEF LLQVHGSEDQ DFGNYYCSVT PWVKSPTGSW QKEAEIHSKP VFITVKMDVL
NAFKYPLLIG VGLSTVIGLL SCLIGYCSSH WCCKKEVQET RRERRRLMSM EMD*

>mIL-12-short PTGFRN; 874 (SEQ ID NO: 6)
MCPQKLTISW FAIVLLVSPL MAMWELEKDV YVVEVDWTPD APGETVNLTC DTPEEDDITW TSDQRHGVIG
SGKTLTITVK EFLDAGQYTC HKGGETLSHS HLLLHKKENG IWSTEILKNF KNKTFLKCEA PNYSGRFTCS
WLVQRNMDLK FNIKSSSSSP DSRAVTCGMA SLSAEKVTLD QRDYEKYSVS CQEDVTCPTA EETLPIELAL
EARQQNKYEN YSTSFFIRDI IKPDPPKNLQ MKPLKNSQVE VSWEYPDSWS TPHSYFSLKF FVRIQRKKEK
MKETEEGCNQ KGAFLVEKTS TEVQCKGGNV CVQAQDRYYN SSCSKWACVP CRVRSGGSGG SGGGGGSGGG
GSGGGGSGGRV IPVSGPARCL SQSRNLLKTT DDMVKTAREK LKHYSCTAED IDHEDITRDQ TSTLKTCLPL
ELHKNESCLA TRETSSTTRG SCLPPQKTSL MMTLCLGSIY EDLKMYQTEF QAINAALQNH NHQQIILDKG
MLVAIDELMQ SLNHNGETLR QKPPVGEADP YRVKMKLCIL LHAFSTRVVT INRVMGYLSS ASAGGGGSGG -continued

SEQUENCE LISTING

GGSGPIFNAS VHSDTPSVIR GDLIKLFCII TVEGAALDPD DMAFDVSWFA VHSFGLDKAP VLLSSLDRKG
IVTTSRRDWK SDLSLERVSV LEFLLQVHGS EDQDFGNYYC SVTPWVKSPT GSWQKEAEIH SKPVFITVKM
DVLNAFKYPL LIGVGLSTVI GLLSCLIGYC SSHWCCKKEV QETRRERRRL MSMEMD*

SEQ ID NO: 7 PTGFRN_IFN_gamma monomer
MGRLASRPLLLALLSLALCRGQDPYVKEAENLKKYFNAGHSDVADNGTLFLGILKNWKEESDRKIMQSQIVSFYFK
LFKNFKDDQSIQKSVETIKEDMNVKFFNSNKKKRDDFEKLTNYSVTDLNVQRKAIHELIQVMAELSPAAKTGSAGG
GGSGGGGSRVVRVPTATLVRVVGTELVIPCNVSDYDGPSEQNFDWSFSSLGSSFVELASTWEVGFPAQLYQERLQR
GEILLRRTANDAVELHIKNVQPSDQGHYKCSTPSTDATVQGNYEDTVQVKVLADSLHVGPSARPPPSLSLREGEPF
ELRCTAASASPLHTHLALLWEVHRGPARRSVLALTHEGRFHPGLGYEQRYHSGDVRLDTVGSDAYRLSVSRALSAD
QGSYRCIVSEWIAEQGNWQEIQEKAVEVATVVIQPSVLRAAVPKNVSVAEGKELDLTCNITTDRADDVRPEVTWSF
SRMPDSTLPGSRVLARLDRDSLVHSSPHVALSHVDARSYHLLVRDVSKENSGYYYCHVSLWAPGHNRSWHKVAEAV
SSPAGVGVTWLEPDYQVYLNASKVPGFADDPTELACRVVDTKSGEANVRFTVSWYYRMNRRSDNVVTSELLAVMDG
DWTLKYGERSKQRAQDGDFIFSKEHTDTFNFRIQRTTEEDRGNYYCVVSAWTKQRNNSWVKSKDVFSKPVNIFWAL
EDSVLVVKARQPKPFFAAGNTFEMTCKVSSKNIKSPRYSVLIMAEKPVGDLSSPNETKYIISLDQDSVVKLENWTD
ASRVDGVVLEKVQEDEFRYRMYQTQVSDAGLYRCMVTAWSPVRGSLWREAATSLSNPIEIDFQTSGPIFNASVHSD
TPSVIRGDLIKLFCIITVEGAALDPDDMAFDVSWFAVHSFGLDKAPVLLSSLDRKGIVTTSRRDWKSDLSLERVSV
LEFLLQVHGSEDQDFGNYYCSVTPWVKSPTGSWQKEAEIHSKPVFITVKMDVLNAFKYPLLIGVGLSTVIGLLSCL
IGYCSSHWCCKKEVQETRRERRRLMSMEMD SEQ ID NO: 8 PTGFRN_IFN_gamma dimer
MGRLASRPLLLALLSLALCRGQDPYVKEAENLKKYFNAGHSDVADNGTLFLGILKNWKEESDRKIMQSQIVSFYFK
LFKNFKDDQSIQKSVETIKEDMNVKFFNSNKKKRDDFEKLTNYSVTDLNVQRKAIHELIQVMAELSPAAKTGGSGG
SGGSGGSGGQDPYVKEAENLKKYFNAGHSDVADNGTLFLGILKNWKEESDRKIMQSQIVSFYFKLFKNFKDDQSIQK
SVETIKEDMNVKFFNSNKKKRDDFEKLTNYSVTDLNVQRKAIHELIQVMAELSPAAKTGSAGGGGSGGGGSRVVRV
PTATLVRVVGTELVIPCNVSDYDGPSEQNFDWSFSSLGSSFVELASTWEVGFPAQLYQERLQRGEILLRRTANDAV
ELHIKNVQPSDQGHYKCSTPSTDATVQGNYEDTVQVKVLADSLHVGPSARPPPSLSLREGEPFELRCTAASASPLH
THLALLWEVHRGPARRSVLALTHEGRFHPGLGYEQRYHSGDVRLDTVGSDAYRLSVSRALSADQGSYRCIVSEWIA
EQGNWQEIQEKAVEVATVVIQPSVLRAAVPKNVSVAEGKELDLTCNITTDRADDVRPEVTWSFSRMPDSTLPGSRV
LARLDRDSLVHSSPHVALSHVDARSYHLLVRDVSKENSGYYYCHVSLWAPGHNRSWHKVAEAVSSPAGVGVTWLEP
DYQVYLNASKVPGFADDPTELACRVVDTKSGEANVRFTVSWYYRMNRRSDNVVTSELLAVMDGDWTLKYGERSKQR
AQDGDFIFSKEHTDTFNFRIQRTTEEDRGNYYCVVSAWTKQRNNSWVKSKDVFSKPVNIFWALEDSVLVVKARQPK
PFFAAGNTFEMTCKVSSKNIKSPRYSVLIMAEKPVGDLSSPNETKYIISLDQDSVVKLENWTDASRVDGVVLEKVQ
EDEFRYRMYQTQVSDAGLYRCMVTAWSPVRGSLWREAATSLSNPIEIDFQTSGPIFNASVHSDTPSVIRGDLIKLF
CIITVEGAALDPDDMAFDVSWFAVHSFGLDKAPVLLSSLDRKGIVTTSRRDWKSDLSLERVSVLEFLLQVHGSEDQ
DFGNYYCSVTPWVKSPTGSWQKEAEIHSKPVFITVKMDVLNAFKYPLLIGVGLSTVIGLLSCLIGYCSSHWCCKKE
VQETRRERRRLMSMEMD SEQ ID NO: 9 PTGFRN_IFN_gamma mouse monomer
MGRLASRPLLLALLSLALCRGRHGTVIESLESLNNYFNSSGIDVEEKSLFLDIWRNWQKDGDMKILQSQIISFYLR
LFEVLKDNQAISNNISVIESHLITTFFSNSKAKKDAFMSIAKFEVNNPQVQRQAFNELIRVVHQLLPESSLRSAGG
GGSGGGGSRVVRVPTATLVRVVGTELVIPCNVSDYDGPSEQNFDWSFSSLGSSFVELASTWEVGFPAQLYQERLQR
GEILLRRTANDAVELHIKNVQPSDQGHYKCSTPSTDATVQGNYEDTVQVKVLADSLHVGPSARPPPSLSLREGEPF
ELRCTAASASPLHTHLALLWEVHRGPARRSVLALTHEGRFHPGLGYEQRYHSGDVRLDTVGSDAYRLSVSRALSAD
QGSYRCIVSEWIAEQGNWQEIQEKAVEVATVVIQPSVLRAAVPKNVSVAEGKELDLTCNITTDRADDVRPEVTWSF
SRMPDSTLPGSRVLARLDRDSLVHSSPHVALSHVDARSYHLLVRDVSKENSGYYYCHVSLWAPGHNRSWHKVAEAV
SSPAGVGVTWLEPDYQVYLNASKVPGFADDPTELACRVVDTKSGEANVRFTVSWYYRMNRRSDNVVTSELLAVMDG
DWTLKYGERSKQRAQDGDFIFSKEHTDTFNFRIQRTTEEDRGNYYCVVSAWTKQRNNSWVKSKDVFSKPVNIFWAL
EDSVLVVKARQPKPFFAAGNTFEMTCKVSSKNIKSPRYSVLIMAEKPVGDLSSPNETKYIISLDQDSVVKLENWTD
ASRVDGVVLEKVQEDEFRYRMYQTQVSDAGLYRCMVTAWSPVRGSLWREAATSLSNPIEIDFQTSGPIFNASVHSD
TPSVIRGDLIKLFCIITVEGAALDPDDMAFDVSWFAVHSFGLDKAPVLLSSLDRKGIVTTSRRDWKSDLSLERVSV
LEFLLQVHGSEDQDFGNYYCSVTPWVKSPTGSWQKEAEIHSKPVFITVKMDVLNAFKYPLLIGVGLSTVIGLLSCL
IGYCSSHWCCKKEVQETRRERRRLMSMEMD SEQ ID NO: 10 PTGFRN_IFN_gamma mouse dimer
MGRLASRPLLLALLSLALCRGRHGTVIESLESLNNYFNSSGIDVEEKSLFLDIWRNWQKDGDMKILQSQIISFYLR
LFEVLKDNQAISNNISVIESHLITTFFSNSKAKKDAFMSIAKFEVNNPQVQRQAFNELIRVVHQLLPESSLRSAGG
SGGSGGSGHGTVIESLESLNNYFNSSGIDVEEKSLFLDIWRNWQKDGDMKILQSQIISFYLRLFEVLKDNQAISNN
ISVIESHLITTFFSNSKAKKDAFMSIAKFEVNNPQVQRQAFNELIRVVHQLLPESSLRSAGGGGSGGGGSRVVRVP
TATLVRVVGTELVIPCNVSDYDGPSEQNFDWSFSSLGSSFVELASTWEVGFPAQLYQERLQRGEILLRRTANDAVE
LHIKNVQPSDQGHYKCSTPSTDATVQGNYEDTVQVKVLADSLHVGPSARPPPSLSLREGEPFELRCTAASASPLHT
HLALLWEVHRGPARRSVLALTHEGRFHPGLGYEQRYHSGDVRLDTVGSDAYRLSVSRALSADQGSYRCIVSEWIAE
QGNWQEIQEKAVEVATVVIQPSVLRAAVPKNVSVAEGKELDLTCNITTDRADDVRPEVTWSFSRMPDSTLPGSRVL
ARLDRDSLVHSSPHVALSHVDARSYHLLVRDVSKENSGYYYCHVSLWAPGHNRSWHKVAEAVSSPAGVGVTWLEPD
YQVYLNASKVPGFADDPTELACRVVDTKSGEANVRFTVSWYYRMNRRSDNVVTSELLAVMDGDWTLKYGERSKQRA
QDGDFIFSKEHTDTFNFRIQRTTEEDRGNYYCVVSAWTKQRNNSWVKSKDVFSKPVNIFWALEDSVLVVKARQPKP
FFAAGNTFEMTCKVSSKNIKSPRYSVLIMAEKPVGDLSSPNETKYIISLDQDSVVKLENWTDASRVDGVVLEKVQE
DEFRYRMYQTQVSDAGLYRCMVTAWSPVRGSLWREAATSLSNPIEIDFQTSGPIFNASVHSDTPSVIRGDLIKLFC
IITVEGAALDPDDMAFDVSWFAVHSFGLDKAPVLLSSLDRKGIVTTSRRDWKSDLSLERVSVLEFLLQVHGSEDQD
FGNYYCSVTPWVKSPTGSWQKEAEIHSKPVFITVKMDVLNAFKYPLLIGVGLSTVIGLLSCLIGYCSSHWCCKKEV
QETRRERRRLMSMEMD SEQ ID NO: 11 IL-15 441
MAPRRARGCRTLGLPALLULLLRPPATRGITCPPPMSVEHADIWVKSYSLYSRERYICNSGFKRKAGTSSLTECVL
NKATNVAHWTTPSLKCIRDPALVHQRPAPPSTVTTAGVTPQPESLSPSGKEPAASSPSSNNTAATTAAIVPGSQLM
PSKSPSTGTTEISSHESSHGTPSQTTAKNWELTASASHQPPGVYPQGHSDTTGGSGGGGSGGGGSGGGGSGGGSGGS
NWVNVISDLKKIEDLIQSMHIDATLYTESDVHPSCKVTAMKCFLLELQVISLESGDASIHDTVENLIILANNSLSS

SEQUENCE LISTING

NGNVTESGCKECEELEEKNIKEFLQSFVHIVQMFINTSSADYKDDDDKFEGGGGSGGGGSAVGQDTQEVIVVPHSL
PFKVVVISAILALVVLTIISLIILIMLWQKKPRSGLLTGRT

SEQ ID NO: 12 IL-15 442
MAPRRARGCRTLGLPALLLLLLRPPATRGHHHHHHITCPPPMSVEHADIWVKSYSLYSRERYICNSGFKRKAGTS
SLTECVLNKATNVAHWTTPSLKCIRDPALVHQRPAPPSTVTTAGVTPQPESLSPSGKEPAASSPSSNNTAATTAAI
VPGSQLMPSKSPSTGTTEISSHESSHGTPSQTTAKNWELTASASHQPPGVYPQGHSDTTGGSGGGSGGGGSTLDPR
SFLLRNPNDKYEPFWEDEEKNESGGGGSGGGGSGGSNWVNVISDLKKIEDLIQSMHIDATLYTESDVHPSCKVTAMK
CFLLELQVISLESGDASIHDTVENLIILANNSLSSNGNVTESGCKECEELEEKNIKEFLQSFVHIVQMFINTSSAD
YKDDDDKFEGGGGSGGGGSAVGQDTQEVIVVPHSLPFKVVVISAILALVVLTIISLIILIMLWQKKPRSGLLTGRT

SEQ ID NO: 13 IL-15 443
METDTLLLWVLLLWVPGSTGNWVNVISDLKKIEDLIQSMHIDATLYTESDVHPSCKVTAMKCFLLELQVISLESGD
ASIHDTVENLIILANNSLSSNGNVTESGCKECEELEEKNIKEFLQSFVHIVQMFINTSGGSGGGSGGGGSGGGGSG
GGSGGSITCPPPMSVEHADIWVKSYSLYSRERYICNSGFKRKAGTSSLTECVLNKATNVAHWTTPSLKCIRDPALV
HQRPAPPSTVTTAGVTPQPESLSPSGKEPAASSPSSNNTAATTAAIVPGSQLMPSKSPSTGTTEISSHESSHGTPS
QTTAKNWELTASASHQPPGVYPQGHSDTTSADYKDDDDKFEGGGGSGGGGSAVGQDTQEVIVVPHSLPFKVVVISA
ILALVVLTIISLIILIMLWQKKPRSGLLTGRT

SEQ ID NO: 14 IL-15 444
METDTLLLWVLLLWVPGSTGNWVNVISDLKKIEDLIQSMHIDATLYTESDVHPSCKVTAMKCFLLELQVISLESGD
ASIHDTVENLIILANNSLSSNGNVTESGCKECEELEEKNIKEFLQSFVHIVQMFINTSDYKDDDDKGGSGGGSGGG
GSTLDPRSFLLRNPNDKYEPFWEDEEKNESGGGGSGGGSGGSITCPPPMSVEHADIWVKSYSLYSRERYICNSGFK
RKAGTSSLTECVLNKATNVAHWTTPSLKCIRDPALVHQRPAPPSTVTTAGVTPQPESLSPSGKEPAASSPSSNNTA
ATTAAIVPGSQLMPSKSPSTGTTEISSHESSHGTPSQTTAKNWELTASASHQPPGVYPQGHSDTTSAFEGGGGSGG
GGSAVGQDTQEVIVVPHSLPFKVVVISAILALVVLTIISLIILIMLWQKKPRSGLLTGRTHHHHHH

SEQ ID NO: 15 IL-15 1009
METDTLLLWVLLLWVPGSTGNWVNVISDLKKIEDLIQSMHIDATLYTESDVHPSCKVTAMKCFLLELQVISLESGD
ASIHDTVENLIILANNSLSSNGNVTESGCKECEELEEKNIKEFLQSFVHIVQMFINTSGGSSGSGSGSTGTSSSGT
GTSAGTTGTSASTSGSGSGGGGSGGGGSAGGTATAGASSGSITCPPPMSVEHADIWVKSYSLYSRERYICNSGFK
RKAGTSSLTECVLNKATNVAHWTTPSLKCIRDPALVHQRPAPPSTVTTAGVTPQPESLSPSGKEPAASSPSSNNTA
ATTAAIVPGSQLMPSKSPSTGTTEISSHESSHGTPSQTTAKNWELTASASHQPPGVYPQGHSDTTSAGGGGSGGGG
SRVVRVPTATLVRVVGTELVIPCNVSDYDGPSEQNFDWSFSSLGSSFVELASTWEVGFPAQLYQERLQRGEILLRR
TANDAVELHIKNVQPSDQGHYKCSTPSTDATVQGNYEDTVQVKVLADSLHVGPSARPPPSLSLREGEPFELRCTAA
SASPLHTHLALLWEVHRGPARRSVLALTHEGRFHPGLGYEQRYHSGDVRLDTVGSDAYRLSVSRALSADQGSYRCI
VSEWIAEQGNWQEIQEKAVEVATVVIQPSVLRAAVPKNVSVAEGKELDLTCNITTDRADDVRPEVTWSFSRMPDST
LPGSRVLARLDRDSLVHSSPHVALSHVDARSYHLLVRDVSKENSGYYYCHVSLWAPGHNRSWHKVAEAVSSPAGVG
VTWLEPDYQVYLNASKVPGFADDPTELACRVVDTKSGEANVRFTVSWYYRMNRRSDNVVTSELLAVMDGDWTLKYG
ERSKQRAQDGDFIFSKEHTDTFNFRIQRTTEEDRGNYYCVVSAWTKQRNNSWVKSKDVFSKPVNIFWALEDSVLVV
KARQPKPFFAAGNTFEMTCKVSSKNIKSPRYSVLIMAEKPVGDLSSPNETKYIISLDQDSVVKLENWTDASRVDGV
VLEKVQEDEFRYRMYQTQVSDAGLYRCMVTAWSPVRGSLWREAATSLSNPIEIDFQTSGPIFNASVHSDTPSVIRG
DLIKLFCIITVEGAALDPDDMAFDVSWFAVHSFGLDKAPVLLSSLDRKGIVTTSRRDWKSDLSLERVSVLEFLLQV
HGSEDQDFGNYYCSVTPWVKSPTGSWQKEAEIHSKPVFITVKMDVLNAFKYPLLIGVGLSTVIGLLSCLIGYCSSH
WCCKKEVQETRRERRRLMSMEMD

SEQ ID NO: 16 IL-15 1010
METDTLLLWVLLLWVPGSTGNWVNVISDLKKIEDLIQSMHIDATLYTESDVHPSCKVTAMKCFLLELQVISLESGD
ASIHDTVENLIILANDSLSSNGNVTESGCKECEELEEKNIKEFLQSFVHIVQMFINTSGGSSGSGSGSTGTSSSGT
GTSAGTTGTSASTSGSGSGGGGSGGGGSAGGTATAGASSGSITCPPPMSVEHADIWVKSYSLYSRERYICNSGFK
RKAGTSSLTECVLNKATNVAHWTTPSLKCIRDPALVHQRPAPPSTVTTAGVTPQPESLSPSGKEPAASSPSSNNTA
ATTAAIVPGSQLMPSKSPSTGTTEISSHESSHGTPSQTTAKNWELTASASHQPPGVYPQGHSDTTSAGGGGSGGGG
SRVVRVPTATLVRVVGTELVIPCNVSDYDGPSEQNFDWSFSSLGSSFVELASTWEVGFPAQLYQERLQRGEILLRR
TANDAVELHIKNVQPSDQGHYKCSTPSTDATVQGNYEDTVQVKVLADSLHVGPSARPPPSLSLREGEPFELRCTAA
SASPLHTHLALLWEVHRGPARRSVLALTHEGRFHPGLGYEQRYHSGDVRLDTVGSDAYRLSVSRALSADQGSYRCI
VSEWIAEQGNWQEIQEKAVEVATVVIQPSVLRAAVPKNVSVAEGKELDLTCNITTDRADDVRPEVTWSFSRMPDST
LPGSRVLARLDRDSLVHSSPHVALSHVDARSYHLLVRDVSKENSGYYYCHVSLWAPGHNRSWHKVAEAVSSPAGVG
VTWLEPDYQVYLNASKVPGFADDPTELACRVVDTKSGEANVRFTVSWYYRMNRRSDNVVTSELLAVMDGDWTLKYG
ERSKQRAQDGDFIFSKEHTDTFNFRIQRTTEEDRGNYYCVVSAWTKQRNNSWVKSKDVFSKPVNIFWALEDSVLVV
KARQPKPFFAAGNTFEMTCKVSSKNIKSPRYSVLIMAEKPVGDLSSPNETKYIISLDQDSVVKLENWTDASRVDGV
VLEKVQEDEFRYRMYQTQVSDAGLYRCMVTAWSPVRGSLWREAATSLSNPIEIDFQTSGPIFNASVHSDTPSVIRG
DLIKLFCIITVEGAALDPDDMAFDVSWFAVHSFGLDKAPVLLSSLDRKGIVTTSRRDWKSDLSLERVSVLEFLLQV
HGSEDQDFGNYYCSVTPWVKSPTGSWQKEAEIHSKPVFITVKMDVLNAFKYPLLIGVGLSTVIGLLSCLIGYCSSH
WCCKKEVQETRRERRRLMSMEMD

SEQ ID NO: 17 pDisplay-anti-CD3
MKIICLALVALLLTAQPAMAEIVLTQSPATLSLSPGERATLSCRASQSVSSYLAWYQQKPGQAPRLLIYDASNRAT
GIPARFSGSGSGTDFTLTISSLEPEDFAVYYCQQRSNWPPLTFGGGTKVEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQGLSSPVTK
SFNRGECGSSGSGSGSTGTSSSGTGTSAGTTGTSASTSGSGSGGGGSGGGGSAGGTATAGASSGSQVQLVESGG
GVVQPGRSLRLSCAASGFKFSGYGMHWVRQAPGKGLEWVAVIWYDGSKKYYVDSVKGRFTISRDNSKNTLYLQMNS
LRAEDTAVYYCARQMGYWHFDLWGRGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSCDKTHTGSGGGSGGGG
SGGGGSGGGSGGGSAVGQDTQEVIVVPHSLPFKVVVISAILALVVLTIISLIILIMLWQKKPRDYKDDDDK -continued

SEQUENCE LISTING

SEQ ID NO: 18 PTGFRN-anti-CD3
MKIICLALVALLLTAQPAMAEIVLTQSPATLSLSPGERATLSCRASQSVSSYLAWYQQKPGQAPRLLIYDASNRAT
GIPARFSGSGSGTDFTLTISSLEPEDFAVYYCQQRSNWPPLTFGGGTKVEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQGLSSPVTK
SFNRGECGGSSGSGSGSTGTSSSGTGTSAGTTGTSASTSGSGSGGGGSGGGGSAGGTATAGASSGSQVQLVESGG
GVVQPGRSLRLSCAASGFKFSGYGMHWVRQAPGKGLEWVAVIWYDGSKKYYVDSVKGRFTISRDNSKNTLYLQMNS
LRAEDTAVYYCARQMGYWHFDLWGRGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSCDKTHTGGSGGGSGGGG
SGGGGSGGGSGGSRVVRVPTATLVRVVGTELVIPCNVSDYDGPSEQNFDWSFSSLGSSFVELASTWEVGFPAQLYQ
ERLQRGEILLRRTANDAVELHIKNVQPSDQGHYKCSTPSTDATVQGNYEDTVQVKVLADSLHVGPSARPPPSLSLR
EGEPFELRCTAASASPLHTHLALLWEVHRGPARRSVLALTHEGRFHPGLGYEQRYHSGDVRLDTVGSDAYRLSVSR
ALSADQGSYRCIVSEWIAEQGNWQEIQEKAVEVATVVIQPSVLRAAVPKNVSVAEGKELDLTCNITTDRADDVRPE
VTWSFSRMPDSTLPGSRVLARLDRDSLVHSSPHVALSHVDARSYHLLVRDVSKENSGYYYCHVSLWAPGHNRSWHK
VAEAVSSPAGVGVTWLEPDYQVYLNASKVPGFADDPTELACRVVDTKSGEANVRFTVSWYYRMNRRSDNVVTSELL
AVMDGDWTLKYGERSKQRAQDGDFIFSKEHTDTFNFRIQRTTEEDRGNYYCVVSAWTKQRNNSWVKSKDVFSKPVN
IFWALEDSVLVVKARQPKPFFAAGNTFEMTCKVSSKNIKSPRYSVLIMAEKPVGDLSSPNETKYIISLDQDSVVKL
ENWTDASRVDGVVLEKVQEDEFRYRMYQTQVSDAGLYRCMVTAWSPVRGSLWREAATSLSNPIEIDFQTSGPIFNA
SVHSDTPSVIRGDLIKLFCIITVEGAALDPDDMAFDVSWFAVHSFGLDKAPVLLSSLDRKGIVTTSRRDWKSDLSL
ERVSVLEFLLQVHGSEDQDFGNYYCSVTPWVKSPTGSWQKEAEIHSKPVFITVKMDVLNAFKYPLLIGVGLSTVIG
LLSCLIGYCSSHWCCKKEVQETRRERRRLMSMEMDTGGSGGSVSKGEELFTGVVPILVELDGDVNGHKFSVSGEGE
GDATYGKLTLKFICTTGKLPVPWPTLVTTLTYGVQCFSRYPDHMKQHDFFKSAMPEGYVQERTIFFKDDGNYKTRA
EVKFEGDTLVNRIELKGIDFKEDGNILGHKLEYNYNSHNVYIMADKQKNGIKVNFKIRHNIEDGSVQLADHYQQNT
PIGDGPVLLPDNHYLSTQSKLSKDPNEKRDHMVLLEFVTAAGITLGMDELYKDYKDDDDK SEQ ID NO: 19 PTGFRN_CD40L trimer mouse
METDTLLLWVLLLWVPGSTGMQRGDEDPQIAAHVVSEANSNAASVLQWAKKGYYTMKSNLVMLENGKQLTVKREGL
YVVYTQVTFCSNREPSSQRPFIVGLWLKPSSGSERILLKAANTHSSSQLCEQQSVHLGGVFELQAGASVFVNVTEA
SQVIHRVGFSSFGLLKLGSGGSGGSGGSGMQRGDEDPQIAAHVVSEANSNAASVLQWAKKGYYTMKSNLVMLENGK
QLTVKREGLYYVYTQVTFCSNREPSSQRPFIVGLWLKPSSGSERILLKAANTHSSSQLCEQQSVHLGGVFELQAGA
SVFVNVTEASQVIHRVGFSSFGLLKLGSGGSGGSGGSGMQRGDEDPQIAAHVVSEANSNAASVLQWAKKGYYTMKS
NLVMLENGKQLTVKREGLYYVYTQVTFCSNREPSSQRPFIVGLWLKPSSGSERILLKAANTHSSSQLCEQQSVHLG
GVFELQAGASVFVNVTEASQVIHRVGFSSFGLLKLSAGGGGSGGGGSRVVRVPTATLVRVVGTELVIPCNVSDYDG
PSEQNFDWSFSSLGSSFVELASTWEVGFPAQLYQERLQRGEILLRRTANDAVELHIKNVQPSDQGHYKCSTPSTDA
TVQGNYEDTVQVKVLADSLHVGPSARPPPSLSLREGEPFELRCTAASASPLHTHLALLWEVHRGPARRSVLALTHE
GRFHPGLGYEQRYHSGDVRLDTVGSDAYRLSVSRALSADQGSYRCIVSEWIAEQGNWQEIQEKAVEVATVVIQPSV
LRAAVPKNVSVAEGKELDLTCNITTDRADDVRPEVTWSFSRMPDSTLPGSRVLARLDRDSLVHSSPHVALSHVDAR
SYHLLVRDVSKENSGYYYCHVSLWAPGHNRSWHKVAEAVSSPAGVGVTWLEPDYQVYLNASKVPGFADDPTELACR
VVDTKSGEANVRFTVSWYYRMNRRSDNVVTSELLAVMDGDWTLKYGERSKQRAQDGDFIFSKEHTDTFNFRIQRTT
EEDRGNYYCVVSAWTKQRNNSWVKSKDVFSKPVNIFWALEDSVLVVKARQPKPFFAAGNTFEMTCKVSSKNIKSPR
YSVLIMAEKPVGDLSSPNETKYIISLDQDSVVKLENWTDASRVDGVVLEKVQEDEFRYRMYQTQVSDAGLYRCMVT
AWSPVRGSLWREAATSLSNPIEIDFQTSGPIFNASVHSDTPSVIRGDLIKLFCIITVEGAALDPDDMAFDVSWFAV
HSFGLDKAPVLLSSLDRKGIVTTSRRDWKSDLSLERVSVLEFLLQVHGSEDQDFGNYYCSVTPWVKSPTGSWQKEA
EIHSKPVFITVKMDVLNAFKYPLLIGVGLSTVIGLLSCLIGYCSSHWCCKKEVQETRRERRRLMSMEMD SEQ ID NO: 20 PTGFRN_CD40L trimer human
METDTLLLWVLLLWVPGSTGMQKGDQNPQIAAHVISEASSKTTSVLQWAEKGYYTMSNNLVTLENGKQLTVKRQGL
YYIYAQVTFCSNREASSQAPFIASLCLKSPGRFERILLRAANTHSSAKPCGQQSIHLGGVFELQPGASVFVNVTDP
SQVSHGTGFTSFGLLKLGSGGSGGSGGSGMQKGDQNPQIAAHVISEASSKTTSVLQWAEKGYYTMSNNLVTLENGK
QLTVKRQGLYYIYAQVTFCSNREASSQAPFIASLCLKSPGRFERILLRAANTHSSAKPCGQQSIHLGGVFELQPGA
SVFVNVTDPSQVSHGTGFTSFGLLKLGSGGSGGSGGSGMQKGDQNPQIAAHVISEASSKTTSVLQWAEKGYYTMSN
NLVTLENGKQLTVKRQGLYYIYAQVTFCSNREASSQAPFIASLCLKSPGRFERILLRAANTHSSAKPCGQQSIHLG
GVFELQPGASVFVNVTDPSQVSHGTGFTSFGLLKLSAGGGGSGGGGSRVVRVPTATLVRVVGTELVIPCNVSDYDG
PSEQNFDWSFSSLGSSFVELASTWEVGFPAQLYQERLQRGEILLRRTANDAVELHIKNVQPSDQGHYKCSTPSTDA
TVQGNYEDTVQVKVLADSLHVGPSARPPPSLSLREGEPFELRCTAASASPLHTHLALLWEVHRGPARRSVLALTHE
GRFHPGLGYEQRYHSGDVRLDTVGSDAYRLSVSRALSADQGSYRCIVSEWIAEQGNWQEIQEKAVEVATVVIQPSV
LRAAVPKNVSVAEGKELDLTCNITTDRADDVRPEVTWSFSRMPDSTLPGSRVLARLDRDSLVHSSPHVALSHVDAR
SYHLLVRDVSKENSGYYYCHVSLWAPGHNRSWHKVAEAVSSPAGVGVTWLEPDYQVYLNASKVPGFADDPTELACR
VVDTKSGEANVRFTVSWYYRMNRRSDNVVTSELLAVMDGDWTLKYGERSKQRAQDGDFIFSKEHTDTFNFRIQRTT
EEDRGNYYCVVSAWTKQRNNSWVKSKDVFSKPVNIFWALEDSVLVVKARQPKPFFAAGNTFEMTCKVSSKNIKSPR
YSVLIMAEKPVGDLSSPNETKYIISLDQDSVVKLENWTDASRVDGVVLEKVQEDEFRYRMYQTQVSDAGLYRCMVT
AWSPVRGSLWREAATSLSNPIEIDFQTSGPIFNASVHSDTPSVIRGDLIKLFCIITVEGAALDPDDMAFDVSWFAV
HSFGLDKAPVLLSSLDRKGIVTTSRRDWKSDLSLERVSVLEFLLQVHGSEDQDFGNYYCSVTPWVKSPTGSWQKEA
EIHSKPVFITVKMDVLNAFKYPLLIGVGLSTVIGLLSCLIGYCSSHWCCKKEVQETRRERRRLMSMEMD SEQ ID NO: 21 PTGFRN_short-anti-CD3
MKIICLALVALLLTAQPAMAEIVLTQSPATLSLSPGERATLSCRASQSVSSYLAWYQQKPGQAPRLLIYDASNRAT
GIPARFSGSGSGTDFTLTISSLEPEDFAVYYCQQRSNWPPLTFGGGTKVEIKRTVAAPSVFIFPPSDEQLKSGTAS
VVCLLNNFYPREAKVQWKVDNALQSGNSQESVTEQDSKDSTYSLSSTLTLSKADYEKHKVYACEVTHQGLSSPVTK
SFNRGECGGSSGSGSGSTGTSSSGTGTSAGTTGTSASTSGSGSGGGGSGGGGSAGGTATAGASSGSQVQLVESGG
GVVQPGRSLRLSCAASGFKFSGYGMHWVRQAPGKGLEWVAVIWYDGSKKYYVDSVKGRFTISRDNSKNTLYLQMNS
LRAEDTAVYYCARQMGYWHFDLWGRGTLVTVSSASTKGPSVFPLAPSSKSTSGGTAALGCLVKDYFPEPVTVSWNS
GALTSGVHTFPAVLQSSGLYSLSSVVTVPSSSLGTQTYICNVNHKPSNTKVDKKVEPKSCDKTHTGGSGGGSGGGG
SGGGGSGGGSGGSGPIFNASVHSDTPSVIRGDLIKLFCIITVEGAALDPDDMAFDVSWFAVHSFGLDKAPVLLSSL
DRKGIVTTSRRDWKSDLSLERVSVLEFLLQVHGSEDQDFGNYYCSVTPWVKSPTGSWQKEAEIHSKPVFITVKMDV
LNAFKYPLLIGVGLSTVIGLLSCLIGYCSSHWCCKKEVQETRRERRRLMSMEMDTGGSGGSVSKGEELFTGVVPIL
VELDGDVNGHKFSVSGEGEGDATYGKLTLKFICTTGKLPVPWPTLVTTLTYGVQCFSRYPDHMKQHDFFKSAMPEG

SEQUENCE LISTING

```
YVQERTIFFKDDGNYKTRAEVKFEGDTLVNRIELKGIDFKEDGNILGHKLEYNYNSHNVYIMADKQKNGIKVNFKI
RHNIEDGSVQLADHYQQNTPIGDGPVLLPDNHYLSTQSKLSKDPNEKRDHMVLLEFVTAAGITLGMDELYKDYKDD
DDK

SEQ ID NO: 22 FLT3L-PTGFRN
MTVLAPAWSPTTYLLLLLLLSSGLSGTQDCSFQHSPISSDFAVKIRELSDYLLQDYPVTVASNLQDEELCGGLWRL
VLAQRWMERLKTVAGSKMQGLLERVNTEIHFVTKCAFQPPPSCLRFVQTNISRLLQETSEQLVALKPWITRQNFSR
CLELQCQPDSSTLPPPWSPRPLEATAPTAPQPPSAGGGGSGGGGSRVVRVPTATLVRVVGTELVIPCNVSDYDGPS
EQNFDWSFSSLGSSFVELASTWEVGFPAQLYQERLQRGEILLRRTANDAVELHIKNVQPSDQGHYKCSTPSTDATV
QGNYEDTVQVKVLADSLHVGPSARPPPSLSLREGEPFELRCTAASASPLHTHLALLWEVHRGPARRSVLALTHEGR
FHPGLGYEQRYHSGDVRLDTVGSDAYRLSVSRALSADQGSYRCIVSEWIAEQGNWQEIQEKAVEVATVVIQPSVLR
AAVPKNVSVAEGKELDLTCNITTDRADDVRPEVTWSFSRMPDSTLPGSRVLARLDRDSLVHSSPHVALSHVDARSY
HLLVRDVSKENSGYYYCHVSLWAPGHNRSWHKVAEAVSSPAGVGVTWLEPDYQVYLNASKVPGFADDPTELACRVV
DTKSGEANVRFTVSWYYRMNRRSDNVVTSELLAVMDGDWTLKYGERSKQRAQDGDFIFSKEHTDTFNFRIQRTTEE
DRGNYYCVVSAWTKQRNNSWVKSKDVFSKPVNIFWALEDSVLVVKARQKPFFAAGNTFEMTCKVSSKNIKSPRYS
VLIMAEKPVGDLSSPNETKYIISLDQDSVVKLENWTDASRVDGVVLEKVQEDEFRYRMYQTQVSDAGLYRCMVTAW
SPVRGSLWREAATSLSNPIEIDFQTSGPIFNASVHSDTPSVIRGDLIKLFCIITVEGAALDPDDMAFDVSWFAVHS
FGLDKAPVLLSSLDRKGIVTTSRRDWKSDLSLERVSVLEFLLQVHGSEDQDFGNYYCSVTPWVKSPTGSWQKEAEI
HSKPVFITVKMDVLNAFKYPLLIGVGLSTVIGLLSCLIGYCSSHWCCKKEVQETRRERRRLMSMEMD
```

Tables

TABLE 1

Exosome lipids

| | |
|---|---|
| Lysobisphosphatidic acid | Ganglioside GM3 24:1 |
| Sphingomyelin (SM) | Ganglioside GM3 16:0 |
| Ganglioside GM3 | PE40:5 |
| Phosphatidylserine (PS) | PE40:6 |
| Phosphatidylinositol (PI) | PE38:3 |
| Phosphatidylcholine (PC) | PE38:4 |
| Phosphatidylethanolamine (PE) | PE36:1 |
| Lysophosphatidylcholine (LPC) | PE36:2 |
| Cholesterol (Chol) | PE34:1 |
| Diacylglycerol (DG) | PE34:2 |
| PI18:0/20:3 | PE-ether38:5 |
| PI18:0/20:4 | PE-ether38:6 |
| PI18:0/18:1 | PE-ether34:1 |
| PI18:1/18:1 | PE-ether34:2 |
| PI18:0/16:0 | PC34:1 |
| PA18:0/18:1 | PC36:4 |
| PS18:0/18:1 | PC34:3 |
| BMP18:0/18:1 | PC32:0 |
| BMP18:1/18:1 | PC30:0 |
| BMP18:1/16:0 | SM24:1 |
| CL(18:1)3/16:1 | SM16:0 |
| CL(18:1)2/(16:1)2 | Dihydrosphingomyelin16:0 |

TABLE 2

Exosome polypeptides

| | | | |
|---|---|---|---|
| ACLY | TCP1 | ACTR1A | LY75 |
| ACTB | PRDX2 | THOC4 | ABCC1 |
| ACTG1 | TSPAN6 | INADL | MYO1E |
| ALB | CCT3 | CTDSPL | NACA |
| ALDOA | TSTA3 | ZMPSTE24 | NAP1L4 |
| ALDOB | TUBA3C | DNAJA2 | NCL |
| AKR1B1 | HIST1H2AK | NDRG1 | NEDD8 |
| AMBP | HIST1H2AJ | RAPGEF3 | YBX1 |
| ANPEP | HIST1H2AB | SPON2 | PA2G4 |
| ANXA2 | HIST2H2AC | UBAC1 | PECAM1 |
| ANXA3 | IFITM1 | N4BP2L2 | PFAS |
| ANXA4 | PDXK | CAP1 | SERPINB9 |
| ANXA5 | LIN7A | VAT1 | PI4KA |
| ANXA6 | BUB3 | NEBL | PLAT |
| ANXA7 | MAP4K4 | DCTN2 | PLCG2 |
| ANXA11 | EDIL3 | ARPC1A | PPA1 |
| | ATP6AP2 | C6orf108 | PPP2CA |
| CAPZB | PSME3 | SMC2 | PRKCB |
| CD63 | TUBB3 | AHSA1 | PSMA6 |
| CD81 | IFITM3 | STAMBP | PSMA7 |
| CKB | ACAA2 | PMVK | PSMB8 |
| CLU | CCT7 | GIPC1 | PSMB9 |
| CLIC1 | CCT4 | HBS1L | PSMD7 |
| TPP1 | IFITM2 | NCKAP1 | PSME1 |
| CLTC | GNA13 | ALDH1L1 | PTPRA |
| CNP | RUVBL2 | FTCD | RAC2 |
| COL6A1 | PRSS23 | FGL2 | RPL3 |
| CR1 | ACOT7 | CFHR3 | RPL4 |
| CTNND1 | CCT5 | MMP24 | RPL5 |
| ACE | DIP2C | COPS8 | RPL11 |
| DDT | ASCC3L1 | CKAP4 | RPL22 |
| DEFA1 | TNIK | C10orf116 | RPL24 |
| DEFA3 | NEDD4L | SLC27A2 | RPL27 |
| DNAH8 | NCSTN | MID2 | RPL30 |
| DPEP1 | TSPAN15 | KIF3A | RPL28 |
| DPP4 | PLXNB2 | NUDT5 | RPL31 |
| EEF1A1 | SDCBP2 | TREH | RPL34 |
| EEF2 | IGKV1-5 | CEP250 | RPL35A |
| EGF | IGHV4-31 | PDCD10 | RPL37A |
| EIF5A | IGKV3-20 | PADI2 | RPS2 |
| ENO1 | IGKV2-24 | PACSIN2 | RPS3A |
| ENO3 | MINK1 | CHP | RPS5 |
| ENPEP | IGKα | SNF8 | RPS9 |
| STOM | VPS36 | DDX19B | RPS19 |
| EPS8 | DERA | SCN11A | RPS25 |
| FABP3 | GOLGA7 | LYPLA2 | RPS26 |
| FGA | KRT76 | PARK7 | RPS28 |
| MLANA | EIF3EIP | COBLL1 | RPS29 |
| FN1 | LSR | CNKSR2 | RSU1 |
| FTL | TUBA8 | ENPP4 | SARS |
| FUS | RAB4B | RAB3GAP1 | SLAMF1 |
| GAA | SETD4 | AKR7A3 | SLC1A4 |
| GAPDH | TOLLIP | SPEN | SLC2A3 |
| GDI2 | PLEKHB2 | GANAB | SNRPD2 |
| GGT1 | VPS37C | MGRN1 | SPINK1 |
| GLB1 | LIN7C | CUX2 | SPN |
| GLG1 | H2AFJ | DNAJC13 | STK10 |
| GNA11 | CAND1 | ZCCHC11 | STXBP3 |
| GNAI1 | PLSCR3 | PHF15 | TALDO1 |
| GNAI2 | KIAA1199 | KIAA0841 | TNFAIP3 |
| GNAI3 | GNB4 | ARHGEF12 | TPM3 |
| GNAS | MYH14 | COTL1 | TPM4 |
| GNB1 | TSPAN14 | ANGPTL2 | TYK2 |
| GNB2 | NCALD | DDAH2 | VIM |
| GNG7 | REG4 | HEBP2 | WARS |
| SFN | VPS25 | CD2AP | WAS |
| GPI | TUBB6 | PLD3 | LAT2 |
| GSTA1 | TUBA1C | TMEM2 | HIST1H2BL |
| GSTA2 | TNKS1BP1 | SH3BP4 | STX7 |
| GSTA3 | FAM125B | BHMT2 | CPNE1 |
| GSTM3 | LRSAM1 | GCA | RPL14 |

TABLE 2-continued

Exosome polypeptides

| | | | |
|---|---|---|---|
| GSTP1 | HIST3H2A | MXRA5 | PDCD5 |
| GUSB | TUBA3E | AHCTF1 | SYNGR2 |
| HIST1H2AD | TUBA3D | PTPN23 | RPL23 |
| HLA-A | DCD | DAK | RAB9A |
| HLA-B | HIST4H4 | ACOT11 | IGSF2 |
| HLA-DQB1 | ALDH16A1 | APPL1 | EEF1E1 |
| HLA-DRA | RPS4Y2 | PHGDH | SCAMP2 |
| HLA-DRB1 | MYL6B | TIAM2 | SCAMP3 |
| HLA-DRB5 | BRI3BP | KCNG2 | DPP3 |
| HPGD | AGR3 | CYFIP2 | ARPC1B |
| HRAS | EEF1AL3 | GHITM | PDIA6 |
| HSPA1A | KRT28 | C11orf54 | WASF2 |
| HSPA1B | KRT24 | DBNL | ANP32B |
| HSPA8 | RPLP0-like | ATAD2 | PAICS |
| HSP90AA1 | RPSAP15 | PHPT1 | AHCYL1 |
| | RANP1 | C16orf80 | VAMP5 |
| KRT1 | PCSK9 | OLA1 | 41891 |
| KRT9 | METRNL | ZDHHC1 | HSPH1 |
| KRT10 | LOC284889 | SNX12 | SUB1 |
| LDHA | KRT6C | PSAT1 | CDC37 |
| LDHB | KRT79 | NT5C | CORO1A |
| TACSTD1 | RAB43 | EHD2 | CD300A |
| MCAM | KRT27 | TAX1BP3 | TMC6 |
| MDH1 | ACTBL2 | CRNN | RFTN1 |
| MEP1A | RP11-631M21.2 | NOX3 | SCRIB |
| MSN | TUBB2B | ATP6V0A4 | SERBP1 |
| 2-Sep | KRT77 | ITSN2 | TTLL3 |
| PGAM1 | AGRN | GEMIN4 | CACYBP |
| PGK1 | RAB15 | LAP3 | SIT1 |
| PKM2 | LOC388524 | CRYL1 | SLC43A3 |
| PPP1CA | LOC388720 | MYO15A | PILRA |
| | HSP90AB2P | ATP6V1D | RPL26L1 |
| PTPRC | ACTBL3 | SNX9 | MPP6 |
| RAN | LOC442497 | PCYOX1 | GNG2 |
| RDX | A26C1A | ANKFY1 | TMED9 |
| SDCBP | HIST2H4B | UFC1 | DOCK10 |
| STX3 | hCG_1757335 | FAM49B | C3orf10 |
| STXBP1 | HLA-A29.1 | CUTA | MYO1G |
| STXBP2 | LOC653269 | ATP6V1H | FLJ21438 |
| TPI1 | A26C1B | VPS24 | SLC38A1 |
| EZR | LOC100128936 | CMPK1 | FERMT3 |
| YWHAE | LOC100130553 | UPB1 | ITFG3 |
| TUBA1A | LOC100133382 | CLIC5 | HIST1H2AH |
| WDR1 | LOC100133739 | MUPCDH | SLAMF6 |
| PDCD6IP | AP2A2 | CLIC6 | TMC8 |
| GPA33 | ALDH3B1 | SIAE | LOC153364 |
| TUBA1B | FASLG | CPVL | SVIP |
| TUBB2C | ATP4A | RHOF | TMEM189-UBE2V1 |
| CAPN7 | CAPS | ARL15 | hCG_16001 |
| DDAH1 | COL12A1 | ZNHIT6 | FABP5L7 |
| PGLS | DMBT1 | GIPC2 | Del(X)1Brd |
| SAMM50 | DSP | PCDH24 | ABP1 |
| CLIC4 | EGFR | VPS13C | ACTN3 |
| CHMP2B | EPHA5 | CC2D1A | AFM |
| ULK3 | EPHB1 | EPS8L1 | AKT1 |
| RNF11 | FAT | C10orf18 | ALDH3A2 |
| VPS4A | HSD17B4 | CHCHD3 | ALOX12P2 |
| ARFIP1 | L1CAM | C2orf18 | ANXA2P1 |
| CHMP2A | LAMA5 | C17orf80 | KRT33B |
| SMPDL3B | MUC4 | EPN3 | MYOC |
| PACSIN3 | NOTCH1 | UACA | SERPINE1 |
| EHD4 | PPP2R1B | VPS13D | PIK3CA |
| EHD3 | PTPRF | APPL2 | NRP1 |
| HEBP1 | SORT1 | ARL8B | SPRY1 |
| VPS28 | SERPINB3 | DDX19A | EMILIN1 |
| DCXR | SELP | NAGK | LRG1 |
| RHCG | FSCN1 | ITLN1 | AZGP1P1 |
| CHMP5 | TGFB1 | CCDC132 | LOC728533 |
| VTA1 | CLTCL1 | OTUB1 | ALDH7A1 |
| RAB14 | CHST1 | CDK5RAP2 | AXL |
| GPRC5B | EIF3I | MBD5 | CFB |
| CAB39 | TNFSF10 | SLC22A11 | C1S |
| RAB8B | MAP7 | SUSD2 | CAT |
| TM7SF3 | COPB2 | SUCNR1 | CD47 |
| MXRA8 | HEPH | BDH2 | CD151 |
| C11orf59 | | NIT2 | CDH13 |
| MOBKL1B | CIB1 | RPL23AP13 | CFTR |

| | | | |
|---|---|---|---|
| UEVLD | SLC34A2 | FAM20C | CEACAM8 |
| TSNAXIP1 | SLC6A14 | SLC12A9 | AP1S1 |
| GPRC5C | DIP2A | RAB25 | CLTA |
| GNG12 | TNPO3 | SMURF1 | CNGB1 |
| BAIAP2L1 | FER1L3 | TMEM27 | COL1A1 |
| MUC13 | CNTLN | RAB22A | COL1A2 |
| CHMP1B | TUBB4Q | NDRG3 | COL2A1 |
| SLC44A2 | KIF15 | ERMN | COL3A1 |
| CPNE5 | SERINC1 | TAOK1 | COL4A1 |
| TMBIM1 | PDIA2 | KIAA1529 | COL4A2 |
| EPS8L3 | EPS8L2 | RNF213 | COL4A3 |
| MMRN2 | PLVAP | WIZ | COL5A1 |
| TTYH3 | MYADM | ACE2 | COL5A2 |
| SLC44A4 | MUC16 | PLEKHA1 | COL7A1 |
| RAB1B | KRT25 | SCPEP1 | COMP |
| RAB33B | SERINC5 | AASDHPPT | CPS1 |
| RBP5 | LOC440264 | FIGNL1 | CSF1 |
| C5orf32 | AGT | PBLD | VCAN |
| ABHD14B | ALPP | KIF9 | SLC25A10 |
| MOBKL1A | APOA2 | LEPRE1 | CTBP2 |
| ARRDC1 | APOB | RAB17 | CTNNA2 |
| | APOE | IKZF5 | DCTN1 |
| FAM125A | SERPING1 | MMP25 | DECR1 |
| SNX18 | C1QB | MPP5 | DNASE1L1 |
| CHMP4B | C1R | TEKT3 | ENG |
| MITD1 | C4A | ALDH8A1 | STX2 |
| S100A16 | C4B | SLC13A3 | ETFB |
| CPNE8 | C4BPA | DUSP26 | F2R |
| C1orf58 | C4BPB | GGCT | F8 |
| GLIPR2 | CD5L | TMEM38A | ACSL1 |
| TUBB | FCN1 | C1orf116 | FAP |
| ATP6V1C2 | FCN2 | GDPD3 | FBLN1 |
| FTLL1 | FGB | OR2A4 | FBN1 |
| PEF1 | FGG | FAM65A | FBN2 |
| SERPINA3 | GRIN1 | NARG1L | FEN1 |
| ACP2 | MSH6 | CHMP6 | FLT1 |
| ACPP | HBA1 | DYNC2H1 | FUCA2 |
| ACTA2 | HBA2 | PRKRIP1 | GAS6 |
| ACTC1 | ITGA2B | GSTCD | GDI1 |
| ACTG2 | PPARG | PIP4K2C | GLDC |
| ACY1 | PDLIM7 | CYBRD1 | GNAL |
| APCS | CD274 | FUZ | GRM2 |
| APOD | A1BG | ARMC9 | GRM3 |
| APRT | ACAT1 | NAT13 | GRM7 |
| AQP1 | ACO1 | COASY | GSTM1 |
| AQP2 | ADCY1 | UBXN6 | GSTM5 |
| ARF1 | ADFP | COL18A1 | H2AFX |
| ARF3 | ADH5 | BHLHB9 | HBE1 |
| ARF4 | ADH6 | WNT5B | HMGCS2 |
| ARF5 | PARP4 | CAB39L | TNC |
| ARF6 | AHSG | ITM2C | IDH3B |
| RHOA | AK1 | LOC81691 | IFRD1 |
| ARL3 | ALAD | AMN | ITGA5 |
| ASAH1 | ALCAM | SH3BGRL3 | ITGB5 |
| ASS1 | ALDH2 | C9orf58 | ITPR2 |
| FXYD2 | ALDH9A1 | BCL2L12 | KRT84 |
| BHMT | ALDOC | RAB34 | LAMB1 |
| BST2 | ALK | TBC1D10A | LCN1 |
| C3 | ALOX12 | GPR98 | LGALS8 |
| CA2 | ALPL | HDHD2 | LMNA |
| CA4 | ANXA13 | ARL6 | LOXL2 |
| CALB1 | AOX1 | IQCG | LTBP2 |
| CALR | APAF1 | C2orf16 | MAP1A |
| CD9 | APOA4 | PARD6B | MAT1A |
| CD59 | SHROOM2 | TXNDC17 | MC1R |
| HSPA5 | RHOB | ABCC11 | MCC |
| HSPA6 | ARHGAP1 | FAM40A | ME1 |
| HSP90AB1 | ARHGDIB | SCIN | MECP2 |
| HSPD1 | ARSE | SCRN2 | MAP3K1 |
| IDH1 | ARSF | ZNF486 | MFAP4 |
| KNG1 | ASL | ACY3 | SCGB2A1 |
| KRAS | ASNA1 | C11orf52 | ALDH6A1 |
| LAMP1 | ATIC | CRB3 | MOS |
| LGALS3BP | ATP6V1A | C20orf114 | CITED1 |
| LRP2 | ATP6V1B1 | NAPRT1 | NEFH |
| MAN1A1 | ATP6V1B2 | RG9MTD2 | OPRM1 |
| RAB8A | ATP6V0C | SAT2 | OTC |
| MIF | ATP6V1C1 | KIF12 | OXTR |

TABLE 2-continued

| Exosome polypeptides | | | |
|---|---|---|---|
| MME | ATP6V1E1 | MAL2 | PAPPA |
| MUC1 | ATP6V0A1 | OSBPL1A | PC |
| MYH9 | ATP6AP1 | VASN | PCOLCE |
| NAGLU | AZU1 | SLC22A12 | PDGFRB |
| NONO | BCR | ACSM1 | PFKB3 |
| NPM1 | BGN | TTC18 | PGAM2 |
| NRAS | BLMH | GSTO2 | SERPINE2 |
| P2RX4 | BLVRA | CLRN3 | PLP2 |
| P4HB | BLVRB | LRRK2 | PPP1CC |
| PEBP1 | BPI | C12orf59 | SRGN |
| SERPINA5 | BTG1 | LOC124220 | MAP2K6 |
| PFN1 | BTN1A1 | SLC5A10 | PSMB7 |
| PFN2 | TSPO | CCDC105 | PSMB10 |
| ABCB1 | C1QC | C1orf93 | PTK7 |
| SERPINA1 | CAPN5 | ARL8A | PTPRK |
| PIGR | C5 | LOC128192 | PZP |
| PIK3C2B | C9 | GALM | RAD21 |
| PKD1 | PTTG1IP | LRRC15 | RASA1 |
| PLSCR1 | CACNA2D1 | LOC131691 | RDH5 |
| PODXL | CALML3 | H1FOO | RPL18 |
| CTSA | CAMK4 | ENPP6 | RPL29 |
| PPIA | CAMP | CMBL | RPS10 |
| PSAP | CAPG | MUM1L1 | RPS24 |
| PSMB3 | CAPN1 | C20orf117 | S100A13 |
| PTBP1 | CAPN2 | SIRPA | SAA4 |
| PTPRJ | CAPZA2 | PLEKHA7 | ATXN1 |
| RAB1A | CD14 | A2ML1 | CLEC11A |
| RAB2A | CD80 | C16orf89 | SDC2 |
| RAB3B | CD36 | TOM1L2 | SMARCA4 |
| RAB5A | SCARB2 | KIF18B | SPOCK1 |
| RAB5B | CD40 | C19orf18 | STAT1 |
| RAB13 | CDC2 | PM20D1 | STC1 |
| RAB27B | CEL | PROM2 | SURF4 |
| RAB5C | CETP | GPR155 | SYT1 |
| RAC1 | CTSC | SLC36A2 | TAGLN |
| RALB | AP2M1 | VPS37D | TCN1 |
| RAP1B | CSN1S1 | SLC5A12 | TERF1 |
| RBM3 | CSN2 | SLC5A8 | TGFB2 |
| RNASE2 | CSN3 | EML5 | TSPAN4 |
| S100A6 | ACSL3 | TBC1D21 | TSN |
| S100A11 | FOLR1 | ZNF114 | TSNAX |
| S100P | B4GALT1 | ANO6 | COL14A1 |
| SLC1A1 | GNAQ | SLC5A9 | WNT5A |
| SLC2A5 | HBB | CRTC2 | ZNF134 |
| SLC12A1 | HBD | C20orf106 | PXDN |
| SLC12A3 | CFH | TMEM192 | SMC1A |
| SNCG | HLA-G | ARMC3 | OFD1 |
| SNRPD1 | HP | NAPEPLD | COPS3 |
| SOD1 | HPR | C10orf30 | STC2 |
| SRI | IGHA1 | ATP6V0D2 | ADAM9 |
| TF | IGJ | STXBP4 | CREG1 |
| THBS1 | IGLC1 | C17orf61 | CDK5R2 |
| THY1 | IGLC2 | TXNDC8 | TNFSF18 |
| TMPRSS2 | IGLC3 | LRRC57 | MPZL1 |
| TSG101 | LAMC1 | HSPA12A | SEMA5A |
| TUBB2A | LPA | MAGI3 | CLDN1 |
| UBE2N | LPL | C11orf47 | RGN |
| UMOD | LRP1 | SLC39A5 | SLC16A3 |
| UPK2 | LTF | C12orf51 | ARHGEF1 |
| VTN | TACSTD2 | SLC46A3 | LRRFIP2 |
| EIF4H | MBL2 | VMO1 | TAAR2 |
| YWHAB | MYH8 | SLC26A11 | CRIPT |
| YWHAG | NEB | LOC284422 | ENTPD4 |
| YWHAZ | PON1 | CRB2 | IFT140 |
| NPHS2 | PKN2 | HIST2H2AB | RNF40 |
| RAB7A | PROS1 | FAM151A | RB1CC1 |
| PSCA | MASP1 | SLC6A19 | PSMD6 |
| CUBN | RELN | PKD1L3 | MRC2 |
| BBOX1 | PTX3 | LOC342897 | HDAC5 |
| RAB11A | RARS | EGFL11 | RASA4 |
| NAPA | SILV | SERINC2 | SLC25A13 |
| PROM1 | THBS2 | PDDC1 | PSMD14 |
| FCGBP | TLR2 | SLCO4C1 | TFG |
| CPNE3 | TTN | SFT2D2 | CDIPT |
| MGAM | TTR | C9orf169 | CRTAP |
| GPRC5A | TYRP1 | LOC377711 | UNC13B |
| RAB11B | VWF | OR11L1 | ARL6IP5 |
| VAMP3 | CLIP2 | RAB19 | TGOLN2 |
| SLC9A3R1 | XDH | LOC440335 | POSTN |
| ITM2B | APOL1 | HIST2H2BF | CLPX |
| NAPSA | FCN3 | LOC441241 | TSPAN9 |
| VPS4B | SELENBP1 | KPRP | TMED10 |
| RAB3D | SMC3 | HSP90AB6P | SLC38A3 |
| PRDX6 | DDX21 | LOC643751 | IL1RAPL1 |
| KIAA0174 | CCPG1 | LOC651536 | GALNT5 |
| PDCD6 | ABCG2 | LOC652968 | PRR4 |
| ARPC4 | SFI1 | AEBP1 | ITGA11 |
| TSPAN1 | MVP | AMY1A | CLASP2 |
| PDZK1IP1 | AKAP9 | AMY1B | EPB41L3 |
| NUTF2 | PRG4 | AMY1C | KIAA0467 |
| FLOT1 | AKR1A1 | AMY2A | DULLARD |
| HRSP12 | ABCA7 | ANGPT1 | NOMO1 |
| A2M | COLEC10 | APLP2 | KIAA0146 |
| ACP1 | GNB5 | APP | SLC39A14 |
| ACTA1 | MMRN1 | AQP5 | DNPEP |
| ACTN4 | CLASP1 | AZGP1 | CASP14 |
| ACTN1 | SYNE1 | CEACAM1 | STX12 |
| ACTN2 | NIPBL | BMP3 | BRMS1 |
| ADAM10 | CHRDL2 | CA6 | ABI3BP |
| AHCY | HSPB8 | DDR1 | PLEKHG3 |
| ALDH1A1 | ANGPTL4 | CAPNS1 | FBXW8 |
| SLC25A4 | NIN | COL6A2 | GAPDHS |
| SLC25A5 | ZNF571 | COPA | GREM1 |
| SLC25A6 | LRP1B | CPD | DKK3 |
| ANXA1 | CNDP2 | DLD | SRPX2 |
| ANXA2P2 | DNAH7 | ETFA | IGHV3-11 |
| APOA1 | HCN3 | GLUD1 | IGHV3-7 |
| ARHGDIA | EXOC4 | HSD17B10 | IGLV4-3 |
| ARVCF | SNX25 | IMPDH2 | IGLV3-21 |
| | TC2N | HTATIP2 | IGLV1-40 |
| | HAPLN3 | MARVELD2 | ST6GALNAC6 |
| ATP1B1 | CD163L1 | CST4 | COPS4 |
| ATP5A1 | HRNR | CST5 | HERC5 |
| ATP5B | P704P | CTSB | NUSAP1 |
| ATP5I | CD24 | DAG1 | PLUNC |
| ATP5O | COL6A3 | DSG2 | PPME1 |
| B2M | COL15A1 | TOR1A | MBD3 |
| CALM1 | COMT | ECM1 | SLC38A2 |
| CALM2 | CP | EIF4G1 | FAM64A |
| CALM3 | CPN2 | EXT2 | GTPBP2 |
| CANX | CRABP2 | FAT2 | DIRAS2 |
| CAPZA1 | CRK | GPC4 | DCHS2 |
| CD2 | CRYAB | FOLH1 | QPCTL |
| CD247 | CRYM | FUT2 | PARP16 |
| CD86 | CSE1L | FUT3 | TMEM51 |
| CD37 | CSK | FUT6 | MCM10 |
| CD44 | CSTB | FUT8 | CHST12 |
| CD53 | CTH | GLRX | LYAR |
| CDC42 | CTNS | GPC1 | ODZ3 |
| CDH1 | CTSD | GPX3 | WDR52 |
| CFL1 | CTSG | IGHA2 | ASH1L |
| CFL2 | DDB1 | IGHVα | UNC45A |
| COX4I1 | DDC | IGLα | SLC7A10 |
| COX5B | DDX3X | IVL | PNO1 |
| CLDN3 | DDX5 | KRT12 | CD248 |
| CSPG4 | CFD | LAMA4 | AHRR |
| CSRP1 | DNM2 | LAMB2 | ZBTB4 |
| CST3 | DPYS | LGALS7 | SPTBN4 |
| CTNNA1 | DSC2 | LMAN1 | LGR6 |
| CTNNB1 | DSG3 | LPO | RNF123 |
| NQO1 | ECE1 | LTBP3 | PRDM16 |
| DYNC1H1 | MEGF8 | DNAJB9 | PARVG |
| EEF1A2 | ELA2 | MEST | RMND5A |
| EFNB1 | SERPINB1 | MGAT1 | FAT4 |
| CTTN | EPHX2 | MGP | FLJ13197 |
| EPHB4 | FBL | MUC5AC | TREML2 |
| ERBB2 | EVPL | MUC7 | SVEP1 |
| F5 | F11 | NEU1 | OBFC1 |
| FASN | FABP1 | NUCB1 | ZNF614 |
| FKBP1A | ACSL4 | NUCB2 | FLJ22184 |
| FLNA | FAH | FURIN | DBF4B |
| FLNB | EFEMP1 | PAM | CD276 |
| G6PD | FBP1 | PLG | CMIP |
| GCNT2 | FKBP4 | FXYD3 | ADAMTS12 |
| PDIA3 | FKBP5 | PLOD2 | SPACA1 |
| GSN | FRK | PLTP | VANGL1 |

TABLE 2-continued

Exosome polypeptides

| | | | | | | | |
|---|---|---|---|---|---|---|---|
| HADHA | FTH1 | PON3 | SPRY4 | SLC1A5 | ENPP3 | TOR3A | LOC400750 |
| HLA-DMB | FUCA1 | PPP1CB | HYI | SLC2A1 | SLC26A4 | VWA1 | LOC400963 |
| HLA-E | GABRB2 | PRELP | FAM108A1 | | PDZK1 | CHID1 | FLJ21767 |
| HNRNPA2B1 | GALK1 | DNAJC3 | TMEM47 | SLC12A2 | PEPD | TMEM109 | LOC401817 |
| HNRNPH2 | GBE1 | HTRA1 | MYCBPAP | SLC16A1 | PFKL | GAL3ST4 | NOMO3 |
| HSPA1L | GDF2 | RARRES1 | RAB6C | SPTBN1 | PGD | THSD4 | LOC439953 |
| HSPA2 | GFRA1 | SAA1 | FAM71F1 | SSBP1 | PGM1 | UXS1 | RPL12P6 |
| HSPA4 | GK2 | SAA2 | ZNF503 | SSR4 | SLC25A3 | TXNDC5 | LOC440589 |
| HSPA7 | GLO1 | SEPP1 | PARP10 | TBCA | SERPINA4 | CRISPLD1 | LOC440917 |
| HSPA9 | GLUL | SFRP1 | SHANK3 | TCEB1 | SERPINB6 | LOXL4 | LOC440991 |
| HSP90AA4P | GM2A | ST3GAL1 | LACRT | TFRC | SERPINB13 | GNPTG | LOC441876 |
| HSP90AA2 | GNG5 | SLC5A5 | TRIM41 | TKT | PIK3C2A | SCGB3A1 | LOC442308 |
| HSP90AB3P | GOT1 | SLC9A1 | OXNAD1 | TSPAN8 | PIP | CHST14 | DIPAS |
| HSPE1 | GPD1 | SLC20A2 | LDHAL6B | TPM1 | PKD2 | C1QTNF1 | LOC643300 |
| HSPG2 | GPM6A | SLPI | LOC92755 | HSP90B1 | PKLR | C1QTNF3 | LOC643358 |
| ICAM1 | GPT | SRPR | CACNA2D4 | TUBA4A | PKHD1 | SLC26A9 | LOC643531 |
| ITGA6 | GPX4 | STAU1 | ARHGAP18 | TUFM | PLCD1 | FAM129A | RPSAP8 |
| ITGA2 | GRB2 | HSPA13 | AHNAK2 | TXN | PLOD1 | HIST2H3C | LOC644464 |
| ITGAV | GRID1 | TGFBI | RPLP0P2 | UBA52 | PLS1 | TPRG1L | LOC644745 |
| | GSR | TGM1 | PGLYRP2 | UBB | UBL3 | TMPRSS11B | LOC645018 |
| ITGB2 | GSS | TGM3 | RAB39B | UBC | PPL | C20orf70 | LOC645548 |
| ITGB4 | GSTM2 | YES1 | GYLTL1B | UBA1 | PPP1R7 | PPM1L | LOC646127 |
| JUP | HGD | HIST2H2AA3 | KRT74 | UBE2V2 | PRCP | GBP6 | LOC646316 |
| CD82 | HINT1 | HIST2H2BE | SLAIN1 | UGDH | PRKCA | KRT78 | LOC646359 |
| KPNB1 | HNMT | GALNT4 | LOC122589 | UQCRC2 | PRKCD | SLC37A2 | LOC646785 |
| KRT2 | HNRNPL | B4GALT3 | NLRP8 | VCP | PRKCH | NPNT | LOC646875 |
| KRT5 | HPD | TNFSF13 | PODN | VIL1 | PRKCI | KRT73 | LOC646949 |
| KRT8 | HPX | TNFSF12 | C5orf24 | YWHAH | PRKCZ | HIST2H3A | LOC647000 |
| KRT13 | HRG | ANGPTL1 | CD109 | CXCR4 | PRNP | VWA2 | LOC647285 |
| KRT14 | DNAJA1 | GCNT3 | TRIM40 | SLC7A5 | PRSS8 | GSTK1 | LOC650405 |
| KRT15 | HSPB1 | TM9SF2 | GPR112 | HIST1H4I | PRTN3 | SBSN | LOC650901 |
| KRT16 | DNAJB1 | DDX23 | KRT72 | HIST1H4A | PSMA1 | C5orf46 | LOC652493 |
| KRT18 | CFI | ADAMTS3 | VTI1A | HIST1H4D | PSMA3 | LRRC26 | LOC652797 |
| KRT19 | IGF2R | GPR64 | SYT9 | HIST1H4F | PSMA4 | C4orf40 | LOC653162 |
| LAMP2 | IGFALS | LHFPL2 | KRT80 | HIST1H4K | PSMA5 | LOC440786 | PPIAL3 |
| LGALS4 | IL1RN | ST3GAL6 | CCDC64B | HIST1H4J | PSMB1 | SCFV | LOC653232 |
| LYZ | IRF6 | PRDX4 | ATP8B3 | HIST1H4C | PSMB2 | LGALS7B | HSPBL2 |
| | ITGA1 | MAN1A2 | C1orf84 | HIST1H4H | PSMB5 | HIST2H3D | LOC728002 |
| MFGE8 | EIF6 | OS9 | LOC149501 | HIST1H4B | PSMB6 | ACAT2 | LOC728088 |
| MMP7 | ITGB8 | MGAT4A | LOC150786 | HIST1H4E | PSMC5 | ACTL6A | LOC728576 |
| MYH10 | ITIH4 | TWF2 | WDR49 | HIST1H4L | PSMD12 | ADK | LOC728590 |
| MYL6 | KHK | CLCA4 | NEK10 | HIST2H4A | PSME2 | ANXA8L2 | LOC728791 |
| MYO1C | KIFC3 | TXNDC4 | STOML3 | TAGLN2 | PTPN6 | | LOC728979 |
| MYO1D | KLK1 | PLCB1 | SASS6 | RUVBL1 | PTPN13 | | ANG |
| NME1 | LBP | CES3 | DCLK2 | VAMP8 | PTPRO | | BDNF |
| NME2 | LCN2 | B3GAT3 | FREM3 | SNAP23 | QDPR | CAV1 | CALU |
| PRDX1 | LCP1 | TOR1B | C9orf91 | IQGAP1 | RAB27A | CD70 | CCR4 |
| PCBP1 | LTA4H | IGHV3OR16-13 | TREML2P | KRT75 | RAP1GDS1 | CS | CCR5 |
| CHMP1A | BCAM | IGLV2-11 | CCDC129 | TJP2 | RBL2 | DARS | CSF2 |
| SERPINF1 | MAN2A1 | IGLV1-44 | PAN3 | ROCK2 | RBP4 | DHX9 | CSF3 |
| PHB | MDH2 | IGKV3D-15 | MAMDC2 | ARPC3 | RENBP | DPYSL2 | DCN |
| PPIB | MFI2 | IGKV4-1 | RCOR2 | ACTR3 | RFC1 | EEF1D | EPO |
| PRKAR2A | MLLT3 | C1GALT1C1 | LOC283412 | LRPPRC | RHEB | EPRS | F3 |
| PRKDC | MLLT4 | RACGAP1 | LOC283523 | TRAP1 | RNH1 | FDPS | GPC5 |
| PSMA2 | MNDA | EFEMP2 | NOMO2 | TUBB4 | RNPEP | FLNC | GDF1 |
| QSOX1 | MPO | DUOX2 | SEC14L4 | GNB2L1 | ROBO2 | XRCC6 | GDF9 |
| PYGB | MPST | SDF4 | LCN1L1 | BAIAP2 | RP2 | GFPT1 | GFRA3 |
| RAB6A | MYO1B | CYB5R1 | LOC286444 | HYOU1 | RPS11 | HIST1H1B | GRN |
| RALA | MSRA | ERAP1 | TAS2R60 | AGR2 | RREB1 | HIST1H2BB | CXCL2 |
| RAP1A | MTAP | NUDT9 | KRT18P19 | OLFM4 | RYR1 | H3F3A | GZMA |
| RPL6 | MTHFD1 | FAM3B | LOC343184 | CCT2 | S100A4 | H3F3B | HIST1H2BD |
| RPL8 | MYH3 | FAM20A | LOC345041 | ATP5L | S100A8 | HNRNPF | HGF |
| RPLP1 | MYO5B | FAM55D | GNAT3 | CCT8 | S100A9 | HNRNPK | IFNG |
| RPLP2 | MYO6 | ANO1 | POLN | SLC12A7 | SERPINB4 | IARS | IGFBP3 |
| RPN1 | NID1 | LRRC16A | LOC376693 | MASP2 | SCN10A | LAMA3 | IGFBP4 |
| RPS3 | NKX6-1 | TTC17 | ARMS2 | IQGAP2 | SEC13 | LAMB3 | IGFBP6 |
| RPS7 | NQO2 | PDGFC | LOC387867 | RAB10 | SECTM1 | LAMC2 | IGFBP7 |
| RPS13 | NP | PCDHGB5 | LOC388339 | PRDX3 | SH3BGRL | LGALS1 | IL1RAP |
| RPS14 | NPC1 | CCL28 | FLG2 | EHD1 | SHMT1 | NBR1 | IL3 |
| RPS15A | NPHS1 | UGCGL1 | LOC388707 | TMED2 | SHMT2 | MARS | IL5 |
| RPS18 | NRF1 | SEMA3G | LOC389141 | LMAN2 | SLC3A1 | MX1 | IL6ST |
| RPS20 | NT5E | CORO1B | LOC390183 | YWHAQ | SLC4A1 | PFKP | IL7 |
| RPS21 | PAFAH1B1 | NDRG2 | KRT8P9 | GCN1L1 | SLC5A1 | PLAU | IL8 |
| RPS27A | PAFAH1B2 | KIAA1324 | LOC391777 | RAB35 | SLC5A2 | PSMB4 | IL10 |
| RRAS | PCBD1 | TXNDC16 | LOC391833 | DSTN | SLC6A13 | PSMC2 | IL11 |
| S100A10 | PCK1 | ARHGAP23 | LOC399942 | UPK1A | SLC9A3 | PSMC4 | IL13 |
| SDC1 | PDCD2 | MUTED | LOC400389 | PHB2 | SLC15A2 | PSMD2 | IL15RA |
| SDC4 | PDE8A | TINAGL1 | LOC400578 | RRAS2 | SLC25A1 | PSMD13 | INHBA |

TABLE 2-continued

Exosome polypeptides

| | | | | | | | | |
|---|---|---|---|---|---|---|---|---|
| SEC31A | SLC22A2 | PYGL | INHBB | | F7 | GGH | EIF4A3 | FGF19 |
| CLSTN1 | SLC22A5 | RPL10 | IPO5 | | FLOT2 | PROZ | ACTR1B | GDF11 |
| PTGR1 | SMO | RPL15 | LIF | | GARS | SQSTM1 | OPTN | FST |
| RAB21 | SORD | STX4 | LRP6 | | GMDS | AP1M1 | NAMPT | LASS1 |
| CYFIP1 | SORL1 | TARS | LTBP1 | | GNB3 | RAB7L1 | MPZL2 | HPSE |
| SLC44A1 | SPAST | CLDN5 | MMP1 | | HIST1H2AE | WASL | STIP1 | ESM1 |
| CORO1C | SPR | TPBG | MMP2 | | HLA-C | PLOD3 | PKP3 | DKK1 |
| MTCH2 | SPRR3 | XPO1 | MMP3 | | HLA-H | PGLYRP1 | POFUT2 | IL17B |
| QPCT | SRC | XRCC5 | MMP10 | | HPCAL1 | KALRN | QPRT | IL19 |
| PRDX5 | ST13 | BAT1 | NBL1 | | | CLIC3 | WBP2 | TNFRSF12A |
| SND1 | STK11 | HIST1H2BG | TNFRSF11B | | IGHα | BAZ1B | ERO1L | IL23A |
| F11R | VAMP7 | HIST1H2BF | OSM | | IGHG1 | SPAG9 | H2AFY2 | FGFRL1 |
| LIMA1 | SYPL1 | HIST1H2BE | PDGFA | | IGHG2 | SLC13A2 | RCC2 | TREM1 |
| RAB6B | SERPINA7 | HIST1H2BI | PRKCSH | | IGHG3 | ATP6V0D1 | RTN4 | IL1F9 |
| KRT20 | TECTA | HIST1H2BC | CCL2 | | IGHG4 | HGS | GLT25D1 | CXCL16 |
| VPS35 | TGM4 | HIST1H4G | CCL7 | | IGHM | AP4M1 | RNASE7 | IL22RA1 |
| TOMM22 | TGFBR3 | EIF3A | CCL20 | | IGKC | ATP6V1F | FCRLA | HIST1H2BK |
| AKR1B10 | TGM2 | EIF3B | SFRP4 | | ITGA3 | PTER | H2AFV | HIST3H2BB |
| S100A14 | TLN1 | EIF3C | SOD3 | | KRT3 | TRIP10 | MRLC2 | LOC440093 |
| DIP2B | DNAJC7 | SLC5A6 | SPARC | | KRT4 | SLC9A3R2 | PAGE2 | PGAM4 |
| RAP2C | UBE2G1 | HIST2H2AA4 | TIMP1 | | KRT6A | SLIT2 | HIST1H2BA | PC-3 |
| FAM129B | UPK1B | LOC728358 | TIMP2 | | KRT6B | SLC22A6 | SNX33 | LOC729500 |
| | UGP2 | LOC730839 | TIMP3 | | KRT7 | KL | PTRF | KRT18P26 |
| AHNAK | UPK3A | LOC100126583 | ICAM5 | | KRT17 | KIF3B | HIST2H2BC | S100A11P |
| VPS37B | UTRN | AARS | TNFRSF1A | | RPSA | SLC22A8 | ANXA8 | LOC729679 |
| TUBA4B | VASP | AK2 | VEGFC | | LFNG | GRHPR | NME1-NME2 | KRT17P3 |
| ARPC5L | VCL | APEH | GDF5 | | LGALS3 | SLC22A13 | EIF2S1 | RCTPI1 |
| EPPK1 | VDAC1 | FAS | HIST3H3 | | LRP4 | TMPRSS11D | EIF2S3 | LOC729903 |
| ADSL | VDAC3 | BAX | HIST1H2AI | | CD46 | GSTO1 | EIF4E | RP11-556K13.1 |
| AP2A1 | XPNPEP2 | FMNL1 | HIST1H2AL | | MICA | NPEPPS | EPB41L2 | LOC100129982 |
| RHOC | BTG2 | CASP9 | HIST1H2AC | | MYH11 | TMEM59 | EVI2B | LOC100130100 |
| RHOG | GCS1 | CD19 | HIST1H2AM | | NARS | ATP6V1G1 | FCER2 | LOC100130446 |
| ASNS | BAT2 | MS4A1 | HIST1H2BN | | NEDD4 | CDC42BPB | FGR | LOC100130562 |
| | PTP4A2 | CD22 | HIST1H2BM | | RPL10A | CREB5 | FH | LOC100130624 |
| CAD | DYSF | TNFRSF8 | HIST1H2BH | | PCNA | CROCC | GART | LOC100130711 |
| CBR1 | EEA1 | SCARB1 | HIST1H2BO | | PLEC1 | DHX34 | GOT2 | LOC100130819 |
| CBR3 | STK24 | ENTPD1 | HIST1H3A | | PLXNA1 | TMEM63A | NCKAP1L | LOC100131713 |
| CCT6A | CUL4B | CD48 | HIST1H3D | | PPP2R1A | SLK | HLA-DPB1 | LOC100131863 |
| CDH17 | CUL3 | CD58 | HIST1H3C | | PSMC6 | RUSC2 | HLA-DQA1 | LOC100132795 |
| CEACAM5 | ATRN | CD74 | HIST1H3E | | PSMD3 | OXSR1 | HNRNPA1 | LOC100133211 |
| COPB1 | CDC42BPA | CD79B | HIST1H3I | | PSMD11 | SLC23A1 | HNRNPC | LOC100133690 |
| CLDN4 | PPFIA2 | CD97 | HIST1H3G | | RAC3 | DOPEY2 | HPRT1 | SET |
| CLDN7 | AKR7A2 | 41889 | HIST1H3J | | RAP2A | ABI1 | ICAM3 | CCT6B |
| CRYZ | PPAP2A | CR2 | HIST1H3H | | RAP2B | GNPDA1 | INSR | ACTR3B |
| CD55 | ABCB11 | CSNK2B | HIST1H3B | | RPL12 | TOM1 | EIF3E | PSMA8 |
| EEF1G | MAP2K1IP1 | DBI | FADD | | RPLP0 | ABCB6 | ITGAL | ARP11 |
| EPHA2 | EIF3H | DHCR7 | IL1RL2 | | RPS4X | ABCC9 | ITGB3 | BCHE |
| EIF4A1 | SLC4A4 | DLG1 | FGF18 | | RPS4Y1 | HUWE1 | ITGB7 | H2AFZ |
| EIF4A2 | SNX3 | DOCK2 | FGF16 | | RPS8 | ARPC5 | ITIH2 | SNRPE |
| ENO2 | MYH13 | DUT | HIST1H3F | | RPS16 | ACTR2 | STMN1 | TFPI |
| SLC29A1 | NAPG | ECH1 | HIST1H2AG | | SPTAN1 | TSPAN3 | LCK | ADAMTS1 |
| EPHB2 | FBP2 | VAPA | HIST1H2BJ | | VAMP1 | ARPC2 | LSP1 | GDF15 |
| EPHB3 | SCEL | H2AFY | NRG2 | | | | | |
| ESD | SUCLA2 | PDIA4 | GDF3 | | | | | |

TABLE 3

Polypeptide payloads and receivers

| Ankyrin repeat proteins | Fibronectins | | Lyases |
|---|---|---|---|
| General Classes | | | |
| Antibodies | Complement receptors | GPI-linked polypeptides | Nanobodies |
| Aptamers | Cyclic peptides | HEAT repeat proteins | Nucleic Acids |
| ARM repeat proteins | DARPins | Hydrolases | Polypeptides |
| Carbohydrates | DNAses | Kinases | Single-chain variable fragments (scFv) |
| Cell surface receptors | Enzymes | Lipoproteins | Tetratri copeptide repeat proteins |
| Complement | | | |
| C1 inhibitor | C4 binding protein | CR3 | Factor I |
| C3 Beta chain Receptor | CD59 | CR4 | Homologous |

TABLE 3-continued

Polypeptide payloads and receivers

| Ankyrin repeat proteins | | Fibronectins | Lyases |
|---|---|---|---|
| C3aR | CR1 | Decay-accelerating factor (DAF) | restriction factor Membrane cofactor protein (MCP) |
| C3eR | CR2 | Factor H | PRELP |

Enzymes

| | | | |
|---|---|---|---|
| triacylglycerol lipase | bile-acid-CoA hydrolase | feruloyl esterase | phosphatidate phosphatase |
| (S)-methylmalonyl-CoA hydrolase | bis(2-ethylhexyl)phthalate esterase | formyl-CoA hydrolase | phosphatidylglycero phosphatase |
| [acyl-carrier-protein] phosphodiesterase | bisphosphoglycerate phosphatase | fructose-bisphosphatase | phosphatidylinositol deacylase |
| [phosphorylase] phosphatase | Carboxylic-Ester Hydrolases | fumarylacetoacetase | phosphodiesterase I |
| 1,4-lactonase | carboxymethylenebutenolidase | fusarinine-C omithinesterase | phosphoglycerate phosphatase |
| 11-cis-retinyl-palmitate hydrolase | cellulose-polysulfatase | galactolipase | phosphoglycolate phosphatase |
| 1-alkyl-2-acetylglycerophosphocholine esterase | cephalosporin-C deacetylase | gluconolactonase | phosphoinositide phospholipase C |
| 2'-hydroxybiphenyl-2-sulfinate desulfinase | cerebroside-sulfatase | glucose-1-phosphatase | phospholipase A1 |
| 2-pyrone-4,6-dicarboxylate lactonase | cetraxate benzylesterase | glucose-6-phosphatase | phospholipase A2 |
| 3',5'-bisphosphate nucleotidase | chlorogenate hydrolase | glutathione thiolesterase | phospholipase C |
| 3-hydroxyisobutyryl-CoA hydrolase | chlorophyllase | glycerol-1-phosphatase | phospholipase D |
| 3'-nucleotidase | cholinesterase | glycerol-2-phosphatase | phosphonoacetaldehyde hydrolase |
| 3-oxoadipate enol-lactonase | choline-sulfatase | glycerophosphocholine phosphodiesterase | phosphonoacetate hydrolase |
| 3-phytase | choloyl-CoA hydrolase | Glycosidases, i.e. enzymes that hydrolyse O- and S-glycosyl compounds | phosphonopyruvate hydrolase |
| 4-hydroxybenzoyl-CoA thioesterase | chondro-4-sulfatase | glycosulfatase | phosphoprotein phosphatase |
| 4-methyloxaloacetate esterase | chondro-6-sulfatase | Glycosylases | Phosphoric-diester hydrolases |
| 4-phytase | citrate-lyase deacetylase | histidinol-phosphatase | Phosphoric-monoester hydrolases |
| 4-pyridoxolactonase | cocaine esterase | hormone-sensitive lipase | Phosphoric-triester hydrolases |
| 5'-nucleotidase | cutinase | Hydrolysing N-glycosyl compounds | phosphoserine phosphatase |
| 6-acetylglucose deacetylase | cyclamate sulfohydrolase | Hydrolysing S-glycosyl compounds | poly(3-hydroxybutyrate) depolymerase |
| 6-phosphogluconolactonase | Cysteine endopeptidases | hydroxy acylglutathione hydrolase | poly(3-hydroxyoctanoate) depolymerase |
| a-amino-acid esterase | Cysteine-type carboxypeptidases | hydroxybutyrate-dimer hydrolase | polyneuridine-aldehyde esterase |
| a-Amino-acyl-peptide hydrolases | D-arabinonolactonase | hydroxymethylglutaryl-CoA hydrolase | protein-glutamate methylesterase |
| acetoacetyl-CoA hydrolase | deoxylimonate A-ring-lactonase | iduronate-2-sulfatase | quorum-quenching N-acyl-homoserine lactonase |
| acetoxybutynylbithiophene deacetylase | dGTPase | inositol-phosphate phosphatase | retinyl-palmitate esterase |
| acetylajmalineesterase | dihydrocoumarin hydrolase | juvenile-hormone esterase | Serine dehyrdatase or serine hydroxymethyl transferase |
| acetylalkylglycerol acetylhydrolase | Dipeptidases | kynureninase | Serine endopeptidases |
| acetylcholinesterase | Dipeptide hydrolases | L-arabinonolactonase | serine-ethanolamine-phosphate phosphodiesterase |

TABLE 3-continued

| Polypeptide payloads and receivers | | | |
|---|---|---|---|
| Ankyrin repeat proteins | | Fibronectins | Lyases |
| acetyl-CoA hydrolase | Dipeptidyl-peptidases and tripeptidyl-peptidases | limonin-D-ring-lactonase | Serine-type carboxypeptidases |
| acetylesterase | Diphosphoric-monoester hydrolases | lipoprotein lipase | S-formylglutathione hydrolase |
| acetylpyruvate hydrolase | disulfoglucosamine-6-sulfatase | L-rhamnono-1,4-lactonase | sialate O-acetylesterase |
| acetylsalicylate deacetylase | dodecanoyl-[acyl-carrier-protein] hydrolase | lysophospholipase | sinapine esterase |
| acetylxylan esterase | Endodeoxyribonucleases producing 3'-phosphomonoesters | mannitol-1-phosphatase | Site specific endodeoxyribo-nucleases: cleavage is not sequence specific |
| acid phosphatase | Endodeoxyribonucleases producing 5'-phosphomonoesters | Metallocarboxypeptidases | Site-specific endodeoxyribo-nucleases that are specific for altered bases. |
| Acting on acid anhydrides to catalyse transmembrane movement of substances | Endopeptidases of unknown catalytic mechanism | Metalloendopeptidases. | Site-specific endodeoxyribo-nucleases: cleavage is sequence specific |
| Acting on acid anhydrides to facilitate cellular and subcellular movement | Endoribonucleases producing 3'-phosphomonoesters | methylphosphothioglycerate phosphatase | sphingomyelin phosphodiesterase |
| Acting on GTP to facilitate cellular and subcellular movement | Endoribonucleases producing 5'-phosphomonoesters | methylumbelliferyl-acetate deacetylase | S-succinylglutathione hydrolase |
| Acting on phosphorus-nitrogen bonds | Endoribonucleases that are active with either ribo- or deoxyribonucleic acids and produce 3'-phosphomonoesters | monoterpene e-lactone hydrolase | steroid-lactonase |
| Acting on sulfur-nitrogen bonds | Endoribonucleases that are active with either ribo- or deoxyribonucleic acids and produce 5'-phosphomonoesters | N-acetylgalactosamine-4-sulfatase | sterol esterase |
| actinomycin lactonase | Enzymes acting on acid anhydrides | N-acetylgalactosamine-6-sulfatase | steryl-sulfatase |
| acylcarnitine hydrolase | Enzymes Acting on carbon-carbon bonds | N-acetylgalactosaminoglycan deacetylase | succinyl-CoA hydrolase |
| acyl-CoA hydrolase | Enzymes acting on carbon-nitrogen bonds, other than peptide bonds | N-acetylglucosamine-6-sulfatase | sucrose-phosphate phosphatase |
| acylglycerol lipase | Enzymes acting on carbon-phosphorus bonds | N-sulfoglucosamine sulfohydrolase | sugar-phosphatase |
| acyloxyacyl hydrolase | Enzymes acting on carbon-sulfur bonds | oleoyl-[acyl-carrier-protein] hydrolase | Sulfuric-ester hydrolases |
| acylpyruvate hydrolase | Enzymes Acting on ether bonds | Omega peptidases | tannase |
| ADAMTS13 | Enzymes acting on halide bonds | orsellinate-depside hydrolase | Thioester hydrolases |
| Adenosine deaminase | Enzymes acting on peptide bonds (peptidases) | oxaloacetase | Thioether and trialkylsulfonium hydrolases |
| adenylyl-[glutamate-ammonia ligase] hydrolase | Enzymes acting on phosphorus-nitrogen bonds | palmitoyl[protein] hydrolase | Threonine endopeptidases |
| ADP-dependent medium-chain-acyl-CoA hydrolase | Enzymes acting on sulfur-nitrogen bonds | palmitoyl-CoA hydrolase | thymidine phosphorylase |

TABLE 3-continued

| Polypeptide payloads and receivers | | | |
|---|---|---|---|
| Ankyrin repeat proteins | | Fibronectins | Lyases |
| ADP-dependent short-chain-acyl-CoA hydrolase | Enzymes acting on sulfur-sulfur bonds | pectinesterase | trehalose-phosphatase |
| ADP-phosphoglycerate phosphatase | Ether hydrolases. | Peptidyl peptide hydrolases | triacetate-lactonase |
| alkaline phosphatase | Exodeoxyribonucleases producing 5'-phosphomonoesters | Peptidyl-amino-acid hydrolases | Triphosphoric-monoester hydrolases |
| all-trans-retinyl-palmitate hydrolase | Exonucleases that are active with either ribo- or deoxyribonucleic acids and produce 3'-phosphomonoesters | Peptidylamino-acid hydrolases or acylamino-acid hydrolases | trithionate hydrolase |
| aminoacyl-tRNA hydrolase | Exonucleases that are active with either ribo- or deoxyribonucleic acids and produce 5'-phosphomonoesters | Peptidyl-dipeptidases | tropinesterase |
| Aminopeptidases | Exoribonucleases producing 3'-phosphomonoesters | phenylacetyl-CoA hydrolase | ubiquitin thiolesterase |
| arylesterase | Exoribonucleases producing 5'-phosphomonoesters. | Phenylalanine ammonia lyase | UDP-sulfoquinovose synthase |
| arylsulfatase | Factor IX | Phenylalanine hydroxylase | uricase |
| Asparaginase | Factor VIII | pheophorbidase | uronolactonase |
| Aspartic endopeptidases | fatty-acyl-ethyl-ester synthase | phloretin hydrolase | wax-ester hydrolase |
| | b-diketone hydrolase | phorbol-diester hydrolase | xylono-1,4-lactonase |

TABLE 4

| Targets | | | |
|---|---|---|---|
| General Classes of Targets | | | |
| Microbes | Polypeptides | DNA | Amino Acids |
| Fungi | Toxins | RNA | Prions |
| Bacteria | Lipids | Parasites | Cytokines |
| Virus | Cells | Cellular Debris | |
| Infectious Disease-Related Targets | | | |
| Lipopolysaccharides | Cell invasion protein | Intermedilysin | Secreted effector protein sptP |
| Zona occludens toxin | Cholera enterotoxin | Invasion protein sipA | Seeligeriolysin |
| Actin polymerization protein RickA | Cysteine protease | Iota toxin component Ia | Serine protease |
| Actin polymerization protein RickA | Cytolethal distending toxin | Ivanolysin | Shiga toxin |
| Adenosine monophosphate-protein transferase vopS | Cytolysin | LepB | Sphingomyelinase |
| adenylate cyclase | Cytotoxic necrotizing factor | Lethal factor | Staphylokinase |
| Adenylate cyclase ExoY | Cytotoxin | Leukotoxin | Streptokinase |
| ADP-ribosyltransferase enzymatic component | Dermonecrotic toxin | Listeriolysin | Streptolysin |
| Aerolysin | Deubiquitinase | Microbial collagenase | Streptopain |
| Alpha-toxin | Diphtheria toxin | Outer membrane protein IcsA autotransporter | Suilysin |

TABLE 4-continued

| Targets | | | |
|---|---|---|---|
| Alveolysin | Enterohemolysin | Panton-Valentine Leucocidin F | Superantigen |
| Alveolysin | Enterotoxin | Perfringolysin | T3SS secreted effector EspF |
| Anthrolysin O | Epidermal cell differentiation inhibitor | Pertussis toxin | Tetanus toxin |
| Arp2/3 complex-activating protein rickA | Exoenzyme | Phospholipase | Tir |
| Binary ADP-ribosyltransferase CDT toxin | Exotoxin | Plasminogen activator | TolC |
| Botulinum neurotoxin | G-nucleotide exchange factor | Pneumolysin | Toxic shock syndrome toxin |
| C2 toxin, component II | Guanine nucleotide exchange factor sopE | Protective antigen | Zink-carboxypeptidase |
| CagA | Heat stable enterotoxin | Protein kinase | Zink-carboxypeptidase |
| Calmodulin-sensitive adenylate cyclase | IgA-specific serine endopeptidase autotransporter | Pyolysin | Zn-dependent peptidase |
| Cell cycle inhibiting factor | Inositol phosphate phosphatase sopB | RTX toxin | |
| Lipid & Cell Targets | | | |
| Circulating tumor cells | very low density lipid (VLDL) | triglycerides | Fatty acids |
| Metastases | high density lipoprotein | chylomicrons | Cholesterol |
| Eukaryotic cells | low density lipoprotein | apolipoproteins | |

TABLE 5

| Cancers | | | |
|---|---|---|---|
| Acute lymphoblastic leukaemia (ALL) | Colorectal cancer | Macroglobulinemia, Waldenström | Pleuropulmonary Blastoma, Childhood |
| Acute myeloid leukaemia (AML) | Craniopharyngioma, Childhood | Male Breast Cancer | Pregnancy and Breast Cancer |
| Adrenocortical Carcinoma | Cutaneous T-Cell Lymphoma | Malignant Fibrous Histiocytoma of Bone and Osteosarcoma | Primary Central Nervous System (CNS) Lymphoma |
| AIDS-Related Kaposi Sarcoma | Ductal Carcinoma In Situ (DCIS) | Melanoma | Prostate Cancer |
| AIDS-Related lymphoma | Embryonal Tumors, Childhood | Merkel Cell Carcinoma | Rare cancers |
| Anal Cancer | Endometrial Cancer | Mesothelioma | Rectal Cancer |
| Appendix Cancer | Ependymoma, Childhood | Metastatic Squamous Neck Cancer with Occult Primary | Renal cell carcinoma |
| Astrocytomas, Childhood | Epithelial cancer | Midline Tract Carcinoma Involving NUT Gene | Renal Pelvis and Ureter, Transitional Cell Cancer |
| Atypical Teratoid/Rhabdoid Tumor, Childhood | Esophageal Cancer | Molar pregnancy | Retinoblastoma |
| Basal Cell Carcinoma | Esthesioneuroblastoma, Childhood | Mouth and oropharyngeal cancer | Rhabdomyosarcoma |
| Bile duct cancer | Ewing sarcoma | Multiple Endocrine Neoplasia Syndromes, Childhood | Salivary Gland Cancer |
| Bladder cancer | Extragonadal Germ Cell Tumor | Multiple Myeloma/Plasma Cell Neoplasm | Sarcoma |
| Bone cancer | Extrahepatic Bile Duct Cancer | Mycosis Fungoides | Secondary cancers |
| Bowel cancer | Eye Cancer | Myelodysplastic Syndromes | Sézary Syndrome |
| Brain Stem Glioma, Childhood | Gallbladder Cancer | Myelodysplastic/Myeloproliferative Neoplasms | Skin Cancer |
| Brain tumours | Gastric cancer | Myeloproliferative Disorders, Chronic | Skin cancer (non melanoma) |
| Breast cancer | Gastrointestinal Carcinoid Tumor | Nasal Cavity and Paranasal Sinus Cancer | Small Cell Lung Cancer |

TABLE 5-continued

| Cancers | | | |
|---|---|---|---|
| Bronchial Tumors, Childhood | Germ Cell Tumor | Nasopharyngeal cancer | Small Intestine Cancer |
| Burkitt Lymphoma | Gestational trophoblastic tumours (GTT) | Neuroblastoma | Soft Tissue Sarcoma |
| Cancer of unknown primary | Glioma | Non-Hodgkin Lymphoma | Squamous Cell Carcinoma |
| Cancer spread to bone | Hairy cell leukaemia | Non-Small Cell Lung Cancer | Squamous Neck Cancer with Occult Primary, Metastatic |
| Cancer spread to brain | Head and neck cancer | Oesophageal cancer | Stomach (Gastric) Cancer |
| Cancer spread to liver | Heart Cancer, Childhood | Oral Cancer | Stomach cancer |
| Cancer spread to lung | Hepatocellular (Liver) Cancer | Oral Cavity Cancer | T-Cell Lymphoma, Cutaneous - see Mycosis Fungoides and Sézary Syndrome |
| Carcinoid Tumor | Histiocytosis, Langerhans Cell | Oropharyngeal Cancer | Testicular cancer |
| Carcinoma of Unknown Primary | Hodgkin Lymphoma | Osteosarcoma (Bone Cancer) | Throat Cancer |
| Cardiac (Heart) Tumors, Childhood | Hypopharyngeal Cancer | Osteosarcoma and Malignant Fibrous Histiocytoma | Thymoma and Thymic Carcinoma |
| Central Nervous System Atypical Teratoid/Rhabdoid Tumor, Childhood | Intraocular Melanoma | Ovarian Cancer | Thyroid Cancer |
| Central Nervous System Embryonal Tumors, Childhood | Islet Cell Tumors, Pancreatic Neuroendocrine Tumors | Pancreatic Cancer | Transitional Cell Cancer of the Renal Pelvis and Ureter |
| Central Nervous System, Childhood | Kidney cancer | Pancreatic Neuroendocrine Tumors (Islet Cell Tumors) | Unknown primary cancer |
| Cervical cancer | Langerhans Cell Histiocytosis | Papillomatosis, Childhood | Ureter and Renal Pelvis, Transitional Cell Cancer |
| Chordoma, Childhood | Laryngeal Cancer | Paraganglioma | Urethral Cancer |
| Choriocarcinoma | Leukemia | Parathyroid Cancer | Uterine Cancer, Endometrial |
| Chronic Lymphocytic Leukemia (CLL) | Lip and Oral Cavity Cancer | Penile Cancer | Uterine Sarcoma |
| Chronic myeloid leukaemia (CML) | Liver cancer | Pharyngeal Cancer | Vaginal cancer |
| Chronic Myeloproliferative Disorders | Lobular Carcinoma In Situ (LCIS) | Pheochromocytoma | Vulvar Cancer |
| Colon cancer | Low Malignant Potential Tumor | Pituitary Tumor | Waldenström Macroglobulinemia |
| Lymphoma | Lung Cancer | Plasma Cell Neoplasm/Multiple Myeloma | Wilms Tumor |

What is claimed is:

1. A composition comprising:
   an extracellular vesicle comprising a cell membrane bounding an enclosed volume, wherein the extracellular vesicle comprises a fusion protein comprising a prostaglandin F2 receptor negative regulator (PTG-FRN) or a fragment thereof fused to an immunomodulating component.

2. The composition of claim 1, wherein the immunomodulating component comprises a cytokine.

3. The composition of claim 2, wherein the cytokine is IL-7.

4. The composition of claim 2, wherein the cytokine is IL-12.

5. The composition of claim 2, wherein the cytokine is IL-15.

6. The composition of claim 2, wherein the cytokine is IL-2, IL-7, IL-10, IL-12, or IL-15.

7. The composition of claim 1, wherein the extracellular vesicle is an exosome.

8. The composition of claim 1, wherein the extracellular vesicle is a nanovesicle.

9. The composition of claim 1, further comprising a pharmaceutically-acceptable carrier.

10. The composition of claim 1, wherein the immunomodulating component is an activator for a positive co-stimulatory molecule or an activator for a binding partner of a positive co-stimulatory molecule.

11. The composition of claim 10, wherein the immunomodulating component comprises a TNF receptor superfamily member.

12. The composition of claim 11, wherein the TNF receptor superfamily member comprises CD120a, CD120b, CD18, OX40, CD40, Fas receptor, M68, CD27, CD30, 4-1BB, TRAILR1, TRAILR2, TRAILR3, TRAILR4, RANK, OCIF, TWEAK receptor, TACI, BAFF receptor, ATAR, CD271, CD269, GITR, TROY, CD358, TRAMP, or XEDAR.

13. The composition of claim 1, wherein the immunomodulating component comprises a TNF superfamily member.

14. The composition of claim 13, wherein the TNF superfamily member comprises TNFα, TNF-C, OX40L, CD40L, FasL, LIGHT, TL1A, CD27L, Siva, CD153, 4-1BB ligand, TRAIL, RANKL, TWEAK, APRIL, BAFF, CAMLG, NGF, BDNF, NT-3, NT-4, GITR ligand, or EDA-2.

15. The composition of claim 14, wherein the TNF superfamily member is CD40L.

16. The composition of claim 1, wherein the immunomodulating component comprises IFNγ.

17. The composition of claim 1, wherein the fragment of the PTGFRN comprises the region before the C-terminal-most IgV domain, the transmembrane domain, and the intracellular domain of PTGFRN.

18. The composition of claim 1, wherein the PTGFRN comprises the full-length PTGFRN.

19. The composition of claim 1, wherein the immunomodulating component comprises an inhibitor of cytotoxic T-lymphocyte-associate protein 4 (CTLA-4), programmed cell death protein 1 (PD-1), programmed death-ligand 1 (PD-L1), programmed death-ligand 2 (PD-L2), lymphocyte-activated gene 3 (LAG3), T-cell immunoglobulin mucin-containing protein 3 (TIM-3), B and T lymphocyte attenuator (BTLA), T cell immunoreceptor with Ig and ITIM domains (TIGIT), V-domain Ig suppressor of T cell activation (VISTA), adenosine A2a receptor (A2aR), killer cell immunoglobulin like receptor (KIR), indoleamine 2,3-dioxygenase (IDO), CD20, CD39, or CD73.

* * * * *

SEQUENCE LISTING

<160> NUMBER OF SEQ ID NOS: 26

<210> SEQ ID NO 1
<211> LENGTH: 390
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 1

```
Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His Ser Ala Gly Gly Gly Ser Asp Tyr Lys Asp Asp Asp Lys
            180                 185                 190

Gly Gly Gly Gly Ser Gly Pro Ile Phe Asn Ala Ser Val His Ser Asp
    195                 200                 205

Thr Pro Ser Val Ile Arg Gly Asp Leu Ile Lys Leu Phe Cys Ile Ile
    210                 215                 220

Thr Val Glu Gly Ala Ala Leu Asp Pro Asp Asp Met Ala Phe Asp Val
225                 230                 235                 240

Ser Trp Phe Ala Val His Ser Phe Gly Leu Asp Lys Ala Pro Val Leu
                245                 250                 255

Leu Ser Ser Leu Asp Arg Lys Gly Ile Val Thr Thr Ser Arg Arg Asp
            260                 265                 270

Trp Lys Ser Asp Leu Ser Leu Glu Arg Val Ser Val Leu Glu Phe Leu
    275                 280                 285

Leu Gln Val His Gly Ser Glu Asp Gln Asp Phe Gly Asn Tyr Tyr Cys
    290                 295                 300

Ser Val Thr Pro Trp Val Lys Ser Pro Thr Gly Ser Trp Gln Lys Glu
305                 310                 315                 320

Ala Glu Ile His Ser Lys Pro Val Phe Ile Thr Val Lys Met Asp Val
                325                 330                 335

Leu Asn Ala Phe Lys Tyr Pro Leu Leu Ile Gly Val Gly Leu Ser Thr
            340                 345                 350

Val Ile Gly Leu Leu Ser Cys Leu Ile Gly Tyr Cys Ser Ser His Trp
    355                 360                 365

Cys Cys Lys Lys Glu Val Gln Glu Thr Arg Arg Glu Arg Arg Arg Leu
    370                 375                 380

Met Ser Met Glu Met Asp
385                 390

<210> SEQ ID NO 2
<211> LENGTH: 382
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 2
```

| | | | | | | | | | | | | | | |
|---|---|---|---|---|---|---|---|---|---|---|---|---|---|---|
| Met | Phe | His | Val | Ser | Phe | Arg | Tyr | Ile | Phe | Gly | Leu | Pro | Pro | Leu | Ile |
| 1 | | | | 5 | | | | | 10 | | | | | 15 | |

Leu Val Leu Leu Pro Val Ala Ser Ser Asp Cys Asp Ile Glu Gly Lys
          20                  25                  30

Asp Gly Lys Gln Tyr Glu Ser Val Leu Met Val Ser Ile Asp Gln Leu
         35                  40                  45

Leu Asp Ser Met Lys Glu Ile Gly Ser Asn Cys Leu Asn Asn Glu Phe
 50                  55                  60

Asn Phe Phe Lys Arg His Ile Cys Asp Ala Asn Lys Glu Gly Met Phe
 65                  70                  75                  80

Leu Phe Arg Ala Ala Arg Lys Leu Arg Gln Phe Leu Lys Met Asn Ser
                 85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His Ser Ala Gly Gly Gly Ser Gly Gly Gly Ser Gly Pro Ile
            180                 185                 190

Phe Asn Ala Ser Val His Ser Asp Thr Pro Ser Val Ile Arg Gly Asp
            195                 200                 205

Leu Ile Lys Leu Phe Cys Ile Ile Thr Val Glu Gly Ala Ala Leu Asp
210                 215                 220

Pro Asp Asp Met Ala Phe Asp Val Ser Trp Phe Ala Val His Ser Phe
225                 230                 235                 240

Gly Leu Asp Lys Ala Pro Val Leu Leu Ser Ser Leu Asp Arg Lys Gly
                245                 250                 255

Ile Val Thr Thr Ser Arg Arg Asp Trp Lys Ser Asp Leu Ser Leu Glu
            260                 265                 270

Arg Val Ser Val Leu Glu Phe Leu Leu Gln Val His Gly Ser Glu Asp
            275                 280                 285

Gln Asp Phe Gly Asn Tyr Tyr Cys Ser Val Thr Pro Trp Val Lys Ser
290                 295                 300

Pro Thr Gly Ser Trp Gln Lys Glu Ala Glu Ile His Ser Lys Pro Val
305                 310                 315                 320

Phe Ile Thr Val Lys Met Asp Val Leu Asn Ala Phe Lys Tyr Pro Leu
                325                 330                 335

Leu Ile Gly Val Gly Leu Ser Thr Val Ile Gly Leu Leu Ser Cys Leu
            340                 345                 350

Ile Gly Tyr Cys Ser Ser His Trp Cys Cys Lys Lys Glu Val Gln Glu
            355                 360                 365

Thr Arg Arg Glu Arg Arg Arg Leu Met Ser Met Glu Met Asp
370                 375                 380

```
<210> SEQ ID NO 3
<211> LENGTH: 1418
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser Gly Gly Gly Gly Ser Gly
                325                 330                 335

Gly Gly Gly Ser Gly Gly Gly Ser Gly Gly Ser Gly Gly Arg
            340                 345                 350

Asn Leu Pro Val Ala Thr Pro Asp Pro Gly Met Phe Pro Cys Leu His
        355                 360                 365
```

-continued

His Ser Gln Asn Leu Leu Arg Ala Val Ser Asn Met Leu Gln Lys Ala
    370                 375                 380

Arg Gln Thr Leu Glu Phe Tyr Pro Cys Thr Ser Glu Glu Ile Asp His
385                 390                 395                 400

Glu Asp Ile Thr Lys Asp Lys Thr Ser Thr Val Glu Ala Cys Leu Pro
                405                 410                 415

Leu Glu Leu Thr Lys Asn Glu Ser Cys Leu Asn Ser Arg Glu Thr Ser
            420                 425                 430

Phe Ile Thr Asn Gly Ser Cys Leu Ala Ser Arg Lys Thr Ser Phe Met
        435                 440                 445

Met Ala Leu Cys Leu Ser Ser Ile Tyr Glu Asp Leu Lys Met Tyr Gln
    450                 455                 460

Val Glu Phe Lys Thr Met Asn Ala Lys Leu Leu Met Asp Pro Lys Arg
465                 470                 475                 480

Gln Ile Phe Leu Asp Gln Asn Met Leu Ala Val Ile Asp Glu Leu Met
                485                 490                 495

Gln Ala Leu Asn Phe Asn Ser Glu Thr Val Pro Gln Lys Ser Ser Leu
            500                 505                 510

Glu Glu Pro Asp Phe Tyr Lys Thr Lys Ile Lys Leu Cys Ile Leu Leu
        515                 520                 525

His Ala Phe Arg Ile Arg Ala Val Thr Ile Asp Arg Val Met Ser Tyr
    530                 535                 540

Leu Asn Ala Ser Ser Ala Gly Gly Gly Ser Gly Gly Gly Gly Ser
545                 550                 555                 560

Arg Val Val Arg Val Pro Thr Ala Thr Leu Val Arg Val Val Gly Thr
                565                 570                 575

Glu Leu Val Ile Pro Cys Asn Val Ser Asp Tyr Asp Gly Pro Ser Glu
            580                 585                 590

Gln Asn Phe Asp Trp Ser Phe Ser Ser Leu Gly Ser Ser Phe Val Glu
        595                 600                 605

Leu Ala Ser Thr Trp Glu Val Gly Phe Pro Ala Gln Leu Tyr Gln Glu
    610                 615                 620

Arg Leu Gln Arg Gly Glu Ile Leu Leu Arg Arg Thr Ala Asn Asp Ala
625                 630                 635                 640

Val Glu Leu His Ile Lys Asn Val Gln Pro Ser Asp Gln Gly His Tyr
                645                 650                 655

Lys Cys Ser Thr Pro Ser Thr Asp Ala Thr Val Gln Gly Asn Tyr Glu
            660                 665                 670

Asp Thr Val Gln Val Lys Val Leu Ala Asp Ser Leu His Val Gly Pro
        675                 680                 685

Ser Ala Arg Pro Pro Pro Ser Leu Ser Leu Arg Glu Gly Glu Pro Phe
    690                 695                 700

Glu Leu Arg Cys Thr Ala Ala Ser Ala Ser Pro Leu His Thr His Leu
705                 710                 715                 720

Ala Leu Leu Trp Glu Val His Arg Gly Pro Ala Arg Arg Ser Val Leu
                725                 730                 735

Ala Leu Thr His Glu Gly Arg Phe His Pro Gly Leu Gly Tyr Glu Gln
            740                 745                 750

Arg Tyr His Ser Gly Asp Val Arg Leu Asp Thr Val Gly Ser Asp Ala
        755                 760                 765

Tyr Arg Leu Ser Val Ser Arg Ala Leu Ser Ala Asp Gln Gly Ser Tyr
    770                 775                 780

```
Arg Cys Ile Val Ser Glu Trp Ile Ala Glu Gln Gly Asn Trp Gln Glu
785             790             795             800

Ile Gln Glu Lys Ala Val Glu Val Ala Thr Val Val Ile Gln Pro Ser
        805             810             815

Val Leu Arg Ala Ala Val Pro Lys Asn Val Ser Val Ala Glu Gly Lys
            820             825             830

Glu Leu Asp Leu Thr Cys Asn Ile Thr Thr Asp Arg Ala Asp Asp Val
            835             840             845

Arg Pro Glu Val Thr Trp Ser Phe Ser Arg Met Pro Asp Ser Thr Leu
    850             855             860

Pro Gly Ser Arg Val Leu Ala Arg Leu Asp Arg Asp Ser Leu Val His
865             870             875             880

Ser Ser Pro His Val Ala Leu Ser His Val Asp Ala Arg Ser Tyr His
                885             890             895

Leu Leu Val Arg Asp Val Ser Lys Glu Asn Ser Gly Tyr Tyr Tyr Cys
            900             905             910

His Val Ser Leu Trp Ala Pro Gly His Asn Arg Ser Trp His Lys Val
        915             920             925

Ala Glu Ala Val Ser Ser Pro Ala Gly Val Gly Val Thr Trp Leu Glu
930             935             940

Pro Asp Tyr Gln Val Tyr Leu Asn Ala Ser Lys Val Pro Gly Phe Ala
945             950             955             960

Asp Asp Pro Thr Glu Leu Ala Cys Arg Val Asp Thr Lys Ser Gly
                965             970             975

Glu Ala Asn Val Arg Phe Thr Val Ser Trp Tyr Tyr Arg Met Asn Arg
            980             985             990

Arg Ser Asp Asn Val Val Thr Ser  Glu Leu Leu Ala Val  Met Asp Gly
        995             1000             1005

Asp Trp  Thr Leu Lys Tyr  Gly  Glu Arg Ser Lys Gln  Arg Ala Gln
    1010             1015              1020

Asp Gly  Asp Phe Ile Phe  Ser  Lys Glu His Thr Asp   Thr Phe Asn
    1025             1030              1035

Phe Arg  Ile Gln Arg Thr  Thr  Glu Glu Asp Arg Gly   Asn Tyr Tyr
    1040             1045              1050

Cys Val  Val Ser Ala Trp  Thr  Lys Gln Arg Asn Asn   Ser Trp Val
    1055             1060              1065

Lys Ser  Lys Asp Val Phe  Ser  Lys Pro Val Asn Ile   Phe Trp Ala
    1070             1075              1080

Leu Glu  Asp Ser Val Leu  Val  Val Lys Ala Arg Gln   Pro Lys Pro
    1085             1090              1095

Phe Phe  Ala Ala Gly Asn  Thr  Phe Glu Met Thr Cys   Lys Val Ser
    1100             1105              1110

Ser Lys  Asn Ile Lys Ser  Pro  Arg Tyr Ser Val Leu   Ile Met Ala
    1115             1120              1125

Glu Lys  Pro Val Gly Asp  Leu  Ser Ser Pro Asn Glu   Thr Lys Tyr
    1130             1135              1140

Ile Ile  Ser Leu Asp Gln  Asp  Ser Val Val Lys Leu   Glu Asn Trp
    1145             1150              1155

Thr Asp  Ala Ser Arg Val  Asp  Gly Val Val Leu Glu   Lys Val Gln
    1160             1165              1170

Glu Asp  Glu Phe Arg Tyr  Arg  Met Tyr Gln Thr Gln   Val Ser Asp
    1175             1180              1185

Ala Gly  Leu Tyr Arg Cys  Met  Val Thr Ala Trp Ser   Pro Val Arg
```

| | | 1190 | | | | 1195 | | | | 1200 | | |

Gly Ser Leu Trp Arg Glu Ala Ala Thr Ser Leu Ser Asn Pro Ile
    1205                1210                1215

Glu Ile Asp Phe Gln Thr Ser Gly Pro Ile Phe Asn Ala Ser Val
    1220                1225                1230

His Ser Asp Thr Pro Ser Val Ile Arg Gly Asp Leu Ile Lys Leu
    1235                1240                1245

Phe Cys Ile Ile Thr Val Glu Gly Ala Ala Leu Asp Pro Asp Asp
    1250                1255                1260

Met Ala Phe Asp Val Ser Trp Phe Ala Val His Ser Phe Gly Leu
    1265                1270                1275

Asp Lys Ala Pro Val Leu Leu Ser Ser Leu Asp Arg Lys Gly Ile
    1280                1285                1290

Val Thr Thr Ser Arg Arg Asp Trp Lys Ser Asp Leu Ser Leu Glu
    1295                1300                1305

Arg Val Ser Val Leu Glu Phe Leu Leu Gln Val His Gly Ser Glu
    1310                1315                1320

Asp Gln Asp Phe Gly Asn Tyr Tyr Cys Ser Val Thr Pro Trp Val
    1325                1330                1335

Lys Ser Pro Thr Gly Ser Trp Gln Lys Glu Ala Glu Ile His Ser
    1340                1345                1350

Lys Pro Val Phe Ile Thr Val Lys Met Asp Val Leu Asn Ala Phe
    1355                1360                1365

Lys Tyr Pro Leu Leu Ile Gly Val Gly Leu Ser Thr Val Ile Gly
    1370                1375                1380

Leu Leu Ser Cys Leu Ile Gly Tyr Cys Ser Ser His Trp Cys Cys
    1385                1390                1395

Lys Lys Glu Val Gln Glu Thr Arg Arg Glu Arg Arg Arg Leu Met
    1400                1405                1410

Ser Met Glu Met Asp
    1415

<210> SEQ ID NO 4
<211> LENGTH: 1421
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Ile Thr Trp Thr Ser Asp Gln
    50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

```
Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
        130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
                325                 330                 335

Gly Ser Gly Gly Gly Ser Gly Gly Gly Ser Gly Gly Gly Ser
            340                 345                 350

Gly Gly Gly Ser Gly Gly Arg Val Ile Pro Val Ser Gly Pro Ala Arg
        355                 360                 365

Cys Leu Ser Gln Ser Arg Asn Leu Leu Lys Thr Thr Asp Asp Met Val
370                 375                 380

Lys Thr Ala Arg Glu Lys Leu Lys His Tyr Ser Cys Thr Ala Glu Asp
385                 390                 395                 400

Ile Asp His Glu Asp Ile Thr Arg Asp Gln Thr Ser Thr Leu Lys Thr
                405                 410                 415

Cys Leu Pro Leu Glu Leu His Lys Asn Glu Ser Cys Leu Ala Thr Arg
            420                 425                 430

Glu Thr Ser Ser Thr Thr Arg Gly Ser Cys Leu Pro Pro Gln Lys Thr
        435                 440                 445

Ser Leu Met Met Thr Leu Cys Leu Gly Ser Ile Tyr Glu Asp Leu Lys
450                 455                 460

Met Tyr Gln Thr Glu Phe Gln Ala Ile Asn Ala Ala Leu Gln Asn His
465                 470                 475                 480

Asn His Gln Gln Ile Ile Leu Asp Lys Gly Met Leu Val Ala Ile Asp
                485                 490                 495

Glu Leu Met Gln Ser Leu Asn His Asn Gly Glu Thr Leu Arg Gln Lys
            500                 505                 510

Pro Pro Val Gly Glu Ala Asp Pro Tyr Arg Val Lys Met Lys Leu Cys
        515                 520                 525

Ile Leu Leu His Ala Phe Ser Thr Arg Val Val Thr Ile Asn Arg Val
```

-continued

```
            530                 535                 540
Met Gly Tyr Leu Ser Ser Ala Ser Ala Gly Gly Gly Ser Gly Gly
545                 550                 555                 560

Gly Gly Ser Arg Val Arg Val Pro Thr Ala Thr Leu Val Arg Val
                565                 570                 575

Val Gly Thr Glu Leu Val Ile Pro Cys Asn Val Ser Asp Tyr Asp Gly
                580                 585                 590

Pro Ser Glu Gln Asn Phe Asp Trp Ser Phe Ser Ser Leu Gly Ser Ser
                595                 600                 605

Phe Val Glu Leu Ala Ser Thr Trp Glu Val Gly Phe Pro Ala Gln Leu
                610                 615                 620

Tyr Gln Glu Arg Leu Gln Arg Gly Glu Ile Leu Leu Arg Arg Thr Ala
625                 630                 635                 640

Asn Asp Ala Val Glu Leu His Ile Lys Asn Val Gln Pro Ser Asp Gln
                645                 650                 655

Gly His Tyr Lys Cys Ser Thr Pro Ser Thr Asp Ala Thr Val Gln Gly
                660                 665                 670

Asn Tyr Glu Asp Thr Val Gln Val Lys Val Leu Ala Asp Ser Leu His
                675                 680                 685

Val Gly Pro Ser Ala Arg Pro Pro Ser Leu Ser Leu Arg Glu Gly
                690                 695                 700

Glu Pro Phe Glu Leu Arg Cys Thr Ala Ala Ser Ala Ser Pro Leu His
705                 710                 715                 720

Thr His Leu Ala Leu Leu Trp Glu Val His Arg Gly Pro Ala Arg Arg
                725                 730                 735

Ser Val Leu Ala Leu Thr His Glu Gly Arg Phe His Pro Gly Leu Gly
                740                 745                 750

Tyr Glu Gln Arg Tyr His Ser Gly Asp Val Arg Leu Thr Val Gly
                755                 760                 765

Ser Asp Ala Tyr Arg Leu Ser Val Ser Arg Ala Leu Ser Ala Asp Gln
                770                 775                 780

Gly Ser Tyr Arg Cys Ile Val Ser Glu Trp Ile Ala Glu Gln Gly Asn
785                 790                 795                 800

Trp Gln Glu Ile Gln Glu Lys Ala Val Glu Val Ala Thr Val Val Ile
                805                 810                 815

Gln Pro Ser Val Leu Arg Ala Ala Val Pro Lys Asn Val Ser Val Ala
                820                 825                 830

Glu Gly Lys Glu Leu Asp Leu Thr Cys Asn Ile Thr Thr Asp Arg Ala
                835                 840                 845

Asp Asp Val Arg Pro Glu Val Thr Trp Ser Phe Ser Arg Met Pro Asp
850                 855                 860

Ser Thr Leu Pro Gly Ser Arg Val Leu Ala Arg Leu Asp Arg Asp Ser
865                 870                 875                 880

Leu Val His Ser Ser Pro His Val Ala Leu Ser His Val Asp Ala Arg
                885                 890                 895

Ser Tyr His Leu Leu Val Arg Asp Val Ser Lys Glu Asn Ser Gly Tyr
                900                 905                 910

Tyr Tyr Cys His Val Ser Leu Trp Ala Pro Gly His Asn Arg Ser Trp
                915                 920                 925

His Lys Val Ala Glu Ala Val Ser Ser Pro Ala Gly Val Gly Val Thr
                930                 935                 940

Trp Leu Glu Pro Asp Tyr Gln Val Tyr Leu Asn Ala Ser Lys Val Pro
945                 950                 955                 960
```

```
Gly Phe Ala Asp Asp Pro Thr Glu Leu Ala Cys Arg Val Val Asp Thr
                965                 970                 975
Lys Ser Gly Glu Ala Asn Val Arg Phe Thr Val Ser Trp Tyr Tyr Arg
            980                 985                 990
Met Asn Arg Arg Ser Asp Asn Val Val Thr Ser Glu Leu Leu Ala Val
        995                 1000                1005
Met Asp Gly Asp Trp Thr Leu Lys Tyr Gly Glu Arg Ser Lys Gln
    1010                1015                1020
Arg Ala Gln Asp Gly Asp Phe Ile Phe Ser Lys Glu His Thr Asp
    1025                1030                1035
Thr Phe Asn Phe Arg Ile Gln Arg Thr Thr Glu Glu Asp Arg Gly
    1040                1045                1050
Asn Tyr Tyr Cys Val Val Ser Ala Trp Thr Lys Gln Arg Asn Asn
    1055                1060                1065
Ser Trp Val Lys Ser Lys Asp Val Phe Ser Lys Pro Val Asn Ile
    1070                1075                1080
Phe Trp Ala Leu Glu Asp Ser Val Leu Val Val Lys Ala Arg Gln
    1085                1090                1095
Pro Lys Pro Phe Phe Ala Ala Gly Asn Thr Phe Glu Met Thr Cys
    1100                1105                1110
Lys Val Ser Ser Lys Asn Ile Lys Ser Pro Arg Tyr Ser Val Leu
    1115                1120                1125
Ile Met Ala Glu Lys Pro Val Gly Asp Leu Ser Ser Pro Asn Glu
    1130                1135                1140
Thr Lys Tyr Ile Ile Ser Leu Asp Gln Asp Ser Val Val Lys Leu
    1145                1150                1155
Glu Asn Trp Thr Asp Ala Ser Arg Val Asp Gly Val Val Leu Glu
    1160                1165                1170
Lys Val Gln Glu Asp Glu Phe Arg Tyr Arg Met Tyr Gln Thr Gln
    1175                1180                1185
Val Ser Asp Ala Gly Leu Tyr Arg Cys Met Val Thr Ala Trp Ser
    1190                1195                1200
Pro Val Arg Gly Ser Leu Trp Arg Glu Ala Ala Thr Ser Leu Ser
    1205                1210                1215
Asn Pro Ile Glu Ile Asp Phe Gln Thr Ser Gly Pro Ile Phe Asn
    1220                1225                1230
Ala Ser Val His Ser Asp Thr Pro Ser Val Ile Arg Gly Asp Leu
    1235                1240                1245
Ile Lys Leu Phe Cys Ile Ile Thr Val Glu Gly Ala Ala Leu Asp
    1250                1255                1260
Pro Asp Asp Met Ala Phe Asp Val Ser Trp Phe Ala Val His Ser
    1265                1270                1275
Phe Gly Leu Asp Lys Ala Pro Val Leu Leu Ser Ser Leu Asp Arg
    1280                1285                1290
Lys Gly Ile Val Thr Thr Ser Arg Arg Asp Trp Lys Ser Asp Leu
    1295                1300                1305
Ser Leu Glu Arg Val Ser Val Leu Glu Phe Leu Leu Gln Val His
    1310                1315                1320
Gly Ser Glu Asp Gln Asp Phe Gly Asn Tyr Tyr Cys Ser Val Thr
    1325                1330                1335
Pro Trp Val Lys Ser Pro Thr Gly Ser Trp Gln Lys Glu Ala Glu
    1340                1345                1350
```

-continued

```
Ile His Ser Lys Pro Val Phe Ile Thr Val Lys Met Asp Val Leu
    1355                1360                1365

Asn Ala Phe Lys Tyr Pro Leu Leu Ile Gly Val Gly Leu Ser Thr
    1370                1375                1380

Val Ile Gly Leu Leu Ser Cys Leu Ile Gly Tyr Cys Ser Ser His
    1385                1390                1395

Trp Cys Cys Lys Lys Glu Val Gln Glu Thr Arg Arg Glu Arg Arg
    1400                1405                1410

Arg Leu Met Ser Met Glu Met Asp
    1415                1420

<210> SEQ ID NO 5
<211> LENGTH: 753
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285
```

```
Val Phe Thr Asp Lys Thr Ser Ala Thr Val Ile Cys Arg Lys Asn Ala
    290                 295                 300
Ser Ile Ser Val Arg Ala Gln Asp Arg Tyr Tyr Ser Ser Ser Trp Ser
305                 310                 315                 320
Glu Trp Ala Ser Val Pro Cys Ser Gly Gly Ser Gly Gly Gly Ser Gly
                325                 330                 335
Gly Gly Gly Ser Gly Gly Gly Gly Ser Gly Gly Gly Ser Gly Gly Arg
            340                 345                 350
Asn Leu Pro Val Ala Thr Pro Asp Pro Gly Met Phe Pro Cys Leu His
            355                 360                 365
His Ser Gln Asn Leu Leu Arg Ala Val Ser Asn Met Leu Gln Lys Ala
    370                 375                 380
Arg Gln Thr Leu Glu Phe Tyr Pro Cys Thr Ser Glu Glu Ile Asp His
385                 390                 395                 400
Glu Asp Ile Thr Lys Asp Lys Thr Ser Thr Val Glu Ala Cys Leu Pro
                405                 410                 415
Leu Glu Leu Thr Lys Asn Glu Ser Cys Leu Asn Ser Arg Glu Thr Ser
            420                 425                 430
Phe Ile Thr Asn Gly Ser Cys Leu Ala Ser Arg Lys Thr Ser Phe Met
    435                 440                 445
Met Ala Leu Cys Leu Ser Ser Ile Tyr Glu Asp Leu Lys Met Tyr Gln
    450                 455                 460
Val Glu Phe Lys Thr Met Asn Ala Lys Leu Leu Met Asp Pro Lys Arg
465                 470                 475                 480
Gln Ile Phe Leu Asp Gln Asn Met Leu Ala Val Ile Asp Glu Leu Met
                485                 490                 495
Gln Ala Leu Asn Phe Asn Ser Glu Thr Val Pro Gln Lys Ser Ser Leu
            500                 505                 510
Glu Glu Pro Asp Phe Tyr Lys Thr Lys Ile Lys Leu Cys Ile Leu Leu
            515                 520                 525
His Ala Phe Arg Ile Arg Ala Val Thr Ile Asp Arg Val Met Ser Tyr
    530                 535                 540
Leu Asn Ala Ser Ser Ala Gly Gly Gly Ser Gly Gly Gly Gly Ser
545                 550                 555                 560
Gly Pro Ile Phe Asn Ala Ser Val His Ser Asp Thr Pro Ser Val Ile
                565                 570                 575
Arg Gly Asp Leu Ile Lys Leu Phe Cys Ile Ile Thr Val Glu Gly Ala
            580                 585                 590
Ala Leu Asp Pro Asp Asp Met Ala Phe Asp Val Ser Trp Phe Ala Val
            595                 600                 605
His Ser Phe Gly Leu Asp Lys Ala Pro Val Leu Leu Ser Ser Leu Asp
    610                 615                 620
Arg Lys Gly Ile Val Thr Thr Ser Arg Arg Asp Trp Lys Ser Asp Leu
625                 630                 635                 640
Ser Leu Glu Arg Val Ser Val Leu Glu Phe Leu Leu Gln Val His Gly
                645                 650                 655
Ser Glu Asp Gln Asp Phe Gly Asn Tyr Tyr Cys Ser Val Thr Pro Trp
            660                 665                 670
Val Lys Ser Pro Thr Gly Ser Trp Gln Lys Glu Ala Glu Ile His Ser
            675                 680                 685
Lys Pro Val Phe Ile Thr Val Lys Met Asp Val Leu Asn Ala Phe Lys
    690                 695                 700
```

```
Tyr Pro Leu Leu Ile Gly Val Gly Leu Ser Thr Val Ile Gly Leu Leu
705                 710                 715                 720

Ser Cys Leu Ile Gly Tyr Cys Ser Ser His Trp Cys Cys Lys Lys Glu
            725                 730                 735

Val Gln Glu Thr Arg Arg Glu Arg Arg Arg Leu Met Ser Met Glu Met
        740                 745                 750

Asp

<210> SEQ ID NO 6
<211> LENGTH: 756
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
            20                  25                  30

Val Glu Val Asp Trp Thr Pro Asp Ala Pro Gly Glu Thr Val Asn Leu
        35                  40                  45

Thr Cys Asp Thr Pro Glu Glu Asp Asp Ile Thr Trp Thr Ser Asp Gln
50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110

Ser Thr Glu Ile Leu Lys Asn Phe Lys Asn Lys Thr Phe Leu Lys Cys
        115                 120                 125

Glu Ala Pro Asn Tyr Ser Gly Arg Phe Thr Cys Ser Trp Leu Val Gln
130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
290                 295                 300
```

```
Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser Gly
            325                 330                 335

Gly Ser Gly Gly Ser Gly Gly Gly Ser Gly Gly Gly Ser
        340             345             350

Gly Gly Gly Ser Gly Gly Arg Val Ile Pro Val Ser Gly Pro Ala Arg
        355                 360                 365

Cys Leu Ser Gln Ser Arg Asn Leu Leu Lys Thr Thr Asp Asp Met Val
    370                 375                 380

Lys Thr Ala Arg Glu Lys Leu Lys His Tyr Ser Cys Thr Ala Glu Asp
385                 390                 395                 400

Ile Asp His Glu Asp Ile Thr Arg Asp Gln Thr Ser Thr Leu Lys Thr
                405                 410                 415

Cys Leu Pro Leu Glu Leu His Lys Asn Glu Ser Cys Leu Ala Thr Arg
                420                 425                 430

Glu Thr Ser Ser Thr Thr Arg Gly Ser Cys Leu Pro Pro Gln Lys Thr
        435                 440                 445

Ser Leu Met Met Thr Leu Cys Leu Gly Ser Ile Tyr Glu Asp Leu Lys
450                 455                 460

Met Tyr Gln Thr Glu Phe Gln Ala Ile Asn Ala Ala Leu Gln Asn His
465                 470                 475                 480

Asn His Gln Gln Ile Ile Leu Asp Lys Gly Met Leu Val Ala Ile Asp
                485                 490                 495

Glu Leu Met Gln Ser Leu Asn His Asn Gly Glu Thr Leu Arg Gln Lys
                500                 505                 510

Pro Pro Val Gly Glu Ala Asp Pro Tyr Arg Val Lys Met Lys Leu Cys
                515                 520                 525

Ile Leu Leu His Ala Phe Ser Thr Arg Val Val Thr Ile Asn Arg Val
            530                 535                 540

Met Gly Tyr Leu Ser Ser Ala Ser Ala Gly Gly Gly Ser Gly Gly
545                 550                 555                 560

Gly Gly Ser Gly Pro Ile Phe Asn Ala Ser Val His Ser Asp Thr Pro
                565                 570                 575

Ser Val Ile Arg Gly Asp Leu Ile Lys Leu Phe Cys Ile Ile Thr Val
            580                 585                 590

Glu Gly Ala Ala Leu Asp Pro Asp Asp Met Ala Phe Asp Val Ser Trp
        595                 600                 605

Phe Ala Val His Ser Phe Gly Leu Asp Lys Ala Pro Val Leu Leu Ser
610                 615                 620

Ser Leu Asp Arg Lys Gly Ile Val Thr Thr Ser Arg Arg Asp Trp Lys
625                 630                 635                 640

Ser Asp Leu Ser Leu Glu Arg Val Ser Val Leu Glu Phe Leu Leu Gln
            645                 650                 655

Val His Gly Ser Glu Asp Gln Asp Phe Gly Asn Tyr Tyr Cys Ser Val
            660                 665                 670

Thr Pro Trp Val Lys Ser Pro Thr Gly Ser Trp Gln Lys Glu Ala Glu
        675                 680                 685

Ile His Ser Lys Pro Val Phe Ile Thr Val Lys Met Asp Val Leu Asn
        690                 695                 700

Ala Phe Lys Tyr Pro Leu Leu Ile Gly Val Gly Leu Ser Thr Val Ile
705                 710                 715                 720

Gly Leu Leu Ser Cys Leu Ile Gly Tyr Cys Ser Ser His Trp Cys Cys
```

-continued

```
                        725                 730                 735
Lys Lys Glu Val Gln Glu Thr Arg Arg Glu Arg Arg Leu Met Ser
                    740                 745                 750

Met Glu Met Asp
        755

<210> SEQ ID NO 7
<211> LENGTH: 1018
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Arg Leu Ala Ser Arg Pro Leu Leu Ala Leu Leu Ser Leu
1               5                   10                  15

Ala Leu Cys Arg Gly Gln Asp Pro Tyr Val Lys Glu Ala Glu Asn Leu
            20                  25                  30

Lys Lys Tyr Phe Asn Ala Gly His Ser Asp Val Ala Asp Asn Gly Thr
            35                  40                  45

Leu Phe Leu Gly Ile Leu Lys Asn Trp Lys Glu Ser Asp Arg Lys
    50                  55                  60

Ile Met Gln Ser Gln Ile Val Ser Phe Tyr Phe Lys Leu Phe Lys Asn
65                  70                  75                  80

Phe Lys Asp Asp Gln Ser Ile Gln Lys Ser Val Glu Thr Ile Lys Glu
                85                  90                  95

Asp Met Asn Val Lys Phe Phe Asn Ser Asn Lys Lys Lys Arg Asp Asp
            100                 105                 110

Phe Glu Lys Leu Thr Asn Tyr Ser Val Thr Asp Leu Asn Val Gln Arg
        115                 120                 125

Lys Ala Ile His Glu Leu Ile Gln Val Met Ala Glu Leu Ser Pro Ala
130                 135                 140

Ala Lys Thr Gly Ser Ala Gly Gly Gly Ser Gly Gly Gly Gly Ser
145                 150                 155                 160

Arg Val Val Arg Val Pro Thr Ala Thr Leu Val Arg Val Gly Thr
                165                 170                 175

Glu Leu Val Ile Pro Cys Asn Val Ser Asp Tyr Asp Gly Pro Ser Glu
            180                 185                 190

Gln Asn Phe Asp Trp Ser Phe Ser Ser Leu Gly Ser Ser Phe Val Glu
        195                 200                 205

Leu Ala Ser Thr Trp Glu Val Gly Phe Pro Ala Gln Leu Tyr Gln Glu
    210                 215                 220

Arg Leu Gln Arg Gly Glu Ile Leu Leu Arg Arg Thr Ala Asn Asp Ala
225                 230                 235                 240

Val Glu Leu His Ile Lys Asn Val Gln Pro Ser Asp Gln Gly His Tyr
                245                 250                 255

Lys Cys Ser Thr Pro Ser Thr Asp Ala Thr Val Gln Gly Asn Tyr Glu
            260                 265                 270

Asp Thr Val Gln Val Lys Val Leu Ala Asp Ser Leu His Val Gly Pro
        275                 280                 285

Ser Ala Arg Pro Pro Pro Ser Leu Ser Leu Arg Glu Gly Glu Pro Phe
    290                 295                 300

Glu Leu Arg Cys Thr Ala Ala Ser Ala Ser Pro Leu His Thr His Leu
305                 310                 315                 320
```

Ala Leu Leu Trp Glu Val His Arg Gly Pro Ala Arg Ser Val Leu
            325                 330                 335

Ala Leu Thr His Glu Gly Arg Phe His Pro Gly Leu Gly Tyr Glu Gln
        340                 345                 350

Arg Tyr His Ser Gly Asp Val Arg Leu Asp Thr Val Gly Ser Asp Ala
            355                 360                 365

Tyr Arg Leu Ser Val Ser Arg Ala Leu Ser Ala Asp Gln Gly Ser Tyr
370                 375                 380

Arg Cys Ile Val Ser Glu Trp Ile Ala Glu Gln Gly Asn Trp Gln Glu
385                 390                 395                 400

Ile Gln Glu Lys Ala Val Glu Val Ala Thr Val Val Ile Gln Pro Ser
                405                 410                 415

Val Leu Arg Ala Ala Val Pro Lys Asn Val Ser Val Ala Glu Gly Lys
            420                 425                 430

Glu Leu Asp Leu Thr Cys Asn Ile Thr Thr Asp Arg Ala Asp Asp Val
        435                 440                 445

Arg Pro Glu Val Thr Trp Ser Phe Ser Arg Met Pro Asp Ser Thr Leu
    450                 455                 460

Pro Gly Ser Arg Val Leu Ala Arg Leu Asp Arg Asp Ser Leu Val His
465                 470                 475                 480

Ser Ser Pro His Val Ala Leu Ser His Val Asp Ala Arg Ser Tyr His
                485                 490                 495

Leu Leu Val Arg Asp Val Ser Lys Glu Asn Ser Gly Tyr Tyr Tyr Cys
            500                 505                 510

His Val Ser Leu Trp Ala Pro Gly His Asn Arg Ser Trp His Lys Val
        515                 520                 525

Ala Glu Ala Val Ser Ser Pro Ala Gly Val Gly Val Thr Trp Leu Glu
    530                 535                 540

Pro Asp Tyr Gln Val Tyr Leu Asn Ala Ser Lys Val Pro Gly Phe Ala
545                 550                 555                 560

Asp Asp Pro Thr Glu Leu Ala Cys Arg Val Val Asp Thr Lys Ser Gly
                565                 570                 575

Glu Ala Asn Val Arg Phe Thr Val Ser Trp Tyr Tyr Arg Met Asn Arg
            580                 585                 590

Arg Ser Asp Asn Val Val Thr Ser Glu Leu Leu Ala Val Met Asp Gly
        595                 600                 605

Asp Trp Thr Leu Lys Tyr Gly Glu Arg Ser Lys Gln Arg Ala Gln Asp
    610                 615                 620

Gly Asp Phe Ile Phe Ser Lys Glu His Thr Asp Thr Phe Asn Phe Arg
625                 630                 635                 640

Ile Gln Arg Thr Thr Glu Glu Asp Arg Gly Asn Tyr Tyr Cys Val Val
                645                 650                 655

Ser Ala Trp Thr Lys Gln Arg Asn Asn Ser Trp Val Lys Ser Lys Asp
            660                 665                 670

Val Phe Ser Lys Pro Val Asn Ile Phe Trp Ala Leu Glu Asp Ser Val
        675                 680                 685

Leu Val Val Lys Ala Arg Gln Pro Lys Pro Phe Phe Ala Ala Gly Asn
    690                 695                 700

Thr Phe Glu Met Thr Cys Lys Val Ser Ser Lys Asn Ile Lys Ser Pro
705                 710                 715                 720

Arg Tyr Ser Val Leu Ile Met Ala Glu Lys Pro Val Gly Asp Leu Ser
                725                 730                 735

Ser Pro Asn Glu Thr Lys Tyr Ile Ile Ser Leu Asp Gln Asp Ser Val

```
                    740                 745                 750
Val Lys Leu Glu Asn Trp Thr Asp Ala Ser Arg Val Asp Gly Val Val
                755                 760                 765

Leu Glu Lys Val Gln Glu Asp Glu Phe Arg Tyr Arg Met Tyr Gln Thr
    770                 775                 780

Gln Val Ser Asp Ala Gly Leu Tyr Arg Cys Met Val Thr Ala Trp Ser
785                 790                 795                 800

Pro Val Arg Gly Ser Leu Trp Arg Glu Ala Ala Thr Ser Leu Ser Asn
                805                 810                 815

Pro Ile Glu Ile Asp Phe Gln Thr Ser Gly Pro Ile Phe Asn Ala Ser
                820                 825                 830

Val His Ser Asp Thr Pro Ser Val Ile Arg Gly Asp Leu Ile Lys Leu
                835                 840                 845

Phe Cys Ile Ile Thr Val Glu Gly Ala Ala Leu Asp Pro Asp Asp Met
850                 855                 860

Ala Phe Asp Val Ser Trp Phe Ala Val His Ser Phe Gly Leu Asp Lys
865                 870                 875                 880

Ala Pro Val Leu Leu Ser Ser Leu Asp Arg Lys Gly Ile Val Thr Thr
                885                 890                 895

Ser Arg Arg Asp Trp Lys Ser Asp Leu Ser Leu Glu Arg Val Ser Val
                900                 905                 910

Leu Glu Phe Leu Leu Gln Val His Gly Ser Glu Asp Gln Asp Phe Gly
                915                 920                 925

Asn Tyr Tyr Cys Ser Val Thr Pro Trp Val Lys Ser Pro Thr Gly Ser
            930                 935                 940

Trp Gln Lys Glu Ala Glu Ile His Ser Lys Pro Val Phe Ile Thr Val
945                 950                 955                 960

Lys Met Asp Val Leu Asn Ala Phe Lys Tyr Pro Leu Leu Ile Gly Val
                965                 970                 975

Gly Leu Ser Thr Val Ile Gly Leu Leu Ser Cys Leu Ile Gly Tyr Cys
            980                 985                 990

Ser Ser His Trp Cys Cys Lys Lys Glu Val Gln Glu Thr Arg Arg Glu
            995                 1000                1005

Arg Arg Arg Leu Met Ser Met Glu Met Asp
    1010                1015

<210> SEQ ID NO 8
<211> LENGTH: 1157
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Gly Arg Leu Ala Ser Arg Pro Leu Leu Leu Ala Leu Leu Ser Leu
1               5                   10                  15

Ala Leu Cys Arg Gly Gln Asp Pro Tyr Val Lys Glu Ala Glu Asn Leu
                20                  25                  30

Lys Lys Tyr Phe Asn Ala Gly His Ser Asp Val Ala Asp Asn Gly Thr
            35                  40                  45

Leu Phe Leu Gly Ile Leu Lys Asn Trp Lys Glu Glu Ser Asp Arg Lys
    50                  55                  60

Ile Met Gln Ser Gln Ile Val Ser Phe Tyr Phe Lys Leu Phe Lys Asn
65                  70                  75                  80
```

```
Phe Lys Asp Asp Gln Ser Ile Gln Lys Ser Val Glu Thr Ile Lys Glu
                85                  90                  95

Asp Met Asn Val Lys Phe Phe Asn Ser Asn Lys Lys Arg Asp Asp
            100                 105                 110

Phe Glu Lys Leu Thr Asn Tyr Ser Val Thr Asp Leu Asn Val Gln Arg
            115                 120                 125

Lys Ala Ile His Glu Leu Ile Gln Val Met Ala Glu Leu Ser Pro Ala
130                 135                 140

Ala Lys Thr Gly Gly Ser Gly Gly Ser Gly Gly Ser Gly Gly Ser Gly
145                 150                 155                 160

Gln Asp Pro Tyr Val Lys Glu Ala Glu Asn Leu Lys Lys Tyr Phe Asn
                165                 170                 175

Ala Gly His Ser Asp Val Ala Asp Asn Gly Thr Leu Phe Leu Gly Ile
            180                 185                 190

Leu Lys Asn Trp Lys Glu Glu Ser Asp Arg Lys Ile Met Gln Ser Gln
            195                 200                 205

Ile Val Ser Phe Tyr Phe Lys Leu Phe Lys Asn Phe Lys Asp Asp Gln
            210                 215                 220

Ser Ile Gln Lys Ser Val Glu Thr Ile Lys Glu Asp Met Asn Val Lys
225                 230                 235                 240

Phe Phe Asn Ser Asn Lys Lys Arg Asp Asp Phe Glu Lys Leu Thr
                245                 250                 255

Asn Tyr Ser Val Thr Asp Leu Asn Val Gln Arg Lys Ala Ile His Glu
            260                 265                 270

Leu Ile Gln Val Met Ala Glu Leu Ser Pro Ala Ala Lys Thr Gly Ser
            275                 280                 285

Ala Gly Gly Gly Ser Gly Gly Gly Ser Arg Val Val Arg Val
290                 295                 300

Pro Thr Ala Thr Leu Val Arg Val Val Gly Thr Glu Leu Val Ile Pro
305                 310                 315                 320

Cys Asn Val Ser Asp Tyr Asp Gly Pro Ser Glu Gln Asn Phe Asp Trp
                325                 330                 335

Ser Phe Ser Ser Leu Gly Ser Ser Phe Val Glu Leu Ala Ser Thr Trp
            340                 345                 350

Glu Val Gly Phe Pro Ala Gln Leu Tyr Gln Glu Arg Leu Gln Arg Gly
            355                 360                 365

Glu Ile Leu Leu Arg Arg Thr Ala Asn Asp Ala Val Glu Leu His Ile
            370                 375                 380

Lys Asn Val Gln Pro Ser Asp Gln Gly His Tyr Lys Cys Ser Thr Pro
385                 390                 395                 400

Ser Thr Asp Ala Thr Val Gln Gly Asn Tyr Glu Asp Thr Val Gln Val
                405                 410                 415

Lys Val Leu Ala Asp Ser Leu His Val Gly Pro Ser Ala Arg Pro Pro
            420                 425                 430

Pro Ser Leu Ser Leu Arg Glu Gly Glu Pro Phe Glu Leu Arg Cys Thr
            435                 440                 445

Ala Ala Ser Ala Ser Pro Leu His Thr His Leu Ala Leu Leu Trp Glu
            450                 455                 460

Val His Arg Gly Pro Ala Arg Arg Ser Val Leu Ala Leu Thr His Glu
465                 470                 475                 480

Gly Arg Phe His Pro Gly Leu Gly Tyr Glu Gln Arg Tyr His Ser Gly
                485                 490                 495

Asp Val Arg Leu Asp Thr Val Gly Ser Asp Ala Tyr Arg Leu Ser Val
```

-continued

```
            500                 505                 510
Ser Arg Ala Leu Ser Ala Asp Gln Gly Ser Tyr Arg Cys Ile Val Ser
            515                 520                 525
Glu Trp Ile Ala Glu Gln Gly Asn Trp Gln Glu Ile Gln Glu Lys Ala
            530                 535                 540
Val Glu Val Ala Thr Val Ile Gln Pro Ser Val Leu Arg Ala Ala
545                 550                 555                 560
Val Pro Lys Asn Val Ser Val Ala Glu Gly Lys Glu Leu Asp Leu Thr
                565                 570                 575
Cys Asn Ile Thr Thr Asp Arg Ala Asp Asp Val Arg Pro Glu Val Thr
                580                 585                 590
Trp Ser Phe Ser Arg Met Pro Asp Ser Thr Leu Pro Gly Ser Arg Val
                595                 600                 605
Leu Ala Arg Leu Asp Arg Asp Ser Leu Val His Ser Ser Pro His Val
                610                 615                 620
Ala Leu Ser His Val Asp Ala Arg Ser Tyr His Leu Leu Val Arg Asp
625                 630                 635                 640
Val Ser Lys Glu Asn Ser Gly Tyr Tyr Tyr Cys His Val Ser Leu Trp
                645                 650                 655
Ala Pro Gly His Asn Arg Ser Trp His Lys Val Ala Glu Ala Val Ser
                660                 665                 670
Ser Pro Ala Gly Val Gly Val Thr Trp Leu Glu Pro Asp Tyr Gln Val
                675                 680                 685
Tyr Leu Asn Ala Ser Lys Val Pro Gly Phe Ala Asp Asp Pro Thr Glu
                690                 695                 700
Leu Ala Cys Arg Val Val Asp Thr Lys Ser Gly Glu Ala Asn Val Arg
705                 710                 715                 720
Phe Thr Val Ser Trp Tyr Tyr Arg Met Asn Arg Arg Ser Asp Asn Val
                725                 730                 735
Val Thr Ser Glu Leu Leu Ala Val Met Asp Gly Asp Trp Thr Leu Lys
                740                 745                 750
Tyr Gly Glu Arg Ser Lys Gln Arg Ala Gln Asp Gly Asp Phe Ile Phe
                755                 760                 765
Ser Lys Glu His Thr Asp Thr Phe Asn Phe Arg Ile Gln Arg Thr Thr
                770                 775                 780
Glu Glu Asp Arg Gly Asn Tyr Tyr Cys Val Val Ser Ala Trp Thr Lys
785                 790                 795                 800
Gln Arg Asn Asn Ser Trp Val Lys Ser Lys Asp Val Phe Ser Lys Pro
                805                 810                 815
Val Asn Ile Phe Trp Ala Leu Glu Asp Ser Val Leu Val Lys Ala
                820                 825                 830
Arg Gln Pro Lys Pro Phe Phe Ala Gly Asn Thr Phe Glu Met Thr
                835                 840                 845
Cys Lys Val Ser Ser Lys Asn Ile Lys Ser Pro Arg Tyr Ser Val Leu
                850                 855                 860
Ile Met Ala Glu Lys Pro Val Gly Asp Leu Ser Ser Pro Asn Glu Thr
865                 870                 875                 880
Lys Tyr Ile Ile Ser Leu Asp Gln Asp Ser Val Val Lys Leu Glu Asn
                885                 890                 895
Trp Thr Asp Ala Ser Arg Val Asp Gly Val Val Leu Glu Lys Val Gln
                900                 905                 910
Glu Asp Glu Phe Arg Tyr Arg Met Tyr Gln Thr Gln Val Ser Asp Ala
                915                 920                 925
```

```
Gly Leu Tyr Arg Cys Met Val Thr Ala Trp Ser Pro Val Arg Gly Ser
            930                 935                 940

Leu Trp Arg Glu Ala Ala Thr Ser Leu Ser Asn Pro Ile Glu Ile Asp
945                 950                 955                 960

Phe Gln Thr Ser Gly Pro Ile Phe Asn Ala Ser Val His Ser Asp Thr
                965                 970                 975

Pro Ser Val Ile Arg Gly Asp Leu Ile Lys Leu Phe Cys Ile Ile Thr
            980                 985                 990

Val Glu Gly Ala Ala Leu Asp Pro Asp Asp Met Ala Phe Asp Val Ser
        995                 1000                1005

Trp Phe Ala Val His Ser Phe Gly Leu Asp Lys Ala Pro Val Leu
    1010                1015                1020

Leu Ser Ser Leu Asp Arg Lys Gly Ile Val Thr Thr Ser Arg Arg
    1025                1030                1035

Asp Trp Lys Ser Asp Leu Ser Leu Glu Arg Val Ser Val Leu Glu
    1040                1045                1050

Phe Leu Leu Gln Val His Gly Ser Glu Asp Gln Asp Phe Gly Asn
    1055                1060                1065

Tyr Tyr Cys Ser Val Thr Pro Trp Val Lys Ser Pro Thr Gly Ser
    1070                1075                1080

Trp Gln Lys Glu Ala Glu Ile His Ser Lys Pro Val Phe Ile Thr
    1085                1090                1095

Val Lys Met Asp Val Leu Asn Ala Phe Lys Tyr Pro Leu Leu Ile
    1100                1105                1110

Gly Val Gly Leu Ser Thr Val Ile Gly Leu Leu Ser Cys Leu Ile
    1115                1120                1125

Gly Tyr Cys Ser Ser His Trp Cys Cys Lys Lys Glu Val Gln Glu
    1130                1135                1140

Thr Arg Arg Glu Arg Arg Arg Leu Met Ser Met Glu Met Asp
    1145                1150                1155

<210> SEQ ID NO 9
<211> LENGTH: 1018
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Gly Arg Leu Ala Ser Arg Pro Leu Leu Leu Ala Leu Leu Ser Leu
1               5                   10                  15

Ala Leu Cys Arg Gly Arg His Gly Thr Val Ile Glu Ser Leu Glu Ser
                20                  25                  30

Leu Asn Asn Tyr Phe Asn Ser Ser Gly Ile Asp Val Glu Glu Lys Ser
            35                  40                  45

Leu Phe Leu Asp Ile Trp Arg Asn Trp Gln Lys Asp Gly Asp Met Lys
        50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Thr Phe Phe Ser Asn Ser Lys Ala Lys Lys Asp Ala
            100                 105                 110

Phe Met Ser Ile Ala Lys Phe Glu Val Asn Asn Pro Gln Val Gln Arg
```

```
              115                 120                 125
Gln Ala Phe Asn Glu Leu Ile Arg Val Val His Gln Leu Leu Pro Glu
        130                 135                 140
Ser Ser Leu Arg Ser Ala Gly Gly Gly Ser Gly Gly Gly Gly Gly Ser
145                 150                 155                 160
Arg Val Val Arg Val Pro Thr Ala Thr Leu Val Arg Val Val Gly Thr
                    165                 170                 175
Glu Leu Val Ile Pro Cys Asn Val Ser Asp Tyr Asp Gly Pro Ser Glu
                180                 185                 190
Gln Asn Phe Asp Trp Ser Phe Ser Ser Leu Gly Ser Ser Phe Val Glu
            195                 200                 205
Leu Ala Ser Thr Trp Glu Val Gly Phe Pro Ala Gln Leu Tyr Gln Glu
        210                 215                 220
Arg Leu Gln Arg Gly Glu Ile Leu Leu Arg Arg Thr Ala Asn Asp Ala
225                 230                 235                 240
Val Glu Leu His Ile Lys Asn Val Gln Pro Ser Asp Gln Gly His Tyr
                    245                 250                 255
Lys Cys Ser Thr Pro Ser Thr Asp Ala Thr Val Gln Gly Asn Tyr Glu
                260                 265                 270
Asp Thr Val Gln Val Lys Val Leu Ala Asp Ser Leu His Val Gly Pro
            275                 280                 285
Ser Ala Arg Pro Pro Pro Ser Leu Ser Leu Arg Glu Gly Glu Pro Phe
        290                 295                 300
Glu Leu Arg Cys Thr Ala Ala Ser Ala Ser Pro Leu His Thr His Leu
305                 310                 315                 320
Ala Leu Leu Trp Glu Val His Arg Gly Pro Ala Arg Arg Ser Val Leu
                    325                 330                 335
Ala Leu Thr His Glu Gly Arg Phe His Pro Gly Leu Gly Tyr Glu Gln
                340                 345                 350
Arg Tyr His Ser Gly Asp Val Arg Leu Asp Thr Val Gly Ser Asp Ala
            355                 360                 365
Tyr Arg Leu Ser Val Ser Arg Ala Leu Ser Ala Asp Gln Gly Ser Tyr
        370                 375                 380
Arg Cys Ile Val Ser Glu Trp Ile Ala Glu Gln Gly Asn Trp Gln Glu
385                 390                 395                 400
Ile Gln Glu Lys Ala Val Glu Val Ala Thr Val Val Ile Gln Pro Ser
                    405                 410                 415
Val Leu Arg Ala Ala Val Pro Lys Asn Val Ser Val Ala Glu Gly Lys
                420                 425                 430
Glu Leu Asp Leu Thr Cys Asn Ile Thr Thr Asp Arg Ala Asp Asp Val
            435                 440                 445
Arg Pro Glu Val Thr Trp Ser Phe Ser Arg Met Pro Asp Ser Thr Leu
        450                 455                 460
Pro Gly Ser Arg Val Leu Ala Arg Leu Asp Arg Asp Ser Leu Val His
465                 470                 475                 480
Ser Ser Pro His Val Ala Leu Ser His Val Asp Ala Arg Ser Tyr His
                    485                 490                 495
Leu Leu Val Arg Asp Val Ser Lys Glu Asn Ser Gly Tyr Tyr Tyr Cys
                500                 505                 510
His Val Ser Leu Trp Ala Pro Gly His Asn Arg Ser Trp His Lys Val
            515                 520                 525
Ala Glu Ala Val Ser Ser Pro Ala Gly Val Gly Val Thr Trp Leu Glu
        530                 535                 540
```

```
Pro Asp Tyr Gln Val Tyr Leu Asn Ala Ser Lys Val Pro Gly Phe Ala
545                 550                 555                 560

Asp Asp Pro Thr Glu Leu Ala Cys Arg Val Asp Thr Lys Ser Gly
                565                 570                 575

Glu Ala Asn Val Arg Phe Thr Val Ser Trp Tyr Tyr Arg Met Asn Arg
            580                 585                 590

Arg Ser Asp Asn Val Val Thr Ser Glu Leu Leu Ala Val Met Asp Gly
            595                 600                 605

Asp Trp Thr Leu Lys Tyr Gly Glu Arg Ser Lys Gln Arg Ala Gln Asp
        610                 615                 620

Gly Asp Phe Ile Phe Ser Lys Glu His Thr Asp Thr Phe Asn Phe Arg
625                 630                 635                 640

Ile Gln Arg Thr Thr Glu Glu Asp Arg Gly Asn Tyr Tyr Cys Val Val
                645                 650                 655

Ser Ala Trp Thr Lys Gln Arg Asn Asn Ser Trp Val Lys Ser Lys Asp
            660                 665                 670

Val Phe Ser Lys Pro Val Asn Ile Phe Trp Ala Leu Glu Asp Ser Val
        675                 680                 685

Leu Val Val Lys Ala Arg Gln Pro Lys Pro Phe Phe Ala Ala Gly Asn
690                 695                 700

Thr Phe Glu Met Thr Cys Lys Val Ser Ser Lys Asn Ile Lys Ser Pro
705                 710                 715                 720

Arg Tyr Ser Val Leu Ile Met Ala Glu Lys Pro Val Gly Asp Leu Ser
                725                 730                 735

Ser Pro Asn Glu Thr Lys Tyr Ile Ile Ser Leu Asp Gln Asp Ser Val
            740                 745                 750

Val Lys Leu Glu Asn Trp Thr Asp Ala Ser Arg Val Asp Gly Val Val
        755                 760                 765

Leu Glu Lys Val Gln Glu Asp Glu Phe Arg Tyr Arg Met Tyr Gln Thr
770                 775                 780

Gln Val Ser Asp Ala Gly Leu Tyr Arg Cys Met Val Thr Ala Trp Ser
785                 790                 795                 800

Pro Val Arg Gly Ser Leu Trp Arg Glu Ala Ala Thr Ser Leu Ser Asn
                805                 810                 815

Pro Ile Glu Ile Asp Phe Gln Thr Ser Gly Pro Ile Phe Asn Ala Ser
            820                 825                 830

Val His Ser Asp Thr Pro Ser Val Ile Arg Gly Asp Leu Ile Lys Leu
        835                 840                 845

Phe Cys Ile Ile Thr Val Glu Gly Ala Ala Leu Asp Pro Asp Asp Met
850                 855                 860

Ala Phe Asp Val Ser Trp Phe Ala Val His Ser Phe Gly Leu Asp Lys
865                 870                 875                 880

Ala Pro Val Leu Leu Ser Ser Leu Asp Arg Lys Gly Ile Val Thr Thr
                885                 890                 895

Ser Arg Arg Asp Trp Lys Ser Asp Leu Ser Leu Glu Arg Val Ser Val
            900                 905                 910

Leu Glu Phe Leu Leu Gln Val His Gly Ser Glu Asp Gln Asp Phe Gly
        915                 920                 925

Asn Tyr Tyr Cys Ser Val Thr Pro Trp Val Lys Ser Pro Thr Gly Ser
930                 935                 940

Trp Gln Lys Glu Ala Glu Ile His Ser Lys Pro Val Phe Ile Thr Val
945                 950                 955                 960
```

```
Lys Met Asp Val Leu Asn Ala Phe Lys Tyr Pro Leu Leu Ile Gly Val
            965                 970                 975

Gly Leu Ser Thr Val Ile Gly Leu Leu Ser Cys Leu Ile Gly Tyr Cys
        980                 985                 990

Ser Ser His Trp Cys Cys Lys Lys  Glu Val Gln Glu Thr Arg Arg Glu
        995                 1000                1005

Arg Arg  Arg Leu Met Ser Met  Glu Met Asp
    1010                1015

<210> SEQ ID NO 10
<211> LENGTH: 1156
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Met Gly Arg Leu Ala Ser Arg Pro Leu Leu Ala Leu Leu Ser Leu
1               5                   10                  15

Ala Leu Cys Arg Gly Arg His Gly Thr Val Ile Glu Ser Leu Glu Ser
            20                  25                  30

Leu Asn Tyr Phe Asn Ser Gly Ile Asp Val Glu Glu Lys Ser
        35                  40                  45

Leu Phe Leu Asp Ile Trp Arg Asn Trp Gln Lys Asp Gly Asp Met Lys
50                  55                  60

Ile Leu Gln Ser Gln Ile Ile Ser Phe Tyr Leu Arg Leu Phe Glu Val
65                  70                  75                  80

Leu Lys Asp Asn Gln Ala Ile Ser Asn Asn Ile Ser Val Ile Glu Ser
                85                  90                  95

His Leu Ile Thr Thr Phe Phe Ser Asn Ser Lys Ala Lys Lys Asp Ala
            100                 105                 110

Phe Met Ser Ile Ala Lys Phe Glu Val Asn Asn Pro Gln Val Gln Arg
        115                 120                 125

Gln Ala Phe Asn Glu Leu Ile Arg Val Val His Gln Leu Leu Pro Glu
130                 135                 140

Ser Ser Leu Arg Gly Ser Gly Gly Ser Gly Gly Ser Gly Gly Ser Gly
145                 150                 155                 160

His Gly Thr Val Ile Glu Ser Leu Glu Ser Leu Asn Asn Tyr Phe Asn
                165                 170                 175

Ser Ser Gly Ile Asp Val Glu Glu Lys Ser Leu Phe Leu Asp Ile Trp
            180                 185                 190

Arg Asn Trp Gln Lys Asp Gly Asp Met Lys Ile Leu Gln Ser Gln Ile
        195                 200                 205

Ile Ser Phe Tyr Leu Arg Leu Phe Glu Val Leu Lys Asp Asn Gln Ala
        210                 215                 220

Ile Ser Asn Asn Ile Ser Val Ile Glu Ser His Leu Ile Thr Thr Phe
225                 230                 235                 240

Phe Ser Asn Ser Lys Ala Lys Lys Asp Ala Phe Met Ser Ile Ala Lys
                245                 250                 255

Phe Glu Val Asn Asn Pro Gln Val Gln Arg Gln Ala Phe Asn Glu Leu
            260                 265                 270

Ile Arg Val Val His Gln Leu Leu Pro Glu Ser Ser Leu Arg Ser Ala
        275                 280                 285

Gly Gly Gly Gly Ser Gly Gly Gly Ser Arg Val Val Arg Val Pro
        290                 295                 300
```

```
Thr Ala Thr Leu Val Arg Val Gly Thr Glu Leu Val Ile Pro Cys
305                 310                 315                 320

Asn Val Ser Asp Tyr Asp Gly Pro Ser Glu Gln Asn Phe Asp Trp Ser
            325                 330                 335

Phe Ser Ser Leu Gly Ser Ser Phe Val Glu Leu Ala Ser Thr Trp Glu
        340                 345                 350

Val Gly Phe Pro Ala Gln Leu Tyr Gln Glu Arg Leu Gln Arg Gly Glu
    355                 360                 365

Ile Leu Leu Arg Arg Thr Ala Asn Asp Ala Val Glu Leu His Ile Lys
370                 375                 380

Asn Val Gln Pro Ser Asp Gln Gly His Tyr Lys Cys Ser Thr Pro Ser
385                 390                 395                 400

Thr Asp Ala Thr Val Gln Gly Asn Tyr Glu Asp Thr Val Gln Val Lys
            405                 410                 415

Val Leu Ala Asp Ser Leu His Val Gly Pro Ser Ala Arg Pro Pro Pro
        420                 425                 430

Ser Leu Ser Leu Arg Glu Gly Glu Pro Phe Glu Leu Arg Cys Thr Ala
    435                 440                 445

Ala Ser Ala Ser Pro Leu His Thr His Leu Ala Leu Leu Trp Glu Val
450                 455                 460

His Arg Gly Pro Ala Arg Arg Ser Val Leu Ala Leu Thr His Glu Gly
465                 470                 475                 480

Arg Phe His Pro Gly Leu Gly Tyr Glu Gln Arg Tyr His Ser Gly Asp
            485                 490                 495

Val Arg Leu Asp Thr Val Gly Ser Asp Ala Tyr Arg Leu Ser Val Ser
        500                 505                 510

Arg Ala Leu Ser Ala Asp Gln Gly Ser Tyr Arg Cys Ile Val Ser Glu
    515                 520                 525

Trp Ile Ala Glu Gln Gly Asn Trp Gln Glu Ile Gln Glu Lys Ala Val
530                 535                 540

Glu Val Ala Thr Val Val Ile Gln Pro Ser Val Leu Arg Ala Ala Val
545                 550                 555                 560

Pro Lys Asn Val Ser Val Ala Glu Gly Lys Glu Leu Asp Leu Thr Cys
            565                 570                 575

Asn Ile Thr Thr Asp Arg Ala Asp Asp Val Arg Pro Glu Val Thr Trp
        580                 585                 590

Ser Phe Ser Arg Met Pro Asp Ser Thr Leu Pro Gly Ser Arg Val Leu
    595                 600                 605

Ala Arg Leu Asp Arg Asp Ser Leu Val His Ser Ser Pro His Val Ala
610                 615                 620

Leu Ser His Val Asp Ala Arg Ser Tyr His Leu Leu Val Arg Asp Val
625                 630                 635                 640

Ser Lys Glu Asn Ser Gly Tyr Tyr Tyr Cys His Val Ser Leu Trp Ala
            645                 650                 655

Pro Gly His Asn Arg Ser Trp His Lys Val Ala Glu Ala Val Ser Ser
        660                 665                 670

Pro Ala Gly Val Gly Val Thr Trp Leu Glu Pro Asp Tyr Gln Val Tyr
    675                 680                 685

Leu Asn Ala Ser Lys Val Pro Gly Phe Ala Asp Asp Pro Thr Glu Leu
690                 695                 700

Ala Cys Arg Val Val Asp Thr Lys Ser Gly Glu Ala Asn Val Arg Phe
705                 710                 715                 720
```

```
Thr Val Ser Trp Tyr Tyr Arg Met Asn Arg Ser Asp Asn Val Val
            725                 730                 735

Thr Ser Glu Leu Leu Ala Val Met Asp Gly Asp Trp Thr Leu Lys Tyr
            740                 745                 750

Gly Glu Arg Ser Lys Gln Arg Ala Gln Asp Gly Asp Phe Ile Phe Ser
            755                 760                 765

Lys Glu His Thr Asp Thr Phe Asn Phe Arg Ile Gln Arg Thr Thr Glu
770                 775                 780

Glu Asp Arg Gly Asn Tyr Tyr Cys Val Val Ser Ala Trp Thr Lys Gln
785                 790                 795                 800

Arg Asn Asn Ser Trp Val Lys Ser Lys Asp Val Phe Ser Lys Pro Val
                805                 810                 815

Asn Ile Phe Trp Ala Leu Glu Asp Ser Val Leu Val Val Lys Ala Arg
                820                 825                 830

Gln Pro Lys Pro Phe Phe Ala Ala Gly Asn Thr Phe Glu Met Thr Cys
            835                 840                 845

Lys Val Ser Ser Lys Asn Ile Lys Ser Pro Arg Tyr Ser Val Leu Ile
            850                 855                 860

Met Ala Glu Lys Pro Val Gly Asp Leu Ser Ser Pro Asn Glu Thr Lys
865                 870                 875                 880

Tyr Ile Ile Ser Leu Asp Gln Asp Ser Val Val Lys Leu Glu Asn Trp
                885                 890                 895

Thr Asp Ala Ser Arg Val Asp Gly Val Val Leu Glu Lys Val Gln Glu
                900                 905                 910

Asp Glu Phe Arg Tyr Arg Met Tyr Gln Thr Gln Val Ser Asp Ala Gly
            915                 920                 925

Leu Tyr Arg Cys Met Val Thr Ala Trp Ser Pro Val Arg Gly Ser Leu
            930                 935                 940

Trp Arg Glu Ala Ala Thr Ser Leu Ser Asn Pro Ile Glu Ile Asp Phe
945                 950                 955                 960

Gln Thr Ser Gly Pro Ile Phe Asn Ala Ser Val His Ser Asp Thr Pro
                965                 970                 975

Ser Val Ile Arg Gly Asp Leu Ile Lys Leu Phe Cys Ile Ile Thr Val
                980                 985                 990

Glu Gly Ala Ala Leu Asp Pro Asp Asp Met Ala Phe Asp Val Ser Trp
            995                 1000                1005

Phe Ala Val His Ser Phe Gly Leu Asp Lys Ala Pro Val Leu Leu
            1010                1015                1020

Ser Ser Leu Asp Arg Lys Gly Ile Val Thr Thr Ser Arg Arg Asp
            1025                1030                1035

Trp Lys Ser Asp Leu Ser Leu Glu Arg Val Ser Val Leu Glu Phe
            1040                1045                1050

Leu Leu Gln Val His Gly Ser Glu Asp Gln Asp Phe Gly Asn Tyr
            1055                1060                1065

Tyr Cys Ser Val Thr Pro Trp Val Lys Ser Pro Thr Gly Ser Trp
            1070                1075                1080

Gln Lys Glu Ala Glu Ile His Ser Lys Pro Val Phe Ile Thr Val
            1085                1090                1095

Lys Met Asp Val Leu Asn Ala Phe Lys Tyr Pro Leu Leu Ile Gly
            1100                1105                1110

Val Gly Leu Ser Thr Val Ile Gly Leu Leu Ser Cys Leu Ile Gly
            1115                1120                1125

Tyr Cys Ser Ser His Trp Cys Cys Lys Lys Glu Val Gln Glu Thr
```

```
                    1130               1135               1140
Arg Arg Glu Arg Arg Arg Leu Met Ser Met Glu Met Asp
        1145               1150               1155

<210> SEQ ID NO 11
<211> LENGTH: 422
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ala Pro Arg Arg Ala Arg Gly Cys Arg Thr Leu Gly Leu Pro Ala
1               5                   10                  15

Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65                  70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Gly Gly Ser
        195                 200                 205

Gly Gly Gly Ser Gly Gly Gly Ser Gly Gly Gly Ser Gly Gly
210                 215                 220

Gly Ser Gly Gly Ser Asn Trp Val Asn Val Ile Ser Asp Leu Lys Lys
225                 230                 235                 240

Ile Glu Asp Leu Ile Gln Ser Met His Ile Asp Ala Thr Leu Tyr Thr
                245                 250                 255

Glu Ser Asp Val His Pro Ser Cys Lys Val Thr Ala Met Lys Cys Phe
            260                 265                 270

Leu Leu Glu Leu Gln Val Ile Ser Leu Glu Ser Gly Asp Ala Ser Ile
        275                 280                 285

His Asp Thr Val Glu Asn Leu Ile Ile Leu Ala Asn Asn Ser Leu Ser
    290                 295                 300

Ser Asn Gly Asn Val Thr Glu Ser Gly Cys Lys Glu Cys Glu Glu Leu
305                 310                 315                 320

Glu Glu Lys Asn Ile Lys Glu Phe Leu Gln Ser Phe Val His Ile Val
                325                 330                 335
```

```
Gln Met Phe Ile Asn Thr Ser Ser Ala Asp Tyr Lys Asp Asp Asp
                340                 345                 350

Lys Phe Glu Gly Gly Gly Gly Ser Gly Gly Gly Ser Ala Val Gly
                355                 360                 365

Gln Asp Thr Gln Glu Val Ile Val Val Pro His Ser Leu Pro Phe Lys
            370                 375                 380

Val Val Val Ile Ser Ala Ile Leu Ala Leu Val Val Leu Thr Ile Ile
385                 390                 395                 400

Ser Leu Ile Ile Leu Ile Met Leu Trp Gln Lys Lys Pro Arg Ser Gly
                405                 410                 415

Leu Leu Thr Gly Arg Thr
            420

<210> SEQ ID NO 12
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly His His
                20                  25                  30

His His His His Ile Thr Cys Pro Pro Pro Met Ser Val Glu His Ala
            35                  40                  45

Asp Ile Trp Val Lys Ser Tyr Ser Leu Tyr Ser Arg Glu Arg Tyr Ile
50                  55                  60

Cys Asn Ser Gly Phe Lys Arg Lys Ala Gly Thr Ser Ser Leu Thr Glu
65                  70                  75                  80

Cys Val Leu Asn Lys Ala Thr Asn Val Ala His Trp Thr Thr Pro Ser
                85                  90                  95

Leu Lys Cys Ile Arg Asp Pro Ala Leu Val His Gln Arg Pro Ala Pro
            100                 105                 110

Pro Ser Thr Val Thr Thr Ala Gly Val Thr Pro Gln Pro Glu Ser Leu
        115                 120                 125

Ser Pro Ser Gly Lys Glu Pro Ala Ala Ser Ser Pro Ser Ser Asn Asn
    130                 135                 140

Thr Ala Ala Thr Thr Ala Ala Ile Val Pro Gly Ser Gln Leu Met Pro
145                 150                 155                 160

Ser Lys Ser Pro Ser Thr Gly Thr Thr Glu Ile Ser Ser His Glu Ser
                165                 170                 175

Ser His Gly Thr Pro Ser Gln Thr Thr Ala Lys Asn Trp Glu Leu Thr
            180                 185                 190

Ala Ser Ala Ser His Gln Pro Pro Gly Val Tyr Pro Gln Gly His Ser
        195                 200                 205

Asp Thr Thr Gly Gly Ser Gly Gly Ser Gly Gly Gly Ser Thr
    210                 215                 220

Leu Asp Pro Arg Ser Phe Leu Leu Arg Asn Pro Asn Asp Lys Tyr Glu
225                 230                 235                 240

Pro Phe Trp Glu Asp Glu Glu Lys Asn Glu Ser Gly Gly Gly Gly Ser
                245                 250                 255

Gly Gly Gly Ser Gly Gly Ser Asn Trp Val Asn Val Ile Ser Asp Leu
            260                 265                 270
```

-continued

```
Lys Lys Ile Glu Asp Leu Ile Gln Ser Met His Ile Asp Ala Thr Leu
        275                 280                 285

Tyr Thr Glu Ser Asp Val His Pro Ser Cys Lys Val Thr Ala Met Lys
290                 295                 300

Cys Phe Leu Leu Glu Leu Gln Val Ile Ser Leu Glu Ser Gly Asp Ala
305                 310                 315                 320

Ser Ile His Asp Thr Val Glu Asn Leu Ile Ile Leu Ala Asn Asn Ser
                325                 330                 335

Leu Ser Ser Asn Gly Asn Val Thr Glu Ser Gly Cys Lys Glu Cys Glu
            340                 345                 350

Glu Leu Glu Glu Lys Asn Ile Lys Glu Phe Leu Gln Ser Phe Val His
        355                 360                 365

Ile Val Gln Met Phe Ile Asn Thr Ser Ser Ala Asp Tyr Lys Asp Asp
    370                 375                 380

Asp Asp Lys Phe Glu Gly Gly Gly Ser Gly Gly Gly Ser Ala
385                 390                 395                 400

Val Gly Gln Asp Thr Gln Glu Val Ile Val Val Pro His Ser Leu Pro
                405                 410                 415

Phe Lys Val Val Val Ile Ser Ala Ile Leu Ala Leu Val Val Leu Thr
            420                 425                 430

Ile Ile Ser Leu Ile Ile Leu Ile Met Leu Trp Gln Lys Lys Pro Arg
        435                 440                 445

Ser Gly Leu Leu Thr Gly Arg Thr
450                 455

<210> SEQ ID NO 13
<211> LENGTH: 412
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
            20                  25                  30

Glu Asp Leu Ile Gln Ser Met His Ile Asp Ala Thr Leu Tyr Thr Glu
        35                  40                  45

Ser Asp Val His Pro Ser Cys Lys Val Thr Ala Met Lys Cys Phe Leu
50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asn Ser Leu Ser Ser
                85                  90                  95

Asn Gly Asn Val Thr Glu Ser Gly Cys Lys Cys Glu Glu Leu Glu
            100                 105                 110

Glu Lys Asn Ile Lys Glu Phe Leu Gln Ser Phe Val His Ile Val Gln
        115                 120                 125

Met Phe Ile Asn Thr Ser Gly Gly Ser Gly Gly Gly Ser Gly Gly Gly
    130                 135                 140

Gly Ser Gly Gly Gly Ser Gly Gly Gly Ser Gly Gly Ser Ile Thr
145                 150                 155                 160

Cys Pro Pro Pro Met Ser Val Glu His Ala Asp Ile Trp Val Lys Ser
```

```
                165                 170                 175
Tyr Ser Leu Tyr Ser Arg Glu Arg Tyr Ile Cys Asn Ser Gly Phe Lys
            180                 185                 190

Arg Lys Ala Gly Thr Ser Ser Leu Thr Glu Cys Val Leu Asn Lys Ala
            195                 200                 205

Thr Asn Val Ala His Trp Thr Thr Pro Ser Leu Lys Cys Ile Arg Asp
            210                 215                 220

Pro Ala Leu Val His Gln Arg Pro Ala Pro Ser Thr Val Thr Thr
225                 230                 235                 240

Ala Gly Val Thr Pro Gln Pro Glu Ser Leu Ser Pro Ser Gly Lys Glu
            245                 250                 255

Pro Ala Ala Ser Ser Pro Ser Ser Asn Asn Thr Ala Ala Thr Thr Ala
            260                 265                 270

Ala Ile Val Pro Gly Ser Gln Leu Met Pro Ser Lys Ser Pro Ser Thr
            275                 280                 285

Gly Thr Thr Glu Ile Ser Ser His Glu Ser Ser His Gly Thr Pro Ser
            290                 295                 300

Gln Thr Thr Ala Lys Asn Trp Glu Leu Thr Ala Ser Ala Ser His Gln
305                 310                 315                 320

Pro Pro Gly Val Tyr Pro Gln Gly His Ser Asp Thr Thr Ser Ala Asp
            325                 330                 335

Tyr Lys Asp Asp Asp Asp Lys Phe Glu Gly Gly Gly Ser Gly Gly
            340                 345                 350

Gly Gly Ser Ala Val Gly Gln Asp Thr Gln Glu Val Ile Val Val Pro
            355                 360                 365

His Ser Leu Pro Phe Lys Val Val Val Ile Ser Ala Ile Leu Ala Leu
            370                 375                 380

Val Val Leu Thr Ile Ile Ser Leu Ile Ile Leu Ile Met Leu Trp Gln
385                 390                 395                 400

Lys Lys Pro Arg Ser Gly Leu Leu Thr Gly Arg Thr
            405                 410

<210> SEQ ID NO 14
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
            20                  25                  30

Glu Asp Leu Ile Gln Ser Met His Ile Asp Ala Thr Leu Tyr Thr Glu
            35                  40                  45

Ser Asp Val His Pro Ser Cys Lys Val Thr Ala Met Lys Cys Phe Leu
            50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asn Ser Leu Ser Ser
            85                  90                  95

Asn Gly Asn Val Thr Glu Ser Gly Cys Lys Glu Cys Glu Glu Leu Glu
            100                 105                 110
```

```
Glu Lys Asn Ile Lys Glu Phe Leu Gln Ser Phe Val His Ile Val Gln
            115                 120                 125

Met Phe Ile Asn Thr Ser Asp Tyr Lys Asp Asp Asp Lys Gly Gly
130                 135                 140

Ser Gly Gly Gly Ser Gly Gly Gly Ser Thr Leu Asp Pro Arg Ser
145                 150                 155                 160

Phe Leu Leu Arg Asn Pro Asn Asp Lys Tyr Glu Pro Phe Trp Glu Asp
            165                 170                 175

Glu Glu Lys Asn Glu Ser Gly Gly Gly Ser Gly Gly Gly Ser Gly
            180                 185                 190

Gly Ser Ile Thr Cys Pro Pro Pro Met Ser Val Glu His Ala Asp Ile
            195                 200                 205

Trp Val Lys Ser Tyr Ser Leu Tyr Ser Arg Glu Arg Tyr Ile Cys Asn
            210                 215                 220

Ser Gly Phe Lys Arg Lys Ala Gly Thr Ser Ser Leu Thr Glu Cys Val
225                 230                 235                 240

Leu Asn Lys Ala Thr Asn Val Ala His Trp Thr Thr Pro Ser Leu Lys
            245                 250                 255

Cys Ile Arg Asp Pro Ala Leu Val His Gln Arg Pro Ala Pro Pro Ser
            260                 265                 270

Thr Val Thr Thr Ala Gly Val Thr Pro Gln Pro Glu Ser Leu Ser Pro
            275                 280                 285

Ser Gly Lys Glu Pro Ala Ala Ser Ser Pro Ser Ser Asn Asn Thr Ala
            290                 295                 300

Ala Thr Thr Ala Ala Ile Val Pro Gly Ser Gln Leu Met Pro Ser Lys
305                 310                 315                 320

Ser Pro Ser Thr Gly Thr Thr Glu Ile Ser Ser His Glu Ser Ser His
            325                 330                 335

Gly Thr Pro Ser Gln Thr Thr Ala Lys Asn Trp Glu Leu Thr Ala Ser
            340                 345                 350

Ala Ser His Gln Pro Pro Gly Val Tyr Pro Gln Gly His Ser Asp Thr
            355                 360                 365

Thr Ser Ala Phe Glu Gly Gly Gly Ser Gly Gly Gly Ser Ala
            370                 375                 380

Val Gly Gln Asp Thr Gln Glu Val Ile Val Val Pro His Ser Leu Pro
385                 390                 395                 400

Phe Lys Val Val Val Ile Ser Ala Ile Leu Ala Leu Val Val Leu Thr
            405                 410                 415

Ile Ile Ser Leu Ile Ile Leu Ile Met Leu Trp Gln Lys Lys Pro Arg
            420                 425                 430

Ser Gly Leu Leu Thr Gly Arg Thr His His His His His His
            435                 440                 445

<210> SEQ ID NO 15
<211> LENGTH: 1239
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
            20                  25                  30
```

```
Glu Asp Leu Ile Gln Ser Met His Ile Asp Ala Thr Leu Tyr Thr Glu
             35                  40                  45

Ser Asp Val His Pro Ser Cys Lys Val Thr Ala Met Lys Cys Phe Leu
         50                  55                  60

Leu Glu Leu Gln Val Ile Ser Leu Glu Ser Gly Asp Ala Ser Ile His
 65                  70                  75                  80

Asp Thr Val Glu Asn Leu Ile Ile Leu Ala Asn Asn Ser Leu Ser Ser
                 85                  90                  95

Asn Gly Asn Val Thr Glu Ser Gly Cys Lys Glu Cys Glu Glu Leu Glu
                100                 105                 110

Glu Lys Asn Ile Lys Glu Phe Leu Gln Ser Phe Val His Ile Val Gln
             115                 120                 125

Met Phe Ile Asn Thr Ser Gly Gly Ser Gly Ser Gly Ser Gly Ser Ser
130                 135                 140

Thr Gly Thr Ser Ser Ser Gly Thr Gly Thr Ser Ala Gly Thr Thr Gly
145                 150                 155                 160

Thr Ser Ala Ser Thr Ser Gly Ser Gly Ser Gly Gly Gly Gly Gly Ser
                165                 170                 175

Gly Gly Gly Gly Ser Ala Gly Gly Thr Ala Thr Ala Gly Ala Ser Ser
            180                 185                 190

Gly Ser Ile Thr Cys Pro Pro Pro Met Ser Val Glu His Ala Asp Ile
            195                 200                 205

Trp Val Lys Ser Tyr Ser Leu Tyr Ser Arg Glu Arg Tyr Ile Cys Asn
            210                 215                 220

Ser Gly Phe Lys Arg Lys Ala Gly Thr Ser Ser Leu Thr Glu Cys Val
225                 230                 235                 240

Leu Asn Lys Ala Thr Asn Val Ala His Trp Thr Thr Pro Ser Leu Lys
                245                 250                 255

Cys Ile Arg Asp Pro Ala Leu Val His Gln Arg Pro Ala Pro Pro Ser
            260                 265                 270

Thr Val Thr Thr Ala Gly Val Thr Pro Gln Pro Glu Ser Leu Ser Pro
            275                 280                 285

Ser Gly Lys Glu Pro Ala Ala Ser Ser Pro Ser Ser Asn Asn Thr Ala
            290                 295                 300

Ala Thr Thr Ala Ala Ile Val Pro Gly Ser Gln Leu Met Pro Ser Lys
305                 310                 315                 320

Ser Pro Ser Thr Gly Thr Thr Glu Ile Ser Ser His Glu Ser Ser His
                325                 330                 335

Gly Thr Pro Ser Gln Thr Thr Ala Lys Asn Trp Glu Leu Thr Ala Ser
            340                 345                 350

Ala Ser His Gln Pro Pro Gly Val Tyr Pro Gln Gly His Ser Asp Thr
            355                 360                 365

Thr Ser Ala Gly Gly Gly Gly Ser Gly Gly Gly Gly Ser Arg Val Val
370                 375                 380

Arg Val Pro Thr Ala Thr Leu Val Arg Val Val Gly Thr Glu Leu Val
385                 390                 395                 400

Ile Pro Cys Asn Val Ser Asp Tyr Asp Gly Pro Ser Glu Gln Asn Phe
                405                 410                 415

Asp Trp Ser Phe Ser Ser Leu Gly Ser Ser Phe Val Glu Leu Ala Ser
            420                 425                 430

Thr Trp Glu Val Gly Phe Pro Ala Gln Leu Tyr Gln Glu Arg Leu Gln
            435                 440                 445
```

-continued

Arg Gly Glu Ile Leu Leu Arg Arg Thr Ala Asn Asp Ala Val Glu Leu
450                 455                 460

His Ile Lys Asn Val Gln Pro Ser Asp Gln Gly His Tyr Lys Cys Ser
465                 470                 475                 480

Thr Pro Ser Thr Asp Ala Thr Val Gln Gly Asn Tyr Glu Asp Thr Val
            485                 490                 495

Gln Val Lys Val Leu Ala Asp Ser Leu His Val Gly Pro Ser Ala Arg
        500                 505                 510

Pro Pro Pro Ser Leu Ser Leu Arg Glu Gly Pro Phe Glu Leu Arg
        515                 520                 525

Cys Thr Ala Ala Ser Ala Ser Pro Leu His Thr His Leu Ala Leu Leu
530                 535                 540

Trp Glu Val His Arg Gly Pro Ala Arg Arg Ser Val Leu Ala Leu Thr
545                 550                 555                 560

His Glu Gly Arg Phe His Pro Gly Leu Gly Tyr Glu Gln Arg Tyr His
                565                 570                 575

Ser Gly Asp Val Arg Leu Asp Thr Val Gly Ser Asp Ala Tyr Arg Leu
            580                 585                 590

Ser Val Ser Arg Ala Leu Ser Ala Asp Gln Gly Ser Tyr Arg Cys Ile
        595                 600                 605

Val Ser Glu Trp Ile Ala Glu Gln Gly Asn Trp Gln Glu Ile Gln Glu
610                 615                 620

Lys Ala Val Glu Val Ala Thr Val Val Ile Gln Pro Ser Val Leu Arg
625                 630                 635                 640

Ala Ala Val Pro Lys Asn Val Ser Val Ala Glu Gly Lys Glu Leu Asp
                645                 650                 655

Leu Thr Cys Asn Ile Thr Thr Asp Arg Ala Asp Asp Val Arg Pro Glu
            660                 665                 670

Val Thr Trp Ser Phe Ser Arg Met Pro Asp Ser Thr Leu Pro Gly Ser
        675                 680                 685

Arg Val Leu Ala Arg Leu Asp Arg Asp Ser Leu Val His Ser Ser Pro
690                 695                 700

His Val Ala Leu Ser His Val Asp Ala Arg Ser Tyr His Leu Leu Val
705                 710                 715                 720

Arg Asp Val Ser Lys Glu Asn Ser Gly Tyr Tyr Tyr Cys His Val Ser
                725                 730                 735

Leu Trp Ala Pro Gly His Asn Arg Ser Trp His Lys Val Ala Glu Ala
            740                 745                 750

Val Ser Ser Pro Ala Gly Val Gly Val Thr Trp Leu Glu Pro Asp Tyr
        755                 760                 765

Gln Val Tyr Leu Asn Ala Ser Lys Val Pro Gly Phe Ala Asp Asp Pro
770                 775                 780

Thr Glu Leu Ala Cys Arg Val Val Asp Thr Lys Ser Gly Glu Ala Asn
785                 790                 795                 800

Val Arg Phe Thr Val Ser Trp Tyr Tyr Arg Met Asn Arg Arg Ser Asp
                805                 810                 815

Asn Val Val Thr Ser Glu Leu Leu Ala Val Met Asp Gly Asp Trp Thr
            820                 825                 830

Leu Lys Tyr Gly Glu Arg Ser Lys Gln Arg Ala Gln Asp Gly Asp Phe
        835                 840                 845

Ile Phe Ser Lys Glu His Thr Asp Thr Phe Asn Phe Arg Ile Gln Arg
850                 855                 860

Thr Thr Glu Glu Asp Arg Gly Asn Tyr Tyr Cys Val Val Ser Ala Trp

```
                865                 870                 875                 880
Thr Lys Gln Arg Asn Asn Ser Trp Val Lys Ser Lys Asp Val Phe Ser
                    885                 890                 895
Lys Pro Val Asn Ile Phe Trp Ala Leu Glu Asp Ser Val Leu Val Val
                900                 905                 910
Lys Ala Arg Gln Pro Lys Pro Phe Ala Ala Gly Asn Thr Phe Glu
            915                 920                 925
Met Thr Cys Lys Val Ser Ser Lys Asn Ile Lys Ser Pro Arg Tyr Ser
    930                 935                 940
Val Leu Ile Met Ala Glu Lys Pro Val Gly Asp Leu Ser Ser Pro Asn
945                 950                 955                 960
Glu Thr Lys Tyr Ile Ile Ser Leu Asp Gln Asp Ser Val Val Lys Leu
                965                 970                 975
Glu Asn Trp Thr Asp Ala Ser Arg Val Asp Gly Val Val Leu Glu Lys
            980                 985                 990
Val Gln Glu Asp Glu Phe Arg Tyr Arg Met Tyr Gln Thr Gln Val Ser
            995                 1000                1005
Asp Ala Gly Leu Tyr Arg Cys Met Val Thr Ala Trp Ser Pro Val
    1010                1015                1020
Arg Gly Ser Leu Trp Arg Glu Ala Ala Thr Ser Leu Ser Asn Pro
    1025                1030                1035
Ile Glu Ile Asp Phe Gln Thr Ser Gly Pro Ile Phe Asn Ala Ser
    1040                1045                1050
Val His Ser Asp Thr Pro Ser Val Ile Arg Gly Asp Leu Ile Lys
    1055                1060                1065
Leu Phe Cys Ile Ile Thr Val Glu Gly Ala Ala Leu Asp Pro Asp
    1070                1075                1080
Asp Met Ala Phe Asp Val Ser Trp Phe Ala Val His Ser Phe Gly
    1085                1090                1095
Leu Asp Lys Ala Pro Val Leu Leu Ser Ser Leu Asp Arg Lys Gly
    1100                1105                1110
Ile Val Thr Thr Ser Arg Arg Asp Trp Lys Ser Asp Leu Ser Leu
    1115                1120                1125
Glu Arg Val Ser Val Leu Glu Phe Leu Leu Gln Val His Gly Ser
    1130                1135                1140
Glu Asp Gln Asp Phe Gly Asn Tyr Tyr Cys Ser Val Thr Pro Trp
    1145                1150                1155
Val Lys Ser Pro Thr Gly Ser Trp Gln Lys Glu Ala Glu Ile His
    1160                1165                1170
Ser Lys Pro Val Phe Ile Thr Val Lys Met Asp Val Leu Asn Ala
    1175                1180                1185
Phe Lys Tyr Pro Leu Leu Ile Gly Val Gly Leu Ser Thr Val Ile
    1190                1195                1200
Gly Leu Leu Ser Cys Leu Ile Gly Tyr Cys Ser Ser His Trp Cys
    1205                1210                1215
Cys Lys Lys Glu Val Gln Glu Thr Arg Arg Glu Arg Arg Arg Leu
    1220                1225                1230
Met Ser Met Glu Met Asp
    1235

<210> SEQ ID NO 16
<211> LENGTH: 1239
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 16

Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
            20                  25                  30

Glu Asp Leu Ile Gln Ser Met His Ile Asp Ala Thr Leu Tyr Thr Glu
        35                  40                  45

Ser Asp Val His Pro Ser Cys Lys Val Thr Ala Met Lys Cys Phe Leu
50                  55                  60

Leu Glu Leu Gln Val Ile Ser Leu Glu Ser Gly Asp Ala Ser Ile His
65                  70                  75                  80

Asp Thr Val Glu Asn Leu Ile Ile Leu Ala Asn Asp Ser Leu Ser Ser
                85                  90                  95

Asn Gly Asn Val Thr Glu Ser Gly Cys Lys Glu Cys Glu Glu Leu Glu
            100                 105                 110

Glu Lys Asn Ile Lys Glu Phe Leu Gln Ser Phe Val His Ile Val Gln
        115                 120                 125

Met Phe Ile Asn Thr Ser Gly Gly Ser Ser Gly Ser Gly Ser Gly Ser
130                 135                 140

Thr Gly Thr Ser Ser Ser Gly Thr Gly Thr Ser Ala Gly Thr Thr Gly
145                 150                 155                 160

Thr Ser Ala Ser Thr Ser Gly Ser Gly Ser Gly Gly Gly Gly Gly Ser
                165                 170                 175

Gly Gly Gly Gly Ser Ala Gly Gly Thr Ala Thr Ala Gly Ala Ser Ser
            180                 185                 190

Gly Ser Ile Thr Cys Pro Pro Pro Met Ser Val Glu His Ala Asp Ile
        195                 200                 205

Trp Val Lys Ser Tyr Ser Leu Tyr Ser Arg Glu Arg Tyr Ile Cys Asn
210                 215                 220

Ser Gly Phe Lys Arg Lys Ala Gly Thr Ser Ser Leu Thr Glu Cys Val
225                 230                 235                 240

Leu Asn Lys Ala Thr Asn Val Ala His Trp Thr Thr Pro Ser Leu Lys
                245                 250                 255

Cys Ile Arg Asp Pro Ala Leu Val His Gln Arg Pro Ala Pro Pro Ser
            260                 265                 270

Thr Val Thr Thr Ala Gly Val Thr Pro Gln Pro Glu Ser Leu Ser Pro
        275                 280                 285

Ser Gly Lys Glu Pro Ala Ala Ser Ser Pro Ser Ser Asn Asn Thr Ala
290                 295                 300

Ala Thr Thr Ala Ala Ile Val Pro Gly Ser Gln Leu Met Pro Ser Lys
305                 310                 315                 320

Ser Pro Ser Thr Gly Thr Thr Glu Ile Ser Ser His Glu Ser Ser His
                325                 330                 335

Gly Thr Pro Ser Gln Thr Thr Ala Lys Asn Trp Glu Leu Thr Ala Ser
            340                 345                 350

Ala Ser His Gln Pro Pro Gly Val Tyr Pro Gln Gly His Ser Asp Thr
        355                 360                 365

Thr Ser Ala Gly Gly Gly Ser Gly Gly Gly Ser Arg Val Val
370                 375                 380

Arg Val Pro Thr Ala Thr Leu Val Arg Val Val Gly Thr Glu Leu Val

```
385                 390                 395                 400
Ile Pro Cys Asn Val Ser Asp Tyr Asp Gly Pro Ser Glu Gln Asn Phe
                    405                 410                 415
Asp Trp Ser Phe Ser Ser Leu Gly Ser Ser Phe Val Glu Leu Ala Ser
                420                 425                 430
Thr Trp Glu Val Gly Phe Pro Ala Gln Leu Tyr Gln Glu Arg Leu Gln
                435                 440                 445
Arg Gly Glu Ile Leu Leu Arg Arg Thr Ala Asn Asp Ala Val Glu Leu
            450                 455                 460
His Ile Lys Asn Val Gln Pro Ser Asp Gln Gly His Tyr Lys Cys Ser
465                 470                 475                 480
Thr Pro Ser Thr Asp Ala Thr Val Gln Gly Asn Tyr Glu Asp Thr Val
                        485                 490                 495
Gln Val Lys Val Leu Ala Asp Ser Leu His Val Gly Pro Ser Ala Arg
                500                 505                 510
Pro Pro Pro Ser Leu Ser Leu Arg Glu Gly Glu Pro Phe Glu Leu Arg
            515                 520                 525
Cys Thr Ala Ala Ser Ala Ser Pro Leu His Thr His Leu Ala Leu Leu
    530                 535                 540
Trp Glu Val His Arg Gly Pro Ala Arg Arg Ser Val Leu Ala Leu Thr
545                 550                 555                 560
His Glu Gly Arg Phe His Pro Gly Leu Gly Tyr Glu Gln Arg Tyr His
                    565                 570                 575
Ser Gly Asp Val Arg Leu Asp Thr Val Gly Ser Asp Ala Tyr Arg Leu
                580                 585                 590
Ser Val Ser Arg Ala Leu Ser Ala Asp Gln Gly Ser Tyr Arg Cys Ile
            595                 600                 605
Val Ser Glu Trp Ile Ala Glu Gln Gly Asn Trp Gln Glu Ile Gln Glu
        610                 615                 620
Lys Ala Val Glu Val Ala Thr Val Val Ile Gln Pro Ser Val Leu Arg
625                 630                 635                 640
Ala Ala Val Pro Lys Asn Val Ser Val Ala Glu Gly Lys Glu Leu Asp
                    645                 650                 655
Leu Thr Cys Asn Ile Thr Thr Asp Arg Ala Asp Asp Val Arg Pro Glu
                660                 665                 670
Val Thr Trp Ser Phe Ser Arg Met Pro Asp Ser Thr Leu Pro Gly Ser
            675                 680                 685
Arg Val Leu Ala Arg Leu Asp Arg Asp Ser Leu Val His Ser Ser Pro
    690                 695                 700
His Val Ala Leu Ser His Val Asp Ala Arg Ser Tyr His Leu Leu Val
705                 710                 715                 720
Arg Asp Val Ser Lys Glu Asn Ser Gly Tyr Tyr Tyr Cys His Val Ser
                    725                 730                 735
Leu Trp Ala Pro Gly His Asn Arg Ser Trp His Lys Val Ala Glu Ala
                740                 745                 750
Val Ser Ser Pro Ala Gly Val Gly Val Thr Trp Leu Glu Pro Asp Tyr
            755                 760                 765
Gln Val Tyr Leu Asn Ala Ser Lys Val Pro Gly Phe Ala Asp Asp Pro
    770                 775                 780
Thr Glu Leu Ala Cys Arg Val Val Asp Thr Lys Ser Gly Glu Ala Asn
785                 790                 795                 800
Val Arg Phe Thr Val Ser Trp Tyr Tyr Arg Met Asn Arg Arg Ser Asp
                    805                 810                 815
```

-continued

```
Asn Val Val Thr Ser Glu Leu Ala Val Met Asp Gly Asp Trp Thr
            820                 825                 830

Leu Lys Tyr Gly Glu Arg Ser Lys Gln Arg Ala Gln Asp Gly Asp Phe
            835                 840                 845

Ile Phe Ser Lys Glu His Thr Asp Thr Phe Asn Phe Arg Ile Gln Arg
            850                 855                 860

Thr Thr Glu Glu Asp Arg Gly Asn Tyr Tyr Cys Val Val Ser Ala Trp
865                 870                 875                 880

Thr Lys Gln Arg Asn Asn Ser Trp Val Lys Ser Lys Asp Val Phe Ser
                885                 890                 895

Lys Pro Val Asn Ile Phe Trp Ala Leu Glu Asp Ser Val Leu Val Val
            900                 905                 910

Lys Ala Arg Gln Pro Lys Pro Phe Ala Ala Gly Asn Thr Phe Glu
            915                 920                 925

Met Thr Cys Lys Val Ser Ser Lys Asn Ile Lys Ser Pro Arg Tyr Ser
    930                 935                 940

Val Leu Ile Met Ala Glu Lys Pro Val Gly Asp Leu Ser Ser Pro Asn
945                 950                 955                 960

Glu Thr Lys Tyr Ile Ile Ser Leu Asp Gln Asp Ser Val Val Lys Leu
                965                 970                 975

Glu Asn Trp Thr Asp Ala Ser Arg Val Asp Gly Val Val Leu Glu Lys
            980                 985                 990

Val Gln Glu Asp Glu Phe Arg Tyr Arg Met Tyr Gln Thr Gln Val Ser
            995                 1000                1005

Asp Ala Gly Leu Tyr Arg Cys Met Val Thr Ala Trp Ser Pro Val
        1010                1015                1020

Arg Gly Ser Leu Trp Arg Glu Ala Ala Thr Ser Leu Ser Asn Pro
        1025                1030                1035

Ile Glu Ile Asp Phe Gln Thr Ser Gly Pro Ile Phe Asn Ala Ser
        1040                1045                1050

Val His Ser Asp Thr Pro Ser Val Ile Arg Gly Asp Leu Ile Lys
        1055                1060                1065

Leu Phe Cys Ile Ile Thr Val Glu Gly Ala Ala Leu Asp Pro Asp
        1070                1075                1080

Asp Met Ala Phe Asp Val Ser Trp Phe Ala Val His Ser Phe Gly
        1085                1090                1095

Leu Asp Lys Ala Pro Val Leu Leu Ser Ser Leu Asp Arg Lys Gly
        1100                1105                1110

Ile Val Thr Thr Ser Arg Arg Asp Trp Lys Ser Asp Leu Ser Leu
        1115                1120                1125

Glu Arg Val Ser Val Leu Glu Phe Leu Leu Gln Val His Gly Ser
        1130                1135                1140

Glu Asp Gln Asp Phe Gly Asn Tyr Tyr Cys Ser Val Thr Pro Trp
        1145                1150                1155

Val Lys Ser Pro Thr Gly Ser Trp Gln Lys Glu Ala Glu Ile His
        1160                1165                1170

Ser Lys Pro Val Phe Ile Thr Val Lys Met Asp Val Leu Asn Ala
        1175                1180                1185

Phe Lys Tyr Pro Leu Leu Ile Gly Val Gly Leu Ser Thr Val Ile
        1190                1195                1200

Gly Leu Leu Ser Cys Leu Ile Gly Tyr Cys Ser Ser His Trp Cys
        1205                1210                1215
```

```
Cys Lys Lys Glu Val Gln Glu Thr Arg Arg Glu Arg Arg Arg Leu
    1220                1225                1230

Met Ser Met Glu Met Asp
    1235

<210> SEQ ID NO 17
<211> LENGTH: 602
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Met Lys Ile Ile Cys Leu Ala Leu Val Ala Leu Leu Leu Thr Ala Gln
1               5                   10                  15

Pro Ala Met Ala Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys Gly Gly Ser Ser Gly
225                 230                 235                 240

Ser Gly Ser Gly Ser Thr Gly Thr Ser Ser Gly Thr Gly Thr Ser
                245                 250                 255

Ala Gly Thr Thr Gly Thr Ser Ala Ser Thr Ser Gly Ser Gly Ser Gly
            260                 265                 270

Gly Gly Gly Gly Ser Gly Gly Gly Ser Ala Gly Thr Ala Thr
        275                 280                 285

Ala Gly Ala Ser Ser Gly Ser Gln Val Gln Leu Val Glu Ser Gly Gly
    290                 295                 300

Gly Val Val Gln Pro Gly Arg Ser Leu Arg Leu Ser Cys Ala Ala Ser
305                 310                 315                 320

Gly Phe Lys Phe Ser Gly Tyr Gly Met His Trp Val Arg Gln Ala Pro
                325                 330                 335
```

Gly Lys Gly Leu Glu Trp Val Ala Val Ile Trp Tyr Asp Gly Ser Lys
            340                 345                 350

Lys Tyr Tyr Val Asp Ser Val Lys Gly Arg Phe Thr Ile Ser Arg Asp
            355                 360                 365

Asn Ser Lys Asn Thr Leu Tyr Leu Gln Met Asn Ser Leu Arg Ala Glu
370                 375                 380

Asp Thr Ala Val Tyr Tyr Cys Ala Arg Gln Met Gly Tyr Trp His Phe
385                 390                 395                 400

Asp Leu Trp Gly Arg Gly Thr Leu Val Thr Val Ser Ser Ala Ser Thr
            405                 410                 415

Lys Gly Pro Ser Val Phe Pro Leu Ala Pro Ser Ser Lys Ser Thr Ser
            420                 425                 430

Gly Gly Thr Ala Ala Leu Gly Cys Leu Val Lys Asp Tyr Phe Pro Glu
            435                 440                 445

Pro Val Thr Val Ser Trp Asn Ser Gly Ala Leu Thr Ser Gly Val His
            450                 455                 460

Thr Phe Pro Ala Val Leu Gln Ser Ser Gly Leu Tyr Ser Leu Ser Ser
465                 470                 475                 480

Val Val Thr Val Pro Ser Ser Ser Leu Gly Thr Gln Thr Tyr Ile Cys
            485                 490                 495

Asn Val Asn His Lys Pro Ser Asn Thr Lys Val Asp Lys Lys Val Glu
            500                 505                 510

Pro Lys Ser Cys Asp Lys Thr His Thr Gly Gly Ser Gly Gly Gly Ser
            515                 520                 525

Gly Gly Gly Gly Ser Gly Gly Gly Ser Gly Gly Gly Ser Gly Gly
            530                 535                 540

Ser Ala Val Gly Gln Asp Thr Gln Glu Val Ile Val Val Pro His Ser
545                 550                 555                 560

Leu Pro Phe Lys Val Val Val Ile Ser Ala Ile Leu Ala Leu Val Val
            565                 570                 575

Leu Thr Ile Ile Ser Leu Ile Ile Leu Ile Met Leu Trp Gln Lys Lys
            580                 585                 590

Pro Arg Asp Tyr Lys Asp Asp Asp Lys
            595                 600

<210> SEQ ID NO 18
<211> LENGTH: 1656
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Lys Ile Ile Cys Leu Ala Leu Val Ala Leu Leu Leu Thr Ala Gln
1               5                   10                  15

Pro Ala Met Ala Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
            35                  40                  45

Val Ser Ser Tyr Leu Ala Trp Tyr Gln Gln Lys Pro Gly Gln Ala Pro
            50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser

```
            85                  90                  95
Ser Leu Glu Pro Glu Asp Phe Ala Val Tyr Tyr Cys Gln Gln Arg Ser
            100                 105                 110

Asn Trp Pro Pro Leu Thr Phe Gly Gly Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
            165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
            210                 215                 220

Pro Val Thr Lys Ser Phe Asn Arg Gly Glu Cys Gly Gly Ser Ser Gly
225                 230                 235                 240

Ser Gly Ser Gly Ser Thr Gly Thr Ser Ser Ser Gly Thr Gly Thr Ser
            245                 250                 255

Ala Gly Thr Thr Gly Thr Ser Ala Ser Thr Ser Gly Ser Gly Ser Gly
            260                 265                 270

Gly Gly Gly Gly Ser Gly Gly Gly Ser Ala Gly Gly Thr Ala Thr
            275                 280                 285

Ala Gly Ala Ser Ser Gly Ser Gln Val Gln Leu Val Glu Ser Gly Gly
            290                 295                 300

Gly Val Val Gln Pro Gly Arg Ser Leu Arg Leu Ser Cys Ala Ala Ser
305                 310                 315                 320

Gly Phe Lys Phe Ser Gly Tyr Gly Met His Trp Val Arg Gln Ala Pro
            325                 330                 335

Gly Lys Gly Leu Glu Trp Val Ala Val Ile Trp Tyr Asp Gly Ser Lys
            340                 345                 350

Lys Tyr Tyr Val Asp Ser Val Lys Gly Arg Phe Thr Ile Ser Arg Asp
            355                 360                 365

Asn Ser Lys Asn Thr Leu Tyr Leu Gln Met Asn Ser Leu Arg Ala Glu
            370                 375                 380

Asp Thr Ala Val Tyr Tyr Cys Ala Arg Gln Met Gly Tyr Trp His Phe
385                 390                 395                 400

Asp Leu Trp Gly Arg Gly Thr Leu Val Thr Val Ser Ser Ala Ser Thr
            405                 410                 415

Lys Gly Pro Ser Val Phe Pro Leu Ala Pro Ser Ser Lys Ser Thr Ser
            420                 425                 430

Gly Gly Thr Ala Ala Leu Gly Cys Leu Val Lys Asp Tyr Phe Pro Glu
            435                 440                 445

Pro Val Thr Val Ser Trp Asn Ser Gly Ala Leu Thr Ser Gly Val His
            450                 455                 460

Thr Phe Pro Ala Val Leu Gln Ser Ser Gly Leu Tyr Ser Leu Ser Ser
465                 470                 475                 480

Val Val Thr Val Pro Ser Ser Ser Leu Gly Thr Gln Thr Tyr Ile Cys
            485                 490                 495

Asn Val Asn His Lys Pro Ser Asn Thr Lys Val Asp Lys Lys Val Glu
            500                 505                 510
```

```
Pro Lys Ser Cys Asp Lys Thr His Thr Gly Gly Ser Gly Gly Gly Ser
    515                 520                 525

Gly Gly Gly Gly Ser Gly Gly Gly Ser Gly Gly Gly Ser Gly Gly
530                 535                 540

Ser Arg Val Val Arg Val Pro Thr Ala Thr Leu Val Arg Val Val Gly
545                 550                 555                 560

Thr Glu Leu Val Ile Pro Cys Asn Val Ser Asp Tyr Asp Gly Pro Ser
                565                 570                 575

Glu Gln Asn Phe Asp Trp Ser Phe Ser Ser Leu Gly Ser Ser Phe Val
            580                 585                 590

Glu Leu Ala Ser Thr Trp Glu Val Gly Phe Pro Ala Gln Leu Tyr Gln
        595                 600                 605

Glu Arg Leu Gln Arg Gly Glu Ile Leu Leu Arg Arg Thr Ala Asn Asp
    610                 615                 620

Ala Val Glu Leu His Ile Lys Asn Val Gln Pro Ser Asp Gln Gly His
625                 630                 635                 640

Tyr Lys Cys Ser Thr Pro Ser Thr Asp Ala Thr Val Gln Gly Asn Tyr
                645                 650                 655

Glu Asp Thr Val Gln Val Lys Val Leu Ala Asp Ser Leu His Val Gly
            660                 665                 670

Pro Ser Ala Arg Pro Pro Ser Leu Ser Leu Arg Glu Gly Glu Pro
        675                 680                 685

Phe Glu Leu Arg Cys Thr Ala Ala Ser Ala Ser Pro Leu His Thr His
    690                 695                 700

Leu Ala Leu Leu Trp Glu Val His Arg Gly Pro Ala Arg Arg Ser Val
705                 710                 715                 720

Leu Ala Leu Thr His Glu Gly Arg Phe His Pro Gly Leu Gly Tyr Glu
                725                 730                 735

Gln Arg Tyr His Ser Gly Asp Val Arg Leu Asp Thr Val Gly Ser Asp
            740                 745                 750

Ala Tyr Arg Leu Ser Val Ser Arg Ala Leu Ser Ala Asp Gln Gly Ser
        755                 760                 765

Tyr Arg Cys Ile Val Ser Glu Trp Ile Ala Glu Gln Gly Asn Trp Gln
    770                 775                 780

Glu Ile Gln Glu Lys Ala Val Glu Val Ala Thr Val Val Ile Gln Pro
785                 790                 795                 800

Ser Val Leu Arg Ala Ala Val Pro Lys Asn Val Ser Val Ala Glu Gly
                805                 810                 815

Lys Glu Leu Asp Leu Thr Cys Asn Ile Thr Thr Asp Arg Ala Asp Asp
            820                 825                 830

Val Arg Pro Glu Val Thr Trp Ser Phe Ser Arg Met Pro Asp Ser Thr
        835                 840                 845

Leu Pro Gly Ser Arg Val Leu Ala Arg Leu Asp Arg Asp Ser Leu Val
    850                 855                 860

His Ser Ser Pro His Val Ala Leu Ser His Val Asp Ala Arg Ser Tyr
865                 870                 875                 880

His Leu Leu Val Arg Asp Val Ser Lys Glu Asn Ser Gly Tyr Tyr Tyr
                885                 890                 895

Cys His Val Ser Leu Trp Ala Pro Gly His Asn Arg Ser Trp His Lys
            900                 905                 910

Val Ala Glu Ala Val Ser Ser Pro Ala Gly Val Gly Val Thr Trp Leu
        915                 920                 925
```

```
Glu Pro Asp Tyr Gln Val Tyr Leu Asn Ala Ser Lys Val Pro Gly Phe
    930             935             940

Ala Asp Asp Pro Thr Glu Leu Ala Cys Arg Val Val Asp Thr Lys Ser
945             950             955             960

Gly Glu Ala Asn Val Arg Phe Thr Val Ser Trp Tyr Tyr Arg Met Asn
            965             970             975

Arg Arg Ser Asp Asn Val Val Thr Ser Glu Leu Leu Ala Val Met Asp
        980             985             990

Gly Asp Trp Thr Leu Lys Tyr Gly Glu Arg Ser Lys Gln Arg Ala Gln
    995             1000            1005

Asp Gly Asp Phe Ile Phe Ser Lys Glu His Thr Asp Thr Phe Asn
1010            1015            1020

Phe Arg Ile Gln Arg Thr Thr Glu Glu Asp Arg Gly Asn Tyr Tyr
1025            1030            1035

Cys Val Val Ser Ala Trp Thr Lys Gln Arg Asn Asn Ser Trp Val
1040            1045            1050

Lys Ser Lys Asp Val Phe Ser Lys Pro Val Asn Ile Phe Trp Ala
1055            1060            1065

Leu Glu Asp Ser Val Leu Val Val Lys Ala Arg Gln Pro Lys Pro
1070            1075            1080

Phe Phe Ala Ala Gly Asn Thr Phe Glu Met Thr Cys Lys Val Ser
1085            1090            1095

Ser Lys Asn Ile Lys Ser Pro Arg Tyr Ser Val Leu Ile Met Ala
1100            1105            1110

Glu Lys Pro Val Gly Asp Leu Ser Ser Pro Asn Glu Thr Lys Tyr
1115            1120            1125

Ile Ile Ser Leu Asp Gln Asp Ser Val Val Lys Leu Glu Asn Trp
1130            1135            1140

Thr Asp Ala Ser Arg Val Asp Gly Val Val Leu Glu Lys Val Gln
1145            1150            1155

Glu Asp Glu Phe Arg Tyr Arg Met Tyr Gln Thr Gln Val Ser Asp
1160            1165            1170

Ala Gly Leu Tyr Arg Cys Met Val Thr Ala Trp Ser Pro Val Arg
1175            1180            1185

Gly Ser Leu Trp Arg Glu Ala Ala Thr Ser Leu Ser Asn Pro Ile
1190            1195            1200

Glu Ile Asp Phe Gln Thr Ser Gly Pro Ile Phe Asn Ala Ser Val
1205            1210            1215

His Ser Asp Thr Pro Ser Val Ile Arg Gly Asp Leu Ile Lys Leu
1220            1225            1230

Phe Cys Ile Ile Thr Val Glu Gly Ala Ala Leu Asp Pro Asp Asp
1235            1240            1245

Met Ala Phe Asp Val Ser Trp Phe Ala Val His Ser Phe Gly Leu
1250            1255            1260

Asp Lys Ala Pro Val Leu Leu Ser Ser Leu Asp Arg Lys Gly Ile
1265            1270            1275

Val Thr Thr Ser Arg Arg Asp Trp Lys Ser Asp Leu Ser Leu Glu
1280            1285            1290

Arg Val Ser Val Leu Glu Phe Leu Leu Gln Val His Gly Ser Glu
1295            1300            1305

Asp Gln Asp Phe Gly Asn Tyr Tyr Cys Ser Val Thr Pro Trp Val
1310            1315            1320

Lys Ser Pro Thr Gly Ser Trp Gln Lys Glu Ala Glu Ile His Ser
```

1325                1330                1335

Lys Pro Val Phe Ile Thr Val Lys Met Asp Val Leu Asn Ala Phe
    1340                1345                1350

Lys Tyr Pro Leu Leu Ile Gly Val Gly Leu Ser Thr Val Ile Gly
    1355                1360                1365

Leu Leu Ser Cys Leu Ile Gly Tyr Cys Ser Ser His Trp Cys Cys
    1370                1375                1380

Lys Lys Glu Val Gln Glu Thr Arg Arg Glu Arg Arg Leu Met
    1385                1390                1395

Ser Met Glu Met Asp Thr Gly Gly Ser Gly Gly Ser Val Ser Lys
    1400                1405                1410

Gly Glu Glu Leu Phe Thr Gly Val Val Pro Ile Leu Val Glu Leu
    1415                1420                1425

Asp Gly Asp Val Asn Gly His Lys Phe Ser Val Ser Gly Glu Gly
    1430                1435                1440

Glu Gly Asp Ala Thr Tyr Gly Lys Leu Thr Leu Lys Phe Ile Cys
    1445                1450                1455

Thr Thr Gly Lys Leu Pro Val Pro Trp Pro Thr Leu Val Thr Thr
    1460                1465                1470

Leu Thr Tyr Gly Val Gln Cys Phe Ser Arg Tyr Pro Asp His Met
    1475                1480                1485

Lys Gln His Asp Phe Phe Lys Ser Ala Met Pro Glu Gly Tyr Val
    1490                1495                1500

Gln Glu Arg Thr Ile Phe Phe Lys Asp Asp Gly Asn Tyr Lys Thr
    1505                1510                1515

Arg Ala Glu Val Lys Phe Glu Gly Asp Thr Leu Val Asn Arg Ile
    1520                1525                1530

Glu Leu Lys Gly Ile Asp Phe Lys Glu Asp Gly Asn Ile Leu Gly
    1535                1540                1545

His Lys Leu Glu Tyr Asn Tyr Asn Ser His Asn Val Tyr Ile Met
    1550                1555                1560

Ala Asp Lys Gln Lys Asn Gly Ile Lys Val Asn Phe Lys Ile Arg
    1565                1570                1575

His Asn Ile Glu Asp Gly Ser Val Gln Leu Ala Asp His Tyr Gln
    1580                1585                1590

Gln Asn Thr Pro Ile Gly Asp Gly Pro Val Leu Leu Pro Asp Asn
    1595                1600                1605

His Tyr Leu Ser Thr Gln Ser Lys Leu Ser Lys Asp Pro Asn Glu
    1610                1615                1620

Lys Arg Asp His Met Val Leu Leu Glu Phe Val Thr Ala Ala Gly
    1625                1630                1635

Ile Thr Leu Gly Met Asp Glu Leu Tyr Lys Asp Tyr Lys Asp Asp
    1640                1645                1650

Asp Asp Lys
    1655

<210> SEQ ID NO 19
<211> LENGTH: 1361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Glu Thr Asp Thr Leu Leu Leu Trp Val Leu Leu Leu Trp Val Pro
1               5                   10                  15

Gly Ser Thr Gly Met Gln Arg Gly Asp Glu Asp Pro Gln Ile Ala Ala
            20                  25                  30

His Val Val Ser Glu Ala Asn Ser Asn Ala Ala Ser Val Leu Gln Trp
            35                  40                  45

Ala Lys Lys Gly Tyr Tyr Thr Met Lys Ser Asn Leu Val Met Leu Glu
50              55                  60

Asn Gly Lys Gln Leu Thr Val Lys Arg Glu Gly Leu Tyr Tyr Val Tyr
65                  70                  75                  80

Thr Gln Val Thr Phe Cys Ser Asn Arg Glu Pro Ser Ser Gln Arg Pro
                85                  90                  95

Phe Ile Val Gly Leu Trp Leu Lys Pro Ser Ser Gly Ser Glu Arg Ile
            100                 105                 110

Leu Leu Lys Ala Ala Asn Thr His Ser Ser Gln Leu Cys Glu Gln
            115                 120                 125

Gln Ser Val His Leu Gly Gly Val Phe Glu Leu Gln Ala Gly Ala Ser
    130                 135                 140

Val Phe Val Asn Val Thr Glu Ala Ser Gln Val Ile His Arg Val Gly
145                 150                 155                 160

Phe Ser Ser Phe Gly Leu Leu Lys Leu Gly Ser Gly Ser Gly Gly
                165                 170                 175

Ser Gly Gly Ser Gly Met Gln Arg Gly Asp Glu Asp Pro Gln Ile Ala
            180                 185                 190

Ala His Val Val Ser Glu Ala Asn Ser Asn Ala Ala Ser Val Leu Gln
        195                 200                 205

Trp Ala Lys Lys Gly Tyr Tyr Thr Met Lys Ser Asn Leu Val Met Leu
    210                 215                 220

Glu Asn Gly Lys Gln Leu Thr Val Lys Arg Glu Gly Leu Tyr Tyr Val
225                 230                 235                 240

Tyr Thr Gln Val Thr Phe Cys Ser Asn Arg Glu Pro Ser Ser Gln Arg
                245                 250                 255

Pro Phe Ile Val Gly Leu Trp Leu Lys Pro Ser Ser Gly Ser Glu Arg
                260                 265                 270

Ile Leu Leu Lys Ala Ala Asn Thr His Ser Ser Gln Leu Cys Glu
                275                 280                 285

Gln Gln Ser Val His Leu Gly Gly Val Phe Glu Leu Gln Ala Gly Ala
    290                 295                 300

Ser Val Phe Val Asn Val Thr Glu Ala Ser Gln Val Ile His Arg Val
305                 310                 315                 320

Gly Phe Ser Ser Phe Gly Leu Leu Lys Leu Gly Ser Gly Gly Ser Gly
                325                 330                 335

Gly Ser Gly Gly Ser Gly Met Gln Arg Gly Asp Glu Asp Pro Gln Ile
            340                 345                 350

Ala Ala His Val Val Ser Glu Ala Asn Ser Asn Ala Ala Ser Val Leu
        355                 360                 365

Gln Trp Ala Lys Lys Gly Tyr Tyr Thr Met Lys Ser Asn Leu Val Met
    370                 375                 380

Leu Glu Asn Gly Lys Gln Leu Thr Val Lys Arg Glu Gly Leu Tyr Tyr
385                 390                 395                 400

Val Tyr Thr Gln Val Thr Phe Cys Ser Asn Arg Glu Pro Ser Ser Gln
                405                 410                 415

Arg Pro Phe Ile Val Gly Leu Trp Leu Lys Pro Ser Ser Gly Ser Glu
```

```
                420             425             430
Arg Ile Leu Leu Lys Ala Ala Asn Thr His Ser Ser Ser Gln Leu Cys
            435                 440                 445

Glu Gln Gln Ser Val His Leu Gly Gly Val Phe Glu Leu Gln Ala Gly
    450                 455                 460

Ala Ser Val Phe Val Asn Val Thr Glu Ala Ser Gln Val Ile His Arg
465                 470                 475                 480

Val Gly Phe Ser Ser Phe Gly Leu Leu Lys Leu Ser Ala Gly Gly Gly
            485                 490                 495

Gly Ser Gly Gly Gly Ser Arg Val Val Arg Val Pro Thr Ala Thr
            500                 505                 510

Leu Val Arg Val Val Gly Thr Glu Leu Val Ile Pro Cys Asn Val Ser
        515                 520                 525

Asp Tyr Asp Gly Pro Ser Glu Gln Asn Phe Asp Trp Ser Phe Ser Ser
    530                 535                 540

Leu Gly Ser Ser Phe Val Glu Leu Ala Ser Thr Trp Glu Val Gly Phe
545                 550                 555                 560

Pro Ala Gln Leu Tyr Gln Glu Arg Leu Gln Arg Gly Glu Ile Leu Leu
                565                 570                 575

Arg Arg Thr Ala Asn Asp Ala Val Glu Leu His Ile Lys Asn Val Gln
            580                 585                 590

Pro Ser Asp Gln Gly His Tyr Lys Cys Ser Thr Pro Ser Thr Asp Ala
        595                 600                 605

Thr Val Gln Gly Asn Tyr Glu Asp Thr Val Gln Val Lys Val Leu Ala
    610                 615                 620

Asp Ser Leu His Val Gly Pro Ser Ala Arg Pro Pro Pro Ser Leu Ser
625                 630                 635                 640

Leu Arg Glu Gly Glu Pro Phe Glu Leu Arg Cys Thr Ala Ala Ser Ala
                645                 650                 655

Ser Pro Leu His Thr His Leu Ala Leu Leu Trp Glu Val His Arg Gly
            660                 665                 670

Pro Ala Arg Arg Ser Val Leu Ala Leu Thr His Glu Gly Arg Phe His
        675                 680                 685

Pro Gly Leu Gly Tyr Glu Gln Arg Tyr His Ser Gly Asp Val Arg Leu
    690                 695                 700

Asp Thr Val Gly Ser Asp Ala Tyr Arg Leu Ser Val Ser Arg Ala Leu
705                 710                 715                 720

Ser Ala Asp Gln Gly Ser Tyr Arg Cys Ile Val Ser Glu Trp Ile Ala
                725                 730                 735

Glu Gln Gly Asn Trp Gln Glu Ile Gln Glu Lys Ala Val Glu Val Ala
            740                 745                 750

Thr Val Val Ile Gln Pro Ser Val Leu Arg Ala Ala Val Pro Lys Asn
        755                 760                 765

Val Ser Val Ala Glu Gly Lys Glu Leu Asp Leu Thr Cys Asn Ile Thr
    770                 775                 780

Thr Asp Arg Ala Asp Asp Val Arg Pro Glu Val Thr Trp Ser Phe Ser
785                 790                 795                 800

Arg Met Pro Asp Ser Thr Leu Pro Gly Ser Arg Val Leu Ala Arg Leu
                805                 810                 815

Asp Arg Asp Ser Leu Val His Ser Ser Pro His Val Ala Leu Ser His
            820                 825                 830

Val Asp Ala Arg Ser Tyr His Leu Leu Val Arg Asp Val Ser Lys Glu
        835                 840                 845
```

```
Asn Ser Gly Tyr Tyr Tyr Cys His Val Ser Leu Trp Ala Pro Gly His
850                 855                 860

Asn Arg Ser Trp His Lys Val Ala Glu Ala Val Ser Ser Pro Ala Gly
865                 870                 875                 880

Val Gly Val Thr Trp Leu Glu Pro Asp Tyr Gln Val Tyr Leu Asn Ala
                885                 890                 895

Ser Lys Val Pro Gly Phe Ala Asp Asp Pro Thr Glu Leu Ala Cys Arg
                900                 905                 910

Val Val Asp Thr Lys Ser Gly Glu Ala Asn Val Arg Phe Thr Val Ser
            915                 920                 925

Trp Tyr Tyr Arg Met Asn Arg Arg Ser Asp Asn Val Val Thr Ser Glu
    930                 935                 940

Leu Leu Ala Val Met Asp Gly Asp Trp Thr Leu Lys Tyr Gly Glu Arg
945                 950                 955                 960

Ser Lys Gln Arg Ala Gln Asp Gly Asp Phe Ile Phe Ser Lys Glu His
                965                 970                 975

Thr Asp Thr Phe Asn Phe Arg Ile Gln Arg Thr Thr Glu Glu Asp Arg
                980                 985                 990

Gly Asn Tyr Tyr Cys Val Val Ser Ala Trp Thr Lys Gln Arg Asn Asn
        995                 1000                1005

Ser Trp Val Lys Ser Lys Asp Val Phe Ser Lys Pro Val Asn Ile
    1010                1015                1020

Phe Trp Ala Leu Glu Asp Ser Val Leu Val Lys Ala Arg Gln
    1025                1030                1035

Pro Lys Pro Phe Phe Ala Ala Gly Asn Thr Phe Glu Met Thr Cys
    1040                1045                1050

Lys Val Ser Ser Lys Asn Ile Lys Ser Pro Arg Tyr Ser Val Leu
    1055                1060                1065

Ile Met Ala Glu Lys Pro Val Gly Asp Leu Ser Ser Pro Asn Glu
    1070                1075                1080

Thr Lys Tyr Ile Ile Ser Leu Asp Gln Asp Ser Val Val Lys Leu
    1085                1090                1095

Glu Asn Trp Thr Asp Ala Ser Arg Val Asp Gly Val Val Leu Glu
    1100                1105                1110

Lys Val Gln Glu Asp Glu Phe Arg Tyr Arg Met Tyr Gln Thr Gln
    1115                1120                1125

Val Ser Asp Ala Gly Leu Tyr Arg Cys Met Val Thr Ala Trp Ser
    1130                1135                1140

Pro Val Arg Gly Ser Leu Trp Arg Glu Ala Ala Thr Ser Leu Ser
    1145                1150                1155

Asn Pro Ile Glu Ile Asp Phe Gln Thr Ser Gly Pro Ile Phe Asn
    1160                1165                1170

Ala Ser Val His Ser Asp Thr Pro Ser Val Ile Arg Gly Asp Leu
    1175                1180                1185

Ile Lys Leu Phe Cys Ile Ile Thr Val Glu Gly Ala Ala Leu Asp
    1190                1195                1200

Pro Asp Asp Met Ala Phe Asp Val Ser Trp Phe Ala Val His Ser
    1205                1210                1215

Phe Gly Leu Asp Lys Ala Pro Val Leu Leu Ser Ser Leu Asp Arg
    1220                1225                1230

Lys Gly Ile Val Thr Thr Ser Arg Arg Asp Trp Lys Ser Asp Leu
    1235                1240                1245
```

-continued

```
Ser Leu Glu Arg Val Ser Val Leu Glu Phe Leu Leu Gln Val His
    1250                1255                1260

Gly Ser Glu Asp Gln Asp Phe Gly Asn Tyr Tyr Cys Ser Val Thr
    1265                1270                1275

Pro Trp Val Lys Ser Pro Thr Gly Ser Trp Gln Lys Glu Ala Glu
    1280                1285                1290

Ile His Ser Lys Pro Val Phe Ile Thr Val Lys Met Asp Val Leu
    1295                1300                1305

Asn Ala Phe Lys Tyr Pro Leu Leu Ile Gly Val Gly Leu Ser Thr
    1310                1315                1320

Val Ile Gly Leu Leu Ser Cys Leu Ile Gly Tyr Cys Ser Ser His
    1325                1330                1335

Trp Cys Cys Lys Lys Glu Val Gln Glu Thr Arg Arg Glu Arg Arg
    1340                1345                1350

Arg Leu Met Ser Met Glu Met Asp
    1355                1360

<210> SEQ ID NO 20
<211> LENGTH: 1361
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Met Glu Thr Asp Thr Leu Leu Leu Trp Val Leu Leu Leu Trp Val Pro
1               5                   10                  15

Gly Ser Thr Gly Met Gln Lys Gly Asp Gln Asn Pro Gln Ile Ala Ala
            20                  25                  30

His Val Ile Ser Glu Ala Ser Ser Lys Thr Thr Ser Val Leu Gln Trp
        35                  40                  45

Ala Glu Lys Gly Tyr Tyr Thr Met Ser Asn Asn Leu Val Thr Leu Glu
    50                  55                  60

Asn Gly Lys Gln Leu Thr Val Lys Arg Gln Gly Leu Tyr Tyr Ile Tyr
65                  70                  75                  80

Ala Gln Val Thr Phe Cys Ser Asn Arg Glu Ala Ser Ser Gln Ala Pro
                85                  90                  95

Phe Ile Ala Ser Leu Cys Leu Lys Ser Pro Gly Arg Phe Glu Arg Ile
            100                 105                 110

Leu Leu Arg Ala Ala Asn Thr His Ser Ser Ala Lys Pro Cys Gly Gln
        115                 120                 125

Gln Ser Ile His Leu Gly Gly Val Phe Glu Leu Gln Pro Gly Ala Ser
    130                 135                 140

Val Phe Val Asn Val Thr Asp Pro Ser Gln Val Ser His Gly Thr Gly
145                 150                 155                 160

Phe Thr Ser Phe Gly Leu Leu Lys Leu Gly Ser Gly Ser Gly Gly Gly
                165                 170                 175

Ser Gly Gly Ser Gly Met Gln Lys Gly Asp Gln Asn Pro Gln Ile Ala
            180                 185                 190

Ala His Val Ile Ser Glu Ala Ser Ser Lys Thr Thr Ser Val Leu Gln
        195                 200                 205

Trp Ala Glu Lys Gly Tyr Tyr Thr Met Ser Asn Asn Leu Val Thr Leu
    210                 215                 220

Glu Asn Gly Lys Gln Leu Thr Val Lys Arg Gln Gly Leu Tyr Tyr Ile
225                 230                 235                 240
```

```
Tyr Ala Gln Val Thr Phe Cys Ser Asn Arg Glu Ala Ser Gln Ala
            245                 250                 255

Pro Phe Ile Ala Ser Leu Cys Leu Lys Ser Pro Gly Arg Phe Glu Arg
        260                 265                 270

Ile Leu Leu Arg Ala Ala Asn Thr His Ser Ser Ala Lys Pro Cys Gly
            275                 280                 285

Gln Gln Ser Ile His Leu Gly Gly Val Phe Glu Leu Gln Pro Gly Ala
        290                 295                 300

Ser Val Phe Val Asn Val Thr Asp Pro Ser Gln Val Ser His Gly Thr
305                 310                 315                 320

Gly Phe Thr Ser Phe Gly Leu Leu Lys Leu Ser Gly Gly Ser Gly
            325                 330                 335

Gly Ser Gly Gly Ser Gly Met Gln Lys Gly Asp Gln Asn Pro Gln Ile
            340                 345                 350

Ala Ala His Val Ile Ser Glu Ala Ser Ser Lys Thr Thr Ser Val Leu
        355                 360                 365

Gln Trp Ala Glu Lys Gly Tyr Tyr Thr Met Ser Asn Asn Leu Val Thr
    370                 375                 380

Leu Glu Asn Gly Lys Gln Leu Thr Val Lys Arg Gln Gly Leu Tyr Tyr
385                 390                 395                 400

Ile Tyr Ala Gln Val Thr Phe Cys Ser Asn Arg Glu Ala Ser Ser Gln
            405                 410                 415

Ala Pro Phe Ile Ala Ser Leu Cys Leu Lys Ser Pro Gly Arg Phe Glu
            420                 425                 430

Arg Ile Leu Leu Arg Ala Ala Asn Thr His Ser Ser Ala Lys Pro Cys
        435                 440                 445

Gly Gln Gln Ser Ile His Leu Gly Gly Val Phe Glu Leu Gln Pro Gly
    450                 455                 460

Ala Ser Val Phe Val Asn Val Thr Asp Pro Ser Gln Val Ser His Gly
465                 470                 475                 480

Thr Gly Phe Thr Ser Phe Gly Leu Leu Lys Leu Ser Ala Gly Gly Gly
            485                 490                 495

Gly Ser Gly Gly Gly Gly Ser Arg Val Val Arg Val Pro Thr Ala Thr
            500                 505                 510

Leu Val Arg Val Val Gly Thr Glu Leu Val Ile Pro Cys Asn Val Ser
        515                 520                 525

Asp Tyr Asp Gly Pro Ser Glu Gln Asn Phe Asp Trp Ser Phe Ser Ser
    530                 535                 540

Leu Gly Ser Ser Phe Val Glu Leu Ala Ser Thr Trp Glu Val Gly Phe
545                 550                 555                 560

Pro Ala Gln Leu Tyr Gln Glu Arg Leu Gln Arg Gly Glu Ile Leu Leu
            565                 570                 575

Arg Arg Thr Ala Asn Asp Ala Val Glu Leu His Ile Lys Asn Val Gln
        580                 585                 590

Pro Ser Asp Gln Gly His Tyr Lys Cys Ser Thr Pro Ser Thr Asp Ala
    595                 600                 605

Thr Val Gln Gly Asn Tyr Glu Asp Thr Val Gln Val Lys Val Leu Ala
        610                 615                 620

Asp Ser Leu His Val Gly Pro Ser Ala Arg Pro Pro Pro Ser Leu Ser
625                 630                 635                 640

Leu Arg Glu Gly Glu Pro Phe Glu Leu Arg Cys Thr Ala Ala Ser Ala
            645                 650                 655
```

-continued

Ser Pro Leu His Thr His Leu Ala Leu Leu Trp Glu Val His Arg Gly
            660                 665                 670

Pro Ala Arg Arg Ser Val Leu Ala Leu Thr His Glu Gly Arg Phe His
            675                 680                 685

Pro Gly Leu Gly Tyr Glu Gln Arg Tyr His Ser Gly Asp Val Arg Leu
            690                 695                 700

Asp Thr Val Gly Ser Asp Ala Tyr Arg Leu Ser Val Ser Arg Ala Leu
705                 710                 715                 720

Ser Ala Asp Gln Gly Ser Tyr Arg Cys Ile Val Ser Glu Trp Ile Ala
            725                 730                 735

Glu Gln Gly Asn Trp Gln Glu Ile Gln Glu Lys Ala Val Glu Val Ala
            740                 745                 750

Thr Val Val Ile Gln Pro Ser Val Leu Arg Ala Ala Val Pro Lys Asn
            755                 760                 765

Val Ser Val Ala Glu Gly Lys Glu Leu Asp Leu Thr Cys Asn Ile Thr
            770                 775                 780

Thr Asp Arg Ala Asp Val Arg Pro Glu Val Thr Trp Ser Phe Ser
785                 790                 795                 800

Arg Met Pro Asp Ser Thr Leu Pro Gly Ser Arg Val Leu Ala Arg Leu
            805                 810                 815

Asp Arg Asp Ser Leu Val His Ser Ser Pro His Val Ala Leu Ser His
            820                 825                 830

Val Asp Ala Arg Ser Tyr His Leu Leu Val Arg Asp Val Ser Lys Glu
            835                 840                 845

Asn Ser Gly Tyr Tyr Tyr Cys His Val Ser Leu Trp Ala Pro Gly His
850                 855                 860

Asn Arg Ser Trp His Lys Val Ala Glu Ala Val Ser Ser Pro Ala Gly
865                 870                 875                 880

Val Gly Val Thr Trp Leu Glu Pro Asp Tyr Gln Val Tyr Leu Asn Ala
            885                 890                 895

Ser Lys Val Pro Gly Phe Ala Asp Asp Pro Thr Glu Leu Ala Cys Arg
            900                 905                 910

Val Val Asp Thr Lys Ser Gly Glu Ala Asn Val Arg Phe Thr Val Ser
            915                 920                 925

Trp Tyr Tyr Arg Met Asn Arg Arg Ser Asp Asn Val Val Thr Ser Glu
            930                 935                 940

Leu Leu Ala Val Met Asp Gly Asp Trp Thr Leu Lys Tyr Gly Glu Arg
945                 950                 955                 960

Ser Lys Gln Arg Ala Gln Asp Gly Asp Phe Ile Phe Ser Lys Glu His
            965                 970                 975

Thr Asp Thr Phe Asn Phe Arg Ile Gln Arg Thr Thr Glu Glu Asp Arg
            980                 985                 990

Gly Asn Tyr Tyr Cys Val Val Ser Ala Trp Thr Lys Gln Arg Asn Asn
            995                 1000                1005

Ser Trp Val Lys Ser Lys Asp Val Phe Ser Lys Pro Val Asn Ile
   1010                1015                1020

Phe Trp Ala Leu Glu Asp Ser Val Leu Val Val Lys Ala Arg Gln
   1025                1030                1035

Pro Lys Pro Phe Phe Ala Ala Gly Asn Thr Phe Glu Met Thr Cys
   1040                1045                1050

Lys Val Ser Ser Lys Asn Ile Lys Ser Pro Arg Tyr Ser Val Leu
   1055                1060                1065

Ile Met Ala Glu Lys Pro Val Gly Asp Leu Ser Ser Pro Asn Glu

```
            1070                1075                1080

Thr Lys Tyr Ile Ile Ser Leu Asp Gln Asp Ser Val Val Lys Leu
        1085                1090                1095

Glu Asn Trp Thr Asp Ala Ser Arg Val Asp Gly Val Val Leu Glu
    1100                1105                1110

Lys Val Gln Glu Asp Glu Phe Arg Tyr Arg Met Tyr Gln Thr Gln
1115                1120                1125

Val Ser Asp Ala Gly Leu Tyr Arg Cys Met Val Thr Ala Trp Ser
        1130                1135                1140

Pro Val Arg Gly Ser Leu Trp Arg Glu Ala Ala Thr Ser Leu Ser
    1145                1150                1155

Asn Pro Ile Glu Ile Asp Phe Gln Thr Ser Gly Pro Ile Phe Asn
1160                1165                1170

Ala Ser Val His Ser Asp Thr Pro Ser Val Ile Arg Gly Asp Leu
        1175                1180                1185

Ile Lys Leu Phe Cys Ile Ile Thr Val Glu Gly Ala Ala Leu Asp
    1190                1195                1200

Pro Asp Asp Met Ala Phe Asp Val Ser Trp Phe Ala Val His Ser
1205                1210                1215

Phe Gly Leu Asp Lys Ala Pro Val Leu Leu Ser Ser Leu Asp Arg
        1220                1225                1230

Lys Gly Ile Val Thr Thr Ser Arg Arg Asp Trp Lys Ser Asp Leu
    1235                1240                1245

Ser Leu Glu Arg Val Ser Val Leu Glu Phe Leu Leu Gln Val His
1250                1255                1260

Gly Ser Glu Asp Gln Asp Phe Gly Asn Tyr Tyr Cys Ser Val Thr
        1265                1270                1275

Pro Trp Val Lys Ser Pro Thr Gly Ser Trp Gln Lys Glu Ala Glu
    1280                1285                1290

Ile His Ser Lys Pro Val Phe Ile Thr Val Lys Met Asp Val Leu
1295                1300                1305

Asn Ala Phe Lys Tyr Pro Leu Leu Ile Gly Val Gly Leu Ser Thr
        1310                1315                1320

Val Ile Gly Leu Leu Ser Cys Leu Ile Gly Tyr Cys Ser Ser His
    1325                1330                1335

Trp Cys Cys Lys Lys Glu Val Gln Glu Thr Arg Arg Glu Arg Arg
1340                1345                1350

Arg Leu Met Ser Met Glu Met Asp
        1355                1360

<210> SEQ ID NO 21
<211> LENGTH: 991
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Lys Ile Ile Cys Leu Ala Leu Val Ala Leu Leu Thr Ala Gln
1               5                   10                  15

Pro Ala Met Ala Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45
```

-continued

```
Val Ser Ser Tyr Leu Ala Trp Tyr Gln Gln Lys Pro Gly Gln Ala Pro
 50              55                  60

Arg Leu Leu Ile Tyr Asp Ala Ser Asn Arg Ala Thr Gly Ile Pro Ala
 65              70                  75                  80

Arg Phe Ser Gly Ser Gly Ser Gly Thr Asp Phe Thr Leu Thr Ile Ser
                 85                  90                  95

Ser Leu Glu Pro Glu Asp Phe Ala Val Tyr Tyr Cys Gln Gln Arg Ser
            100                 105                 110

Asn Trp Pro Pro Leu Thr Phe Gly Gly Gly Thr Lys Val Glu Ile Lys
            115                 120                 125

Arg Thr Val Ala Ala Pro Ser Val Phe Ile Phe Pro Pro Ser Asp Glu
130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
            195                 200                 205

Lys His Lys Val Tyr Ala Cys Glu Val Thr His Gln Gly Leu Ser Ser
210                 215                 220

Pro Val Thr Lys Ser Phe Asn Arg Gly Glu Cys Gly Gly Ser Ser Gly
225                 230                 235                 240

Ser Gly Ser Gly Ser Thr Gly Thr Ser Ser Gly Thr Gly Thr Ser
                245                 250                 255

Ala Gly Thr Thr Gly Thr Ser Ala Ser Thr Ser Gly Ser Gly Ser Gly
            260                 265                 270

Gly Gly Gly Gly Ser Gly Gly Gly Ser Ala Gly Thr Ala Thr
            275                 280                 285

Ala Gly Ala Ser Ser Gly Ser Gln Val Gln Leu Val Glu Ser Gly Gly
            290                 295                 300

Gly Val Val Gln Pro Gly Arg Ser Leu Arg Leu Ser Cys Ala Ala Ser
305                 310                 315                 320

Gly Phe Lys Phe Ser Gly Tyr Gly Met His Trp Val Arg Gln Ala Pro
                325                 330                 335

Gly Lys Gly Leu Glu Trp Val Ala Val Ile Trp Tyr Asp Gly Ser Lys
            340                 345                 350

Lys Tyr Tyr Val Asp Ser Val Lys Gly Arg Phe Thr Ile Ser Arg Asp
            355                 360                 365

Asn Ser Lys Asn Thr Leu Tyr Leu Gln Met Asn Ser Leu Arg Ala Glu
            370                 375                 380

Asp Thr Ala Val Tyr Tyr Cys Ala Arg Gln Met Gly Tyr Trp His Phe
385                 390                 395                 400

Asp Leu Trp Gly Arg Gly Thr Leu Val Thr Val Ser Ser Ala Ser Thr
                405                 410                 415

Lys Gly Pro Ser Val Phe Pro Leu Ala Pro Ser Ser Lys Ser Thr Ser
            420                 425                 430

Gly Gly Thr Ala Ala Leu Gly Cys Leu Val Lys Asp Tyr Phe Pro Glu
            435                 440                 445

Pro Val Thr Val Ser Trp Asn Ser Gly Ala Leu Thr Ser Gly Val His
450                 455                 460

Thr Phe Pro Ala Val Leu Gln Ser Ser Gly Leu Tyr Ser Leu Ser Ser
```

```
                465                 470                 475                 480
Val Val Thr Val Pro Ser Ser Leu Gly Thr Gln Thr Tyr Ile Cys
                    485                 490                 495

Asn Val Asn His Lys Pro Ser Asn Thr Lys Val Asp Lys Val Glu
                    500                 505                 510

Pro Lys Ser Cys Asp Lys Thr His Thr Gly Gly Ser Gly Gly Ser
                    515                 520                 525

Gly Gly Gly Gly Ser Gly Gly Gly Ser Gly Gly Ser Gly Gly
                    535                 540
530

Ser Gly Pro Ile Phe Asn Ala Ser Val His Ser Asp Thr Pro Ser Val
545                 550                 555                 560

Ile Arg Gly Asp Leu Ile Lys Leu Phe Cys Ile Ile Thr Val Glu Gly
                565                 570                 575

Ala Ala Leu Asp Pro Asp Asp Met Ala Phe Asp Val Ser Trp Phe Ala
                580                 585                 590

Val His Ser Phe Gly Leu Asp Lys Ala Pro Val Leu Leu Ser Ser Leu
        595                 600                 605

Asp Arg Lys Gly Ile Val Thr Thr Ser Arg Arg Asp Trp Lys Ser Asp
        610                 615                 620

Leu Ser Leu Glu Arg Val Ser Val Leu Glu Phe Leu Leu Gln Val His
625                 630                 635                 640

Gly Ser Glu Asp Gln Asp Phe Gly Asn Tyr Tyr Cys Ser Val Thr Pro
                645                 650                 655

Trp Val Lys Ser Pro Thr Gly Ser Trp Gln Lys Glu Ala Glu Ile His
                660                 665                 670

Ser Lys Pro Val Phe Ile Thr Val Lys Met Asp Val Leu Asn Ala Phe
            675                 680                 685

Lys Tyr Pro Leu Leu Ile Gly Val Gly Leu Ser Thr Val Ile Gly Leu
            690                 695                 700

Leu Ser Cys Leu Ile Gly Tyr Cys Ser Ser His Trp Cys Cys Lys Lys
705                 710                 715                 720

Glu Val Gln Glu Thr Arg Arg Glu Arg Arg Arg Leu Met Ser Met Glu
                725                 730                 735

Met Asp Thr Gly Gly Ser Gly Gly Ser Val Ser Lys Gly Glu Glu Leu
                740                 745                 750

Phe Thr Gly Val Val Pro Ile Leu Val Glu Leu Asp Gly Asp Val Asn
                755                 760                 765

Gly His Lys Phe Ser Val Ser Gly Glu Gly Glu Gly Asp Ala Thr Tyr
            770                 775                 780

Gly Lys Leu Thr Leu Lys Phe Ile Cys Thr Thr Gly Lys Leu Pro Val
785                 790                 795                 800

Pro Trp Pro Thr Leu Val Thr Thr Leu Thr Tyr Gly Val Gln Cys Phe
                805                 810                 815

Ser Arg Tyr Pro Asp His Met Lys Gln His Asp Phe Phe Lys Ser Ala
                820                 825                 830

Met Pro Glu Gly Tyr Val Gln Glu Arg Thr Ile Phe Phe Lys Asp Asp
            835                 840                 845

Gly Asn Tyr Lys Thr Arg Ala Glu Val Lys Phe Glu Gly Asp Thr Leu
850                 855                 860

Val Asn Arg Ile Glu Leu Lys Gly Ile Asp Phe Lys Glu Asp Gly Asn
865                 870                 875                 880

Ile Leu Gly His Lys Leu Glu Tyr Asn Tyr Asn Ser His Asn Val Tyr
                885                 890                 895
```

```
Ile Met Ala Asp Lys Gln Lys Asn Gly Ile Lys Val Asn Phe Lys Ile
            900                 905                 910

Arg His Asn Ile Glu Asp Gly Ser Val Gln Leu Ala Asp His Tyr Gln
            915                 920                 925

Gln Asn Thr Pro Ile Gly Asp Gly Pro Val Leu Leu Pro Asp Asn His
            930                 935                 940

Tyr Leu Ser Thr Gln Ser Lys Leu Ser Lys Asp Pro Asn Glu Lys Arg
945                 950                 955                 960

Asp His Met Val Leu Leu Glu Phe Val Thr Ala Ala Gly Ile Thr Leu
            965                 970                 975

Gly Met Asp Glu Leu Tyr Lys Asp Tyr Lys Asp Asp Asp Lys
            980                 985                 990

<210> SEQ ID NO 22
<211> LENGTH: 1055
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Met Thr Val Leu Ala Pro Ala Trp Ser Pro Thr Thr Tyr Leu Leu Leu
1               5                   10                  15

Leu Leu Leu Leu Ser Ser Gly Leu Ser Gly Thr Gln Asp Cys Ser Phe
            20                  25                  30

Gln His Ser Pro Ile Ser Ser Asp Phe Ala Val Lys Ile Arg Glu Leu
            35                  40                  45

Ser Asp Tyr Leu Leu Gln Asp Tyr Pro Val Thr Val Ala Ser Asn Leu
50                  55                  60

Gln Asp Glu Glu Leu Cys Gly Gly Leu Trp Arg Leu Val Leu Ala Gln
65                  70                  75                  80

Arg Trp Met Glu Arg Leu Lys Thr Val Ala Gly Ser Lys Met Gln Gly
            85                  90                  95

Leu Leu Glu Arg Val Asn Thr Glu Ile His Phe Val Thr Lys Cys Ala
            100                 105                 110

Phe Gln Pro Pro Pro Ser Cys Leu Arg Phe Val Gln Thr Asn Ile Ser
            115                 120                 125

Arg Leu Leu Gln Glu Thr Ser Glu Gln Leu Val Ala Leu Lys Pro Trp
            130                 135                 140

Ile Thr Arg Gln Asn Phe Ser Arg Cys Leu Glu Leu Gln Cys Gln Pro
145                 150                 155                 160

Asp Ser Ser Thr Leu Pro Pro Pro Trp Ser Pro Arg Pro Leu Glu Ala
            165                 170                 175

Thr Ala Pro Thr Ala Pro Gln Pro Pro Ser Ala Gly Gly Gly Gly Ser
            180                 185                 190

Gly Gly Gly Gly Ser Arg Val Val Arg Val Pro Thr Ala Thr Leu Val
            195                 200                 205

Arg Val Val Gly Thr Glu Leu Val Ile Pro Cys Asn Val Ser Asp Tyr
            210                 215                 220

Asp Gly Pro Ser Glu Gln Asn Phe Asp Trp Ser Phe Ser Ser Leu Gly
225                 230                 235                 240

Ser Ser Phe Val Glu Leu Ala Ser Thr Trp Glu Val Gly Phe Pro Ala
            245                 250                 255

Gln Leu Tyr Gln Glu Arg Leu Gln Arg Gly Glu Ile Leu Leu Arg Arg
```

```
              260                 265                 270
Thr Ala Asn Asp Ala Val Glu Leu His Ile Lys Asn Val Gln Pro Ser
            275                 280                 285
Asp Gln Gly His Tyr Lys Cys Ser Thr Pro Ser Thr Asp Ala Thr Val
        290                 295                 300
Gln Gly Asn Tyr Glu Asp Thr Val Gln Val Lys Val Leu Ala Asp Ser
305                 310                 315                 320
Leu His Val Gly Pro Ser Ala Arg Pro Pro Ser Leu Ser Leu Arg
                325                 330                 335
Glu Gly Glu Pro Phe Glu Leu Arg Cys Thr Ala Ala Ser Ala Ser Pro
                340                 345                 350
Leu His Thr His Leu Ala Leu Leu Trp Glu Val His Arg Gly Pro Ala
                355                 360                 365
Arg Arg Ser Val Leu Ala Leu Thr His Glu Gly Arg Phe His Pro Gly
            370                 375                 380
Leu Gly Tyr Glu Gln Arg Tyr His Ser Gly Asp Val Arg Leu Asp Thr
385                 390                 395                 400
Val Gly Ser Asp Ala Tyr Arg Leu Ser Val Ser Arg Ala Leu Ser Ala
                405                 410                 415
Asp Gln Gly Ser Tyr Arg Cys Ile Val Ser Glu Trp Ile Ala Glu Gln
                420                 425                 430
Gly Asn Trp Gln Glu Ile Gln Glu Lys Ala Val Glu Val Ala Thr Val
            435                 440                 445
Val Ile Gln Pro Ser Val Leu Arg Ala Ala Val Pro Lys Asn Val Ser
450                 455                 460
Val Ala Glu Gly Lys Glu Leu Asp Leu Thr Cys Asn Ile Thr Thr Asp
465                 470                 475                 480
Arg Ala Asp Asp Val Arg Pro Glu Val Thr Trp Ser Phe Ser Arg Met
                485                 490                 495
Pro Asp Ser Thr Leu Pro Gly Ser Arg Val Leu Ala Arg Leu Asp Arg
                500                 505                 510
Asp Ser Leu Val His Ser Ser Pro His Val Ala Leu Ser His Val Asp
            515                 520                 525
Ala Arg Ser Tyr His Leu Leu Val Arg Asp Val Ser Lys Glu Asn Ser
            530                 535                 540
Gly Tyr Tyr Tyr Cys His Val Ser Leu Trp Ala Pro Gly His Asn Arg
545                 550                 555                 560
Ser Trp His Lys Val Ala Glu Ala Val Ser Ser Pro Ala Gly Val Gly
                565                 570                 575
Val Thr Trp Leu Glu Pro Asp Tyr Gln Val Tyr Leu Asn Ala Ser Lys
            580                 585                 590
Val Pro Gly Phe Ala Asp Asp Pro Thr Glu Leu Ala Cys Arg Val Val
            595                 600                 605
Asp Thr Lys Ser Gly Glu Ala Asn Val Arg Phe Thr Val Ser Trp Tyr
        610                 615                 620
Tyr Arg Met Asn Arg Arg Ser Asp Asn Val Val Thr Ser Glu Leu Leu
625                 630                 635                 640
Ala Val Met Asp Gly Asp Trp Thr Leu Lys Tyr Gly Glu Arg Ser Lys
                645                 650                 655
Gln Arg Ala Gln Asp Gly Asp Phe Ile Phe Ser Lys Glu His Thr Asp
            660                 665                 670
Thr Phe Asn Phe Arg Ile Gln Arg Thr Thr Glu Glu Asp Arg Gly Asn
            675                 680                 685
```

Tyr Tyr Cys Val Val Ser Ala Trp Thr Lys Gln Arg Asn Asn Ser Trp
690             695                 700

Val Lys Ser Lys Asp Val Phe Ser Lys Pro Val Asn Ile Phe Trp Ala
705             710                 715                 720

Leu Glu Asp Ser Val Leu Val Val Lys Ala Arg Gln Pro Lys Pro Phe
            725                 730                 735

Phe Ala Ala Gly Asn Thr Phe Glu Met Thr Cys Lys Val Ser Ser Lys
            740                 745                 750

Asn Ile Lys Ser Pro Arg Tyr Ser Val Leu Ile Met Ala Glu Lys Pro
            755                 760                 765

Val Gly Asp Leu Ser Ser Pro Asn Glu Thr Lys Tyr Ile Ile Ser Leu
770             775                 780

Asp Gln Asp Ser Val Val Lys Leu Glu Asn Trp Thr Asp Ala Ser Arg
785             790                 795                 800

Val Asp Gly Val Val Leu Glu Lys Val Gln Glu Asp Glu Phe Arg Tyr
            805                 810                 815

Arg Met Tyr Gln Thr Gln Val Ser Asp Ala Gly Leu Tyr Arg Cys Met
            820                 825                 830

Val Thr Ala Trp Ser Pro Val Arg Gly Ser Leu Trp Arg Glu Ala Ala
            835                 840                 845

Thr Ser Leu Ser Asn Pro Ile Glu Ile Asp Phe Gln Thr Ser Gly Pro
850             855                 860

Ile Phe Asn Ala Ser Val His Ser Asp Thr Pro Ser Val Ile Arg Gly
865             870                 875                 880

Asp Leu Ile Lys Leu Phe Cys Ile Ile Thr Val Glu Gly Ala Ala Leu
            885                 890                 895

Asp Pro Asp Asp Met Ala Phe Asp Val Ser Trp Phe Ala Val His Ser
            900                 905                 910

Phe Gly Leu Asp Lys Ala Pro Val Leu Leu Ser Ser Leu Asp Arg Lys
            915                 920                 925

Gly Ile Val Thr Thr Ser Arg Arg Asp Trp Lys Ser Asp Leu Ser Leu
930             935                 940

Glu Arg Val Ser Val Leu Glu Phe Leu Leu Gln Val His Gly Ser Glu
945             950                 955                 960

Asp Gln Asp Phe Gly Asn Tyr Tyr Cys Ser Val Thr Pro Trp Val Lys
            965                 970                 975

Ser Pro Thr Gly Ser Trp Gln Lys Glu Ala Glu Ile His Ser Lys Pro
            980                 985                 990

Val Phe Ile Thr Val Lys Met Asp Val Leu Asn Ala Phe Lys Tyr Pro
            995                 1000                1005

Leu Leu Ile Gly Val Gly Leu Ser Thr Val Ile Gly Leu Leu Ser
    1010                1015                1020

Cys Leu Ile Gly Tyr Cys Ser Ser His Trp Cys Cys Lys Lys Glu
    1025                1030                1035

Val Gln Glu Thr Arg Arg Glu Arg Arg Arg Leu Met Ser Met Glu
    1040                1045                1050

Met Asp
    1055

<210> SEQ ID NO 23
<211> LENGTH: 38
<212> TYPE: PRT
<213> ORGANISM: Artificial Sequence
<220> FEATURE:

```
<223> OTHER INFORMATION: Description of Artificial Sequence: Synthetic
      polypeptide

<400> SEQUENCE: 23

Glu His Ser Ala Gly Gly Gly Gly Ser Asp Tyr Lys Asp Asp Asp Asp
1               5                   10                  15

Lys Gly Gly Gly Gly Ser Leu Ser Asn Pro Ile Glu Ile Asp Phe Gln
                20                  25                  30

Thr Ser Gly Pro Ile Phe
            35

<210> SEQ ID NO 24
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu His Ser Ala Gly Gly Gly Gly Ser Asp Tyr Lys Asp Asp Asp Asp
1               5                   10                  15

Lys Gly Gly Gly Gly Ser Ile Glu Ile Asp Phe Gln Thr Ser Gly Pro
                20                  25                  30

Ile Phe

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu His Ser Ala Gly Gly Gly Gly Ser Asp Tyr Lys Asp Asp Asp Asp
1               5                   10                  15

Lys Gly Gly Gly Gly Ser Phe Gln Thr Ser Gly Pro Ile Phe
                20                  25                  30

<210> SEQ ID NO 26
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu His Ser Ala Gly Gly Gly Gly Ser Asp Tyr Lys Asp Asp Asp Asp
1               5                   10                  15

Lys Gly Gly Gly Gly Ser Gly Pro Ile Phe
                20                  25
```